US008748627B2

(12) United States Patent
Gu et al.

(10) Patent No.: US 8,748,627 B2
(45) Date of Patent: Jun. 10, 2014

(54) ACETYL-COA CARBOXYLASE (ACC) INHIBITORS AND THEIR USE IN DIABETES, OBESITY AND METABOLIC SYNDROME

(75) Inventors: Yu Gui Gu, Libertyville, IL (US);
Moshe Weitzberg, Highland Park, IL (US); Xiangdong Xu, Buffalo Grove, IL (US); Richard F. Clark, Gurnee, IL (US); Tianyuan Zhang, Gurnee, IL (US); Qun Li, Libertyville, IL (US); Todd M. Hansen, Grayslake, IL (US); Hing Sham, South San Francisco, CA (US); Bruce A. Beutel, Lake Forest, IL (US); Heidi S. Camp, Winnetka, IL (US); Xiaojun Wang, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 1696 days.

(21) Appl. No.: 11/675,410

(22) Filed: Feb. 15, 2007

(65) Prior Publication Data

US 2007/0225332 A1 Sep. 27, 2007

Related U.S. Application Data

(60) Provisional application No. 60/773,436, filed on Feb. 15, 2006.

(51) Int. Cl.
| | |
|---|---|
| *A61K 31/427* | (2006.01) |
| *A61K 31/433* | (2006.01) |
| *A61K 31/4245* | (2006.01) |
| *A61K 31/4439* | (2006.01) |
| *A61K 31/444* | (2006.01) |
| *C07D 417/12* | (2006.01) |
| *C07D 417/14* | (2006.01) |
| *C07D 417/04* | (2006.01) |
| *C07D 413/12* | (2006.01) |
| *C07D 413/14* | (2006.01) |

(52) U.S. Cl.
USPC ........... 548/182; 548/247; 548/131; 548/136; 546/256; 546/269.7; 546/272.1; 514/333; 514/369; 514/364; 514/378; 514/363; 514/340; 514/342; 514/361

(58) Field of Classification Search
USPC ....................................................... 548/182
See application file for complete search history.

(56) References Cited

U.S. PATENT DOCUMENTS

| | | | | |
|---|---|---|---|---|
| 4,720,493 | A * | 1/1988 | Kawakita et al. .......... 514/236.8 |
| 5,177,067 | A | 1/1993 | Guerry et al. | |
| 5,750,470 | A | 5/1998 | Morimoto et al. | |
| 5,760,032 | A * | 6/1998 | Kitajima et al. ............. 514/220 |
| 6,441,177 | B1 | 8/2002 | Aebi et al. | |
| 6,586,453 | B2 | 7/2003 | Chanoa et al. | |
| 6,620,828 | B2 * | 9/2003 | Chu et al. ..................... 514/364 |
| 6,979,741 | B2 * | 12/2005 | Perry et al. .................... 548/229 |
| 8,207,350 | B2 | 6/2012 | Gu et al. | |
| 2004/0176409 | A1 | 9/2004 | McGee et al. | |
| 2005/0203146 | A1 | 9/2005 | Herpin et al. | |
| 2005/0288340 | A1 | 12/2005 | Hamanaka | |
| 2006/0178400 | A1 * | 8/2006 | Beutel et al. ................. 514/317 |
| 2007/0219251 | A1 | 9/2007 | Gu et al. | |
| 2008/0161368 | A1 * | 7/2008 | Gu et al. ....................... 514/365 |
| 2009/0239830 | A1 * | 9/2009 | Munger et al. ............... 514/129 |

FOREIGN PATENT DOCUMENTS

| | | | |
|---|---|---|---|
| CA | 2231493 | * | 4/1997 |
| EP | 1553091 | | 7/2005 |
| GB | 2404855 A | * | 2/2005 |
| JP | 59-196876 | | 10/2005 |
| JP | 2006022065 | | 1/2006 |
| WO | 96/04278 | | 2/1996 |
| WO | 97/12879 | | 4/1997 |
| WO | 98/08845 | | 3/1998 |
| WO | 02/051355 | | 7/2002 |
| WO | 02/083643 | | 10/2002 |
| WO | 02/100403 | | 12/2002 |
| WO | 03/009841 | | 2/2003 |
| WO | 03/015773 | | 2/2003 |
| WO | 03/072100 | | 9/2003 |
| WO | 2004/052840 | | 6/2004 |
| WO | 2004/106307 | | 12/2004 |
| WO | WO-2004/113331 A1 | * | 12/2004 |
| WO | 2005007647 | | 1/2005 |
| WO | 2005/044793 | | 5/2005 |
| WO | 2005/051945 | | 6/2005 |
| WO | 2005/063729 | | 7/2005 |
| WO | 2005/070920 | | 8/2005 |
| WO | 2005/113069 | | 12/2005 |
| WO | 2006/002099 | | 1/2006 |
| WO | 2006/011631 | | 2/2006 |

OTHER PUBLICATIONS

Chemical Abstracts Registry No. 52170-13-5, indexed in the Registry file on STN Nov. 16, 1984.*
Turkoglu et al., "Effect of Abdominal Obesity on Insulin Resistance and the Components of the Metabolics Syndrome: Evidence Supporting Obesity as the Central Feature" Obes. Surg. 13: 699-705 (2003).
Steyn et al., "Diet, Nutrition and the Prevention of Type 2 Diabetes" Public Health Nutr. 7: 146-165 (2004).
Hulver et al., "Skeletal Muscle Lipid Metabolism with Obesity" Am. J. Physiol. Endocrinol Metab. 284: E741-747 (2003).

(Continued)

*Primary Examiner* — Laura L. Stockton
(74) *Attorney, Agent, or Firm* — Lisa V. Mueller; Michael Best & Friedrich LLP

(57) ABSTRACT

The present invention relates to compounds of formula (I),

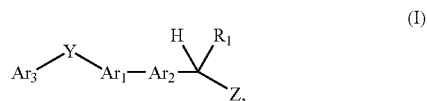

which inhibit acetyl-CoA carboxylase (ACC) and are useful for the prevention or treatment of metabolic syndrome, type II diabetes, obesity, atherosclerosis and cardiovascular diseases in humans.

29 Claims, No Drawings

(56) References Cited

OTHER PUBLICATIONS

Sinha, et al., "Assessment of Skeletal Muscle Triglyceride Content by 1H Nuclear Magnetic Resonance Spectroscopy in Lean and Obese Adolescents: Relationships to Insulin Sensitivity, Total Body Fat, and Central Adiposity" Diabetes 51: 1022-1027 (2002).
Friedman et al., "Fat in all the Wrong Places" Nature 415: 268-269 (2002).
Ruderman et al., "AMP Kinase and Malonyl-CoA: Targets for Therapy of the Metabolic Syndrome" Nature Rev. Drug Discov. 3: 340-351 (2004).
Mao et al., "Human Acetyl-CoA Carboxylase 1 Gene: Presence of Three Promoters and Heterogeneity at the 5-untranslated mRNA Region" Proc. Natl. Acad. Sci. USA 100: 7515-7520 (2003).
Abu-Elheiga et al., "Continuous Fatty Acid Oxidation and Reduced Fat Storage in Mice Lacking Acetyl-CoA Carboxylase 2" Science 291: 2613-2616 (2001).
Abu-Elheiga et al., "Acetyl-CoA Carboxylase 2 Mutant Mice are Protected Against Obesity and Diabetes Induced by High-Fat/High-Carbohydrate Diets" Proc. Natl. Acad. Sci. USA 100: 10207-10212 (2003).
Yamauchi et al., "The Fat-derived Hormone Adiponectin Reverses Insulin Resistance Associated with both Lipoatrophy and Obesity" Nat. Med. 7: 941-946 (2001).
Higuchi and Stella, Pro-drugs as Novel Delivery Systems, vol. 14 of the A.C.S. Symposium Series, Table of Contents.
Abu-Elheiga et al., "The Subcellular Localization of Acetyl-CoA Carboxylase 2" Proc. Natl. Acad. Sci. USA 97: 1444-1449 (2000).
Abu-Elheiga et al., "Human Acetyl-CoA Carboxylase 2: Molecular Cloning, Characterization, Chromosomal Mapping, and Evidence for Two Isoforms" J. Biol. Chem. 272: 10669-10699 (1997).
XP002448591, Derwent Publications Ltd., London, GB.
Gu et al., "N-{3-[2-(4-Alkoxyphenoxy)thiazol-5-yl]-1-methylprop-2-ynyl}carboxy Derivatives as Acrtyl-CoA Carboxylase Inhibitors—Improvement of Caridovascular and Neurological Liabilities via Structural Modifications", Journal of Medicinal Chemistry 50:5, 1078-1082, XP002448589 (2007).
Aicher, T.D. et al., "Substituted tetrahydropyrrolo[2,1-b]oxazol-5(6H)-ones and tetrahydropyrrolo[2,1-b]thiazol-5(6H)- ones as hypoglycemic agents," J. Med. Chem. (1998) 41(23):4556-4566.
Brown et al., "Diacid bases. Part II. Curarising Agents. Derivatives of Diphenyl Ether," J. Of the Chem. Soc. (1954) 76(3):873-880.
Clark et al., Bioorg. Chem. Med. Chem. Lett. (2006) 16(23):6078-6081.
El Kazzouli et al., J. Marocain de Chimie Heterocyclique (2004) 3(1):1-7.
Greene et al., Protecting Groups in Chemical Synthesis, 3rd edition, John Wiley & Sons, Ny (1999) Table of Contents.
Gu et al., J. Med. Chem. (2006) 49(13):3770-3773.
Wade, L.G., Jr., Organic Chemistry, 3rd Edition, Chapter 13 entitled "Ethers and epoxides," p. 594; Chapter 18 entitled "Ketones and aldehydes," p. 810; Chapter 19 entitled "Structure of amines," p. 871; and Chapter 19 entitled: "Basicity of amines," p. 879 (Dec. 22, 1994).
United States Patent Office Action for U.S. Appl. No. 11/950,692 dated Aug. 2, 2010 (17 pages).
United States Patent Office Action for U.S. Appl. No. 12/259,090 dated Jun. 13, 2011 (9 pages).
United States Patent Office Action for U.S. Appl. No. 11/675,406 dated Jun. 23, 2010 (14 pages).
United States Patent Office Action for U.S. Appl. No. 11/675,406 dated Mar. 9, 2011 (14 pages).
United States Patent Office Action for U.S. Appl. No. 11/675,406 dated May 16, 2013 (21 pages).
United States Patent Office Notice of Allowance for U.S. Appl. No. 11/675,406 dated Sep. 11, 2013 (15 pages).

\* cited by examiner

ACETYL-COA CARBOXYLASE (ACC) INHIBITORS AND THEIR USE IN DIABETES, OBESITY AND METABOLIC SYNDROME

CROSS-REFERENCE SECTION TO RELATED APPLICATIONS

This application claims the benefit of priority of U.S. Provisional Application Ser. No. 60/773,436, which was filed Feb. 15, 2006, and is incorporated herein by reference in its entirety.

FIELD OF THE INVENTION

The present invention relates to compounds that inhibit acetyl-CoA carboxylase (ACC) and are useful for the prevention or treatment of diseases including, but not limited to, metabolic syndrome, type 2 diabetes, obesity, atherosclerosis, and cardiovascular diseases in mammals

BACKGROUND OF THE INVENTION

The incidence of type 2 diabetes has dramatically increased over the past decade. This epidemic is largely attributed to proliferation of key risk factors, which include a sedentary lifestyle, a high fat diet, obesity and the demographic shift to a more aged population. There is ample evidence to indicate that increased abdominal obesity and physical inactivity contribute significantly to the development of type 2 diabetes (Turkoglu C, Duman B S, Gunay D, Cagatay P, Ozcan R, Buyukdevrim A S: Effect of abdominal obesity on insulin resistance and the components of the metabolic syndrome: evidence supporting obesity as the central feature. Obes Surg 2003; 13: 699-705 Steyn N P, Mann J, Bennett P H, Temple N, Zimmet P, Tuomilehto J, Lindstrom J, Louheranta A: Diet, nutrition and the prevention of type 2 diabetes Public Health Nutr 2004; 7; 147-65).

At the cellular level, an increase in ectopic fat storage in nonadipose tissues such as in muscle, liver and pancreas is a strong predictor of the development of insulin resistance and type 2 diabetes (Hulver M W, Berggren J R, Cortright R N, Dudek R W, Thompson R P, Pories W J, MacDonald K G, Cline G W, Shulman G I, Dolm G L, Houmard J A: Skeletal muscle lipid metabolism with obesity. Am J Physiol Endocrinol Metab 2003; 284: E741-7. Sinha R, Dufour. S, Petersen K F, LeBon V, Enoksson S, Ma Y Z, Savoye M, Rothman D L, Shulman G I, Caprio S: Assessment of skeletal muscle triglyceride content by $^1$H nuclear magnetic resonance spectroscopy in lean and obese adolescents: relationships to insulin sensitivity, total body fat, and central adiposity. Diabetes 2002; 51: 1022-7). The precise mechanism of how increased intracellular lipid content exacerbates whole body insulin sensitivity is unclear at present but it has been postulated that increased long chain fatty acyl-CoAs, ceramide or diacylglycerol, whose contents are proportional to the accumulation of intramyocellular triglyceride, antagonizes metabolic actions of insulin, reduces muscle glucose uptake and inhibits hepatic glucose production (Sinha R, Dufour S, Petersen K F, LeBon V, Enoksson S, Ma Y Z, Savoye M, Rothman D L, Shulman G I, Caprio S: Assessment of skeletal muscle triglyceride content by $^1$H nuclear magnetic resonance spectroscopy in lean and obese adolescents: relationships to insulin sensitivity, total body fat, and central adiposity. Diabetes 2002; 51: 1022-7. Friedman J: Fat in all the wrong places. Nature 2002; 415: 268-9). As muscle is the primary site of metabolic action of insulin, the development of muscle insulin resistance along with liver insulin resistance are thus inherently linked to the development of whole body insulin resistance.

In order to increase muscle and liver fat oxidation and thus limit the concentration of LCFACoA's we aim to inhibit the activity of Acetyl CoA Carboxylase (ACC), which catalyzes the production of malonyl-CoA from acetyl-CoA. Malonyl-CoA is an intermediate substrate that plays an important role in the overall fatty acid metabolism: Malonyl-CoA is utilized by fatty acid synthase for de novo lipogenesis, and also acts as a potent allosteric inhibitor of carnitine palmitoyltransferase 1 (CPT1), a mitochondrial membrane protein that shuttles long chain fatty acyl CoAs into the mitochondrial where they are oxidized (Ruderman N, Prentki M: AMP kinase and malonyl-CoA: targets for therapy of the metabolic syndrome. Nat Rev Drug Discov 2004; 3: 340-51). A small molecule inhibitor, of ACC would thus limit de novo lipid synthesis, de-inhibit CPT1 and subsequently increase fat oxidation.

In rodents and in humans, there are two known isoforms of ACC that are encoded by distinct genes and share approximately 70% amino acids identity. ACC1, which encodes a 265 KD protein, is highly expressed in the cytosol of lipogenic tissues such as liver and adipose, whereas 280 KD ACC2 protein is preferentially expressed in oxidative tissues, skeletal muscle and heart (Mao J, Chirala S S, Wakil S J: Human acetyl-CoA carboxylase 1 gene: presence of three promoters and heterogeneity at the 5'-untranslated mRNA region. Proc Natl Acad Sci USA 2003; 100: 7515-20. Abu-Elheiga L, Almarza-Ortega D B, Baldini A, Wakil S J: Human acetyl-CoA carboxylase 2. Molecular cloning, characterization, chromosomal mapping, and evidence for two isoforms. J Biol Chem 1997; 272: 10669-77). ACC2 has a unique 114 amino acid N-terminus with a putative transmembrane domain (TM), which is thought to be responsible for mitochondrial targeting (Abu-Elheiga L, Brinkley W R, Zhong L, Chirala S S, Woldegiorgis G, Wakil S J: The subcellular localization of acetyl-CoA carboxylase 2 Proc Natl Acad Sci USA 2000; 97: 1444-9). Based on tissue distribution and subcellular localization of these two isoforms, the current hypothesis is that a distinct pool of Malonyl-CoA produced by ACC1 is preferentially converted into fatty acids by fatty acid synthase, whereas another pool of Malonyl-CoA synthesized primarily by ACC2, presumed localized in near mitochondria, is involved in the inhibition of CPT1 (Abu-Elheiga L, Brinkley W R, Zhong L, Chirala S S, Woldegiorgis G, Wakil S J: The subcellular localization of acetyl-CoA carboxylase 2. Proc Natl Acad Sci USA 2000; 97: 1444-9) Therefore, ACC1 inhibition reduces fatty acid synthesis and is beneficial for use in treating diseases such as metabolic syndrome.

Genetic studies have demonstrated that ACC2 knockout mice are healthy and fertile with a favorable metabolic phenotype, increased fatty acid oxidation, increased thermogenesis, reduced hepatic TG content and subsequent decrease in body weight despite increase in food intake compared to their littermates (Abu-Elheiga L, Matzuk M M, Abo-Hashema K A, Wakil S J: Continuous fatty acid oxidation and reduced fat storage in mice lacking acetyl-CoA carboxylase 2. Science 2001; 291: 2613-6). In addition, these mice are resistant against high fat diet-induced obesity and insulin resistance (Abu-Elheiga L, Oh W, Kordari P, Wakil S J: Acetyl-CoA carboxylase 2 mutant mice are protected against obesity and diabetes induced by high-fat/high-carbohydrate diets. Proc Natl Acad Sci USA 2003; 100: 10207-12) Also, recently it was demonstrated that the effects of leptin and adiponectin, cytokines secreted from adipose tissue, to increase fatty acid oxidation are at least due in part to the inhibition of ACC in liver and skeletal muscle (Yamauchi T, Kamon J, Waki H, Terauchi Y, Kubota N, Hara K, Mori Y, Ide T, Murakami K, Tsuboyama-Kasaoka N, Ezaki O, Akanuma Y, Gavrilova O, Vinson C, Reitman M L, Kagechika H, Shudo I C, Yoda M, Nakano Y, Tobe K, Nagai R, Kimura S, Tomita M, Froguel P, Kadowaki T: The fat-derived hormone adiponectin reverses insulin resistance associated with both lipoatrophy and obesity. Nat Med 2001; 7; 941-6). Taken together these data support that the discovery of small molecular inhibitors of ACC2 can provide a favorable metabolic profile against obesity induced type 2 diabetic patients. Further-more, the dual inhibition of ACC1 and ACC2 can provide the profile needed to demonstrate benefit for patients exhibiting conditions of metabolic syndrome.

SUMMARY OF THE INVENTION

The present invention is directed to compounds of formula (I),

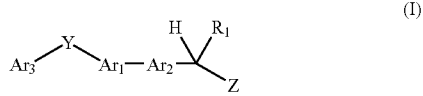

or a pharmaceutically acceptable salt, prodrug, salt of a prodrug, or combination thereof, wherein $R_1$ is selected from the group consisting of hydrogen, cycloalkyl, alkyl and haloalkyl;

Y is selected from the group consisting of —$(CR_{4a}R_{4b})_m$—, —C(O)—, —O—, —N(H)—, —N(alkyl)- and —S—; wherein m is 1, 2 or 3;

each of $R_{4a}$, $R_{4b}$, at each occurrence, is independently selected from the group consisting of hydrogen, alkyl, hydroxyalkyl, and haloalkyl when m is 1, 2 or 3;

alternatively, $R_{4a}$ and $R_{4b}$ together with the carbon to which they are attached form a monocyclic cycloalkyl or heterocycle ring when m is 1;

$Ar_3$ is phenyl or monocyclic heteroaryl; wherein $Ar_3$ is substituted with 1, 2 or 3 or 4 substituents independently selected from the group consisting of alkyl, alkenyl, —CN, —$NO_2$, halogen, —$OR_5$, —O—N=$CH(R_2)$, —$OC(O)R_2$, —$OC(O)N(R_3)(R_5)$, —$OC(O)OR_2$, —$OS(O)_2R_5$, —$SR_2$, —$S(O)R_2$, —$S(O)_2R_5$, —$S(O)_2OR_5$, —$S(O)_2N(R_3)(R_5)$, —$C(O)R_5$, —$C(O)N(R_3)(R_5)$, —$C(O)OR_5$, —$C(O)N(R_3)(R_5)$, —$N(R_3)(R_5)$, —N(H)—N=$CH(R_2)$, —$N(R_3)C(O)R_2$, —$N(R_3)C(O)OR_5$, —$N(R_3)S(O)_2R_5$, —$N(R_3)C(O)N(R_3)(R_5)$, —$N(R_3)S(O)_2N(R_3)(R_5)$, —$R_8$, haloalkyl, cyanoalkyl, nitroalkyl, hydroxyalkyl, alkoxyalkyl, haloalkoxyalkyl, -alkylenyl-$OC(O)R_2$, -alkylenyl-$OC(O)N(R_3)(R_5)$, -alkylenyl-$OC(O)OR_2$, -alkylenyl-$OS(O)_2R_5$, -alkylenyl-$SR_2$, -alkylenyl-$S(O)R_2$, -alkylenyl-$S(O)_2R_5$, -alkylenyl-$S(O)_2OR_5$, -alkylenyl-$S(O)_2N(R_3)(R_5)$, -alkylenyl-$C(O)R_5$, -alkylenyl-$C(O)N(R_3)(R_5)$, -alkylenyl-$C(O)OR_5$, -alkylenyl-$C(O)N(R_3)(R_5)$, -alkylenyl-$N(R_3)(R_5)$, -alkylenyl-$N(R_3)C(O)R_2$, -alkylenyl-$N(R_3)C(O)OR_5$, -alkylenyl-$N(R_3)S(O)_2R_5$, -alkylenyl-$N(R_3)C(O)N(R_3)(R_5)$, -alkylenyl-$N(R_3)S(O)_2N(R_3)(R_5)$, and -alkylenyl-$R_8$;

$R_2$, at each occurrence, is independently selected from the group consisting of alkyl, alkenyl, haloalkyl, alkoxyalkyl, haloalkoxyalkyl, —$R_8$, and -alkylenyl-$R_8$;

$R_3$, at each occurrence, is independently selected from the group consisting of hydrogen, alkyl, arylalkyl, haloalkyl, and heteroarylalkyl;

$R_5$, at each occurrence, is independently selected from the group consisting of hydrogen, alkyl, alkenyl, haloalkyl, alkoxyalkyl, haloalkoxyalkyl, —$R_8$, and -alkylenyl-$R_8$;

$Ar_1$ is selected from the group consisting of phenyl and a monocyclic, five or six-membered heteroaryl;

$Ar_2$ is a monocyclic five membered heteroaryl, wherein each $Ar_2$ is independently unsubstituted or substituted with 1 or 2 substituents selected from the group consisting of alkyl, alkenyl, halogen, —CN, —$NO_2$, hydroxy, alkoxy, —$NH_2$, —N(H)(alkyl), —$N(alkyl)_2$, —C(O)OH, —C(O)Oalkyl, —C(O)H, —C(O)alkyl, and haloalkyl;

Z is selected from the group consisting of —$OR_{9a}$, -alkylenyl-$OR_{9a}$, —$NR_6R_{9b}$ and -alkylenyl-$NR_6R_{9b}$;

$R_6$, at each occurrence, is independently selected from the group consisting of hydrogen, alkyl and haloalkyl;

$R_{9a}$, at each occurrence, is independently selected from the group consisting of hydrogen, alkyl, haloalkyl, $R_8$, —C(O)$OR_{10}$, —$S(O)_2R_{10}$, —$C(O)NR_7R_{11}$, —$S(O)_2NR_7R_{11}$, —$C(O)R_{10}$, -alkylenyl-$OR_{10}$, -alkylenyl-$NR_7R_{11}$, -alkylenyl-$N(R_7)C(O)OR_{10}$, -alkylenyl-$N(R_7)C(O)R_{10}$, -alkylenyl-$C(O)OR_{10}$, -alkylenyl-$S(O)_2R_{10}$, -alkylenyl-$S(O)_2NR_7R_{11}$, -alkylenyl-$C(O)NR_7R_{11}$, -alkylenyl-$C(O)R_{10}$, and -alkylenyl-$R_8$, $R_{9b}$, at each occurrence, is independently selected from the group consisting of hydrogen, alkyl, hydroxy, alkoxy, $R_8$, —C(=NH)$NH_2$, —$C(O)OR_{10}$, —$S(O)_2R_{10}$, —C(O)$NR_7R_{12}$, —$C(O)ONH_2$, —$S(O)_2NR_7R_{12}$, —$C(O)R_{10}$, —$C(O)CH_2C(O)R_{10}$, haloalkyl, -alkylenyl-$OR_{10}$, -alkylenyl-$NR_7R_{12}$, -alkylenyl-$N(R_7)C(O)OR_{10}$, -alkylenyl-$N(R_7)C(O)R_{10}$, -alkylenyl-$C(O)OR_{10}$, -alkylenyl-$S(O)_2R_{10}$, -alkylenyl-$S(O)_2NR_7R_{12}$, -alkylenyl-$C(O)NR_7R_{12}$, -alkylenyl-$C(O)R_{10}$, and -alkylenyl-$R_8$, $R_7$, at each occurrence, are each independently selected from the group consisting of hydrogen, alkyl and haloalkyl;

$R_{10}$, at each occurrence, is independently selected from the group consisting of hydrogen, alkyl, alkoxyalkyl, cyanoalkyl, haloalkyl, —$R_8$, and alkylenyl-$R_8$;

$R_{11}$, at each occurrence, is independently selected from the group consisting of hydrogen, alkyl, hydroxy, alkoxy, alkoxyalkyl, cyanoalkyl, haloalkyl, —$R_8$, and -alkylenyl-$R_8$;

$R_{12}$, at each occurrence, is independently selected from the group consisting of hydrogen, alkyl, hydroxy, alkoxy, —$R_8$, alkoxyalkyl, cyanoalkyl, haloalkyl, -alkylenyl-$C(O)NH_2$, -alkylenyl-$C(O)N(H)(alkyl)$, -alkylenyl-$C(O)N(alkyl)_2$, -alkylenyl-$N(H)C(O)Oalkyl$, -alkylenyl-$N(alkyl)C(O)Oalkyl$, and -alkylenyl-$R_8$; and $R_8$, at each occurrence, is independently selected from the group consisting of aryl, heteroaryl, heterocycle, cycloalkyl and cycloalkenyl; and the phenyl, cycloalkyl, cycloalkenyl, aryl, heteroaryl, heterocycle, aryl moiety of the arylalkyl, and the heteroaryl moiety of the heteroarylalkyl represented by $Ar_1$, $R_3$ and $R_8$, are each independently unsubstituted or substituted with 1, 2, 3 or 4 substituents independently selected from the group consisting of alkyl, alkenyl, —CN, —$NO_2$, halogen, ethylenedioxy, methylenedioxy, oxo, —$OR_a$, —$OC(O)R_a$, —$OC(O)OR_a$, —$OS(O)_2R_a$, —S(alkyl), —S(O)alkyl, —$S(O)_2$alkyl, —$S(O)_2OR_a$, —$S(O)_2NR_aR_b$, —$C(O)OR_a$, —$C(O)NR_aR_b$, —$C(O)OR_a$, —$C(O)NR_aR_b$, —$NR_aR_b$, —$NOR_a$, —$N(R_b)C(O)R_a$, —$N(R_b)C(O)OR_a$, —$N(R_b)S(O)_2R_a$, —$N(R_b)C(O)NR_aR_b$, —$N(R_b)S(O)_2NR_aR_b$, haloalkyl, cyanoalkyl, nitroalkyl, hydroxyalkyl, alkoxyalkyl, haloalkoxyalkyl, -alkylenyl-$OC(O)R_a$, -alkylenyl-$OC(O)OR_a$, -alkylenyl-$OS(O)_2$alkyl, -alkylenyl-$S(alkyl)$, -alkylenyl-$S(O)$alkyl, -alkylenyl-$S(O)_2$alkyl, -alkylenyl-$S(O)_2OR_a$, -alkylenyl-$S(O)_2NR_aR_b$, -alkylenyl-$C(O)R_a$, -alkylenyl-$C(O)NR_aR_b$, -alkylenyl-$C(O)OR_a$, -alkylenyl-$C(O)NR_aR_b$, -alkylenyl-NR$_a$R$_b$, -alkylenyl-N(R$_b$)C(O)R$_a$, -alkylenyl-N(R$_b$)C(O)OR$_a$, -alkylenyl-N(R$_b$)S(O)$_2$R$_a$, -alkylenyl-N(R$_b$)C(O)NR$_a$R$_b$, and -alkylenyl-N(R$_b$)S(O)$_2$NR$_a$R$_b$; wherein R$_a$ at each occurrence is independently selected from the group consisting of hydrogen, alkyl, alkenyl and haloalkyl, and R$_b$ at each occurrence is independently selected from the group consisting of hydrogen and alkyl. The invention is also directed towards pharmaceutical compositions including the compounds of the present invention. Such compositions can be administered in accordance with methods of the present invention, typically as part of a therapeutic regimen for, treatment or prevention of conditions and disorders related to ACC. Another aspect of the present invention relates to a method of inhibiting ACC activity. The method is useful for treating, or preventing conditions and disorders related to ACC in mammals. More particularly, the method is useful for treating or preventing conditions and disorders related to metabolic syndrome, type II diabetes, obesity, atherosclerosis and cardiovascular diseases in mammals. Accordingly, the compounds and compositions of the invention are useful as a medicament for treating or preventing disease modulated by ACC. Further, the present invention provides for processes for making the compounds of the present invention.

DETAILED DESCRIPTION OF THE INVENTION

For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds, which can be isolated in a useful degree of purity from a reaction mixture. Certain terms as used in the specification are intended to refer to the following definitions, as detailed below.

The term "alkoxy" as used herein, means an alkyl group, as defined herein, appended to the parent molecular moiety through an oxygen atom. Representative examples of alkoxy include, but are not limited to, methoxy, ethoxy, propoxy, isopropoxy, butoxy, isobutoxy, tert-butoxy, pentyloxy, and hexyloxy.

The term "alkoxyalkyl" as used herein, means an alkyl group, as defined herein, in which one or two hydrogen atoms are replaced by alkoxy groups as defined herein. Representative examples of alkoxyalkyl include, but are not limited to, methoxyethyl and ethoxymethyl.

The term "alkyl" as used herein, means a straight or branched chain hydrocarbon containing from 1 to 10 carbon atoms. Representative examples of alkyl include, but are not limited to, methyl, ethyl, n-propyl, isopropyl, n-butyl, sec-butyl, isobutyl (2-methylpropyl), tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "C$_1$-C$_6$ alkyl" as used herein, means a straight or branched chain hydrocarbon containing from 1 to 6 carbon atoms.

The term "C$_1$-C$_9$ alkyl" as used herein, means a straight or branched chain hydrocarbon containing from 1 to 9 carbon atoms.

The term "alkylenyl" as used herein, means a divalent group derived from a straight or branched chain hydrocarbon of from 1 to 6 carbon atoms. Representative examples of alkylenyl include, but are not limited to, —CH$_2$—, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— and —CH$_2$CH(CH$_3$)CH$_2$—.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. The phenyl and the bicyclic aryl groups of the present invention are unsubstituted or substituted. The bicyclic aryl is attached to the parent molecular moiety through any carbon atom contained within the bicyclic aryl. Representative examples of the aryl groups include, but are not limited to, dihydroindenyl, indenyl, naphthyl, dihydronaphthalenyl, and 5,6,7,8-tetrahydronaphthalenyl.

The term "cyano" as used herein, means —CN.

The term "cyanoalkyl" as used herein, means an alkyl group as defined herein, in which one or two hydrogen atoms are replaced by cyano. Representative examples of cyanoalkyl include, but are not limited to, 1-methyl-1-cyanoethyl and cyanoethyl.

The term "cycloalkyl" or "cycloalkane" as used herein, means a monocyclic or bicyclic cycloalkyl. The monocyclic cycloalkyl has three to eight carbon atoms, zero heteroatom and zero double bond. The monocyclic cycloalkyl can be attached to the parent molecular moiety through any substitutable atom contained within the monocyclic cycloalkyl. Examples of monocyclic cycloalkyls include, but are not limited to, cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl. The bicyclic cycloalkyl can be attached to the parent molecular moiety through any substitutable atom contained within the bicyclic cycloalkyl. The monocyclic and bicyclic cycloalkyl groups of the present invention can be unsubstituted or substituted.

The term "cycloalkenyl" or "cycloalkene" as used herein, means a monocyclic or a bicyclic hydrocarbon ring system The monocyclic cycloalkenyl has four-, five-, six-, seven- or eight carbon atoms and zero heteroatom. The four-membered ring systems have one double bond, the five- or six-membered ring systems have one or two double bonds, and the seven- or eight-membered ring systems have one, two or three double bonds. The monocyclic cycloalkenyl can be attached to the parent molecular moiety through any substitutable atom contained within the monocyclic cycloalkenyl. Representative examples of monocyclic cycloalkenyl groups include, but not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The bicyclic cycloalkenyl can be attached to the parent molecular moiety through any substitutable atom contained within the bicyclic cycloalkenyl. Representative examples of the bicyclic cycloalkenyl groups include, but not limited to, 4,5,6,7-tetrahydro-3aH-indene, octahydronaphthalenyl and 1,6-dihydro-pentalene. The monocyclic and bicyclic cycloalkenyl groups of the present invention can be unsubstituted or substituted.

The term "ethylenedioxy" as used herein, means a —O—(CH$_2$)$_2$—O— group wherein the oxygen atoms of the ethylenedioxy group are attached to two adjacent carbon atoms of the parent molecular moiety, forming a six membered ring with the parent molecular moiety.

The term "halo" or "halogen" as used herein, means —Cl, —Br, —I or —F.

The term "haloalkoxy" as used herein, means an alkoxy group, as defined herein, in which one, two, three or four hydrogen atoms are replaced by halogen Representative examples of haloalkoxy include, but are not limited to, chloromethoxy, 2-fluoroethoxy, trifluoromethoxy, 2-chloro-3-fluoropentyloxy, and pentafluoroethoxy.

The term "haloalkoxyalkyl" as used herein, means a haloalkoxy group, as defined herein, appended to the parent moiety through an alkyl group, as defined herein.

The term "haloalkyl" as used herein, means an alkyl group, as defined herein, in which one, two, three, four, five or six hydrogen atoms are replaced by halogen. Representative examples of haloalkyl include, but are not limited to, chloromethyl, 2-fluoroethyl, trifluoromethyl, pentafluoroethyl, and 2-chloro-3-fluoropentyl.

The term "heterocycle" or "heterocyclic" as used herein, means a monocyclic heterocycle or a bicyclic heterocycle. The monocyclic heterocycle is a three-, four-, five-, six- or seven-membered ring containing at least one heteroatom independently selected from the group consisting of O, N, and S. The three- or four membered rings contain zero or one double bond, and one heteroatom selected from the group consisting of O, N and S. The five-membered ring contains zero or one double bond and one, two or three heteroatoms selected from the group consisting of O, N and S. The six-membered ring contains zero, one or two double bonds and one, two or three heteroatoms selected from the group consisting of O, N and S. The seven-membered ring contains zero, one, two, or three double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, a monocyclic heterocycle fused to a monocyclic heterocycle, or a monocyclic heterocycle fused to a monocyclic heteroaryl. The bicyclic heterocycle is connected to the parent molecular moiety through any carbon atom or any nitrogen atom contained within the bicyclic heterocycle. Representative examples of bicyclic heterocycle include, but are not limited to, 1,3-benzodithiolyl, benzopyranyl, benzothiopyranyl, 2,3-dihydrobenzofuranyl, 2,3-dihydrobenzothienyl, 2,3-dihydro-1H-indolyl, 2,3-dihydroisoindol-2-yl, 2,3-dihydroisoindol-3-yl, 1,3-dioxo-1H-isoindolyl, 2-(trifluoromethyl)-5,6-dihydroimidazo-[1,2-a]pyrazin-7(8H)-yl, 1-acetyl-2,3-dihydro-1H-indol-6-yl, 3-(trifluoromethyl)-5,6-dihydro[1,2,4]triazolo[4,3-a]pyrazin-7(8H)-yl, 1,2,3,4-tetrahydroisoquinolin-2-yl, and 1,2,3,4-tetrahydroquinolinyl The monocyclic and bicyclic heterocycle of the present invention can be unsubstituted or substituted.

The term "heteroaryl" as used herein, means a monocyclic heteroaryl or a bicyclic heteroaryl. The monocyclic heteroaryl is a five- or six-membered ring with two double bonds and at least one heteroatom selected from oxygen, sulfur or nitrogen. The five-membered ring consists of one heteroatom selected from sulfur, nitrogen or oxygen atom; or two, three or four nitrogen atoms; or one nitrogen atom together with one other heteroatoms selected from oxygen or sulfur, or two nitrogen atoms together with another heteroatom selected from oxygen or sulfur. The six-membered ring consists of three double bonds and one, two, three or four nitrogen atoms. The monocyclic heteroaryl is connected to the parent molecular moiety through any substitutable atom contained within the monocyclic heteroaryl. Representative examples of monocyclic heteroaryl include, but are not limited to, furanyl, imidazolyl, isoxazolyl, isothiazolyl, 1,2,4-oxadiazolyl, oxazolyl, pyridinyl, pyridazinyl, pyrimidinyl, pyrazinyl, pyrazolyl, pyrrolyl, tetrazolyl, 1,3,4-thiadiazolyl, 1,2,4-thiadiazolyl, thiazoly, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl. The bicyclic heteroaryl is connected to the parent molecular moiety through any carbon atom or any nitrogen atom contained within the bicyclic heteroaryl. Representative examples of bicyclic heteroaryl groups include, but not limited to, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphlithyridinyl, pyridoimidazolyl, quinolinyl, and 5,6,7,8-tetrahydroquinolin-5-yl. The monocyclic and bicyclic heteroaryl groups of the present invention can be substituted or unsubstituted.

The term "heteroatom" as used herein, refers to nitrogen, oxygen or sulfur atom.

The term "hydroxy" or "hydroxyl" as used herein, means an —OH group.

The term "hydroxyalkyl" as used herein, means an alkyl group, as defined herein, in which one or two hydrogen atoms are replaced by a hydroxyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "methylenedioxy" as used herein, means a —O—(CH$_2$)—O— group wherein the oxygen atoms of the methylenedioxy group are attached to two adjacent carbon atoms of the parent molecular moiety, forming a five membered ring with the parent molecular moiety.

The term "nitro" as used herein, refers to an —NO$_2$ group.

The term "nitroalkyl" as used herein, means a nitro group, as defined herein, appended to the parent moiety through an alkyl group, as defined herein.

The term "oxo" as used herein, means =O.

In an embodiment of the present invention, compounds of the invention can have the formula (I) as described herein. In one embodiment, in the compounds of formula (I), Ar$_1$ is selected from the group consisting of phenyl and a monocyclic, five or six-membered heteroaryl; each of which is independently unsubstituted or substituted as described in formula (I). Particularly, Ar$_1$ is phenyl, pyridinyl, thienyl, furanyl, thiazolyl, oxazolyl, isoxazolyl, 1,3,4-thiadiazolyl, 1,2,4-thiadiazolyl, or 1,2,4-oxadiazolyl, each of which is independently unsubstituted or substituted as described in formula (I). More particularly, Ar$_1$ is phenyl, pyridinyl, thienyl, furanyl, 1,3-thiazolyl, or 1,3,4-thiadiazolyl, each of which is independently unsubstituted or substituted with one substituent selected from the group consisting of —I, —Br, —Cl, and —F. Preferably, Ar$_1$ is 1,3-thiazolyl.

Ar$_2$ is a monocyclic five membered heteroaryl, unsubstituted or substituted as described in formula (I). Particularly, Ar$_2$ is thienyl, furanyl, thiazolyl, oxazolyl, isoxazolyl, 1,3,4-thiadiazolyl, 1,2,4-thiadiazolyl, or 1,2,4-oxadiazolyl; each of which is independently unsubstituted or substituted as described in formula (I). More particularly, Ar$_2$ is thienyl, 1,3-thiazolyl, isoxazolyl, 1,2,4-thiadiazolyl, or 1,2,4-oxadiazolyl; each of which is independently unsubstituted or substituted with one $C_1$-$C_6$ alkyl. Preferably, $Ar_2$ is thienyl, 1,3-thiazolyl, isoxazolyl, 1,2,4-thiadiazolyl, or 1,2,4-oxadiazolyl; each of which is independently unsubstituted or substituted with one substituent selected from the group consisting of methyl and ethyl.

$Ar_3$ is phenyl or monocyclic heteroaryl; each of which is independently unsubstituted or substituted as described in formula (I). Particularly, $Ar_3$ is selected from the group of formula

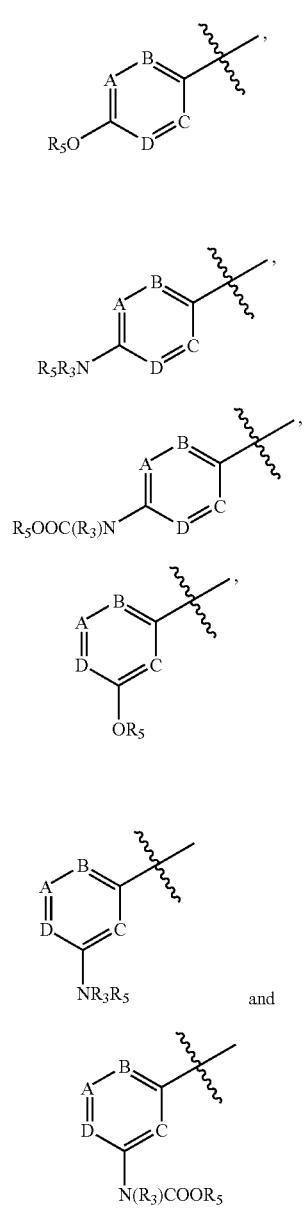

wherein A, B, C and D are —C(R)—; or 1 or 2 of A, B, C and D are N and the others are —C(R)—; wherein R is selected from the group consisting of hydrogen, alkyl, alkenyl, —CN, —$NO_2$, halogen, hydroxy, alkoxy, —$NH_2$, —N(H)(alkyl), —N(alkyl)$_2$, —SH, —S(alkyl), —S(O)$_2$alkyl, —S(O)$_2$OH, —S(O)$_2$Oalkyl, —C(O)OH, —C(O)Oalkyl, —C(O)H, haloalkyl, cyanoalkyl, nitroalkyl, hydroxyalkyl, alkoxyalkyl, and haloalkoxyalkyl; and $R_3$ and $R_5$ are as described in formula (I) More particularly, $Ar_3$ is of formula (a), (b), (c), (d), (e) or (i); wherein A, B, C and D are —C(R)—; or 1 of A, B, C and D are N and the others are —C(R)—; wherein R, $R_3$ and $R_5$ are as described above Preferably, $Ar_3$ is of formula (a), (b), (c), (d), (e) or (f); wherein A, B, C and D are —C(R)—; or 1 of A, B, C and D are N and the others are —C(R)— wherein R is selected from the group consisting of hydrogen, —I, —Br, —Cl, and —F, $R_3$ is hydrogen and $R_5$ at each occurrence is independently selected from the group consisting of alkyl, —$R_8$ and -alkylenyl-$R_8$ wherein $R_8$ is selected from the group consisting of cycloalkyl, heterocycle and aryl, each of which is independently unsubstituted or substituted. More preferably, $Ar_3$ is of formula (a), (b) or (c), wherein A, B, C and D are —C(R)—; or 1 of A, B, C and D are N and the others are —C(R)— wherein R is selected from the group consisting of hydrogen, —I, —Br, —Cl and F; $R_3$ is hydrogen and $R_5$ at each occurrence is independently selected from the group consisting of alkyl, —$R_8$ and -alkylenyl-$R_8$ wherein $R_8$ is selected from the group consisting of cycloalkyl, heterocycle and aryl, each of which is independently unsubstituted or substituted, preferably the alkyl group is $C_1$-$C_6$ alkyl and the cycloalkyl is $C_3$-$C_6$ cycloalkyl. Even more preferably, $Ar_3$ is of formula (a), (b) or (c), wherein A, B, C and D are —C(R)—; or 1 of A, B, C and D) are N and the others are —C(R)— wherein R is selected from the group consisting of hydrogen, —I, —Br, —Cl and —F; $R_3$ is hydrogen and $R_5$ at each occurrence, is independently selected from the group consisting of methyl, ethyl, isopropyl 2-methylpropyl, —$R_8$ and -alkylenyl-$R_8$; wherein $R_8$ at each occurrence is an unsubstituted or substituted ring independently selected from the group consisting of phenyl, cyclopropyl, cyclopentyl, cyclohexyl, tetrahydrofuranyl and tetrahydropyranyl.

$R_1$ is selected from the group consisting of hydrogen, cycloalkyl, alkyl and haloalkyl. Particularly, $R_1$ is selected from the group consisting of $C_1$-$C_6$ alkyl and haloalkyl. More particularly, $R_1$ is methyl or trifluoromethyl.

Y is selected from the group consisting of —(CR$_{4a}$R$_{4b}$)$_m$—, —C(O)—, —O—, —N(H)—, —N(alkyl)- and —S— wherein $R_{4a}$, $R_{4b}$, and m are as described in formula (I). Particularly, Y is —$CH_2$—, —C(O)—, —O—, —N(H)—, —N(alkyl)- or —S—. Preferably, Y is —O—.

Z is selected from the group consisting of —OR$_{9a}$, -alkylenyl-OR$_{9a}$, —NR$_6$R$_{9b}$ and -alkylenyl-NR$_6$R$_{9b}$ wherein R$_{9a}$, R$_{9b}$ and R$_6$ are as described in formula (I). Particularly, Z is selected from the group consisting of —OR$_{9a}$, and —NR$_6$R$_{9b}$; wherein R$_{9a}$ is —S(O)$_2$($C_1$-$C_6$ alkyl), R$_6$ is hydrogen, and R$_{9b}$ is selected from the group consisting of hydrogen, —C(O)NH$_2$, —C(O)N(H)($C_1$-$C_6$ alkyl), —C(O)O($C_1$-$C_6$ alkyl), —S(O)$_2$($C_1$-$C_6$ alkyl), —$CH_2$—C(O)O($C_1$-$C_6$ alkyl), and —C(O)R$_{10}$ wherein R$_{10}$ is $C_1$-$C_6$ alkyl or unsubstituted $C_1$-$C_6$ cycloalkyl. More particularly, Z is selected from the group consisting of —OR$_{9a}$, and —NR$_6$R$_{9b}$; wherein R$_{9a}$ is —S(O)$_2$(methyl), R$_6$ is hydrogen, and R$_{9b}$ is selected from the group consisting of hydrogen, —C(O)NH$_2$, —C(O)N(H)(methyl), —C(O)O(methyl), —S(O)$_2$(methyl), —$CH_2$—C(O)O(methyl), and —C(O)R$_{10}$ wherein R$_{10}$ is methyl, ethyl, isopropyl or unsubstituted cyclopropyl.

It is appreciated that the present invention contemplates compounds of formula (I) with combinations of the above embodiments, including particular, more particular, preferred, mote preferred and most preferred embodiments.

Accordingly, one aspect of the invention is related to compounds of formula (I) wherein $Ar_3$ is selected from the group of formula consisting of

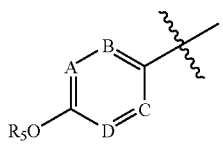
(a)

A, B, C and D are —C(R)—; or 1 or 2 of A, B, C and D are N and the others are —C(R)—; wherein R is selected from the group consisting of hydrogen, alkyl, alkenyl, —CN, —NO$_2$, halogen, hydroxy, alkoxy, —NH$_2$, —N(H)(alkyl), —N(alkyl)$_2$, —SH, —S(alkyl), —S(O)$_2$alkyl, —S(O)$_2$OH, —S(O)$_2$Oalkyl, —C(O)OH, —C(O)Oalkyl, —C(O)H, haloalkyl, cyanoalkyl, nitroalkyl, hydroxyalkyl, alkoxyalkyl, and haloalkoxyalkyl; Y is —O— and R$_1$, R$_5$, Ar$_1$, Ar$_2$, and Z are as described in formula (I). Preferably, A, B, C and D are —C(R)—; or one of A, B, C and D are N and toe others are —C(R)—; wherein R is selected from the group consisting of hydrogen, —I, —Br, —Cl and —F; Y is —O— and R$_1$, R$_5$, Ar$_1$, Ar$_2$, and Z are as described in formula (I).

Another aspect of the invention relates to compounds of formula (I), or a pharmaceutically acceptable salt, prodrug, salt of a prodrug, or a combination thereof wherein Ar$_3$ is

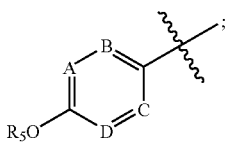
(a);

A, B, C and D are —C(R)—; or 1 or 2 of A, B, C and D are N and the others are —C(R)—; wherein R is selected from the group consisting of hydrogen, alkyl, alkenyl, —CN, —NO$_2$, halogen, hydroxy, alkoxy, —NH$_2$, —N(H)(alkyl), —N(alkyl)$_2$, —SH, —S(alkyl), —S(O)$_2$alkyl, —S(O)$_2$OH, —S(O)$_2$Oalkyl, —C(O)OH, —C(O)Oalkyl, —C(O)H, haloalkyl, cyanoalkyl, nitroalkyl, hydroxyalkyl, alkoxyalkyl, and haloalkoxyalkyl; Y is —O—; Ar$_1$ is phenyl, pyridinyl, thienyl, furanyl, thiazolyl, oxazolyl, isoxazolyl, 1,3,4-thiadiazolyl, 1,2,4-thiadiazolyl, or 1,2,4-oxadiazolyl; each of which is independently unsubstituted or substituted as described in formula (I); and R$_1$, R$_5$, Ar$_2$, and Z are as described in formula (I). Preferably, A, B, C and D are —C(R)—; or one of A, B, C and D are N and the others are —C(R)—; wherein R is selected from the group consisting of hydrogen, —I, —Br, —Cl and —F; Y is —O—; Ar$_1$ is phenyl, pyridinyl, thienyl, furanyl, thiazolyl, or 1,3,4-thiadiazolyl; each of which is independently unsubstituted or substituted with one substituent selected from the group consisting of —I, —Br, —Cl and —F; and R$_1$, R$_5$, Ar$_2$, and Z are as described in formula (I).

Another aspect of the invention relates to compounds of formula (I), or a pharmaceutically acceptable salt, prodrug, salt of a prodrug, or a combination thereof, wherein Ar$_3$ is

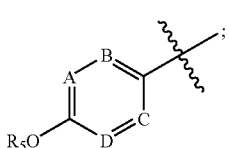
(a)

A, B, C and D are —C(R)—; or 1 or 2 of A, B, C and D are N and the others are —C(R)—; wherein R is selected from the group consisting of hydrogen, alkyl, alkenyl, —CN, —NO$_2$, halogen, hydroxy, alkoxy, —NH$_2$, —N(H)(alkyl), —N(alkyl)$_2$, —SH, —S(alkyl), —S(O)$_2$alkyl, —S(O)$_2$OH, —S(O)$_2$Oalkyl, —C(O)OH, —C(O)Oalkyl, —C(O)H, haloalkyl, cyanoalkyl, nitroalkyl, hydroxyalkyl, alkoxyalkyl, and haloalkoxyalkyl; Y is —O—; Ar$_1$ is thiazolyl unsubstituted or substituted with substituents as described in formula (I); and R$_1$, R$_5$, Ar$_2$, and Z are as described in formula (I). Preferably, A, B, C and D are —C(R)—; or 1 or 2 of A, B, C and D are N and the others are —C(R)—; wherein R is selected from the group consisting of hydrogen, —I, —Br, —Cl and —F; Y is —O—; Ar$_1$ is thiazolyl unsubstituted or substituted with one substituent selected from the group consisting of —I, —Br, —Cl and —F; and R$_1$, R$_5$, Ar$_2$, and Z are as described in formula (I). More preferably, A, B, C and D are —C(R)—; or one of A, B, C and D are N and the others are —(C(R)—; wherein R is selected from the group consisting of hydrogen, —I, —Br, —Cl and —F; Y is —O—; Ar$_1$ is thiazolyl unsubstituted or substituted with one substituent selected from the group consisting of —I, —Br, —Cl and —F; and R$_1$, R$_5$, Ar$_2$, and Z are as described in formula (I).

Another aspect of the invention relates to compounds of formula (I), or a pharmaceutically acceptable salt, prodrug, salt of a prodrug, or a combination thereof, wherein Ar$_3$ is (a)

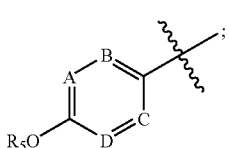

A, B, C and D are —C(R)—; or 1 or 2 of A, B, C and D are N and the others are —C(R)—; wherein R is selected from the group consisting of hydrogen, alkyl, alkenyl, —CN, —NO$_2$, halogen, hydroxy, alkoxy, —NH$_2$, —N(H)(alkyl), —N(alkyl)$_2$, —SH, —S(alkyl), —S(O)$_2$alkyl, —S(O)$_2$OH, —S(O)$_2$Oalkyl, —C(O)OH, —C(O)Oalkyl, —C(O)H, haloalkyl, cyanoalkyl, nitroalkyl, hydroxyalkyl, alkoxyalkyl, and haloalkoxyalkyl; Y is —O—; Ar$_1$ is phenyl, pyridinyl, thienyl, furanyl, thiazolyl, oxazolyl, isoxazolyl, 1,3,4-thiadiazolyl, 1,2,4-thiadiazolyl, or 1,2,4-oxadiazolyl; eat of which is independently unsubstituted or substituted as described in formula (I); Ar$_2$ is thienyl, furanyl, thiazolyl, oxazolyl, isoxazolyl, 1,3,4-thiadiazolyl, 1,2,4-thiadiazolyl, or 1,2,4-oxadiazolyl; each of which is independently unsubstituted or substituted as described in formula (I); and R$_1$, R$_5$ and Z are as described in formula (I). Preferably, A, B, C and D are —C(R)—; or one of A, B, C and D are N and the others are —C(R)—; wherein R is selected from the group consisting of hydrogen, —I, —Br, —Cl and —F; Y is —O—; Ar$_1$ is phenyl, pyridinyl, thienyl, furanyl, thiazolyl, isoxazolyl or 1,3,4-thiadiazolyl; each of which is independently unsubstituted or substituted with one substituent selected from the group consisting of —I, —Br, —Cl and —F; Ar$_2$ is thienyl, thiazolyl, 1,2,4-thiadiazolyl, or 1,2,4-oxadiazolyl, each of which is independently unsubstituted or substituted with one $C_1$-$C_6$ alkyl; and R$_1$, R$_5$, and Z are as described in formula (I).

Another aspect of the invention relates to compounds of formula (I), or a pharmaceutically acceptable salt, prodrug, salt of a prodrug, or a combination thereof, wherein Ar$_3$ is

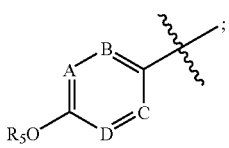

A, B, C and D are —C(R)—; or 1 or 2 of A, B, C and D are N and the others are —C(R)—; wherein R is selected from the group consisting of hydrogen, alkyl, alkenyl, —CN, —NO$_2$, halogen, hydroxy, alkoxy, —NH$_2$, —N(H)(alkyl), —N(alkyl)$_2$, —SH, —S(alkyl), —S(O)$_2$alkyl, —S(O)$_2$OH, —S(O)$_2$Oalkyl, —C(O)OH, —C(O)Oalkyl, —C(O)H, haloalkyl, cyanoalkyl, nitroalkyl, hydroxyalkyl, alkoxyalkyl, and haloalkoxyalkyl; Y is —O—; Ar$_1$ is thiazolyl unsubstituted or substituted with substituents as described in formula (I); Ar$_2$ is isoxazolyl unsubstituted or substituted with substituents as described in formula (I); and R$_1$, R$_5$, and Z are as described in formula (I) Preferably, A, B, C and D are —C(R)—; or 1 or 2 of A, B, C and D are N and the others are —C(R)—; wherein R is selected from the group consisting of hydrogen, —I, —Br, —Cl and —F; Y is —O—; Ar$_1$ is thiazolyl unsubstituted or substituted with one substituent selected from the group consisting of —I, —Br, —Cl and —F; Ar$_2$ is isoxazolyl unsubstituted or substituted with one C$_1$-C$_6$ alkyl; and R$_1$, R$_5$, and Z are as described in formula (I). More preferably, A, B, C and D are —C(R)—; or one of A, B, C and D are N and the others are —C(R)—; wherein R is selected from the group consisting of hydrogen, —I, —Br, —Cl and —F; Y is —O—; Ar$_1$ is thiazolyl unsubstituted or substituted with one substituent selected from the group consisting of —I, —Br, —Cl and —F; Ar$_2$ is isoxazolyl unsubstituted or substituted with one substituent selected from the group consisting of methyl and ethyl; and R$_1$, R$_5$, and Z are as described in formula (I).

Another aspect of the invention relates to compounds of formula (I), or a pharmaceutically acceptable salt, prodrug, salt of a prodrug, or a combination thereof, wherein Ar$_3$ is

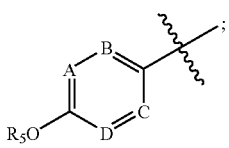

A, B, C and D are —C(R)—; or 1 or 2 of A, B, C and D are N and the others are —C(R)—; wherein R is selected from the group consisting of hydrogen, alkyl, alkenyl, —CN, —NO$_2$, halogen, hydroxy, alkoxy, —NH$_2$, —N(H)(alkyl), —N(alkyl)$_2$, —SH, —S(alkyl), —S(O)$_2$alkyl, —S(O)$_2$OH, —S(O)$_2$Oalkyl, —C(O)OH, —C(O)Oalkyl, —C(O)H, haloalkyl, cyanoalkyl, nitroalkyl, hydroxyalkyl, alkoxyalkyl, and haloalkoxyalkyl; Y is —O—; Ar$_1$ is thiazolyl unsubstituted or substituted with substituents as described in formula (I); Ar$_2$ is 1,2,4-oxadiazolyl unsubstituted or substituted with substituents as described in formula (I); and R$_1$, R$_5$, and Z are as described in formula (I). Preferably, A, B, C and D are —C(R)—; or 1 or 2 of A, B, C and D are N and the others are —C(R)—; wherein R is selected from the group consisting of hydrogen, —I, —Br, —Cl and —F; Y is —O—; Ar$_1$ is thiazolyl unsubstituted or substituted with one substituent selected from the group consisting of —I, —Br, —Cl and —F; Ar$_2$ is 1,2,4-oxadiazolyl unsubstituted or substituted with one C$_1$-C$_6$ alkyl; and R$_1$, R$_5$, and Z are as described in formula (I). More preferably, A, B, C and D are —C(R)—; or one of A, B, C and D are N and the others are —C(R)—; wherein R is selected from the group consisting of hydrogen, —I, —Br, —Cl and —F; Y is —O—; Ar$_1$ is thiazolyl unsubstituted or substituted with one substituent selected from the group consisting of —I, —Br, —Cl and —F; Ar$_2$ is 1,2,4-oxadiazolyl unsubstituted or substituted with one substituent selected from the group consisting of methyl and ethyl; and R$_1$, R$_5$, and Z are as described in formula (I).

Another aspect of the invention relates to compounds of formula (I), or a pharmaceutically acceptable salt, prodrug, salt of a prodrug, or a combination thereof wherein Ar$_3$ is

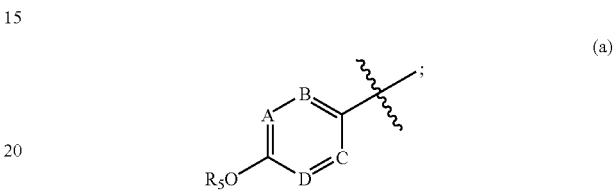

A, B, C and D are —C(R)—; or one of A, B, C and D is N and the others are —C(R)—; wherein R is selected from the group consisting of hydrogen, —I, —Br, —Cl, and —F; Ar$_1$ is selected from the group consisting of phenyl, pyridinyl, thienyl, furanyl, thiazolyl, and 1,3,4-thiadiazolyl; each of which is independently unsubstituted or substituted with one substituent selected from the group consisting of —I, —Br, —Cl, and —F; Ar$_2$ is selected from the group consisting of thienyl, thiazolyl, isoxazolyl, 1,2,4-thiadiazolyl, and 1,2,4-oxadiazolyl; each of which is independently unsubstituted or substituted with one C$_1$-C$_6$ alkyl; R$_1$ is selected from the group consisting of C$_1$-C$_6$ alkyl and haloalkyl; Z is selected from the group consisting of —OR$_{9a}$ and —NR$_6$R$_{9b}$; wherein R$_{9a}$ is —S(O)$_2$(C$_1$-C$_6$ alkyl), R$_6$ is hydrogen, and R$_{9b}$ is selected from the group consisting of hydrogen, —C(O)NH$_2$, —C(O)N(H)(C$_1$-C$_6$ alkyl), —C(O)O(C$_1$-C$_6$ alkyl), —S(O)$_2$(C$_1$-C$_6$ alkyl), —CH$_2$—C(O)O(C$_1$-C$_6$ alkyl), and —C(O)R$_{10}$ wherein R$_{10}$ is C$_1$-C$_6$ alkyl or unsubstituted C$_1$-C$_6$ cycloalkyl; Y is —O—; and R$_5$ is selected from the group consisting of C$_1$-C$_6$ alkyl, —R$_8$, and —(C$_1$-C$_6$ alkylenyl)-R$_8$ wherein R$_8$ at each occurrence is an unsubstituted ring selected from the group consisting of phenyl, cyclopropyl, cyclopentyl, cyclohexyl, tetrahydrofuranyl and tetrahydropyranyl.

Another aspect of the invention relates to compounds of formula (I), or a pharmaceutically acceptable salt, prodrug, salt of a prodrug, or combination thereof, wherein Ar$_3$ is

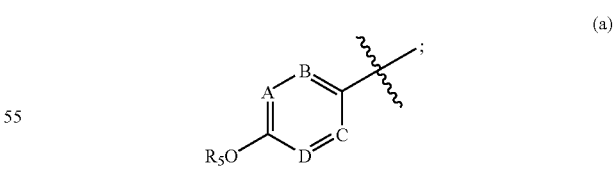

A, B, C and D are —C(R)—, or one of A, B, C and D is N and the others are —C(R)—; wherein R is selected from the group consisting of hydrogen, —I, —Br, —Cl, and —F; Ar$_1$ is selected from the group consisting of phenyl, pyridinyl, thienyl, furanyl, thiazolyl, and 1,3,4-thiadiazolyl; each of which is independently unsubstituted or substituted with one substituent selected from the group consisting of —I, —Br, —Cl, and —F; Ar$_2$ is selected from the group consisting of thienyl, thiazolyl, isoxazolyl, 1,2,4-thiadiazolyl, and 1,2,4- oxadiazolyl; each of which is independently unsubstituted or substituted with one substituent selected from the group consisting of methyl and ethyl; R₁ is selected from the group consisting of methyl and trifluoromethyl; Z is selected from the group consisting of —OR$_{9a}$ and —NR₆R$_{9b}$; wherein R$_{9a}$ is —S(O)₂(methyl), R₆ is hydrogen, and R$_{9b}$ is selected from the group consisting of hydrogen, —C(O)NH₂, —C(O)N(H)(methyl), —C(O)O(methyl), —S(O)₂(methyl), —CH₂—C(O)O(methyl), and —C(O)R₁₀ wherein R₁₀ is methyl, ethyl, isopropyl or unsubstituted cyclopropyl; Y is —O— and R₅ is selected from the group consisting of methyl, ethyl, isopropyl, 2-methylpropyl, —R₈, and —CH₂—R₈ wherein R₈ at each occurrence is an unsubstituted ring selected from the group consisting of phenyl, cyclopropyl, cyclopentyl, cyclohexyl, tetrahydrofuranyl and tetrahydropyranyl.

Another aspect of the invention is related to compounds of formula (I), or a pharmaceutically acceptable salt, prodrug, salt of a prodrug, or a combination thereof, wherein Ar₃ is selected from the group of formula consisting of

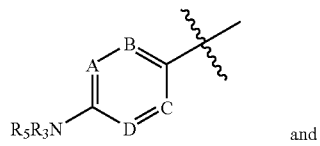

and

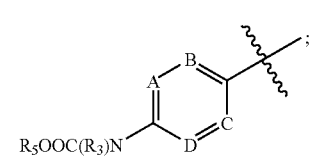

A, B, C and D are —C(R)—; or 1 or 2 of A, B, C and D are N and the others are —C(R)—; wherein R is selected from the group consisting of hydrogen, alkyl, alkenyl, —CN, —NO₂, halogen, hydroxy, alkoxy, —NH₂, —N(H)(alkyl), —N(alkyl)₂, —SH, —S(alkyl), —S(O)₂alkyl, —S(O)₂OH, —S(O)₂Oalkyl, —C(O)OH, —C(O)Oalkyl, —C(O)H, haloalkyl, cyanoalkyl, nitroalkyl, hydroxyalkyl, alkoxyalkyl, and haloalkoxyalkyl; Y is —O— and R₁, R₃, R₅, Ar₁, Ar₂, and Z are as described in formula (I). Preferably, A, B, C and D are —C(R)—; or one of A, B, C and D are N and the others are —C(R)—; wherein R is selected from the group consisting of hydrogen, —I, —Br, —Cl and —F; Y is —O— and R₁, R₃, R₅, Ar₁, Ar₂, and Z are as described in formula (I).

Another aspect of the invention relates to compounds of formula (I), or a pharmaceutically acceptable salt, prodrug, salt of a prodrug, or a combination thereof, wherein Ar₃ is selected from the group consisting of

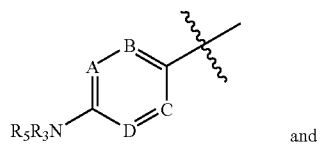

and

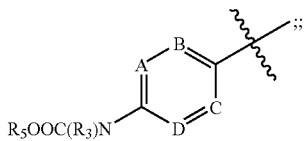

A, B, C and D are —C(R)—; or 1 or 2 of A, B, C and D are N and the others are —C(R)—; wherein R is selected from the group consisting of hydrogen, alkyl, alkenyl, —CN, —NO₂, halogen, hydroxy, alkoxy, —NH₂, —N(H)(alkyl), —N(alkyl)₂, —SH, —S(alkyl), —S(O)₂alkyl, —S(O)₂OH, —S(O)₂Oalkyl, —C(O)OH, —C(O)Oalkyl, —C(O)H, haloalkyl, cyanoalkyl, nitroalkyl, hydroxyalkyl, alkoxyalkyl, and haloalkoxyalkyl; Y is —O—; Art is phenyl, pyridinyl, thienyl, furanyl, thiazolyl, oxazolyl, isoxazolyl, 1,3,4-thiadiazolyl, 1,2,4-thiadiazolyl, or 1,2,4-oxadiazolyl; each of which is independently unsubstituted or substituted as described in formula (I); and R₁, R₃, R₅, Ar₂, and Z are as described in formula (I). Preferably, A, B, C and D are —C(R)—; or one of A, B, C and D are N and the others are —C(R)—; wherein R is selected from the group consisting of hydrogen, —I, —Br, —Cl and —F; Y is —O—; Art is phenyl, pyridinyl, thienyl, furanyl, thiazolyl, or 1,3,4-thiadiazolyl; each of which is independently unsubstituted or substituted with one substituent selected from the group consisting of —I, —Br, —Cl and —F; and R₁, R₃, R₅, Ar₂, and Z are as described in formula (I).

Another aspect of the invention relates to compounds of formula (I), or a pharmaceutically acceptable salt, prodrug, salt of a prodrug, or a combination thereof wherein Ar₃ is selected from the group consisting of

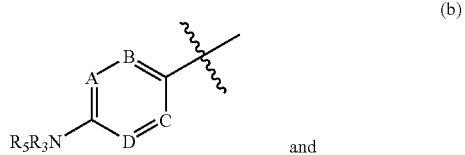

A, B, C and D are —C(R)—; or 1 or 2 of A, B, C and D are N and the others are —C(R)—; wherein R is selected from the group consisting of hydrogen, alkyl, alkenyl, —CN, —NO₂, halogen, hydroxy, alkoxy, —NH₂, —N(H)(alkyl), —N(alkyl)₂, —SH, —S(alkyl), —S(O)₂alkyl, —S(O)₂OH, —S(O)₂Oalkyl, —C(O)OH, —C(O)Oalkyl, —C(O)H, haloalkyl, cyanoalkyl, nitroalkyl, hydroxyalkyl, alkoxyalkyl, and haloalkoxyalkyl; Y is —O—; Ar₁ is thiazolyl unsubstituted or substituted with substituents as described in formula (I); and R₁, R₃, R₅, Ar₂, and Z are as described in formula (I) Preferably, A, B, C and D are —C(R)—; or 1 or 2 of A, B, C and D are N and the others are —C(R)—; wherein R is selected from the group consisting of hydrogen, —I, —Br, —Cl and —F; Y is —O—; Ar₁ is thiazolyl unsubstituted or substituted with one substituent selected from the group consisting of —I, —B, —Cl and —F; and R₁, R₃, R₅, Ar₂, and Z are as described in formula (I). More preferably, A, B, C and D are —C(R)—; or one of A, B, C and D) are N and the others are —C(R)—; wherein R is selected from the group consisting of hydrogen, —I, —Br, —Cl and —F; Y is —O—; Ar$_1$ is thiazolyl unsubstituted or substituted with one substituent selected from the group consisting of —I, —Br, —Cl and —F; and R$_1$, R$_3$, R$_5$, Ar$_2$, and Z are as described in formula (I).

Another aspect of the invention relates to compounds of formula (I), or a pharmaceutically acceptable salt, prodrug, salt of a prodrug, or a combination thereof, wherein Ar$_3$ is selected from the group consisting of

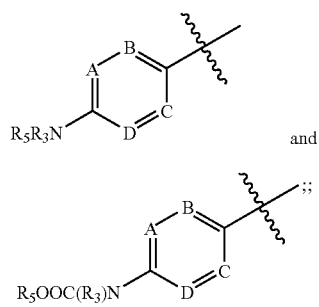

and

A, B, C and D are —C(R)—; or 1 or 2 of A, B, C and D are N and the others are —C(R)—; wherein R is selected from the group consisting of hydrogen, alkyl, alkenyl, —CN, —NO$_2$, halogen, hydroxy, alkoxy, —NH$_2$, —N(H)(alkyl), —N(alkyl)$_2$, —SH, —S(alkyl), —S(O)$_2$alkyl, —S(O)$_2$OH, —S(O)$_2$Oalkyl, —C(O)OH, —C(O)Oalkyl, —C(O)H, haloalkyl, cyanoalkyl, nitroalkyl, hydroxyalkyl, alkoxyalkyl, and haloalkoxyalkyl; Y is —O—; Ar$_1$ is phenyl, pyridinyl, thienyl, furanyl, thiazolyl, oxazolyl, isoxazolyl, 1,3,4-thiadiazolyl, 1,2,4-thiadiazolyl, or 1,2,4-oxadiazolyl; each of which is independently unsubstituted or, substituted as described in formula (I); Ar$_2$ is thienyl, furanyl, thiazolyl, oxazolyl, isoxazolyl, 1,3,4-thiadiazolyl, 1,2,4-thiadiazolyl, or 1,2,4-oxadiazolyl; each of which is independently unsubstituted or substituted as described in formula (I); and R$_1$, R$_3$, R$_5$, and Z are as described in formula (I) Particularly, A, B, C and D are —C(R)—; or one of A, B, C and D are N and the others are —C(R)—; wherein R is selected from the group consisting of hydrogen, —I, —Br, —Cl and —F; Y is —O—; Ar$_1$ is phenyl, pyridinyl, thienyl, furanyl, thiazolyl, or 1,3,4-thiadiazolyl; each of which is independently unsubstituted or substituted with one substituent selected from the group consisting of —I, —Br, —Cl and —F; Ar$_2$ is thienyl, thiazolyl, isoxazolyl, 1,2,4-thiadiazolyl, or 1,2,4-oxadiazolyl, each of which is independently unsubstituted or substituted with one C$_1$-C$_6$ alkyl; and R$_1$, R$_3$, R$_5$, and Z are as described in formula (I).

Another aspect of the invention relates to compounds of formula (I), or a pharmaceutically acceptable salt, prodrug, salt of a prodrug, or a combination thereof, wherein Ar$_3$ is selected from the group consisting of

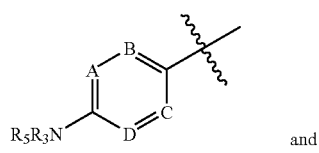

and

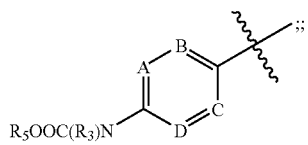

A, B, C and D are —C(R)—; or 1 or 2 of A, B, C and D are N and the others are —C(R)—; wherein R is selected from the group consisting of hydrogen, alkyl, alkenyl, —CN, —NO$_2$, halogen, hydroxy, alkoxy, —NH$_2$, —N(H)(alkyl), —N(alkyl)$_2$, —SH, —S(alkyl), —S(O)$_2$alkyl, —S(O)$_2$OH, —S(O)$_2$Oalkyl, —O(O)OH, —O(O)Oalkyl, —O(O)H, haloalkyl, cyanoalkyl, nitroalkyl, hydroxyalkyl, alkoxyalkyl, and haloalkoxyalkyl; Y is —O—; Ar$_1$ is thiazolyl unsubstituted or substituted with substituents as described in formula (I); Ar$_2$ is isoxazolyl unsubstituted or substituted with substituents as described in formula (I); and R$_1$, R$_3$, R$_5$, and Z are as described in formula (I). Preferably, A, B, C and D are —C(R)—; or 1 or 2 of A, B, C and D are N and the others are —C(R)—; wherein R is selected from the group consisting of hydrogen, —I, —Br, —Cl and —F; Y is —O—; Ar$_1$ is thiazolyl unsubstituted or substituted with one substituent selected from the group consisting of —I, —Br, —Cl and —F; Ar$_2$ is isoxazolyl unsubstituted or substituted with one C$_1$-C$_6$ alkyl; and R$_1$, R$_3$, R$_5$, and Z are as described in formula (I). More preferably, A, B, C and D are —C(R)—; or one of A, B, C and D are N and the others are —C(R)—; wherein R is selected from the group consisting of hydrogen, —I, —Br, —Cl and —F; Y is —O—; Ar$_1$ is thiazolyl unsubstituted or substituted with one substituent selected from the group consisting of —I, —Br, —Cl and —F; Ar$_2$ is isoxazolyl unsubstituted or substituted with one substituent selected from the group consisting of methyl and ethyl; and R$_1$, R$_3$, R$_5$, and Z are as described in formula (I).

Another aspect of the invention relates to compounds of formula (I), or a pharmaceutically acceptable salt, prodrug, salt of a prodrug, or a combination thereof, wherein Ar$_3$ is selected from the group consisting of

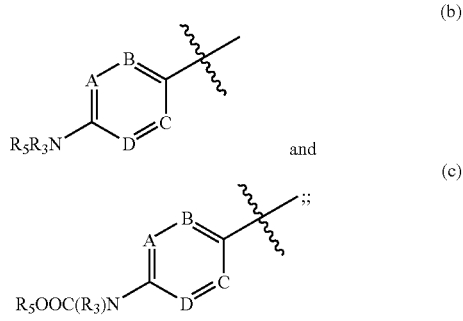

A, B, C and D are —C(R)—; or 1 or 2 of A, B, C and D are N and the others are —C(R)—; wherein R is selected from the group consisting of hydrogen, alkyl, alkenyl, —CN, —NO$_2$, halogen, hydroxy, alkoxy, —NH—, —N(H)(alkyl), —N(alkyl)$_2$, —SH, —S(alkyl), —S(O)$_2$alkyl, —S(O)$_2$OH, —S(O)$_2$Oalkyl, —C(O)OH, —C(O)Oalkyl, —C(O)H, haloalkyl, cyanoalkyl, nitroalkyl, hydroxyalkyl, alkoxyalkyl, and haloalkoxyalkyl; Y is —O—; Ar$_1$ is thiazolyl unsubstituted or substituted with substituents as described in formula (I); Ar$_1$ is 1,2,4-oxadiazolyl unsubstituted or substituted with substituents as described in formula (I); and R$_1$, R$_3$, R$_5$, and Z are as described in formula (I). Preferably, A, B, C and D are —C(R)—; or 1 or 2 of A, B, C and D are N and the others are —C(R)—; wherein R is selected from the group consisting of hydrogen, —I, —Br, —Cl and —F; Y is —O—; $Ar_1$ is thiazolyl unsubstituted or substituted with one substituent selected from the group consisting of —I, —Br, —Cl and —F; $Ar_2$ is 1,2,4-oxadiazolyl unsubstituted or substituted with one $C_1$-$C_6$ alkyl; and $R_1$, $R_3$, $R_5$, and Z are as described in formula (I). More preferably, A, B, C and D are —C(R)—; or one of A, B, C and D are N and the others are —C(R)—; wherein R is selected from the group consisting of hydrogen, —I, —Br, —Cl and —F; Y is —O—; $Ar_1$ is thiazolyl unsubstituted or substituted with one substituent selected from the group consisting of —I, —Br, —Cl and —F; $Ar_2$ is 1,2,4-oxadiazolyl unsubstituted or substituted with one substituent selected from the group consisting of methyl and ethyl; and $R_1$, $R_3$, $R_5$, and Z are as described in formula (I).

Another aspect of the invention relates to compound of formula (I), or a pharmaceutically acceptable salt, prodrug, salt of a prodrug, or combination thereof, wherein $Ar_3$ is selected from the group consisting of

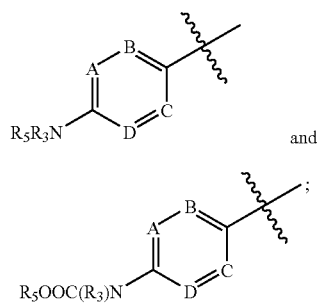

A, B, C and D are —C(R)—, or one of A, B, C and D is N and the others are —C(R)—; wherein R is selected from the group consisting of hydrogen, —I, —Br, —Cl, and —F; $Ar_1$ is selected from the group consisting of phenyl, pyridinyl, thienyl, furanyl, thiazolyl, and 1,3,4-thiadiazolyl; each of which is independently unsubstituted or substituted with one substituent selected from the group consisting of —I, —Br, —Cl, and —F; $Ar_2$ is selected from the group consisting of thienyl, thiazolyl, isoxazolyl, 1,2,4-thiadiazolyl, and 1,2,4-oxadiazolyl; each of which is independently unsubstituted or substituted with one $C_1$-$C_6$ alkyl; $R_1$ is selected from the group consisting of $C_1$-$C_6$ alkyl and haloalkyl; Z is selected from the group consisting of —$OR_{9a}$ and —$NR_6R_{9b}$; wherein $R_{9a}$ is —$S(O)_2$($C_1$-$C_6$ alkyl), $R_6$ is hydrogen, and $R_{9b}$ is selected from the group consisting of hydrogen, —C(O)$NH_2$, —C(O)N(H)($C_1$-$C_6$ alkyl), —C(O)O($C_1$-$C_6$ alkyl), —$S(O)_2$($C_1$-$C_6$ alkyl), —$CH_2$—C(O)O($C_1$-$C_6$ alkyl), and —C(O)$R_{10}$ wherein $R_{10}$ is $C_1$-$C_6$ alkyl or unsubstituted $C_1$-$C_6$ cycloalkyl; Y is —O—; $R_3$ is hydrogen; and $R_5$ at each occurrence is independently selected from the group consisting of $C_1$-$C_9$ alkyl, —$R_8$, and —($C_1$-$C_6$ alkylenyl)-$R_8$ wherein $R_8$ at each occurrence is an unsubstituted ring selected from the group consisting of phenyl, cyclopropyl, cyclopentyl, cyclohexyl, tetrahydrofuranyl and tetrahydropyranyl.

Another aspect of the invention relates to compound of formula (I), or a pharmaceutically acceptable salt, prodrug, salt of a prodrug, or combination thereof, wherein $Ar_3$ is selected from the group of formula consisting of

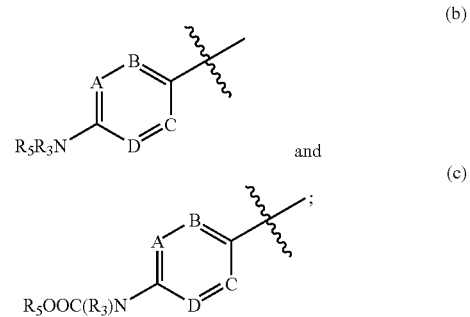

A, B, C and D are —C(R)—, or one of A, B, C and D is N and the others are —C(R)—; wherein R is selected from the group consisting of hydrogen, —I, —Br, —Cl, and —F; $Ar_1$ is selected from the group consisting of phenyl, pyridinyl, thienyl, furanyl, thiazolyl, and 1,3,4-thiadiazolyl; each of which is independently unsubstituted or substituted with one substituent selected from the group consisting of —I, —Br, —Cl, and —F; $Ar_2$ is selected from the group consisting of thienyl, thiazolyl, isoxazolyl, 1,2,4-thiadiazolyl, and 1,2,4-oxadiazolyl; each of which is independently unsubstituted or substituted with one substituent selected from the group consisting of methyl and ethyl; $R_1$ is selected from the group consisting of methyl and trifluoromethyl; Z is selected from the group consisting of —$OR_{9a}$ and —$NR_6R_{9b}$; wherein $R_{9a}$ is —$S(O)_2$(methyl), $R_6$ is hydrogen, and $R_{9b}$ is selected from the group consisting of hydrogen, —C(O)$NH_2$, —C(O)N(H)(methyl), —C(O)O(methyl), —$S(O)_2$(methyl), —$CH_2$—C(O)O(methyl), and —C(O)$R_{10}$ wherein $R_{10}$ is methyl, ethyl, isopropyl or unsubstituted cyclopropyl; Y is —O—; $R_3$ is hydrogen; and $R_5$ at each occurrence is independently selected from the group consisting of methyl, ethyl, isopropyl, 2-methylpropyl, tert-butyl, —$R_8$, and —$CH_2$—$R_8$ wherein $R_8$ at each occurrence is an unsubstituted ring selected from the group consisting of phenyl, cyclopropyl, cyclopentyl, cyclohexyl, tetrahydrofuranyl and tetrahydropyranyl.

Another aspect of the invention is related to compounds of formula (I), or a pharmaceutically acceptable salt, prodrug, salt of a prodrug, or a combination thereof, wherein $Ar_3$ is

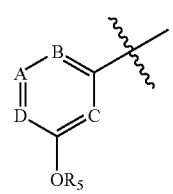

A, B, C and D are —C(R)—; or 1 or 2 of A, B, C and D are N and the others are —C(R)—; wherein R is selected from the group consisting of hydrogen, alkyl, alkenyl, —CN, —$NO_2$, halogen, hydroxy, alkoxy, —$NH_2$, —N(H)(alkyl), —N(alkyl)$_2$, —SH, —S(alkyl), —$S(O)_2$alkyl, —$S(O)_2$OH, —$S(O)_2$Oalkyl, —C(O)OH, —C(O)Oalkyl, —C(O)H, haloalkyl, cyanoalkyl, nitroalkyl, hydroxyalkyl, alkoxyalkyl, and haloalkoxyalkyl; Y is —O— and $R_1$, $R_5$, $Ar_1$, $Ar_2$, and Z are as described in formula (I). Preferably, A, B, C and D are —C(R)—; or one of A, B, C and D are N and the others are —C(R)—; wherein R is selected from the group consisting of hydrogen, —I, —Br, —Cl and —F; Y is —O— and $R_1$, $R_5$, $Ar_1$, $Ar_2$, and Z are as described in formula (I).

Another aspect of the invention relates to compounds of formula (I), or a pharmaceutically acceptable salt, prodrug, salt of a prodrug, or a combination thereof, wherein $Ar_3$ is

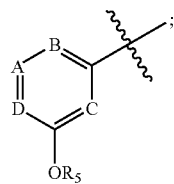

(d)

A, B, C and D are —C(R)—; or 1 or 2 of A, B, C and D are N and the others ate —C(R)—; wherein R is selected from the group consisting of hydrogen, alkyl, alkenyl, —CN, —$NO_2$, halogen, hydroxy, alkoxy, —$NH_2$, —N(H)(alkyl), —N(alkyl)$_2$, —SH, —S(alkyl), —S(O)$_2$alkyl, —S(O)$_2$OH, —S(O)$_2$Oalkyl, —C(O)OH, —C(O)Oalkyl, —C(O)H, haloalkyl, cyanoalkyl, nitroalkyl, hydroxyalkyl, alkoxyalkyl, and haloalkoxyalkyl; Y is —O—; $Ar_1$ is phenyl, pyridinyl, thienyl, furanyl, thiazolyl, oxazolyl, isoxazolyl, 1,3,4-thiadiazolyl, 1,2,4-thiadiazolyl, or 1,2,4-oxadiazolyl; each of which is independently unsubstituted or substituted as described in formula (I); and $R_1$, $R_5$, $Ar_2$, and Z are as described in formula (I). Preferably, A, B, C and D are —C(R)—; or one of A, B, C and D are N and the others are —C(R)—; wherein R is selected from the group consisting of hydrogen, —I, —Br, —Cl and —F; Y is —O—; $Ar_1$ is phenyl, pyridinyl, thienyl, furanyl, thiazolyl, or 1,3,4-thiadiazolyl; each of which is independently unsubstituted or substituted with one substituent selected from the group consisting of —I, —Br, —Cl and —F; and $R_1$, $R_5$, $Ar_2$, and Z are as described in formula (I).

Another aspect of the invention relates to compounds of formula (I), or a pharmaceutically acceptable salt, prodrug, salt of a prodrug, or a combination thereof, wherein $Ar_3$ is

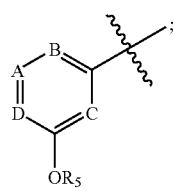

(d)

A, B, C and D are —C(R)—; or 1 or 2 of A, B, C and D are N and the others are —C(R)—; wherein R is selected from the group consisting of hydrogen, alkyl, alkenyl, —CN, —$NO_2$, halogen, hydroxy, alkoxy, —$NH_2$, —N(H)(alkyl), —N(alkyl)$_2$, —SH, —S(alkyl), —S(O)$_2$alkyl, —S(O)$_2$OH, —S(O)$_2$Oalkyl, —C(O)OH, —C(O)Oalkyl, —C(O)H, haloalkyl, cyanoalkyl, nitroalkyl, hydroxyalkyl, alkoxyalkyl, and haloalkoxyalkyl; Y is —O—; $Ar_1$ is thiazolyl unsubstituted or substituted with substituents as described in formula (I); and $R_1$, $R_5$, $Ar_2$, and Z are as described in formula (I). Preferably, A, B, C and D are —C(R)—; or 1 or 2 of A, B, C and D are N and the others are —C(R)—; wherein R is selected from the group consisting of hydrogen, —I, —Br, —Cl and —F; Y is —O—; $Ar_1$ is thiazolyl unsubstituted or substituted with one substituent selected from the group consisting of —I, —Br, —Cl and —F; and $R_1$, $R_5$, $Ar_2$, and Z are as described in formula (I). More preferably, A, B, C and D are —C(R)—; or one of A, B, C and D are N and the others are —C(R)—; wherein R is selected from the group consisting of hydrogen, —I, —Br, —Cl and —F; Y is —O—; $Ar_1$ is thiazolyl unsubstituted or substituted with one substituent selected from the group consisting of —I, —Br, —Cl and —F; and $R_1$, $R_5$, $Ar_2$, and Z are as described in formula (I).

Another aspect of the invention relates to compounds of formula (I), or a pharmaceutically acceptable salt, prodrug, salt of a prodrug, or a combination thereof, wherein $Ar_3$ is

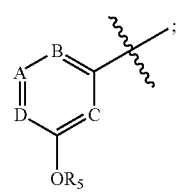

(d)

A, B, C and D are —C(R)—; or 1 or 2 of A, B, C and D are N and the others are —C(R)—; wherein R is selected from the group consisting of hydrogen, alkyl, alkenyl, —CN, —$NO_2$, halogen, hydroxy, alkoxy, —$NH_2$, —N(H)(alkyl), —N(alkyl)$_2$, —SH, —S(alkyl), —S(O)$_2$alkyl, —S(O)$_2$OH, —S(O)$_2$Oalkyl, —C(O)OH, —C(O)Oalkyl, —C(O)H, haloalkyl, cyanoalkyl, nitroalkyl, hydroxyalkyl, alkoxyalkyl, and haloalkoxyalkyl; Y is —O—; $Ar_1$ is phenyl, pyridinyl, thienyl, furanyl, thiazolyl, oxazolyl, isoxazolyl, 1,3,4-thiadiazolyl, 1,2,4-thiadiazolyl, or 1,2,4-oxadiazolyl; each of which is independently unsubstituted or substituted as described in formula (I); $Ar_2$ is thienyl, furanyl, thiazolyl, oxazolyl, isoxazolyl, 1,3,4-thiadiazolyl, 1,2,4-thiadiazolyl, or 1,2,4-oxadiazolyl; each of which is independently unsubstituted or substituted as described in formula (I); and $R_1$, $R_5$ and Z are as described in formula (I). Particularly, A, B, C and D are —C(R)—; or one of A, B, C and D are N and the others are —C(R)—; wherein R is selected from the group consisting of hydrogen, —I, —Br, —Cl and —F; Y is —O—; $Ar_1$ is phenyl, pyridinyl, thienyl, furanyl, thiazolyl, or 1,3,4-thiadiazolyl; each of which is independently unsubstituted or substituted with one substituent selected from the group consisting of —I, —Br, —Cl and —F; $Ar_2$ is thienyl, thiazolyl, isoxazolyl, 1,2,4-thiadiazolyl, or 1,2,4-oxadiazolyl, each of which is independently unsubstituted or substituted with one $C_1$-$C_6$ alkyl; and $R_1$, $R_5$, and Z are as described in formula (I).

Another aspect of the invention relates to compounds of formula (I), or a pharmaceutically acceptable salt, prodrug, salt of a prodrug, or a combination thereof, wherein $Ar_3$ is

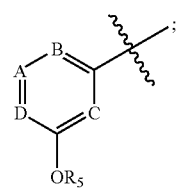

(d)

A, B, C and D are —C(R)—; or 1 or 2 of A, B, C and D are N and the others are —C(R)—; wherein R is selected from the group consisting of hydrogen, alkyl, alkenyl, —CN, —$NO_2$, halogen, hydroxy, alkoxy, —$NH_2$, —N(H)(alkyl), —N(alkyl)$_2$, —SH, —S(alkyl), —S(O)$_2$alkyl, —S(O)$_2$OH, —S(O)$_2$Oalkyl, —C(O)OH, —C(O)Oalkyl, —C(O)H, haloalkyl, cyanoalkyl, nitroalkyl, hydroxyalkyl, alkoxyalkyl, and haloalkoxyalkyl; Y is —O—; $Ar_1$ is thiazolyl unsubstituted or substituted with substituents as described in formula (I); $Ar_2$ is isoxazolyl unsubstituted or substituted with substituents as described in formula (I); and $R_1$, $R_5$, and Z are as described in formula (I). Preferably, A, B, C and D are —C(R)—; or 1 or 2 of A, B, C and D are N and the others are —C(R)—; wherein R is selected from the group consisting of hydrogen, —I, —Br, —Cl and —F; Y is —O—; $Ar_1$ is thiazolyl unsubstituted or substituted with one substituent selected from the group consisting of —I, —Br, —Cl and —F; $Ar_2$ is isoxazolyl unsubstituted or substituted with one $C_1$-$C_6$ alkyl; and $R_1$, $R_5$, and Z are as described in formula (I). More preferably, A, B, C and D are —C(R)—; or one of A, B, C and D are N and the others are —C(R)—; wherein R is selected from the group consisting of hydrogen, —I, —Br, —Cl and —F; Y is —O—; $Ar_1$ is thiazolyl unsubstituted or substituted with one substituent selected from the group consisting of —I, —Br, —Cl and —F; $Ar_2$ is isoxazolyl unsubstituted or substituted with one substituent selected from the group consisting of methyl and ethyl; and $R_1$, $R_5$, and Z are as described in formula (I).

Another aspect of the invention relates to compounds of formula (I), or a pharmaceutically acceptable salt, prodrug, salt of a prodrug, or a combination thereof, wherein $Ar_3$ is

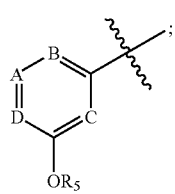

(d)

A, B, C and D are —C(R)—; or 1 or 2 of A, B, C and D are N and the others are —C(R)—; wherein R is selected from the group consisting of hydrogen, alkyl, alkenyl, —CN, —$NO_2$, halogen, hydroxy, alkoxy, —$NH_2$, —N(H)(alkyl), —N(alkyl)$_2$, —SH, —S(alkyl), —S(O)$_2$alkyl, —S(O)$_2$OH, —S(O)$_2$Oalkyl, —C(O)OH, —C(O)Oalkyl, —C(O)H, haloalkyl, cyanoalkyl, nitroalkyl, hydroxyalkyl, alkoxyalkyl, and haloalkoxyalkyl; Y is —O—; $Ar_1$ is thiazolyl unsubstituted or substituted with substituents as described in formula (I); $Ar_2$ is 1,2,4-oxadiazolyl unsubstituted or substituted with substituents as described in formula (I); and $R_1$, $R_5$, and Z are as described in formula (I). Preferably, A, B, C and D are —C(R)—; or 1 or 2 of A, B, C and D are N and the others are —C(R)—; wherein R is selected from the group consisting of hydrogen, —I, —Br, —Cl and —F; Y is —O—; $Ar_1$ is thiazolyl unsubstituted or substituted with one substituent selected from the group consisting of —I, —Br, —Cl and —F; $Ar_1$ is 1,2,4-oxadiazolyl unsubstituted or substituted with one $C_1$-$C_6$ alkyl; and $R_1$, $R_5$, and Z are as described in formula (I). More preferably, A, B, C and D are —C(R)—; or one of A, B, C and D are N and the others are —C(R)—; wherein R is selected from the group consisting of hydrogen, —I, —Br, —Cl and —F; Y is —O—; $Ar_1$ is thiazolyl unsubstituted or substituted with one substituent selected from the group consisting of —I, —Br, —Cl and —F; $Ar_2$ is 1,2,4-oxadiazolyl unsubstituted or substituted with one substituent selected from the group consisting of methyl and ethyl; and $R_1$, $R_5$, and Z are as described in formula (I).

Another aspect of the invention relates to compound of formula (I), or a pharmaceutically acceptable salt, prodrug, salt of a prodrug, or combination thereof, wherein $Ar_3$ is

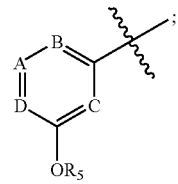

(d)

A, B, C and D are —C(R)—, or one of A, B, C and D is N and the others are —C(R)—; wherein R is selected from the group consisting of hydrogen, —I, —Br, —Cl, and —F; $Ar_1$ is selected from the group consisting of phenyl, pyridinyl, thienyl, furanyl, thiazolyl, and 1,3,4-thiadiazolyl; each of which is independently unsubstituted or substituted with one substituent selected from the group consisting of —I, —Br, —Cl, and —F; $Ar_2$ is selected from the group consisting of thienyl, thiazolyl, isoxazolyl, 1,2,4-thiadiazolyl, and 1,2,4-oxadiazolyl; each of which is independently unsubstituted or substituted with one $C_1$-$C_6$ alkyl; $R_1$ is selected from the group consisting of $C_1$-$C_6$ alkyl and haloalkyl; Z is selected from the group consisting of —$OR_{9a}$ and —$NR_6R_{9b}$; wherein $R_{9a}$ is —S(O)$_2$($C_1$-$C_6$ alkyl), $R_6$ is hydrogen, and $R_{9b}$ is selected from the group consisting of hydrogen, —C(O)$NH_2$, —C(O)N(H)($C_1$-$C_6$ alkyl), —C(O)O($C_1$-$C_6$ alkyl), —S(O)$_2$($C_1$-$C_6$ alkyl), —$CH_2$—C(O)O($C_1$-$C_6$ alkyl), and —C(O)$R_{10}$ wherein $R_{10}$ is $C_1$-$C_6$ alkyl or unsubstituted $C_1$-$C_6$ cycloalkyl; Y is —O—; and $R_5$ is selected from the group consisting of $C_1$-$C_6$ alkyl, —$R_8$, and —($C_1$-$C_6$ alkylenyl)-$R_8$ wherein $R_8$ at each occurrence is an unsubstituted ring selected from the group consisting of phenyl, cyclopropyl, cyclopentyl, cyclohexyl, tetrahydrofuranyl and tetrahydropyranyl.

Another aspect of the invention relates to compound of formula (I), or a pharmaceutically acceptable salt, prodrug, salt of a prodrug, or combination thereof, wherein $Ar_3$ is

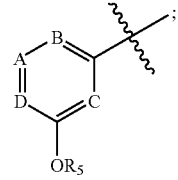

(d)

A, B, C and D are —C(R)—, or one of A, B, C and D is N and the others are —C(R)—; wherein R is selected from the group consisting of hydrogen, —I, —Br, —Cl, and —F; $Ar_1$ is selected from the group consisting of phenyl, pyridinyl, thienyl, furanyl, thiazolyl, and 1,3,4-thiadiazolyl; each of which is independently unsubstituted or substituted with one substituent selected from the group consisting of —I, —Br, —Cl, and —F; $Ar_2$ is selected from the group consisting of thienyl, thiazolyl, isoxazolyl, 1,2,4-thiadiazolyl, and 1,2,4-oxadiazolyl; each of which is independently unsubstituted or substituted with one substituent selected from the group consisting of methyl and ethyl; $R_1$ is selected from the group consisting of methyl and trifluoromethyl; Z is selected from the group consisting of —$OR_{9a}$ and —$NR_6R_{9b}$; wherein $R_{9a}$ is —S(O)$_2$(methyl), $R_6$ is hydrogen, and $R_{9b}$ is selected from the group consisting of hydrogen, —C(O)$NH_2$, —C(O)N(H)(methyl), —C(O)O(methyl), —S(O)$_2$(methyl), —$CH_2$—C(O)O(methyl), and —C(O)$R_{10}$ wherein $R_{10}$ is methyl, ethyl, isopropyl or unsubstituted cyclopropyl; Y is —O— and $R_5$ is selected from the group consisting of methyl, ethyl, isopropyl, 2-methylpropyl, —R$_8$, and —CH$_2$—R$_8$ wherein R$_8$ at each occurrence is an unsubstituted ring selected from the group consisting of phenyl, cyclopropyl, cyclopentyl, cyclohexyl, tetrahydrofuranyl and tetrahydropyranyl.

Another aspect of the invention is related to compounds of formula (I), or a pharmaceutically acceptable salt, prodrug, salt of a prodrug, or a combination thereof, wherein Ar$_3$ is selected from the group of formula consisting of

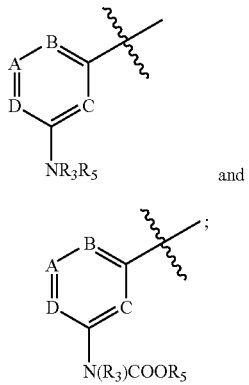

A, B, C and D are —C(R)—; or 1 or 2 of A, B, C and D are N and the others are —C(R)—; wherein R is selected from the group consisting of hydrogen, alkyl, alkenyl, —CN, —NO$_2$, halogen, hydroxy, alkoxy, —NH$_2$, —N(H)(alkyl), —N(alkyl)$_2$, —SH, —S(alkyl), —S(O)$_2$alkyl, —S(O)$_2$OH, —S(O)$_2$Oalkyl, —C(O)OH, —C(O)Oalkyl, —C(O)H, haloalkyl, cyanoalkyl, nitroalkyl, hydroxyalkyl, alkoxyalkyl, and haloalkoxyalkyl; Y is —O— and R$_1$, R$_3$, R$_5$, Ar$_1$, Ar$_2$, and Z are as described in formula (I). Preferably, A, B, C and D are —C(R)—; or one of A, B, C and D are N and the others are —C(R)—; wherein R is selected from the group consisting of hydrogen, —I, —Br, —Cl and —F; Y is —O— and R$_1$, R$_3$, R$_5$, Ar$_1$, Ar$_2$, and Z are as described in formula (I).

Another aspect of the invention relates to compounds of formula (I), or a pharmaceutically acceptable salt, prodrug, salt of a prodrug, or a combination thereof, wherein Ar$_3$ is selected from the group consisting of

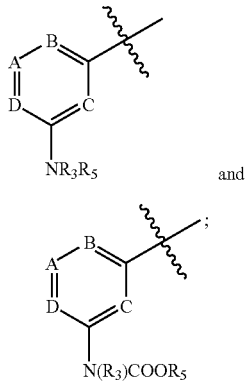

A, B, C and D are —C(R)—; or 1 or 2 of A, B, C and D are N and the others are —C(R)—; wherein R is selected from the group consisting of hydrogen, alkyl, alkenyl, —CN, —NO$_2$, halogen, hydroxy, alkoxy, —NH$_2$, —N(H)(alkyl), —N(alkyl)$_2$, —SH, —S(alkyl), —S(O)$_2$alkyl, —S(O)$_2$OH, —S(O)$_2$Oalkyl, —C(O)OH, —C(O)Oalkyl, —C(O)H, haloalkyl, cyanoalkyl, nitroalkyl, hydroxyalkyl, alkoxyalkyl, and haloalkoxyalkyl; Y is —O—; Ar$_1$ is phenyl, pyridinyl, thienyl, furanyl, thiazolyl, oxazolyl, isoxazolyl, 1,3,4-thiadiazolyl, 1,2,4-thiadiazolyl, or 1,2,4-oxadiazolyl; each of which is independently unsubstituted or substituted as described in formula (I); and R$_1$, R$_3$, R$_5$, Ar$_2$, and Z are as described in formula (I). Preferably, A, B, C and D are —C(R)—; or one of A, B, C and D are N and the others are —C(R)—; wherein R is selected from the group consisting of hydrogen, —I, —Br, —Cl and —F; Y is —O—; Ar$_1$ is phenyl, pyridinyl, thienyl, furanyl, thiazolyl, or 1,3,4-thiadiazolyl; each of which is independently unsubstituted or substituted with one substituent selected from the group consisting of —I, —Br, —Cl and —F; and R$_1$, R$_3$, R$_5$, Ar$_2$, and Z are as described in formula (I).

Another aspect of the invention relates to compounds of formula (I), or a pharmaceutically acceptable salt, prodrug, salt of a prodrug, or a combination thereof, wherein Ar$_3$ is selected from the group consisting of

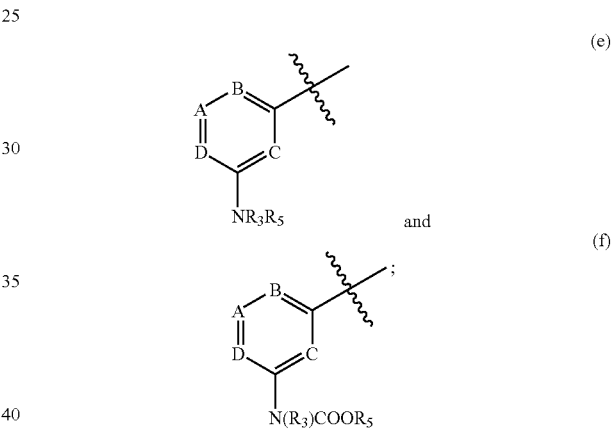

A, B, C and D are —C(R)—; or 1 or 2 of A, B, C and D are N and the others are —C(R)—; wherein R is selected from the group consisting of hydrogen, alkyl, alkenyl, —CN, —NO$_2$, halogen, hydroxy, alkoxy, —NH$_2$—, —N(H)(alkyl), —N(alkyl)$_2$, —SH, —S(alkyl), —S(O)$_2$alkyl, —S(O)$_2$OH, —S(O)$_2$Oalkyl, —C(O)OH, —C(O)Oalkyl, —C(O)H, haloalkyl, cyanoalkyl, nitroalkyl, hydroxyalkyl, alkoxyalkyl, and haloalkoxyalkyl; Y is —O—; Ar$_1$ is thiazolyl unsubstituted or substituted with substituents as described in formula (I); and R$_1$, R$_3$, R$_5$, Ar$_2$, and Z are as described in formula (I). Preferably, A, B, C and D are —C(R)—; or 1 or 2 of A, B, C and D are N and the others are —C(R)—; wherein R is selected from the group consisting of hydrogen, —I, —Br, —Cl and —F; Y is —O—; Ar$_1$ is thiazolyl unsubstituted or substituted with one substituent selected from the group consisting of —I, —Br, —Cl and —F; and R$_1$, R$_3$, R$_5$, Ar$_2$, and Z are as described in formula (I). More preferably, A, B, C and D are —C(R)—; or one of A, B, C and D are N and the others are —C(R)—; wherein R is selected from the group consisting of hydrogen, —I, —Br, —Cl and —F; Y is —O—; Ar$_1$ is thiazolyl unsubstituted or substituted with one substituent selected from the group consisting of —I, —Br, —Cl and —F; and R$_1$, R$_3$, R$_5$, Ar$_2$, and Z are as described in formula (I).

Another aspect of the invention relates to compounds of formula (I), or a pharmaceutically acceptable salt, prodrug, salt of a prodrug, or a combination thereof, wherein Ar₃ is selected from the group consisting of

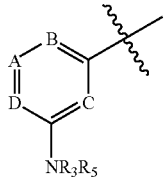

(e)

and

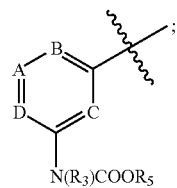

(f)

A, B, C and D are —C(R)—; or 1 or 2 of A, B, C and D are N and the others are —C(R)—; wherein R is selected from the group consisting of hydrogen, alkyl, alkenyl, —CN, —NO₂, halogen, hydroxy, alkoxy, —NH₂, —N(H)(alkyl), —N(alkyl)₂, —SH, —S(alkyl), —S(O)₂alkyl, —S(O)₂OH, —S(O)₂Oalkyl, —C(O)OH, —C(O)Oalkyl, —C(O)H, haloalkyl, cyanoalkyl, nitroalkyl, hydroxyalkyl, alkoxyalkyl, and haloalkoxyalkyl; Y is —O—; Ar₁ is phenyl, pyridinyl, thienyl, furanyl, thiazolyl, oxazolyl, isoxazolyl, 1,3,4-thiadiazolyl, 1,2,4-thiadiazolyl, or 1,2,4-oxadiazolyl; each of which is independently unsubstituted or substituted as described in formula (I); Ar₂ is thienyl, furanyl, thiazolyl, oxazolyl, isoxazolyl, 1,3,4-thiadiazolyl, 1,2,4-thiadiazolyl, or 1,2,4-oxadiazolyl; each of which is independently unsubstituted or substituted as described in formula (I); and R₁, R₃, R₅, and Z are as described in formula (I) Particularly, A, B, C and D are —C(R)—; or one of A, B, C and D are N and the others are —C(R)—; wherein R is selected from the group consisting of hydrogen, —I, —Br, —Cl and —F; Y is —O—; Ar₁ is phenyl, pyridinyl, thienyl, furanyl, thiazolyl, or 1,3,4-thiadiazolyl; each of which is independently unsubstituted or substituted with one substituent selected from the group consisting of —I, —Br, —Cl and —F; Ar₂ is thienyl, thiazolyl, isoxazolyl, 1,2,4-thiadiazolyl, or 1,2,4-oxadiazolyl, each of which is independently unsubstituted or substituted with one C₁-C₆ alkyl; and R₁, R₃, R₅, and Z are as described in formula (I).

Another aspect of the invention relates to compounds of formula (I), or a pharmaceutically acceptable salt, prodrug, salt of a prodrug, or a combination thereof, wherein Ar₃ is selected from the group consisting of

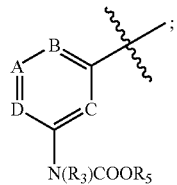

(e)

and

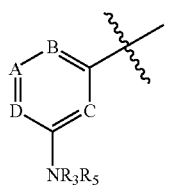

(f)

A, B, C and D are —C(R)—; or 1 or 2 of A, B, C and D are N and the others are —C(R)—; wherein R is selected from the group consisting of hydrogen, alkyl, alkenyl, —CN, —NO₂, halogen, hydroxy, alkoxy, —NH₂, —N(H)(alkyl), —N(alkyl)₂, —SH, —S(alkyl), —S(O)₂alkyl, —S(O)₂OH, —S(O)₂Oalkyl, —C(O)OH, —C(O)Oalkyl, —C(O)H, haloalkyl, cyanoalkyl, nitroalkyl, hydroxyalkyl, alkoxyalkyl, and haloalkoxyalkyl; Y is —O—; Ar₁ is thiazolyl unsubstituted or substituted with substituents as described in formula (I); Ar₂ is isoxazolyl unsubstituted or substituted with substituents as described in formula (I); and R₁, R₃, R₅, and Z are as described in formula (I). Preferably, A, B, C and D are —C(R)—; or 1 or 2 of A, B, C and D are N and the others are —C(R)—; wherein R is selected from the group consisting of hydrogen, —I, —Br, —Cl and —F; Y is —O—; Ar₁ is thiazolyl unsubstituted or substituted with one substituent selected from the group consisting of —I, —Br, —Cl and —F; Ar₂ is isoxazolyl unsubstituted or substituted with one C₁-C₆ alkyl; and R₁, R₃, R₅, and Z are as described in formula (I). More preferably, A, B, C and D are —C(R)—; or one of A, B, C and D are N and the others are —C(R)—; wherein R is selected from the group consisting of hydrogen, —I, —Br, —Cl and —F; Y is —O—; Ar₁ is thiazolyl unsubstituted or substituted with one substituent selected from the group consisting of —I, —Br, —Cl and —F; Ar₂ is isoxazolyl unsubstituted or substituted with one substituent selected from the group consisting of methyl and ethyl; and R₁, R₃, R₅, and Z are as described in formula (I).

Another aspect of the invention relates to compounds of formula (I), or a pharmaceutically acceptable salt, prodrug, salt of a prodrug, or a combination thereof, wherein Ar₃ is selected from the group consisting of

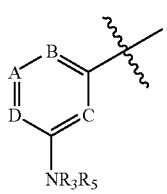

(e)

and

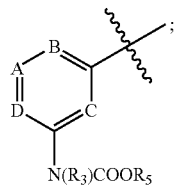

(f)

A, B, C and D are —C(R)—; or 1 or 2 of A, B, C and D are N and the others are —C(R)—; wherein R is selected from the group consisting of hydrogen, alkyl, alkenyl, —CN, —NO₂, halogen, hydroxy, alkoxy, —NH₂, —N(H)(alkyl), —N(alkyl)₂, —SH, —S(alkyl), —S(O)₂alkyl, —S(O)₂OH, —S(O)₂Oalkyl, —C(O)OH, —C(O)Oalkyl, —C(O)H, haloalkyl, cyanoalkyl, nitroalkyl, hydroxyalkyl, alkoxyalkyl, and haloalkoxyalkyl; Y is —O—; $Ar_1$ is thiazolyl unsubstituted or substituted with substituents as described in formula (I); $Ar_2$ is 1,2,4-oxadiazolyl unsubstituted or substituted with substituents as described in formula (I); and $R_1$, $R_3$, $R_5$, and Z are as described in formula (I). Preferably, A, B, C and D are —C(R)—; or 1 or 2 of A, B, C and D are N and the others are —C(R)—; wherein R is selected from the group consisting of hydrogen, —I, —Br, —Cl and —F; Y is —O—; $Ar_1$ is thiazolyl unsubstituted or substituted with one substituent selected from the group consisting of —I, —Br, —Cl and —F; $Ar_2$ is 1,2,4-oxadiazolyl unsubstituted or substituted with one $C_1$-$C_6$ alkyl; and $R_1$, $R_3$, $R_5$, and Z are as described in formula (I). More preferably, A, B, C and D are —C(R)—; or one of A, B, C and D are N and the others are —C(R)—; wherein R is selected from the group consisting of hydrogen, —I, —Br, —Cl and —F; Y is —O—; $Ar_1$ is thiazolyl unsubstituted or substituted with one substituent selected from the group consisting of —I, —Br, —Cl and —F; $Ar_2$ is 1,2,4-oxadiazolyl unsubstituted or substituted with one substituent selected from the group consisting of methyl and ethyl; and $R_1$, $R_3$, $R_5$, and Z are as described in formula (I).

Another aspect of the invention relates to compound of formula (I), or a pharmaceutically acceptable salt, prodrug, salt of a prodrug, or combination thereof, wherein $Ar_3$ is selected from the group of formula consisting of

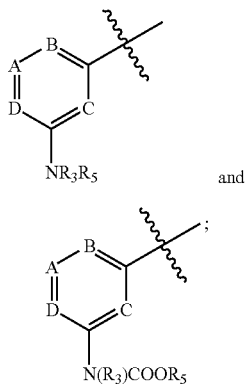

A, B, C and D are —C(R)—, or one of A, B, C and D is N and the others are —C(R)—; wherein R is selected from the group consisting of hydrogen, —I, —Br, —Cl, and —F; $Ar_1$ is selected from the group consisting of phenyl, pyridinyl, thienyl, furanyl, thiazolyl, and 1,3,4-thiadiazolyl; each of which is independently unsubstituted or substituted with one substituent selected from the group consisting of —I, —Br, —Cl, and —F; $Ar_2$ is selected from the group consisting of thienyl, thiazolyl, isoxazolyl, 1,2,4-thiadiazolyl, and 1,2,4-oxadiazolyl; each of which is independently unsubstituted or substituted with one $C_1$-$C_6$ alkyl; $R_1$ is selected from the group consisting of $C_1$-$C_6$ alkyl and haloalkyl; Z is selected from the group consisting of —$OR_{9a}$, and —$NR_6R_{9b}$; wherein $R_{9a}$ is —$S(O)_2(C_1$-$C_6$ alkyl), $R_6$ is hydrogen, and $R_{9b}$ is selected from the group consisting of hydrogen, —C(O)$NH_2$, —C(O)N(H)($C_1$-$C_6$ alkyl), —C(O)O($C_1$-$C_6$ alkyl), —S(O)$_2$($C_1$-$C_6$ alkyl), —$CH_2$—C(O)O($C_1$-$C_6$ alkyl), and —C(O)$R_{10}$ wherein $R_{10}$ is $C_1$-$C_6$ alkyl or unsubstituted $C_1$-$C_6$ cycloalkyl; Y is —O—; $R_3$ is hydrogen; and $R_5$ at each occurrence is independently selected from the group consisting of $C_1$-$C_9$ alkyl, —$R_8$, and —($C_1$-$C_6$ alkylenyl)-$R_8$ wherein $R_8$ at each occurrence is an unsubstituted ring selected from the group consisting of phenyl, cyclopropyl, cyclopentyl, cyclohexyl, tetrahydrofuranyl and tetrahydropyranyl.

Another aspect of the invention relates to compound of formula (I), or a pharmaceutically acceptable salt, prodrug, salt of a prodrug, or combination thereof, wherein $Ar_3$ is selected from the group of formula consisting of

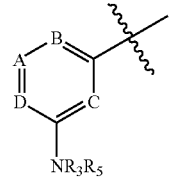

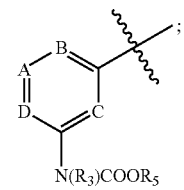

A, B, C and D are —C(R)—, or one of A, B, C and D is N and the others are —C(R)—; wherein R is selected from the group consisting of hydrogen, —I, —Br, —Cl, and —F; $Ar_1$ is selected from the group consisting of phenyl, pyridinyl, thienyl, furanyl, thiazolyl, and 1,3,4-thiadiazolyl; each of which is independently unsubstituted or substituted with one substituent selected from the group consisting of —I, —Br, —Cl, and —F; $Ar_2$ is selected from the group consisting of thienyl, thiazolyl, isoxazolyl, 1,2,4-thiadiazolyl, and 1,2,4-oxadiazolyl; each of which is independently unsubstituted or substituted with one substituent selected from the group consisting of methyl and ethyl; $R_1$ is selected from the group consisting of methyl and trifluoromethyl; Z is selected from the group consisting of —$OR_{9a}$ and —$NR_6R_{9b}$; wherein $R_{9a}$ is —$S(O)_2$(methyl), $R_6$ is hydrogen, and $R_{9b}$ is selected from the group consisting of hydrogen, —C(O)$NH_2$, —C(O)N(H)(methyl), —C(O)O(methyl), —S(O)$_2$(methyl), —$CH_2$—C(O)O(methyl), and —C(O)$R_{10}$ wherein $R_{10}$ is methyl, ethyl, isopropyl or unsubstituted cyclopropyl; Y is —O—; $R_3$ is hydrogen; and $R_5$ at each occurrence is independently selected from the group consisting of methyl, ethyl, isopropyl, 2-methylpropyl, tert-butyl, —$R_8$, and —$CH_2$—$R_8$ wherein $R_8$ at each occurrence is an unsubstituted ring selected from the group consisting of phenyl, cyclopropyl, cyclopentyl, cyclohexyl, tetrahydrofuranyl and tetrahydropyranyl.

Exemplary compounds of the present invention having formula (I) include, but are not limited to, N-(1-{3-[2-(4-isopropoxyphenoxy)-1,3-thiazol-5-yl]isoxazol-5-yl}ethyl)acetamide;

N-(1-{5-[2-(4-phenoxyphenoxy)-1,3-thiazol-5-yl]thien-2-yl}ethyl)urea;

N-(1-{5-[2-(4-isopropoxyphenoxy)-1,3-thiazol-5-yl]thien-2-yl}ethyl)acetamide;

N-{1-[2'-(4-isopropoxyphenoxy)-2,5'-bi-1,3-thiazol-5-yl]ethyl}acetamide;

N-(2,2,2-trifluoro-1-{5-[2-(4-isopropoxyphenoxy)-1,3-thiazol-5-yl]thien-2-yl}ethyl)urea;

N-(1-{3-[2-(4-isopropoxyphenoxy)-1,3-thiazol-5-yl]isoxazol-5-yl}ethyl)propanamide;

N-(1-{3-[2-(4-isopropoxyphenoxy)-1,3-thiazol-5-yl]isoxazol-5-yl}ethyl)urea;

N-(1-{3-[2-(4-isopropoxyphenoxy)-1,3-thiazol-5-yl]isoxazol-5-yl}ethyl)-N'-methylurea;
N-(1-{3-[2-(2-chloro-4-isobutoxyphenoxy)-1,3-thiazol-5-yl]isoxazol-5-yl}ethyl)cyclopropanecarboxamide;
N-(1-{3-[2-(2-chloro-4-isobutoxyphenoxy)-1,3-thiazol-5-yl]isoxazol-5-yl}ethyl)-2-methylpropanamide;
N-(1-{3-[2-(2-chloro-4-isobutoxyphenoxy)-1,3-thiazol-5-yl]isoxazol-5-yl}ethyl)acetamide;
N-(1-{3-[2-(2-chloro-4-isobutoxyphenoxy)-1,3-thiazol-5-yl]isoxazol-5-yl}ethyl)propanamide;
methyl 1-{3-[2-(2-chloro-4-isobutoxyphenoxy)-1,3-thiazol-5-yl]isoxazol-5-yl}ethylcarbamate;
N-(1-{3-[2-(2-chloro-4-isobutoxyphenoxy)-1,3-thiazol-5-yl]isoxazol-5-yl}ethyl)-N'-methylurea;
N-((1R)-1-{3-[2-(4-isopropoxyphenoxy)-1,3-thiazol-5-yl]isoxazol-5-yl}ethyl)acetamide;
N((1S)-1-{3-[2-(4-isopropoxyphenoxy)-1,3-thiazol-5-yl]isoxazol-5-yl}ethyl)acetamide;
N-(1-{3-[4-(4-isopropoxyphenoxy)phenyl]isoxazol-5-yl}ethyl)acetamide;
N-(1-{3-[2-(2-chloro-4-methoxyphenoxy)-1,3-thiazol-5-yl]isoxazol-5-yl}ethyl)acetamide;
methyl 1-{3-[2-(2-chloro-4-methoxyphenoxy)-1,3-thiazol-5-yl]isoxazol-5-yl}ethylcarbamate;
N-(1-{3-[2-(2-chloro-4-methoxyphenoxy)-1,3-thiazol-5-yl]isoxazol-5-yl}ethyl)-2-methylpropanamide;
N-(1-{3-[2-(2-chloro-4-methoxyphenoxy)-1,3-thiazol-5-yl]isoxazol-5-yl}ethyl)cyclopropanecarboxamide;
methyl 1-{3-[4-(4-isopropoxyphenoxy)phenyl]isoxazol-5-yl}ethylcarbamate;
N-(1-{3-[4-(4-isopropoxyphenoxy)phenyl]isoxazol-5-yl}ethyl)urea;
N-(1-{5-[5-(4-isopropoxyphenoxy)-1,3,4-thiadiazol-2-yl]thien-2-yl}ethyl)acetamide;
N-(1-{3-[2-(2-chloro-4-isopropoxyphenoxy)-1,3-thiazol-5-yl]isoxazol-5-yl}ethyl)acetamide;
methyl 1-{3-[2-(2-chloro-4-isopropoxyphenoxy)-1,3-thiazol-5-yl]isoxazol-5-yl}ethylcarbamate;
N-(1-{3-[2-(2-chloro-4-isopropoxyphenoxy)-1,3-thiazol-5-yl]isoxazol-5-yl}ethyl)-2-methylpropanamide;
N-(1-{3-[2-(2-chloro-4-isopropoxyphenoxy)-1,3-thiazol-5-yl]isoxazol-5-yl}ethyl)cyclopropanecarboxamide;
N-[1-(3-{2-[2-chloro-4-(cyclopropylmethoxy)phenoxy]-1,3-thiazol-5-yl}isoxazol-5-yl)ethyl]acetamide;
methyl 1-(3-{2-[2-chloro-4-(cyclopropylmethoxy)phenoxy]-1,3-thiazol-5-yl}isoxazol-5-yl)ethylcarbamate;
N-[1-(3-{2-[2-chloro-4-(cyclopropylmethoxy)phenoxy]-1,3-thiazol-5-yl}isoxazol-5-yl)ethyl]-N'-methylurea;
N-(1-{5-[5-(4-isopropoxyphenoxy)-1,3,4-thiadiazol-2-yl]thien-2-yl}ethyl)-N'-methylurea;
N-(1-{3-[2-(2-chloro-4-isopropoxyphenoxy)-1,3-thiazol-5-yl]isoxazol-5-yl}ethyl)urea;
N-(1-{3-[2-(2-chloro-4-isopropoxyphenoxy)-1,3-thiazol-5-yl]isoxazol-5-yl}ethyl)-N'-methylurea;
N-[1-(3-{2-[2-chloro-4-(tetrahydrofuran-3-ylmethoxy)phenoxy]-1,3-thiazol-5-yl}isoxazol-5-yl)ethyl]acetamide;
N-[1-(3-{2-[2-chloro-4-(tetrahydrofuran-3-yloxy)phenoxy]-1,3-thiazol-5-yl}isoxazol-5-yl)ethyl]acetamide;
N-(1-{3-[2-(2-chloro-4-ethoxyphenoxy)-1,3-thiazol-5-yl]isoxazol-5-yl}ethyl)acetamide;
N-(1-{3-[2-(4-isopropoxyphenoxy)-1,3-thiazol-5-yl]-1,2,4-oxadiazol-5-yl}ethyl)acetamide;
N-(1-{3-[5-(4-isopropoxyphenoxy)thien-2-yl]isoxazol-5-yl}ethyl)acetamide;
N-(1-{3-[5-(4-isopropoxyphenoxy)-2-furyl]isoxazol-5-yl}ethyl)acetamide;
N-(1-{3-[5-(4-isopropoxyphenoxy)-2-furyl]isoxazol-5-yl}ethyl)-N'-methylurea;
N-[1-(3-{2-[2-chloro-4-(cyclohexyloxy)phenoxy]-1,3-thiazol-5-yl}isoxazol-5-yl)ethyl]acetamide;
N-[1-(3-{2-[2-chloro-4-(cyclopentyloxy)phenoxy]-1,3-thiazol-5-yl}isoxazol-5-yl)ethyl]acetamide;
N-[1-(3-{2-[2-chloro-4-(tetrahydro-2H-pyran-4-yloxy)phenoxy]-1,3-thiazol-5-yl}isoxazol-5-yl)ethyl]acetamide;
N-[1-(3-{2-[4-(cyclopropylmethoxy)phenoxy]-1,3-thiazol-5-yl}isoxazol-5-yl)ethyl]acetamide;
methyl 1-(3-{2-[4-(cyclopropylmethoxy)phenoxy]-1,3-thiazol-5-yl}isoxazol-5-yl)ethylcarbamate;
N-[1-(3-{2-[4-(cyclopropylmethoxy)phenoxy]-1,3-thiazol-5-yl}isoxazol-5-yl)ethyl]urea;
N-[1-(3-{2-[4-(cyclopropylmethoxy)phenoxy]-1,3-thiazol-5-yl}isoxazol-5-yl)ethyl]-N'-methylurea;
N-[1-(3-{2-[4-(tetrahydro-2H-pyran-4-yloxy)phenoxy]-1,3-thiazol-5-yl}isoxazol-5-yl)ethyl]acetamide;
N-[1-(3-{2-[4-(tetrahydrofuran-3-yloxy)phenoxy]-1,3-thiazol-5-yl}isoxazol-5-yl)ethyl]acetamide;
N-[1-(3-{2-[4-(cyclohexyloxy)phenoxy]-1,3-thiazol-5-yl}isoxazol-5-yl)ethyl]acetamide;
N-[1-(3-{2-[4-(cyclopentyloxy)phenoxy]-1,3-thiazol-5-yl}isoxazol-5-yl)ethyl]acetamide;
N-(1-{3-[4-chloro-2-(4-isopropoxyphenoxy)-1,3-thiazol-5-yl]isoxazol-5-yl}ethyl)acetamide;
N-(1-{3-[4-chloro-2-(4-isopropoxyphenoxy)-1,3-thiazol-5-yl]isoxazol-5-yl}ethyl)-N'-methylurea;
methyl 1-{3-[4-chloro-2-(4-isopropoxyphenoxy)-1,3-thiazol-5-yl]isoxazol-5-yl}ethylcarbamate;
N-(1-{3-[4-chloro-2-(4-isopropoxyphenoxy)-1,3-thiazol-5-yl]isoxazol-5-yl}ethyl)urea;
methyl 1-{3-[2-(4-isopropoxyphenoxy)-1,3-thiazol-5-yl]-1,2,4-oxadiazol-5-yl}ethylcarbamate;
N-(1-{3-[2-(4-isopropoxyphenoxy)-1,3-thiazol-5-yl]-1,2,4-oxadiazol-5-yl}ethyl)-N'-methylurea;
N-(1-{3-[2-(4-isopropoxyphenoxy)-1,3-thiazol-5-yl]-1,2,4-oxadiazol-5-yl}ethyl)urea;
N-[1-(3-{2-[(6-isopropoxypyridin-3-yl)oxy]-1,3-thiazol-5-yl}isoxazol-5-yl)ethyl]acetamide;
N-[1-(3-{4-[(5-isopropoxypyridin-2-yl)oxy]phenyl}isoxazol-5-yl)ethyl]acetamide;
N-(1-{3-[6-(4-isopropoxyphenoxy)pyridin-3-yl]isoxazol-5-yl}ethyl)acetamide;
1-{3-[2-(4-isopropoxyphenoxy)-1,3-thiazol-5-yl]-1,2,4-oxadiazol-5-yl}ethanamine;
N-(1-{3-[2-(4-isopropoxyphenoxy)-1,3-thiazol-5-yl]-1,2,4-oxadiazol-5-yl}ethyl)cyclopropanecarboxamide;
N-(1-{3-[2-(4-isopropoxyphenoxy)-1,3-thiazol-5-yl]-1,2,4-oxadiazol-5-yl}ethyl)methanesulfonamide;
N-(1-{3-[2-(4-isopropoxyphenoxy)-1,3-thiazol-5-yl]-1,2,4-oxadiazol-5-yl}ethyl)-2-methylpropanamide;
N-[1-(3-{2-[(6-isopropoxypyridin-3-yl)oxy]-1,3-thiazol-5-yl}-1,2,4-oxadiazol-5-yl)ethyl]acetamide;
N-[1-(3-{6-[(6-isopropoxypyridin-3-yl)oxy]pyridin-3-yl}isoxazol-5-yl)ethyl]acetamide;
N-[1-(3-{6-[(6-isopropoxypyridin-3-yl)oxy]pyridin-3-yl}isoxazol-5-yl)ethyl]urea;
N-[1-(3-{6-[(6-isopropoxypyridin-3-yl)oxy]pyridin-3-yl}isoxazol-5-yl)ethyl]-N'-methylurea;
methyl 1-(3-{6-[(6-isopropoxypyridin-3-yl)oxy]pyridin-3-yl}isoxazol-5-yl)ethylcarbamate;
methyl 1-(3-{2-[(6-isopropoxypyridin-3-yl)oxy]-1,3-thiazol-5-yl}-1,2,4-oxadiazol-5-yl)ethylcarbamate;
N-[1-(3-{2-[(6-isopropoxypyridin-3-yl)oxy]-1,3-thiazol-5-yl}-1,2,4-oxadiazol-5-yl)ethyl]urea;

N-[1-(3-{2-[(6-isopropoxypyridin-3-yl)oxy]-1,3-thiazol-5-yl}-1,2,4-oxadiazol-5-yl)ethyl]-N'-methylurea;
1-{3-[2-(4-isopropoxyphenoxy)-1,3-thiazol-5-yl]-1,2,4-thiadiazol-5-yl}ethyl methanesulfonate;
N-(1-{3-[2-(4-isopropoxyphenoxy)-1,3-thiazol-5-yl]-1,2,4-thiadiazol-5-yl}ethyl)acetamide;
methyl 1-{3-[2-(4-isopropoxyphenoxy)-1,3-thiazol-5-yl]-1,2,4-thiadiazol-5-yl}ethylcarbamate;
methyl [(1-{3-[2-(4-isopropoxyphenoxy)-1,3-thiazol-5-yl]-1,2,4-oxadiazol-5-yl}ethyl)amino]acetate;
N-(1-{3-[2-(4-isopropoxyphenoxy)-1,3-thiazol-5-yl]-4-methylisoxazol-5-yl}ethyl)acetamide;
N-(1-{4-ethyl-3-[2-(4-isopropoxyphenoxy)-1,3-thiazol-5-yl]isoxazol-5-yl}ethyl)acetamide;
N-[1-(3-{2-[4-(isopropylamino)phenoxy]-1,3-thiazol-5-yl}isoxazol-5-yl)ethyl]acetamide;
N-{1-[3-(2-{4-[(cyclopropylmethyl)amino]phenoxy}-1,3-thiazol-5-yl)isoxazol-5-yl]ethyl}acetamide;
N-[1-(3-{2-[4-(isobutylamino)phenoxy]-1,3-thiazol-5-yl}isoxazol-5-yl)ethyl]acetamide;
N-{1-[3-(2-{3-chloro-4-[(cyclopropylmethyl)amino]phenoxy}-1,3-thiazol-5-yl)isoxazol-5-yl]ethyl}acetamide;
tert-butyl 4-[(5-{5-[1-(acetylamino)ethyl]-1,2,4-oxadiazol-3-yl}-1,3-thiazol-2-yl)oxy]phenylcarbamate;
N-[1-(3-{2-[4-(isobutylamino)phenoxy]-1,3-thiazol-5-yl}-1,2,4-oxadiazol-5-yl)ethyl]acetamide;
tert-butyl 4-[(5-{5-[1-(acetylamino)ethyl]-1,2,4-oxadiazol-3-yl}-1,3-thiazol-2-yl)oxy]-2-chlorophenylcarbamate;
N-{1-[3-(2-{3-chloro-4-[(cyclopropylmethyl)amino]phenoxy}-1,3-thiazol-5-yl)-1,2,4-oxadiazol-5-yl]ethyl}acetamide;
N-[1-(3-{2-[3-chloro-4-(isobutylamino)phenoxy]-1,3-thiazol-5-yl}-1,2,4-oxadiazol-5-yl)ethyl]acetamide;
N-[1-(3-{2-[3-chloro-4-(isopropylamino)phenoxy]-1,3-thiazol-5-yl}-1,2,4-oxadiazol-5-yl)ethyl]acetamide;
N-[1-(3-{2-[4-(isopropylamino)phenoxy]-1,3-thiazol-5-yl}-1,2,4-oxadiazol-5-yl)ethyl]acetamide;
tert-butyl 4-[(5-{5-[1-(acetylamino)ethyl]-1,2,4-oxadiazol-3-yl}-1,3-thiazol-2-yl)oxy]-3-chlorophenylcarbamate;
N-[1-(3-{2-[2-chloro-4-(isopropylamino)phenoxy]-1,3-thiazol-5-yl}-1,2,4-oxadiazol-5-yl)ethyl]acetamide;
N-{1-[3-(2-{2-chloro-4-[(cyclopropylmethyl)amino]phenoxy}-1,3-thiazol-5-yl)-1,2,4-oxadiazol-5-yl]ethyl}acetamide;
N-[1-(3-{2-[2-chloro-4-(isobutylamino)phenoxy]-1,3-thiazol-5-yl}-1,2,4-oxadiazol-5-yl)ethyl]acetamide;
N-[1-(3-{2-[4-(benzylamino)-2-chlorophenoxy]-1,3-thiazol-5-yl}-1,2,4-oxadiazol-5-yl)ethyl]acetamide;
N-[1-(3-{2-[3-(isobutylamino)phenoxy]-1,3-thiazol-5-yl}isoxazol-5-yl)ethyl]acetamide;
N-{1-[3-(2-{3-[(cyclopropylmethyl)amino]phenoxy}-1,3-thiazol-5-yl)isoxazol-5-yl]ethyl}acetamide;
N-[1-(3-{2-[3-(isopropylamino)phenoxy]-1,3-thiazol-5-yl}isoxazol-5-yl)ethyl]acetamide;
N-[1-(3-{2-[3-(isopropylamino)phenoxy]-1,3-thiazol-5-yl}-1,2,4-oxadiazol-5-yl)ethyl]acetamide;
N-{1-[3-(2-{3-[(cyclopropylmethyl)amino]phenoxy}-1,3-thiazol-5-yl)-1,2,4-oxadiazol-5-yl]ethyl}acetamide; and
N-[1-(3-{2-[3-(isobutylamino)phenoxy]-1,3-thiazol-5-yl}-1,2,4-oxadiazol-5-yl)ethyl]acetamide; or a pharmaceutically acceptable salt, prodrug, salt of a prodrug, or a combination thereof.

Asymmetric centers can exist in the present compounds. Individual stereoisomers of the compounds are prepared by synthesis from chiral starting materials or by preparation of racemic mixtures and separation by conversion to a mixture of diastereomers followed by separation or recrystallization, chromatographic techniques, or direct separation of the enantiomers on chiral chromatographic columns. Starting materials of particular stereochemistry are either commercially available or are made by the methods described herein and resolved by techniques well known in the art.

Geometric isomers can exist in the present compounds. The invention contemplates the various geometric isomers and mixtures thereof resulting from the disposal of substituents around a carbon-carbon double bond, a cycloalkyl group, or a heterocycloalkyl group. Substituents around a carbon-carbon double bond are designated as being of Z or E configuration and substituents around a cycloalkyl or heterocycloalkyl are designated as being of cis or trans configuration.

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "therapeutically acceptable carrier" as used herein, means a non-toxic, solid, semi-solid or liquid filler, diluent, encapsulating material, or formulation auxiliary of any type. Examples of therapeutically suitable excipients include sugars; cellulose and derivatives thereof; oils; glycols; solutions; buffering, coloring, releasing, coating, sweetening, flavoring, and perfuming agents; and the like. These therapeutic compositions can be administered parenterally, intracisternally, orally, rectally, or intraperitoneally.

Liquid dosage forms for oral administration of the present compounds comprise formulations of the same as emulsions, microemulsions, solutions, suspensions, syrups, and elixirs. In addition to the compounds, the liquid dosage forms can contain diluents and/or solubilizing or emulsifying agents. Besides inert diluents, the oral compositions can include wetting, emulsifying, sweetening, flavoring, and perfuming agents.

Injectable preparations of the present compounds comprise sterile, injectable, aqueous and oleaginous solutions, suspensions or emulsions, any of which can be optionally formulated with parenterally suitable diluents, dispersing, wetting, or suspending agents. These injectable preparations can be sterilized by filtration through a bacterial-retaining filter or formulated with sterilizing agents that dissolve or disperse in the injectable media.

Inhibition of ACC by the compounds of the present invention can be delayed by using a liquid suspension of crystalline or amorphous material with poor water solubility. The rate of absorption of the compounds depends upon their rate of dissolution, which, in turn, depends on their crystallinity. Delayed absorption of a parenterally administered compound can be accomplished by dissolving or suspending the compound in oil. Injectable depot forms of the compounds can also be prepared by microencapsulating the same in biodegradable polymers. Depending upon the ratio of compound to polymer and the nature of the polymer employed, the rate of release can be controlled. Depot injectable formulations are also prepared by entrapping the compounds in liposomes or microemulsions that are compatible with body tissues.

Solid dosage forms for oral administration of the present compounds include capsules, tablets, pills, powders, and granules In such forms, the compound is mixed with at least one inert, therapeutically suitable excipient such as a carrier, filler, extender, disintegrating agent, solution retarding agent, wetting agent, absorbent, or lubricant. With capsules, tablets, and pills, the excipient can also contain buffering agents. Suppositories for rectal administration can be prepared by mixing the compounds with a suitable non-irritating excipient that is solid at ordinary temperature but fluid in the rectum.

The present compounds can be microencapsulating with one or more of the excipients discussed previously The solid dosage forms of tablets, dragees, capsules, pills, and granules can be prepared with coatings and shells such as enteric and release controlling In these forms, the compounds can be mixed with at least one inert diluent and can optionally comprise tableting lubricants and aids. Capsules can also optionally contain opacifying agents that delay release of the compounds in a desired part of the intestinal tract.

Transdermal patches have the added advantage of providing controlled delivery of the present compounds to the body. Such dosage forms are prepared by dissolving or dispensing the compounds in the proper medium. Absorption enhancers can also be used to increase the flux of the compounds across the skin, and the rate of absorption can be controlled by providing a rate controlling membrane or by dispersing the compounds in a polymer matrix or gel.

The compounds of the invention can be used in the form of pharmaceutically acceptable salts, esters, or amides derived from inorganic or organic acids. The term "pharmaceutically acceptable salts, esters and amides," as used herein, include salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

Pharmaceutically acceptable salts are well known in the art. The salts can be prepared during the final isolation and purification of the compounds or separately by reacting an amino group of the compounds with a suitable acid. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetic, trifluoroacetic, glutamate, para-toluenesulfonate, undecanoate, hydrochloric, hydrobromic, sulfuric, phosphoric, and the like. The amino groups of the compounds can also be quaternized with alkyl chlorides, bromides, and iodides such as methyl, ethyl, propyl, isopropyl, butyl, lauryl, myristyl, stearyl, and the like. The present invention contemplates pharmaceutically suitable salts formed at the nitrogen of formula (I).

Basic addition salts can be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethyl amine, diethyl amine, ethyl amine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like, are contemplated as being within the scope of the present invention.

The term "pharmaceutically acceptable ester," as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyl iodide, benzyl iodide, cyclopentyl iodide They also can be prepared by reaction of the compound with an acid such as hydrochloric acid and an alkylcarboxylic acid such as acetic acid, or with acid and an arylcarboxylic acid such as benzoic acid.

The term "pharmaceutically acceptable amide," as used herein, refers to non-toxic amides of the invention derived from ammonia, primary $C_1$-to-$C_6$ alkyl amines and secondary $C_1$-to-$C_6$ dialkyl amines. In the case of secondary amines, the amine can also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also can be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis in blood. A thorough discussion is provided in T. Higuchi and V. Stella, Prodrugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention contemplates pharmaceutically active compounds either chemically synthesized or formed by in vivo biotransformation to compounds of formula (I).

The present invention is also directed to a method of inhibiting acetyl-CoA carboxylase (ACC). By inhibiting ACC, the compounds of the present invention can be useful as therapeutic agents for the treatment or prevention of disorders such as but not limited to metabolic syndrome, type II diabetes, obesity, atherosclerosis and cardiovascular disease. Therefore, according to an embodiment of the present invention compounds of formula (I), can be useful for the treatment of metabolic syndrome, type II diabetes, obesity, atherosclerosis and cardiovascular disease.

Compounds and compositions of the invention are useful for inhibiting the effects of ACC, and more particularly that of ACC1 and ACC2. In particular, the compounds and compositions of the invention can be used for treating and preventing disorders modulated by ACC. Typically, such disorders can be ameliorated by selectively inhibiting the ACC in a mammal, preferably by administering a compound or composition of the invention, either alone or in combination with another active agent, for example, as part of a therapeutic regimen.

The compounds of the invention, including but not limited to those specified in the examples, inhibit ACC. As inhibitors of ACC, the compounds of the invention can be useful for the treatment and prevention of a number of ACC mediated diseases or conditions.

Compounds of the invention are particularly useful for the treatment or prevention of metabolic syndrome, type II diabetes, obesity, atherosclerosis and cardiovascular diseases in humans.

Accordingly, the present invention is directed to a method of inhibiting ACC, comprising administrating a therapeutically effective amount of a compound of formula (I).

The present invention is also directed toward a method of inhibiting ACC-1, comprising administering a therapeutically effective amount of a compound of formula (I).

The present invention is also directed toward a method of inhibiting ACC-2, comprising administering a therapeutically effective amount of a compound of formula (I).

Another embodiment of the present invention is directed toward a method of treating metabolic syndrome, comprising administering a therapeutically effective amount of a compound of formula (I).

Another embodiment of the present invention is directed toward a method of treating type II diabetes, comprising administering a therapeutically effective amount of a compound of formula (I).

Another embodiment of the present invention is directed toward a method of treating obesity, comprising administering a therapeutically effective amount of a compound of formula (I).

Disorders that can be treated or prevented in a patient by administering to the patient, a therapeutically effective amount of compound of the present invention in such an amount and for such time as is necessary to achieve the desired result. The term "therapeutically effective amount," refers to a sufficient amount of a compound of formula (I) to effectively ameliorate disorders by inhibiting ACC at a reasonable benefit/risk ratio applicable to any medical treatment. The specific therapeutically effective dose level for any particular patient depends upon a variety of factors including the disorder being treated and the severity of the disorder; the activity of the compound employed; the specific composition employed; the age, body weight, general health, sex, and diet of the patient; the time of administration, route of administration, rate of excretion; the duration of the treatment; and drugs used in combination or coincidental therapy.

The total daily dose of the compounds of the present invention necessary to inhibit the action of ACC in single or divided doses can be in amounts, for example, from about 0.1 to 50 mg/kg body weight. In a more preferred range, compounds of the present invention inhibit the action of ACC in a single or divided doses from about 1 to 25 mg/kg body weight. Single dose compositions can contain such amounts or submultiple doses thereof of the compounds of the present invention to make up the daily dose. In general, treatment regimens comprise administration to a patient in need of such treatment from about 1 mg to about 1000 mg of the compounds per day in single or multiple doses.

Biological Data

The ACC2 enzymatic assay has been developed using either crude digitonin lysates of hACC2 overexpressing HEK 293 cells or recombinant human ACC2 expressed in baculovirus/Sf9 system. In both cases in order to increase the expression and solubility of the protein, a chimeric version of ACC2 ("mito-minus"), in which the N-terminal transmembrane domain (1-275 aa's of ACC2) was replaced with the corresponding ACC1 sequence (1-133 aa's). The enzymatic assay measures ACC mediated incorporation of [$^{14}$C] CO2 into [$^{14}$C]-Malonyl CoA. Mono-Avidin purified rat liver ACC1 was used as ACC1 enzyme source for the ACC-1 activity assay. The assay was preformed in 40 μL reaction in a 96-well plate format. The 1× assay buffer contains 50 mM Hepes/NaOH, pH 7.5, 10 mM citrate, 20 mM $MgCl_2$ and 0.075% BSA. First, 20 μL, of test compounds was dissolved in 1% DMSO in 1× assay buffer was dispensed into 96-well Then, 10 μL of enzyme in 1× assay buffer was dispensed. The reaction was initiated by adding the following substrate mixture in 1× assay buffer: 2 mM ATP, 1 mM acetyl-CoA, and 17.6 mM $NaHCO_3$ (0.12 μCi). The reaction was carried out at room temperature for 40 minutes and the reaction was terminated by adding 50 μL of 1N HCl. The plate was air-dried in a fine hood at room temperature overnight. 20 μL of distilled water was added followed by adding 150 μL of SuperMix liquid scintillation fluid (PerkinElmer). The radioactivity was determined in PerkinElmer microbeta after vigorous shaking. The IC50 value was calculated from 8-dose response curve of test compounds,

TABLE 1

Inhibition of ACC1 and ACC2 Enzymatic Activities

| ACC1 IC50 (μM) | ACC2 IC50 (μM) |
|---|---|
| 1.5 | 0.017 |
| 0.15 | 0.023 |
| 0.13 | 0.020 |
| 0.19 | 0.027 |
| 0.75 | 0.23 |
| 0.16 | 0.026 |
| 0.056 | 0.011 |
| 0.065 | 0.008 |
| 0.086 | 0.008 |
| >30 | 0.33 |
| >30 | 0.14 |
| 1.0 | 0.25 |
| 0.12 | 0.066 |
| 0.40 | 0.03 |
| 0.35 | 0.016 |
| 10.8 | 0.13 |
| 10.3 | 0.095 |
| 16.2 | 0.12 |
| 0.61 | 0.22 |
| >30 | 0.29 |
| 10.2 | 0.042 |
| 0.033 | 0.027 |
| 0.021 | 0.004 |

TABLE 1-continued

Inhibition of ACC1 and ACC2 Enzymatic Activities

| ACC1 IC50 (μM) | ACC2 IC50 (μM) |
|---|---|
| 3.2 | 0.98 |
| 1.5 | 0.012 |
| 0.68 | 0.021 |
| 0.35 | 0.015 |
| 0.080 | 0.005 |
| 1.0 | 0.070 |
| 0.037 | 0.002 |
| 0.058 | 0.003 |
| 1.1 | 0.034 |
| 0.23 | 0.042 |
| 0.69 | 0.070 |
| 0.030 | 0.006 |
| 0.014 | 0.002 |
| 0.093 | 0.040 |
| 1.5 | 0.36 |
| 1.8 | 0.98 |
| 0.14 | 0.005 |
| 1.4 | 0.019 |
| 0.70 | 0.013 |
| 1.1 | 0.089 |
| 0.20 | 0.013 |
| 0.92 | 0.031 |
| 7.0 | 0.029 |
| 0.78 | 0.027 |
| 1.7 | 0.072 |
| 2.7 | 0.010 |
| 0.27 | 0.12 |
| 0.092 | 0.027 |
| 0.12 | 0.023 |
| 0.061 | 0.012 |
| 0.041 | 0.005 |
| 0.12 | 0.031 |
| 0.46 | 0.083 |
| 0.36 | 0.36 |
| 0.032 | 0.008 |
| 1.2 | 1.7 |
| 0.16 | 0.026 |
| 0.006 | 0.008 |
| 0.51 | 0.59 |
| 1.4 | 0.91 |
| 1.7 | 1.2 |
| 6.8 | 2.0 |
| 0.023 | 0.004 |
| 0.14 | 0.015 |
| 1.4 | 0.088 |
| 1.9 | 0.22 |
| 1.3 | 0.39 |
| 0.046 | 0.018 |
| 0.18 | 0.068 |
| 11.1 | 1.1 |
| 0.14 | 0.018 |
| 0.16 | 0.026 |
| 4.5 | 0.079 |
| 0.29 | 0.081 |
| 0.088 | 0.014 |
| 0.71 | 0.076 |
| 0.0.26 | 0.004 |
| 0.13 | 0.024 |
| 0.018 | 0.009 |
| 0.28 | 0.16 |
| 1.1 | 0.41 |
| 0.19 | 0.020 |
| 0.067 | 0.008 |
| 0.57 | 0.056 |
| 0.031 | 0.001 |
| 0.14 | 0.004 |
| 0.024 | 0.006 |
| 0.16 | 0.025 |
| 0.085 | 0.035 |
| 0.065 | 0.018 |
| 0.33 | 0.11 |
| 0.075 | 0.026 |
| 0.030 | 0.019 |
| 0.10 | 0.040 |
| 0.018 | 0.011 |
| 0.035 | 0.032 |
| 0.26 | 0.046 |
| 2.7 | 0.70 |
| 0.48 | 0.075 |
| 0.068 | 0.040 |
| 0.11 | 0.020 |
| 0.77 | 0.0.69 |
| 0.80 | 0.18 |
| 1.5 | 0.39 |
| 0.099 | 0.022 |
| 2.3 | 0.40 |
| 0.52 | 0.23 |

Dysregulation of fatty acids metabolism contributes to decreased insulin sensitivity and the development of metabolic syndrome. ACC is known to modulate fatty acid synthesis and fatty acid oxidation in insulin responsive tissues such as liver, adipose and skeletal muscles. The ACC inhibitors of the present invention, have the potential to decrease de novo lipid synthesis and increase fat oxidation in vivo. Therefore, these chemotypes represent a novel method to treat insulin resistance/type 2 diabetes, as well as obesity, hypertension and hyperlipidemia.

Synthetic Methods

The compounds and processes of the present invention are better understood in connection with the following synthetic schemes, which together illustrate the methods by which the compounds of the invention can be prepared. The synthesis of compounds of formula (I) wherein the groups $R_1$, $R_3$, $R_5$, $R_{9a}$, $R_{9b}$, $Ar_1$, $Ar_2$, $Ar_3$, and Y are as defined above unless otherwise noted, are exemplified in Schemes 1-8.

Starting materials can be obtained from commercial sources or prepared by well-established literature methods known to those of ordinary skill in the art.

This invention is intended to encompass compounds having formula (I) when prepared by synthetic processes or by metabolic processes. Preparation of the compounds of the invention by metabolic processes includes those occurring in the human or animal body (in vivo) or processes occurring in vitro.

As used in the descriptions of the schemes and the examples, certain abbreviations are intended to have the following meanings: DMSO for dimethylsulfoxide; and HPLC for high-pressure liquid chromatography, Scheme 1

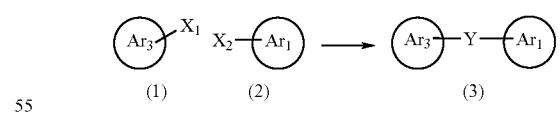

Compounds of formula (3) wherein $Ar_1$, $Ar_3$ are as defined in formula (I) and Y is —O—, —N(alkyl)-, —N(H)— and —S—, can be prepared by reacting compounds of formula (1) wherein $X_1$ is Y—H, with halides of formula (2) wherein $X_2$ is Br, Cl or triflate, in the presence of a base such as, but not limited to sodium hydride or potassium carbonate, and optionally in the presence of 18-crown-6. The reaction can generally be performed in a solvent such as, but not limited to, N,N-dimethylformamide or dimethylsulfoxide, at a temperature from about room temperature to about 180° C. It is appreciated compounds of formula (3) can also be obtained from the reaction of formula (I) wherein $X_1$ is Br, Cl or triflate, and compounds of formula (2) wherein $X_2$ is Y—H.

Alternatively, the transformation can also be effected in the presence of a metal catalyst such as, but not limited to, copper metal, CuI, palladium acetate, optionally in the presence of a ligand such as, but not limited to, 2,2'-bis(diphenylphosphino)-1,1'-binaphthyl or tri-tert-butylphosphine, and optionally in the presence of a base such as, but not limited to, sodium tert-butoxide, cesium carbonate, or sodium hydride. The reaction is generally performed at a temperature from about room temperature to about 180° C., in a solvent such as, but not limited to, toluene or N,N-dimethylformamide.

Conversion of oximes of formula (6) to oximes of formula (7) can be effected by Stirring with N-chlorosuccinimide in a solvent such as, but not limited to, N,N-dimethylformamide at room temperature.

Cycloaddition of oximes of formula (7) and alkynes of formula (12) wherein $P_g$ is phthalimide or acetyl, or a protecting group for an amine such as, but not limited to, t-butoxycarbonyl (BOC), provides isoxazoles of formula (8) The reaction is generally conducted in the presence of a base such as, but not limited to, potassium carbonate, in a solvent such as, but not limited to, toluene or ethyl acetate, at a temperature of about room temperature to about the reflux temperature of

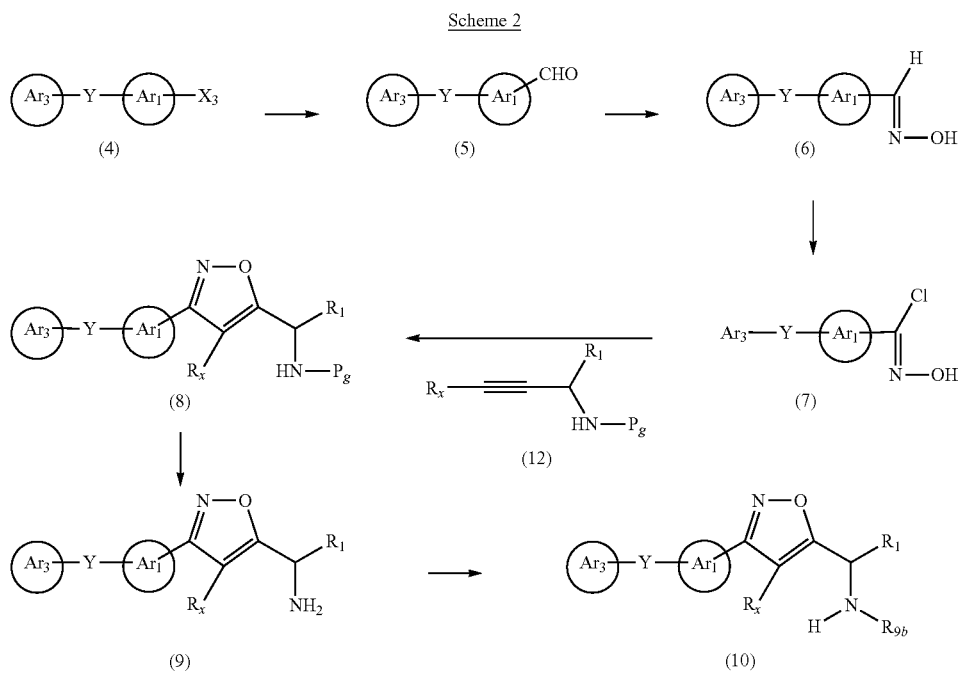

Scheme 2

Compounds of formula (10) wherein Y is —O—, —N(alkyl)-, —N(H)— and —S—, $Ar_1$, $Ar_3$, $R_1$, and $R_{9b}$ are as described in formula (I) and $R_x$ is as described as the substituent of $Ar_2$ in formula (I) can be prepared as outlined in Scheme 2.

Aldehydes of formula (5) can be obtained from the metal-halogen exchange of compounds of formula (4) wherein $X_3$ is halogen, followed by treating the intermediate so obtained with a formylating agent such as, but not limited to, N-formylmorpholine. The first step of the reaction is generally carried out in the presence of n-butyl lithium in a solvent such as, but not limited to, tetrahydrofuran at a temperature of about –78° C. Treatment of the intermediate obtained with N-fomlylmorpholine can be conducted at a temperature from about –78° C. to about room temperature. Compounds of formula (5) can also be obtained from compounds of formula (4) wherein $Ar_1$ is a five membered heteroaryl and $X_3$ is hydrogen by treatment with n-butyl lithium followed by treatment with N-formylmorpholine.

Reaction of aldehydes of formula (5) with hydroxylamine hydrochloride salt in the presence of a base such as, but not limited to, pyridine, and optionally in an appropriate solvent, provides oximes of formula (6). The reaction is generally conducted at a temperature from about room temperature to about 70° C.

the solvent employed. The phthalimide protection of the amino group can be removed by treatment with hydrazine, in a solvent such as, but not limited to, a mixture of dichloromethane and ethanol, at a temperature of about room temperature to about 50° C.

The primary amines of formula (9) obtained can be further derivatized using methodologies known to one skilled in the art. One such manipulation involves acylating the amines with acetic anhydride or acyl halides of formula $R_{9b}C(O)X$ wherein X is Br or Cl; and $R_{9b}$ is as defined in formula (I), in the presence of an organic base such as, but not limited to triethylamine or diisopropyl ethyl amine. The reaction is generally performed in a solvent such as, but not limited to, dichloromethane or tetrahydrofuran, at about room temperature.

Reaction of the primary amines of formula (9) with trichloroacetyl isocyanate in a solvent such as dichloromethane and the like, at room temperature, followed by refluxing in methanol in catalytic amount of sodium carbonate and water, affords compounds of formula (10) wherein $R_{9b}$ is —C(O)NH$_2$. Other ureas of formula (10) wherein $R_{9b}$ is —C(O)N(H)$R_{10}$ and $R_{12}$ is alkyl, haloalkyl, $R_8$ and -alkylenyl-$R_8$ and $R_8$ is as defined in formula (I) can be facilitated by treatment of (9) with isocyanates of formula $R_{12}$NCO in a solvent such as dichloromethane and the like, at room temperature.

Reaction of amines of formula (9) with chloroformates of formula ClC(O)OR$_{10}$ at room temperature and an organic base such as, but not limited to, triethylamine or diisopropyl ethyl amine, and in a solvent such as, but not limited to, dichloromethane affords carbamates of formula (10) wherein R$_{9b}$ is —C(O)OR$_{10}$.

Sulfonamides of formula (10) wherein R$_{9b}$ is SO$_2$R$_{10}$ can be prepared from amines of formula (9) by treatment with sulfonyl chlorides of formula R$_{10}$SO$_2$Cl in the presence of an organic base such as, but not limited to triethylamine or diisopropyl ethyl amine. The reaction is generally performed in a solvent such as, but not limited to, dichloromethane or tetrahydrofuran, at about room temperature.

Compounds of formula (10) wherein R$_{9b}$ is -alkylenyl-C(O)OR$_{10}$ can be prepared from compounds of formula (9) by treatment with halides of formula X-alkylenyl-C(O)OR$_{10}$ wherein X is Cl, Br or I, in the presence of a base such as, but not limited to, potassium carbonate) in a solvent such as acetonitrile and the like, at a temperature from about room temperature to about the reflux temperature of the solvent employed.

Scheme 3

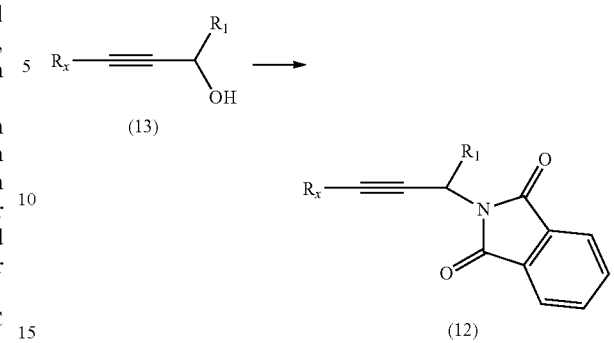

Alkynes of formula (12) wherein P$_g$ is phthalimide can be obtained from the corresponding alcohols of formula (13) by treatment with phthalimide, triphenylphosphine, and diethyl azodicarboxylate in a solvent such as, but not limited to, tetrahydrofuran, at room temperature.

Scheme 5

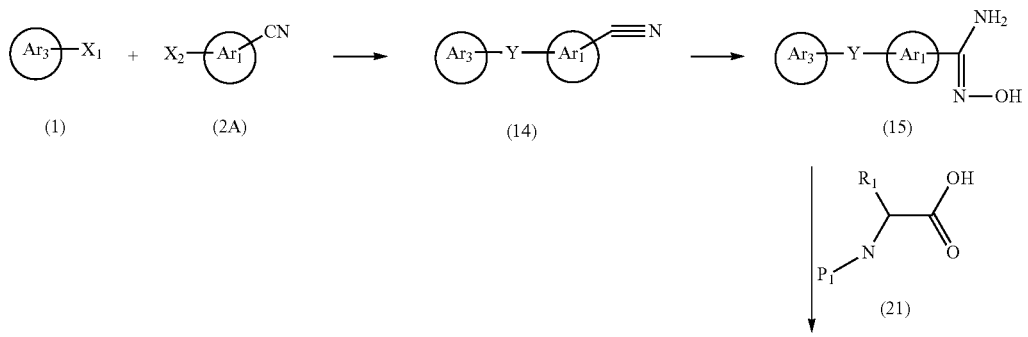

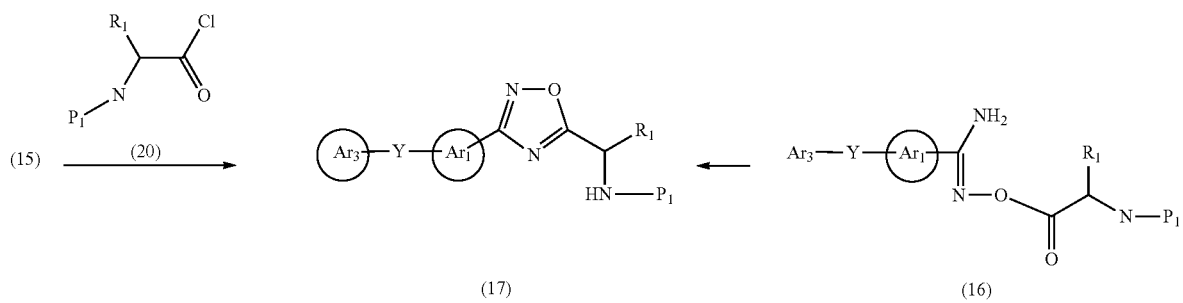

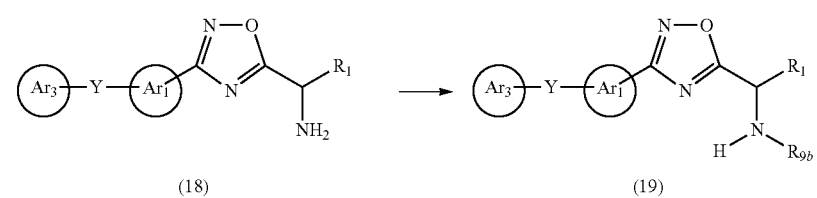

Scheme 4 outlines the synthetic route of oxadiazoles of formula (19) wherein Y is —O—, —N(alkyl)-, —N(H)— and —S—, $Ar_1$, $Ar_3$, $R_1$, and $R_{9b}$ are as defined in formula (I).

Compounds of formula (14) can be prepared from compounds of formula (I) and nitriles of formula (2A) using the reaction conditions as outlined in Scheme 1. Alternatively, compounds of formula (14) can also be prepared from compounds of formula (6) by treatment with reagents such as, but no limited to, methanesulfonyl chloride and pyridine, carbonyl diimidazole, or acetic anhydride and pyridine, at a temperature from about room temperature to about 80° C.

Refluxing compounds of formula (14) with hydroxylamine hydrochloride and an organic base such as triethylamine, in a mixture of ethanol and water provides compounds of formula (15). Treatment of compounds of formula (15) with compounds of formula (20) wherein $P_1$ is an amino protecting group such as, but not limited to, acetyl, phthalimide, Boc (tert-butyloxy carbonyl) or CBZ (benzyloxy carbonyl), provides compounds of formula (17). The reaction is generally performed in pyridine with or without an additional solvent, such as, but not limited to, 1-(3-dimethylaminopropyl)-3-ethylcarbodiimide, 1-hydroxybenzotriazole hydrate (HOBT) and an organic base such as diisopropyl ethyl amine and the like, in a solvent such as, but not limited to, dichloromethane or N,N-dimethylformamide, to provide compounds of formula (16). Cyclization of compounds of formula (16) to afford compounds of formula (17) can be achieved by refluxing in a solvent such as, but not limited to, pyridine or toluene.

Removal of the protecting group in compounds of formula (17) to provide compounds of formula (18) can be effected by employing methodologies known to one skilled in the art. For example, the phthalimide group can be removed by reaction with hydrazine, and the Boc group can be removed by stirring with trifluoroacetic acid in a solvent such as, but not limited to, dichloromethane.

The primary amino group in compounds of formula (18) can be transformed to the corresponding amides, sulfonamides, ureas and carbamates of formula (19) using the reaction conditions for the conversion of compounds of formula (9) to compounds of formula (10) as described in Scheme 2.

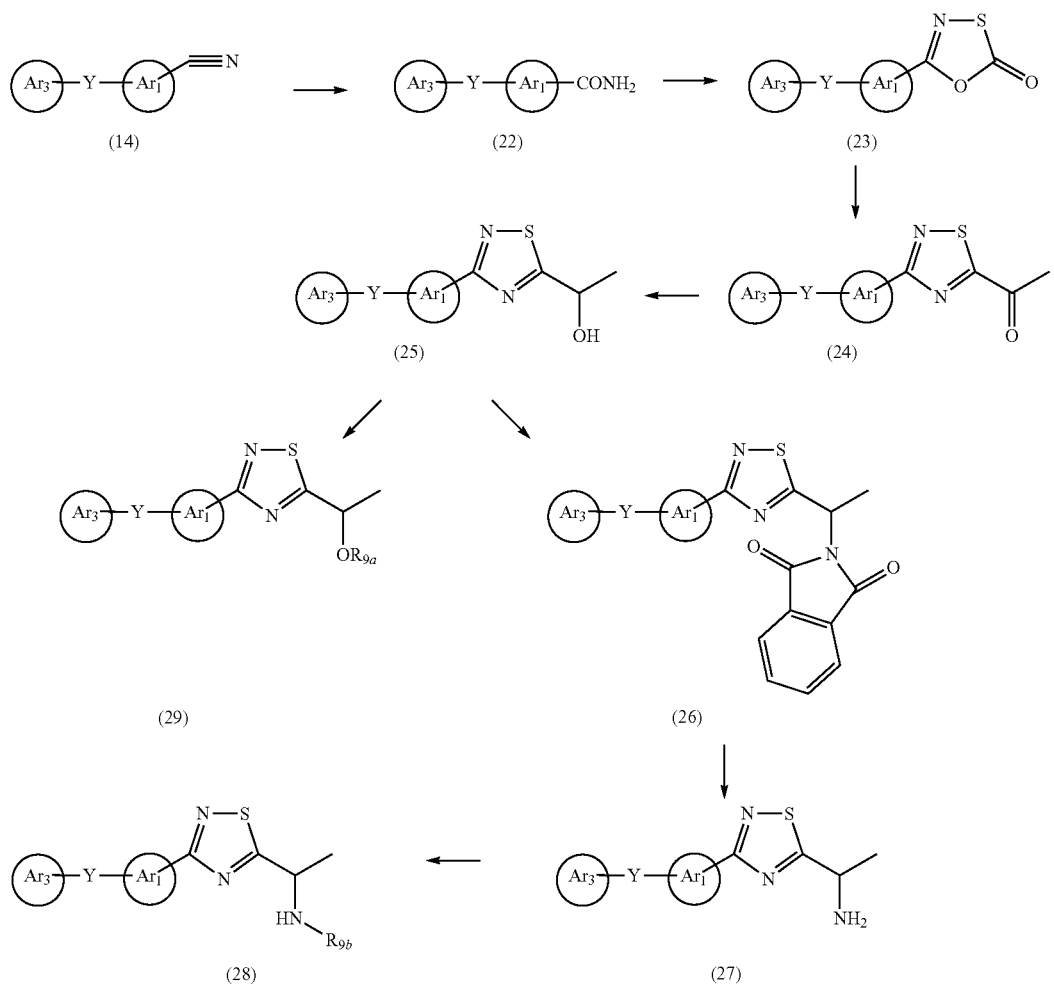

Scheme 5 at a temperature from about room temperature to about the reflux temperature of pyridine. Compounds of formula (15) can also be coupled with amino acids of formula (21) wherein $P_1$ is as previously defined, in the presence of a coupling agent Thiadiazoles of formula (28) and (29) wherein Y is —O—, —N(alkyl)-, —N(H)— and —S—, $Ar_1$, $Ar_3$, $R_{9a}$ and $R_{9b}$ as defined in formula (I) can be prepared from nitrites of formula (14) as shown in Scheme 5.

Nitriles of formula (14) can be treated with concentrated hydrochloric acid at room temperature to afford amides of formula (22). Upon treatment with chlorocarbonylsulfenyl chloride in refluxing toluene, the amides can be transformed to oxathiazol-2-ones of formula (23).

Treatment of oxathiazol-2-ones of formula (23) with pyruvonitrile in xylene at reflux yields thiadiazoles of formula (24). Alcohols of formula (25) can be obtained by reaction of compounds of formula (24) with a reducing agent such as, but not limited to, sodium borohydride, in a solvent such as, but not limited to, methanol, tetrahydrofuran, dichloromethane, or mixture thereof.

Conversion of the alcohols of formula (25) to sulfonates of formula (29) can be achieved by treatment with sulfonyl chlorides of formula $R_{9a}SO_2Cl$ in the presence of an organic base such as, but not limited to, triethylamine, and optionally in the presence of 4-(dimethylamino)pyridine, in a solvent such as, but not limited to, dichloromethane.

Conversion of the alcohols of formula (25) to amines of formula (27) can be achieved by (a) treatment with phthalimide, triphenylphosphine and diethyl azodicarboxylate, in a solvent such as, but not limited to, tetrahydrofuran to provide compounds of formula (26); and (b) treatment of compounds of formula (26) with hydrazine in a mixture of ethanol and dichloromethane at reflux.

The primary amino group in compounds of formula (27) can be transformed to the corresponding amides, sulfonamides, ureas and carbamates of formula (28) using the reaction conditions for the conversion of compounds of formula (9) to compounds of formula (10) as described in Scheme 2.

tri(2-furyl)phosphine or triphenylamine, to provide compounds of formula (32) wherein $X_7$ is hydrogen, formyl, CN or $R_1C(O)$—. The reaction is generally conducted in a solvent such as N,N-dimethylformamide at a temperature from about 25° C. to about 150° C. It is appreciated compounds of formula (32) can also be obtained from the reaction of stannanes of formula (31) wherein $X_6$ is —Sn(alkyl)$_3$ and compounds of formula (30) wherein $X_5$ is Cl, Br or triflate.

Stannanes of formula (30) or (31) can be purchased or prepared from heteroarylhalides, heteroaryltriflates, arylhalides or aryltriflates by reaction with hexa-alkyl distannanes of formula ((alkyl)$_3$Sn)$_2$ in the presence of a palladium source like tetrakis(triphenylphosphine) palladium(0). Alternatively, stannanes of formula (30) or (31) can be obtained from metal-halogen exchange of compounds of formula (30) or (31) wherein $X_5$ or $X_6$ is bromide, with n-butyl lithium at about −78° C., followed by reaction with tributyl tin halide at a temperature from about −78° C. to about room temperature, in a solvent such as tetrahydrofuran.

Conversion of compounds of formula (32) wherein $X_7$ is hydrogen to compounds of formula (32) wherein $X_7$ is formyl group can be effected by employing n-butyl lithium followed by treatment with a formylation agent such as, but not limited to, N-formylmorpholine.

Compounds of formula (32) wherein $X_7$ is hydrogen can be converted to compounds of formula (33) by treatment with a lithium base such as, but not limited to, n-butyl lithium in a solvent such as, but not limited to, tetrahydrofuran or dichloromethane, followed by aldehydes of formula $R_1CHO$.

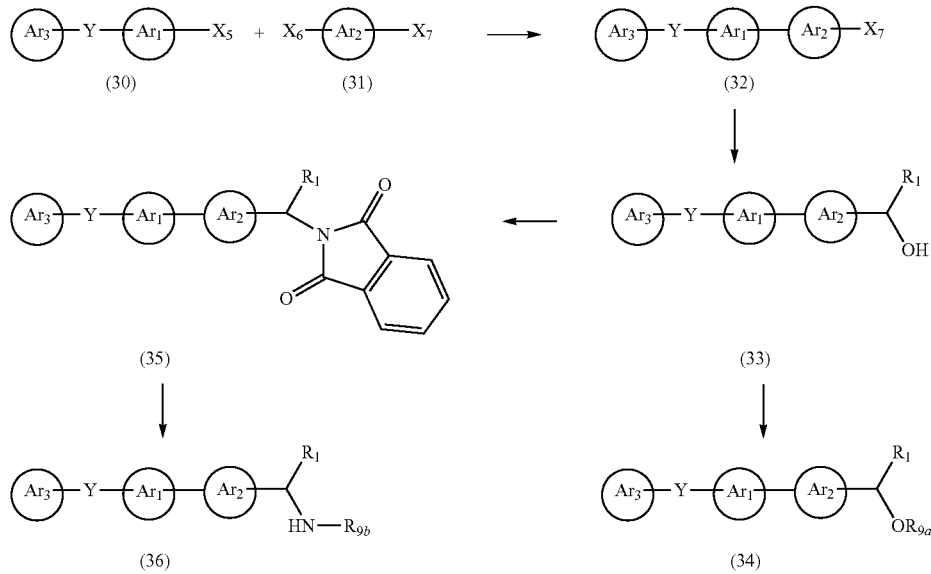

Scheme 6

Compounds of formula (34) and (36) wherein Y is —O—, —N(alkyl)-, —N(H)— and —S—, $Ar_1$, $Ar_2$, $Ar_3$, $R_1$, $R_{9a}$ and $R_{9b}$ are as defined in formula (I) can be prepared as outlined in Scheme 6.

Stannanes of formula (30) wherein $X_5$ is —Sn(alkyl)$_3$ can be reacted with compounds of formula (31) wherein $X_6$ is Cl, Br or triflate, and $X_7$ is hydrogen, formyl, CN or $R_1C(O)$—; in the presence of a palladium source such as tris(dibenzylidineacetone)dipalladium, tetrakis(triphenylphosphine) palladium(0), optionally in the presence of a ligand such as Treatment of compounds of formula (32) wherein $X_7$ is formyl with trimethyl(trifluoromethyl)silane and tetrabutylammonium fluoride in a solvent such as, but not limited to, tetrahydrofuran, provides compounds of formula (33) wherein $R_1$ is trifluoromethyl.

Reduction of compounds of formula (32) wherein $X_7$ is $R_1C(O)$— by reacting with a reducing agent such as, but not limited to, sodium borohydride in a mixture of solvent of methanol and tetrahydrofuran converts to alcohols of formula (33).

Employing reaction conditions as described for the transformation of compounds of formula (25) to (28) or (25) to (29) in Scheme 5, compounds of formula (33) can be converted to compounds of formula (36) or (34) respectively.

Scheme 7

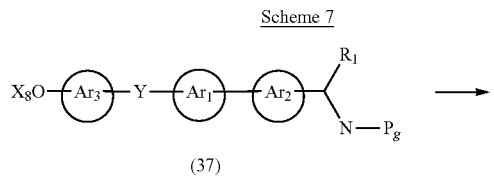

(37)

-continued

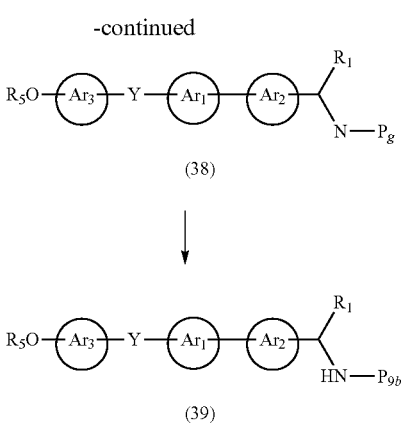

Compounds of formula (37) wherein $X_8$ is hydrogen, obtained from demethylation of compounds of formula (37) wherein $X_8$ is methyl by treatment with boron tribromide in dichloromethane at about room temperature, can be convert to compounds of formula (39) wherein Y, $R_5$, $Ar_3$, $Ar_1$, $Ar_2$, $R_1$ and $R_{9b}$ are as defined in formula (I).

Conversion of compounds of formula (37) wherein $X_8$ is hydrogen to compounds of formula (38) can be achieved by treatment with alcohols of formula $R_5OH$ in the presence of triphenylphosphine and diethyl azodicarboxylate in a solvent such as, but not limited to, tetrahydrofuran at room temperature. Conversion of compounds of formula (38) to compounds of formula (39) can be achieved using general reaction conditions employed for the conversion of compounds of formula (8) to compounds of formula (10) as outlined in Scheme 2.

Scheme 8

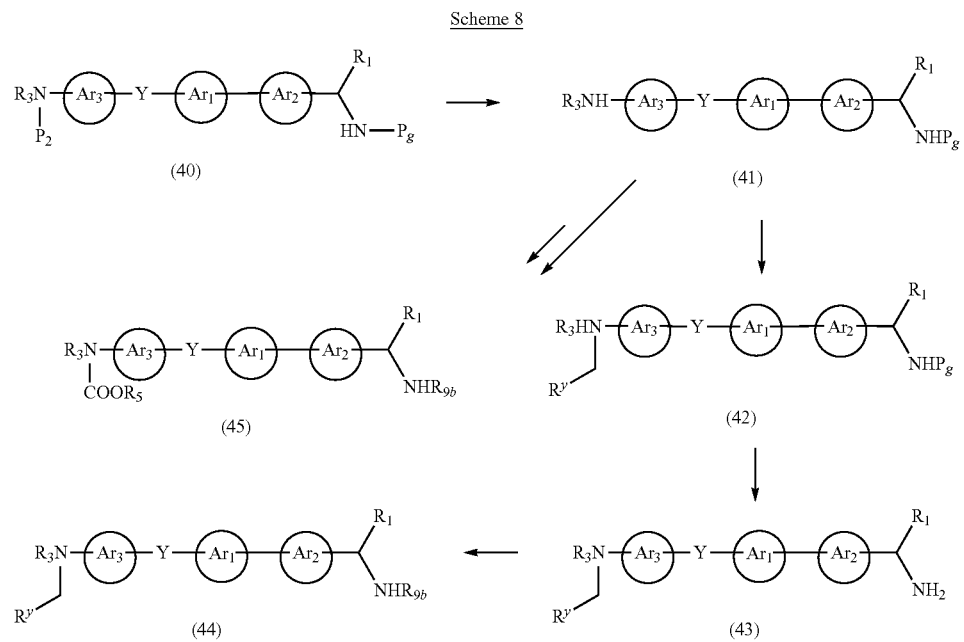

Compounds of formula (45) and (44) wherein $R^y$ is alkyl or —$R_8$, and Y, $R_8$, $R_1$, $R_3$, $R_{9b}$, $Ar_1$, $Ar_2$, $Ar_3$ are as defined in formula (I) can be prepared as outlined in Scheme 8.

Compounds of formula (40) wherein $P_g$ is phthalimide or acetyl, and $P_2$ is an amino protecting group such as, but not limited to, Boc (tert-butyloxy carbonyl) or CBZ (benzyloxy carbonyl), can be deprotected selectively by treatment with an acid such as trifluoroacetic acid at about room temperature (in the case where $P_2$ is Boc) or treatment with hydrogen in the presence of a metal catalyst such as palladium/carbon (in the case where $P_2$ is CBZ) and the like, to afford compounds of formula (41).

Treatment of compounds of formula (41) with aldehydes of formula $R^yCHO$, in the presence of a buffer solution (for example, acetic acid/sodium acetate in methanol and the like) and a reducing agent such as, but not limited to, sodium cyanoborohydride, provides amines of formula (42). The reaction can be performed in a solvent such as, but not limited to, dichloromethane, at a temperature from about room temperature to about 70° C. Using reaction conditions for the transformation of compounds of formula (8) to compounds of formula (10) facilitate the removal of the amino protecting group (for example where $P_g$ is phthalimide) and derivatization of the amino group, providing compounds of formula (44).

Compounds of formula (45) can be obtained by (a) reacting compounds of formula (41) with chloroformates of formula ClC(O)OR$_5$, (b) treating carbamates from step (a) with hydrazine to remove $P_g$ wherein $P_g$ is phthalimide, and (c) derivative the primary amine obtained from step (C) using reaction conditions as outlined in Scheme 2.

The present invention will now be described in connection with certain preferred embodiments which are not intended to limit its scope. On the contrary, the present invention covers all alternatives, modifications, and equivalents as can be included within the scope of the claims. Routine experimentation, including appropriate manipulation of the reaction conditions, solvents and reagents used, and sequence of the synthetic route, protection of any chemical functionality that can not be compatible with the reaction conditions, and deprotection thereafter are included in the scope of the invention. Synthesis of the compounds of formula (I) can be accomplished by methods analogous to those described above and in the following examples. Thus, the following examples, which include preferred embodiments, illustrate the preferred practice of the present invention, it being understood that the examples are for the purpose of illustration of certain preferred embodiments and are presented to provide what is believed to be the most useful and readily understood description of its procedures and conceptual aspects.

Compounds of the invention were named by ACD/ChemSketch version 5.06 (developed by Advanced Chemistry Development, Inc., Toronto, ON, Canada) or were given names consistent with ACD nomenclature.

EXAMPLES

Example 1

N-(1-{3-[2-(4-isopropoxyphenoxy)-1,3-thiazol-5-yl]isoxazol-5-yl}ethyl)acetamide

Example 1A 4-isopropoxyphenol

A solution of potassium hydroxide (78.5 g, 0.5 mol) in water (100 mL) was added to a solution of hydroquinone (55.7 g, 0.5 mol) and 2-iodopropane (57.5 g, 0.33 mol) in ethanol. The dark brown solution was then refluxed for 16 hours Ethanol was removed and the aqueous phase was acidified with 2N HCl and extracted with ethyl acetate (3×200 mL). The combined organic layers were washed with brine, dried over magnesium sulfate and filtered. The filtrate was concentrated to give over 70 g of crude material, which was triturated with dichloromethane and filtered. The filtrate was concentrated and purified on silica gel (ethyl acetate/hexane, 5~35%) to give 23.0 g of product as a brown oil (46% yield). $^1$H NMR (300 MHz, CDCl$_3$) δ ppm 1.30 (d, J=5.88 Hz, 6H) 4.30-4.50 (m, 1H) 4.78 (s, 1H) 6.66-6.86 (m, 4H), MS (ESI): m/z 151 (M−H), Example 1B 2-(4-isopropoxyphenoxy)-1,3-thiazole A mixture of Example 1A (15.5 g, 0.1 mol), 2-bromothiazole (18.2 g, 0.11 mol) and potassium carbonate (15.2 g, 0.11 mol) in dimethylsulfoxide was heated at 160° C. under nitrogen for six hours. After cooling and treating with water, the aqueous phase was extracted with dichloromethane. The organic layer was washed with brine, dried, and concentrated to give 27.5 g of the crude as a dark brown oil, which was purified on a silica gel (ethyl acetate/hexane 5-35%) to afford 21.5 g of the product as a brown oil (91% yield) $^1$H NMR (500 MHz, CDCl$_3$) δ ppm 1.32-1.36 (m, 6H) 1.34 (none, 6H) 1.34 (none, 5 H) 4.45-4.57 (m, 1H) 6.76 (d, J=3.91 Hz, 1H) 6.87-6.93 (m, 2H) 7.15-7.20 (m, 2H) 7.21 (d, J=3.91 Hz, 1H). MS (ESI): m/z 236 (M+H).

Example 1C 2-(4-isopropoxyphenoxy)-1,3-thiazole-5-carbaldehyde

Butyl lithium (20 mL, of 2.5M solution, 0.05 mol) at −78° C. over 15 minutes was added to a solution of Example 1B (11.8 g, 0.05 mol) in dry tetrahydrofuran. After one hour at the same temperature, formylmorpholine (5.8 g, 0.05 mol) was added drop wise and the mixture was stirred for 4 hours and then quenched with sat. NH$_4$Cl. The aqueous layer was extracted with ethyl acetate and the organic phase washed with brine, dried over MgSO$_4$ and filtered. The filtrate was concentrated and purified on silica gel (5~35% ethyl acetate in hexane) to give 13.2 g of product as a yellow oil, $^1$H NMR (300 MHz, CDCl$_3$) δ ppm 1.36 (d, J=5.88 Hz, 6H) 4.46-4.61 (m, 1H) 6.88-6.98 (m, 2H) 7.12-7.23 (m, 2H) 7.93 (s, 1H) 9.83 (s, 1H). MS (ESI), m/z 264.1 (M+H)$^+$.

Example 1D 2-(4-isopropoxyphenoxy)-1,3-thiazole-5-carbaldehyde oxime

To a solution of Example 1C (2.5 g, 0.0095 mol) in pyridine (15 mL, 0.19 mol) was added hydroxylamine hydrochloride (6.6 g, 0.095 mol) portion wise and the mixture was stirred at room temperature for 5 minutes and it solidified. The mixture was then heated at 70° C. for 0.5 hours. Water (300 mL) was added and the reaction was stirred for 20 minutes. The solid was filtered and air-dried to give 2.26 g of product as a white solid (85% yield). $^1$H NMR (500 MHz, DMSO-d$_6$) δ ppm 1.28 (d, J=5.49 Hz, 6H) 4.54-4.68 (m, 1H) 7.00 (d, J=9.16 Hz, 2H) 7.28 (d, J=9.16 Hz, 2H) 7.68 (s, 1H) 7.77 (s, 1H) 11.89 (s, 1H). MS (ESI), m/z 279.0 (M+H)$^+$.

Example 1E

N-hydroxy-2-(4-isopropoxyphenoxy)-1,3-thiazole-5-carboximidoyl chloride

To a solution of Example 1D (7.77 g, 0.028 mol) in N,N-dimethylformamide was added N-chlorosuccinimide (4.0 g, 0.029 mol) and the solution was stirred at room temperature for 6 hours. Water was added and the reaction mixture stirred for 30 minutes. The precipitate was filtered and air-dried to give 8.45 g of product as an off-white solid (96% yield). $^1$H NMR (300 MHz, DMSO-d$_6$) δ ppm 1.28 (d, J=5.88 Hz, 6H) 4.53-4.70 (m, 1 H) 6.95-7.07 (m, 2H) 7.26-7.37 (m, 2H) 7.67 (s, 1H) 12.41 (s, 1H). MS (ESI) m/z 294.0 (M−18)$^+$.

Example 1F 2-(1-{3-[2-(4-isopropoxyphenoxy)-1,3-thiazol-5-yl]isoxazol-5-yl}ethyl)-1H-isoindole-1,3(2H)-dione To a solution of Example 1E (0.65 g, 0.002 mol) and Example 1F-1 (0.4 g, 0.002 mol) in toluene was added potassium carbonate (0.42 g, 0.003 mol), and the reaction was heated at reflux for 6 hours. The reactions was then diluted with dichloromethane and filtered. The filtrate was concentrated and purified on silica gel (10~30% ethyl acetate in hexane) to give 0.33 g of product as a off-white solid (70% yield). $^1$H NMR (300 MHz, CDCl$_3$) δ ppm 1.35 (d, J=5.88 Hz, 6H) 1.91 (d, J=7.35 Hz, 3H) 4.42-4.64 (m, 1H) 5.67 (d, J=8.09 Hz, 1H) 6.51 (s, 1H) 6.86-6.97 (m, 2H) 7.14-7.24 (m, 2H) 7.53 (s, 1H) 7.70-7.80 (m, 2H) 7.82-7.92 (m, 2H). MS (ESI) m/z 476.0 (M+H)$^+$.

Example 1F-1

2-(1-methyl-prop-2-ynyl)-isoindole-1,3-dione

To a solution of but-3-yn-2-ol (13.3 g, 0.19 mol), phthalimide (28.5 g, 0.19 mol) and triphenylphosphine (76.0 g, 0.28 mol) in tetrahydrofuran was added diethyl azodicarboxylate (123.8 g, 0.28 mol, 310 mL of 40% toluene solution) drop wise at room temperature. The reaction mixture was stirred for 16 h. Solvent was removed and the residue was treated with 600 mL mixture of ether and hexane (1:1). The precipitate was filtered off and the filtrate was concentrated to give 90 g of the crude. The crude was then purified on silica gel eluting with 15% ethyl acetate in hexane to give 24 g of the title compound as a white solid (63% yield), $^1$H NMR (300 MHz, CDCl$_3$) δ ppm 1.72 (d, J=6.99 Hz, 3H) 2.35 (d, J=2.21 Hz, 1H) 5.22 (dt, J=14.34, 7.35, 2.57 Hz, 1H) 7.68-7.78 (m, 2H) 7.82-7.90 (m, 2H), MS (ESI), M/Z: 200.0 (M+H)$^+$.

Example 1G

N-(1-{3-[2-(4-isopropoxyphenoxy)-1,3-thiazol-5-yl]isoxazol-5-yl}ethyl)acetamide

Step 1
A mixture of Example 1F (3.9 g, 0.0082 mol) and hydrazine (4.1 g, 0.082 mol) in dichloromethane was heated at reflux for 3 hours. The reaction was cooled and filtered, the filtrated was concentrated, and the residue was suspended in dichloromethane and filtered again. The filtrate was evaporated to give 3.2 g of crude product, which was used without further purification.
Step 2
To a solution of the product of step 1 of Example 1G and triethylamine (excess) in dichloromethane was added acetic anhydride (excess, 1 mL) at room temperature and the mixture was stirred for 0.5 hours. After the removal of solvent, the crude was purified on silica gel (ethyl acetate/hexane, 35~100%) to give 2.34 g of product as a pale yellow solid. $^1$H NMR (300 MHz, DMSO-d$_6$) δ ppm 1.28 (d, J=6.25 Hz, 6H) 1.42 (d, J=6.99 Hz, 3 H) 1.87 (s, 3H) 4.53-4.74 (m, 1H) 5.10 (t, J=7.17 Hz, 1H) 6.89 (s, 1H) 6.97-7.07 (m, 2H) 7.29-7.40 (m, 2H) 7.95 (s, 1H) 8.51 (d, J=8.09 Hz, 1H). MS (ESI) m/z 388.1 (M+H)$^+$. Anal. Calcd: C, 58.90; H, 5.46; N, 10.85; S, 8.28. Found: C, 58.36; H, 5.27; N, 11.03; S, 8.10.

Example 2

N-(1-{5-[2-(4-phenoxyphenoxy)-1,3-thiazol-5-yl]thien-2-yl}ethyl)urea

Example 2A 2-(4-phenoxyphenoxy)-5-(tributylstannyl)-1,3-thiazole

To a solution of Example 2A-1 (5.0 g, 0.0186 mol) in dry tetrahydrofuran was added n-butyl lithium (7.4 mL of 2.5 M in hexane, 0.019 mol) at −78° C. drop wise. After stirring at this temperature, tributyltin chloride (5.25 mL, 0.0186 mol) was added slowly to the mixture. The brown solution was then stirred for 3 hours while warming up to room temperature. Water was added and the reaction was extracted with ethyl acetate. The organic layer was washed with sat, NH$_4$Cl, brine, and then dried over magnesium sulfate. The filtrate was concentrated and the crude material was purified to give 7.5 g of the product as a clear oil (72% yield). $^1$H NMR (300 MHz, CDCl$_3$) δ ppm 0.89 (t, J=7.17 Hz, 9H) 1.04-1.16 (m, 6H) 1.24-1.42 (m, 6H) 1.48-1.61 (m, 6H) 7.03 (d, J=9.19 Hz, 3H) 7.07-7.18 (m, 2H) 7.20-7.29 (m, 3H) 7.30-7.40 (m, 2H); MS (ESI) m/z 560.0 (M+H)$^+$.

Example 2A-1

2-(4-phenoxy-phenoxy)-thiazole

To a solution of 2-bromothiazole (3 g, 18.3 mmol) in dimethylsulfoxide (40 mL) was successively added 4-phenoxyphenol (3.4 g, 18.3 mmol) and potassium carbonate (2.52 g, 18.3 mmol). The reaction mixture was heated at 160° C. for 6.5 hours. The reaction mixture was diluted with methylene chloride and washed with water (×3) and brine. The reaction mixture was dried over magnesium sulfate, filtered and evaporated. The product was purified via silica-gel column, using a gradient of 3 to 10% ethyl acetate in hexane as eluent to afford 4.24 g of the title compound. $^1$H NMR (300 MHz, CDCl$_3$) δ ppm 7.30-7.40 (m, 2H) 7.20-7.30 (m, 3H) 7.08-7.17 (m, 1H) 6.98-7.08 (m, 4H) 6.81 (d, J=3.68 Hz, 1H). MS (ESI): m/z 270 (M+H).

Example 2B

1-{5-[2-(4-phenoxyphenoxy)-1,3-thiazol-5-yl]thien-2-yl}ethanone

A mixture of 1-(5-bromo-thiophen-2-yl)-ethanone (from Aldrich) (1.1 g, 0.005 mol), Example 2A (3.4 g, 0.006 mol) and tetrakis(triphenylphosphine)palladium (0.35 g, 0.0003 mol) was heated at 60° C. under nitrogen overnight in N,N-dimethylformamide. The reaction was then cooled to room temperature and diluted with dichloromethane and then filtered through a pad of Celite. The filtrate was concentrated and purified by recrystallization from ethyl acetate and hexane to give 2.13 g of product as light yellow crystal (90% yield). $^1$H NMR (300 MHz, CDCl$_3$) δ ppm 2.55 (s, 3H) 6.97-7.10 (m, 4H) 7.14 (t, J=7.35 Hz, 1H) 7.22-7.32 (m, 2H) 7.37 (t, J=7.91 Hz, 2H) 7.44 (s, 1H) 7.57 (d, J=4.04 Hz, 1H). MS (ESI), M/Z: 393.9 (M+NH$_4$—H$_2$O)$^+$.

Example 2C

1-{5-[2-(4-phenoxyphenoxy)-1,3-thiazol-5-yl]thien-2-yl}ethanol

To a solution of Example 2B (1.9 g, 0.0048 mol) in a mixture of methanol and tetrahydrofuran was added NaBH$_4$ (0.37 g, 0.0096 mol) portion wise at room temperature. The yellow solution turned reddish immediately upon the addition. Reaction was over after 30 minutes. Water was added and the mixture was stirred at room temperature overnight. Brown solid was filtered and air-dried to give the crude material, which was recrystallized from methanol to give 0.76 g of product as a yellow solid. The filtrate was concentrated and purified on silica gel (20~50% ethyl acetate/hexanes) to give additional 0.65 g of the title compound as a pale white solid (74% yield). ¹H NMR (500 MHz, CDCl₃) δ ppm 1.60 (d, J=6.35 Hz, 3H) 2.05 (d, J=4.88 Hz, 1H) 5.04-5.13 (m, 1H) 6.86 (d, J=4.39 Hz, 1H) 6.90 (d, J=3.42 Hz, 1H) 7.01-7.07 (m, 3H) 7.12 (t, J=7.32 Hz, 1H) 7.24 (s, 1H) 7.25-7.29 (m, 2H) 7.31-7.40 (m, 2H), MS (ESI) m/z 395.9 (M+NH₄—H₂O)⁺.

Example 2D 2-(1-{5-[2-(4-phenoxyphenoxy)-1,3-thiazol-5-yl]thien-2-yl}ethyl)-1H-isoindole-1,3(2H)-dione To a solution of Example 2C (1.2 g, 0.003 mol), triphenylphosphine (1.2 g, 0.0045 mol) and phthalimide (0.55 g, 0.0038 mol) in dry tetrahydrofuran was added a solution of diethyl azodicarboxylate (0.79 g, 0.0038 mol) in toluene drop wise. The mixture was stirred at room temperature for 2 hours. The solvent was removed and the residue was purified on silica gel (ethyl acetate/hexanes, 5~35%) to give 1.04 g of the title compound as a light yellow solid (66% yield). MS (ESI), M/Z: 524.9 (M+NH₄—H₂O)⁺.

Example 2E

1-{5-[2-(4-phenoxyphenoxy)-1,3-thiazol-5-yl]thien-2-yl}ethanamine

To a solution of Example 2D (1.0 g, 0.0019 mol) in a mixture of dichloromethane and ethanol was added hydrazine monohydrate (0.95 g, 0.019 mol) and the reaction mixture was refluxed under nitrogen for 2 hours. The white suspension was cooled, filtered, and washed with more dichloromethane. The filtrate was concentrated and filtered through a pad of silica eluting with 5% methanol in dichloromethane to give g 0.65 of the title compound as a yellow oil (86% yield). ¹H NMR (300 MHz, DMSO-d₆) δ ppm 1.33 (d, J=6.62 Hz, 3H) 2.23 (s, 2H) 4.20 (q, J=6.25 Hz, 1H) 6.86 (d, J=3.68 Hz, 1H) 7.02-7.14 (m, 5H) 7.18 (t, J=7.35 Hz, 1H) 7.37-7.48 (m, 4H). MS (ESI), M/Z; 377.9 (M−17)⁺.

Example 2F

N-(1-{5-[2-(4-phenoxyphenoxy)-1,3-thiazol-5-yl]thien-2-yl}ethyl)urea

To a solution of Example 2E (0.36 g, 0.00091 mol) in dichloromethane was added trichloroacetyl isocyanate (0.26 g, 0.0014 mol) and the mixture was stirred at room temperature for 15 minutes. The solvent was removed and the residue was triturated with methanol to give 0.42 g of intermediate as a light solid. The solid was suspended with methanol (20 mL) and refluxed with catalytic sodium carbonate and several drops of water for 1.5 hours. It was then cooled, and filtered. The filtrate was concentrated to dryness and triturated with methanol to give 0.23 g of the title compound as an off-white solid (58% yield), ¹H NMR (300 MHz, DMSO-d₆) δ ppm 1.41 (d, J=6.99 Hz, 3H) 4.84-5.00 (m, 1 H) 5.51 (s, 2H) 6.50 (d, J=8.09 Hz, 1H) 6.87 (d, J=3.68 Hz, 1H) 7.02-7.14 (m, 5H) 7.18 (t, J=7.35 Hz, 1H) 7.36-7.50 (m, 4H). MS (ESI), m/z 436.2 (M−H)⁺.

Example 3

N-(1-{5-[2-(4-isopropoxyphenoxy)-1,3-thiazol-5-yl]thien-2-yl}ethyl)acetamide

Example 3A

1-{5-[2-(4-isopropoxyphenoxy)-1,3-thiazol-5-yl]thien-2-yl}ethanone

To a degassed solution of Example 2A (550 mg, 1.05 mmol) in N,N-dimethyl formamide (10 mL) at room temperature, was added 1-(5-bromothiophen-2-yl)ethanone (269 mg, 1.31 mmol) followed by dichlorobis(triphenylphosphine)palladium(II) (45 mg, 0.064 mmol). The reaction mixture was heated at 60° C. overnight. The solvent was evaporated under vacuum and the product was purified via silica gel column chromatography using a gradient of 15 to 35% ethyl acetate in hexane to give the desired compound (320 mg). ¹H NMR (300 MHz, CDCl₃) δ ppm 7.56 (d, J=4.04 Hz, 1H) 7.43 (s, 1H) 7.15-7.24 (m, 2H) 7.02 (d, J=4.04 Hz, 1H) 6.88-6.97 (m, 2H) 4.44-4.62 (heptet, J=5.88 Hz, 1H) 2.54 (s, 3H) 1.36 (d, J=5.88 Hz, 6H). MS (ESI) m/z 360 (M+1)⁺.

Example 3B

1-{5-[2-(4-isopropoxyphenoxy)-1,3-thiazol-5-yl]thien-2-yl}ethanol

To a solution of Example 3A (320 mg, 0.89 mmol) in a mixture of 1:1 methanol:tetrahydrofuran (40 mL) was added sodium borohydride (67.5 mg, 1.78 mmol) and stirred at room temperature for 2.5 hours. The reaction mixture was quenched with acetone, the solvent removed in vacuum and the residue dissolved in dichloromethane. The organic phase was washed with water and brine, dried over magnesium sulfate filtered and evaporated, to produce the title compound (317 mg). ¹H NMR (300 MHz, CDCl₃) δ ppm 7.15-7.29 (m, 3H) 6.82-6.97 (m, 4H) 502-5.16 (m, 1H) 4.43-4.61 (heptet, J=6.25 Hz, 1H) 1.60 (d, J=6.62 Hz, 3H) 1.35 (d, J=6.25 Hz, 6H). MS (DCI): m/z 362 (M+H).

Example 3C 2-(1-{5-[2-(4-isopropoxyphenoxy)-1,3-thiazol-5-yl]thien-2-yl}ethyl)-1H-isoindole-1,3(2H)-dione To a solution of Example 3B (314 mg, 0.87 mmol), phthalimide (140 mg, 0.95 mmol) and triphenylphophine (341 mg, 1.3 mmol) in tetrahydrofuran (25 mL), at room temperature was slowly added diethyl azodicarboxylate (205 uL, 1.3 mmol). The reaction mixture was stirred at room temperature, overnight. The solvent was removed under vacuum and the product was purified on a silica-gel column using a gradient of 10-15% ethyl acetate in hexane and yielded the product as white powder (210 mg). ¹H NMR (300 MHz, CDCl₃) δ ppm 7.63-7.97 (m, 5H) 7.12-7.24 (m, 2H) 7.00 (d, J=3.68 Hz, 1H) 6.81-6.96 (m, 3H) 5.73 (q, J=7.35 Hz, 1H) 4.44-4.59 (heptet, J=6.25 Hz, 1H) 196 (d, J=7.35 Hz, 3H) 1.34 (d, J=6.25 Hz, 6H), MS (DCI): m/z 491 (M+H).

Example 3D

N-(1-{5-[2-(4-isopropoxyphenoxy)-1,3-thiazol-5-yl]thien-2-yl}ethyl)acetamide

To a solution of Example 3C (200 mg, 0.41 mmol) at room temperature in dichloromethane (5 mL) was added hydrazine hydrate (197 uL, 4.1 mmol). Ethanol was added until a clear, single phase was formed. After an hour at room temperature, the solvent was removed under vacuum and the reaction mixture was thoroughly dried. To the resulting mixture was added dichloromethane (5 mL), triethylamine (300 uL, 2.15 mmol) and acetic anhydride (150 uL, 1.59 mmol). After two hours at room temperature, methanol was added and the solution was stirred for additional hour. The mixture was concentrated and the product was isolated via silica column chromatography (using a gradient of 25 to 75% ethyl acetate in hexane) and yielded 40 mg of the title compound. ¹H NMR (300 MHz, CDCl$_3$) δ ppm 7.16-7.23 (m, 3H) 6.83-6.95 (m, 4H) 5.66 (d, J=8.09 Hz, 1H) 5.25-5.43 (m, 1H) 4.52 (heptet, J=6.25 Hz, 1H) 2.00 (s, 3H) 1.57 (d, J=6.99 3 H) 1.35 (d, J=6.25 Hz, 6H), MS (DCI): m/z 403 (M+H).

Example 4

N-{1-[2'-(4-isopropoxyphenoxy)-2,5'-bi-1,3-thiazol-5-yl]ethyl}acetamide

Example 4A 2-(4-isopropoxyphenoxy)-5-(tributylstannyl)-1,3-thiazole

To a solution of Example 1B (2.4 g, 0.01 mol) in dry tetrahydrofuran was added n-butyl lithium 4.4 mL, 2.5 M in hexane) at −78° C. drop wise. After stirring at this temperature, tributyltin chloride (3.0 mL, 0.011 mol) was added slowly. The solution was then stirred for 3 hours while warming up to room temperature. Water was added and the solution was extracted with ethyl acetate. The organic layer was washed with sat. NH$_4$Cl, brine, and then dried over magnesium sulfate. The solution was filtered, concentrated, and purified to give 4.85 g of the title compound as a clear oil (93% yield). $^1$H NMR (300 MHz, CDCl$_3$) δ ppm 0.77-1.74 (m, 33H) 4.40-4.63 (m, 1H) 6.84-6.95 (m, 2H) 7.12 (s, 1H) 7.14 (m, 2H). MS (ESI) m/z 526.2 (M+H)$^+$.

Example 4B

2'-(4-isopropoxyphenoxy)-2,5'-bi-1,3-thiazole

The title compound was prepared as described in Example 2B, substituting Example 4A for Example 2A, and substituting 2-bromothiazole for 1-(5-bromo-thiophen-2-yl)-ethanone. The N,N-dimethyl formamide was removed and the residue was purified on silica gel (5~25% ethyl acetate in hexane) to give 0.72 g of product as a clear oil (95% yield), $^1$H NMR (300 MHz, CDCl$_3$) δ ppm 1.35 (d, J=6.25 Hz, 6H) 4.46-4.59 (m, 1H) 6.88-6.97 (m, 2H) 7.18-7.23 (m, 2H) 7.25 (d, J=3.31 Hz, 1H) 7.64 (s, 1H) 7.72 (d, J=3.31 Hz, 1H). MS (ESI) m/z 318.9 (M+H)$^+$.

Example 4C

1-[2'-(4-isopropoxyphenoxy)-2,5'-bi-1,3-thiazol-5-yl]ethanol

To a solution of Example 4B (0.7 g, 0.0022 mol) in dry tetrahydrofuran was added n-butyl lithium 1.0 mL, 2.5 M hexane solution, 0.0025 mol) drop wise at −78° C. This yellow solution was stirred at low temperature for 1 hour then acetaldehyde (0.25 mL, 0.0044 mol) was added. After stirring at room temperature for 1 hour. The reaction was quenched with sat NH$_4$Cl solution and extracted with ethyl acetate. The organic layer was washed with brine, dried over magnesium sulfate and filtered. The filtrate was concentrated and purified on silica gel (20-40% ethyl acetate in hexane) to give 0.66 g of the title compounds a yellow oil (83% yield). $^1$H NMR (300 MHz, CDCl$_3$) δ ppm 1.35 (d, J=5.88 Hz, 6H) 1.58 (s, 1H) 1.62 (d, J=6.25 Hz, 3H) 4.46-4.58 (m, 1H) 5.17 (dd, J=6.07, 4.23 Hz, 1H) 6.87-6.96 (m, 2H) 7.15-7.24 (m, 2H) 7.53 (s, 1H) 7.58 (s, 1H). MS (ESI) m/z 362.9 (M+H)$^+$.

Example 4D

N-{1-[2'-(4-isopropoxyphenoxy)-2,5'-bi-1,3-thiazol-5-yl]ethyl}acetamide

To a solution of Example 4C (0.2 g, 0.0005 mol) in a mixture of dichloromethane and acetonitrile (2:1) was added excess trifluoroboroane dietherate and the reaction mixture was heated at reflux for 6 hours. The solvent was removed and the crude material was purified by HPLC (5-95% acetonitrile: 0.1% aqueous trifluoroacetic acid) to give 0.07 g of the title compound as a white solid (35% yield), $^1$H NMR (300 MHz, DMSO-d$_6$) δ ppm 1.28 (d, J=5.88 Hz, 6H) 1.47 (d, J=6.99 Hz, 3H) 1.83 (s, 3H) 455-4.71 (m, 1H) 5.16 (t, J=7.17 Hz, 1H) 6.96-7.08 (m, 2H) 7.27-7.40 (m, 2H) 7.59 (s, 1H) 7.85 (s, 1H) 8.49 (d, J=8.09 Hz, 1H). MS (ESI), M/Z: 404.0 (M+H)$^+$.

Example 5

N-2,2,2-trifluoro-1-{5-[2-(4-isopropoxyphenoxy)-1,3-thiazol-5-yl]thien-2-yl}ethyl)urea

Example 5A 1-(5-bromothien-2-yl)-2,2,2-trifluoroethanol

To a solution of 2-bromo-2-thiophenecarboxaldehyde (2.1 g, 0.01 mol) and trimethyl(trifluoromethyl)silane (1.7 g, 0.012 mol) in dry tetrahydrofuran at 0° C. was added tetrabutylammonium fluoride (10 mL of 1.0 M tetrahydrofuran solution, 0.01 mol) drop wise. The mixture was warmed to room temperature and stirred for 36 hours. The reaction was then quenched with 6N HCl and stirred for 30 minutes, and then extracted with ethyl acetate. The organic layer was washed with brine, dried over magnesium sulfate and filtered. The filtrate was concentrated to give 3.3 g of crude as a dark brown oil, which was purified through a plug of silica gel eluting with an ethyl acetate and hexane mixture (1:1) to give 2.56 g of the title compound as a yellow liquid (98% yield), $^1$H NMR (300 MHz, CDCl$_3$) δ ppm 2.78 (d, J=5.15 Hz, 1H) 5.14-5.27 (m, 1H) 6.95 (d, J=3.68 Hz, 1H) 7.00 (d, J=3.68 Hz, 1H),

Example 5B 2,2,2-trifluoro-1-{5-[2-(4-isopropoxyphenoxy)-1,3-thiazol-5-yl]thien-2-yl}ethanol The title compound was prepared as described in Example 2B, except for substituting Example 5A for 1-(5-bromo-thiophen-2-yl)-ethanone (from Aldrich), and substituting Example 4A for Example 2A. The N,N-dimethyl formamide was removed and the residue was purified on silica gel (10~35% ethyl acetate in hexane) to afford 1.92 g of product as a light yellow solid (92% yield). $^1$H NMR (300 MHz, CDCl$_3$) δ ppm 1.35 (d, J=5.88 Hz, 6H) 3.07 (s, 1H) 4.53 (dt, J=18.20, 12.13, 6.07 Hz, 1H) 5.23 (q, J=6.25 Hz, 1H) 6.87-6.98 (m, 3H) 7.07 (d, J=3.68 Hz, 1H) 7.16-7.23 (m, 2H) 7.27 (s, 1H). MS (ESI), m/z 415.6 (M+H)$^+$.

Example 5C

5-[5-(1-chloro-2,2,2-trifluoroethyl)thien-2-yl]-2-(4-isopropoxyphenoxy)-1,3-thiazole To a solution of Example 5B (1.67 g, 0.004 mol), triethylamine (1.4 mL, 0.01 mol) and catalytic amount of 4-(dimethylamino)pyridine in dichloromethane at 0° C. was added methanesulfonyl chloride (0.55 g, 0.0048 mol) drop wise and the mixture was stirred for 2 hours at room temperature. The solution was diluted with dichloromethane and washed with water and brine and then dried over magnesium sulfate and filtered. The filtrate was concentrated to give 1.75 g of crude product as a brown oil. $^1$H NMR (300 MHz, CDCl$_3$) δ ppm 1.35 (d, J=5.88 Hz, 6H) 4.48-4.60 (m, 1H) 5.37 (q, J=6.50 Hz, 1H) 6.88-6.96 (m, 3H) 7.13 (d, J=3.68 Hz, 1H) 7.17-7.24 (m, 2H) 7.31 (s, 1H). MS (ESI), m/z 433.9 (M+H)$^+$.

Example 5D

5-[5-(1-azido-2,2,2-trifluoroethyl)thien-2-yl]-2-(4-isopropoxyphenoxy)-1,3-thiazole A mixture of Example 5C (0.6 g, 0.0013 mol) and sodium azide (1.0 g, 0.013 mol) in N,N-dimethylformamide was heated at 80° C. under nitrogen for 4 hours. Water was added and the solution was extracted with ether. The organic layer was then washed with brine, dried and filtered. The filtrate was concentrated to give 0.5 g of crude as a yellow oil, which was purified on silica gel (10~30% ethyl acetate in hexane) to give 0.41 g of pure product as a light yellow oil (72% yield), $^1$H NMR (300 MHz, CDCl$_3$) δ ppm 1.35 (d, J=5.88 Hz, 6H) 4.44-4.61 (m, 1H) 5.10 (q, J=6.62 Hz, 1H) 6.87-6.96 (m, 2H) 6.97 (d, J=3.68 Hz, 1H) 7.08-7.14 (m, 1H) 7.16-7.24 (m, 2H) 7.32 (s, 1H).

Example 5E 2,2,2-trifluoro-1-{5-[2-(4-isopropoxyphenoxy)-1,3-thiazol-5-yl]thien-2-yl}ethanamine Example 5D was hydrogenated at atmospheric pressure with palladium on carbon (10%) as the catalyst overnight. The mixture was filtered through Celite and the filtrate was concentrated and purified on silica gel (10~50% ethyl acetate in hexane) to give 0.22 g of product as a light yellow oil which solidified upon standing (62% yield). $^1$H NMR (300 MHz, CDCl$_3$) δ ppm 1.35 (d, J=5.88 Hz, 6H) 1.58 (s, 2H) 2.05 (none, 1H) 4.47-4.58 (m, 1H) 4.63 (q, J=6.99 Hz, 1H) 6.87-6.96 (m, 2H) 7.02 (d, J=3.68 Hz, 1H) 7.16-7.23 (m, 2H) 7.27 (s, 1H), MS (ESI) m/z 414.9 (M+H)$^+$.

Example 5F

N-(2,2,2-trifluoro-1-{5-[2-(4-isopropoxyphenoxy)-1,3-thiazol-5-yl]thien-2-yl}ethyl)urea The title compound was prepared as described in Example 2F, substituting Example 5E for Example 2E (66% yield), $^1$H NMR (300 MHz, DMSO-d$_6$) δ ppm 1.28 (d, J=5.88 Hz, 6H) 4.53-4.72 (m, 1H) 5.71-5.98 (m, 3H) 6.97-7.05 (m, 2H) 7.13-7.20 (m, 2H) 7.28-7.36 (m, 2H) 7.37 (s, 1H) 75.2 (s, 1H). MS (ESI), M/Z: 457.9 (M+H)$^+$.

Example 6

N-(1-{3-[2-(4-isopropoxyphenoxy)-1,3-thiazol-5-yl]isoxazol-5-yl}ethyl)propanamide The title compound was prepared as described in Example 1G, substituting propionyl chloride for acetic anhydride. After the removal of solvent, the residue was triturated with ethyl acetate and hexane to give 0.04 g of product as a light yellow solid (43% yield). $^1$H NMR (300 MHz, CDCl$_3$) δ ppm 1.17 (t, J=7.54 Hz, 3H) 1.35 (d, J=5.88 Hz, 6H) 1.56 (d, J=7.35 Hz, 3H) 2.25 (q, J=7.48 Hz, 2H) 4.46-4.61 (m, 1H) 5.29-5.44 (m, 1 H) 5.77 (d, J=8.09 Hz, 1H) 6.35 (s, 1H) 6.88-6.97 (m, 2H) 7.16-7.24 (m, 2H) 7.51 (s, 1H). MS (ESI), M/Z: 402.0 (M+H)$^+$.

Example 7

N-(1-{3-[2-(4-isopropoxyphenoxy)-1,3-thiazol-5-yl]isoxazol-5-yl}ethyl)urea

The title compound was synthesized by the method as described in Example 2F, substituting the intermediate obtained from step 1 of Example 1G for Example 2E. $^1$H NMR (300 MHz, DMSO-d$_6$) δ ppm 1.28 (d, J=5.88 Hz, 6H) 1.39 (d, J=6.99 Hz, 3H) 4.55-4.70 (m, 1H) 4.85-4.99 (m, 1H) 5.60 (s, 2H) 6.61 (d, J=8.46 Hz, 1H) 6.83 (s, 1 H) 6.98-7.07 (m, 2H) 7.34 (d, J=8.82 Hz, 2H) 7.96 (s, 1H). MS (ESI) m/z 389.0 (M+H)$^+$.

Example 8

N-(1-{3-[2-(4-isopropoxyphenoxy)-1,3-thiazol-5-yl]isoxazol-5-yl}ethyl)-N'-methylurea To a solution of the intermediate obtained from step 1 of Example 1G (0.08 g, 0.00023 mol) and pyridine (0.18 g, 0.0023 mol) in dichloromethane was added p-nitrophenyl chloroformate (0.06 g, 0.00028 mol) and the reaction was stirred at room temperature for 1 hour. Then a solution of methylamine (2M) in tetrahydrofuran was added and the reaction was stirred overnight. The reaction was filtered and the filtrate was concentrated and purified on silica gel (50~100% ethyl acetate in hexane) to give 0.058 g of product as a white solid (63% yield). $^1$H NMR (300 MHz, DMSO-d$_6$) δ ppm 1.28 (d, J=5.88 Hz, 6H) 1.39 (d, J=6.99 Hz, 3H) 2.56 (d, J=4.41 Hz, 3H) 4.88-5.02 (m, 1H) 5.73-5.86 (m, J=4.78 Hz, 1H) 5.74-5.84 (m, J=4.78 Hz, 1H) 6.57 (d, J=8.09 Hz, 1H) 6.82 (s, 1H) 6.96-7.07 (m, 2 H) 7.28-7.40 (m, 2H) 7.95 (s, 1H). MS (ESI) m/z 403.3 (M+H)$^+$.

Example 9

N-(1-{3-[2-(2-chloro-4-isobutoxyphenoxy)-1,3-thiazol-5-yl]isoxazol-5-yl}ethyl)cyclopropanecarboxamide Example 9A 2-(2-chloro-4-methoxyphenoxy)-1,3-thiazole A mixture of 2-chloro-4-methoxy-phenol (7.93 g, 0.05 mol), 2-bromothiazole (9.0 g, 0.055 mol) and potassium carbonate (7.6 g, 0.055 mol) in dimethyl sulfoxide was heated at 160° C. under nitrogen for 4 hours. The solution was cooled and treated with water, and the aqueous phase was extracted with dichloromethane. The organic layer was washed with brine, dried and concentrated to give 30 g of the crude material, which was purified on a silica gel (ethyl acetate/hexane 5-35%) to afford 10.62 g of the product as a light yellow oil (88% yield), $^1$H NMR (300 MHz, CDCl$_3$) δ ppm 3.81 (s, 3H) 6.80 (d, J=4.04 Hz, 1H) 6.85 (dd, J=9.19, 2.94 Hz, 1H) 7.01

(d, J=2.94 Hz, 1H) 7.19 (d, J=3.68 Hz, 1H) 7.27 (d, J=8.82 Hz, 1H). MS (ESI), m/z 241.9 (M+H)$^+$.

Example 9B 3-chloro-4-(1,3-thiazol-2-yloxy)phenol

To a solution of Example 9A (5.4 g, 0.022 mol) in dichloromethane at −78° C. was added a solution of BBr$_3$ (0.066 mol) drop wise and the reaction mixture was stirred overnight while warming up to room temperature. The mixture was poured into ice and then stirred at room temperature for 24 hours. The organic layer was washed with brine, dried over magnesium sulfate and filtered. The filtrate was concentrated under vacuum to give 3.5 g of product as an off-white solid (70% yield). $^1$H NMR (300 MHz, CDCl$_3$) δ ppm 6.59 (dd, J=8.82, 2.94 Hz, 1H) 6.67 (d, J=2.57 Hz, 1H) 6.88 (d, J=3.68 Hz, 1H) 7.07 (d, J=8.82 Hz, 1H) 7.19 (d, J=3.68 Hz, 1H). MS (ESI) M/z 227.9 (M+H)$^+$.

Example 9C 2-(2-chloro-4-isobutoxyphenoxy)-1,3-thiazole

To a solution of Example 9B (3.4 g, 0.015 mol) in N,N-dimethyl formamide was added sodium hydride (0.7 g, 0.018 mol) in portions at room temperature. After stirring for 15 minutes, isobutyl iodide (4.2 g, 0.023 mol) was added rapidly and the mixture was stirred at room temperature for 24 hours. More sodium hydride and isobutyl iodide were added later to complete the reaction. Water was added and the aqueous layer was extracted with ethyl acetate. The organic layer was washed with brine, dried over magnesium sulfate and filtered. The filtrate was concentrated and purified on silica gel (5~35% ethyl acetate in hexane) to give 1.92 g of product as clear oil (45% yield), $^1$H NMR (300 MHz, CDCl$_3$) δ ppm 1.02 (d, J=6.62 Hz, 6H) 1.98-2.18 (m, 1H) 3.71 (d, J=6.62 Hz, 1H) 6.79 (d, J=4.04 Hz, 1H) 6.83 (d, J=2.94 Hz, 1H) 6.86 (d, J=2.94 Hz, 1H) 7.00 (d, J=2.94 Hz, 1H) 7.19 (d, J=4.04 Hz, 1H) 7.24 (s, 1H). MS (ESI) m/z 284.0 (M+H)$^+$.

Example 9D 2-(2-chloro-4-isobutoxyphenoxy)-1,3-thiazole-5-carbaldehyde

The title compound was prepared as described in Example 1C, substituting Example 9C for Example 1B. $^1$H NMR (300 MHz, DMSO-d$_6$) δ ppm 0.99 (d, J=6.62 Hz, 6H) 1.93-2.12 (m, 1H) 3.82 (d, J=625 Hz, 2H) 7.06 (dd, J=9.19, 2.94 Hz, 1H) 7.27 (d, J=2.94 Hz, 1H) 7.55 (d, J=9.19 Hz, 1H) 8.28 (s, 1H) 9.88 (s, 1H). MS (ESI), M/Z: 344.0 (M+32)$^+$.

Example 9E 2-(2-chloro-4-isobutoxyphenoxy)-1,3-thiazole-5-carbaldehyde oxime The title compound was prepared as described in Example 1D, substituting Example 9D for Example 1C, $^1$H NMR (300 MHz, DMSO-d$_6$) δ ppm 0.98 (d, J=6.62 Hz, 6H) 1.94-2.10 (m, 1H), 3.81 (d, J=6.62 Hz, 2H) 7.02 (dd, J=9.19, 2.94 Hz, 1H) 7.23 (d, J=2.94 Hz, 1H) 7.49 (d, J=9.19 Hz, 1H) 7.68 (s, 1H) 7.81 (s, 1H) 12.02 (s, 1H). MS (ESI), M/Z: 327.0 (M+H)$^+$.

Example 9F 2-(2-chloro-4-isobutoxyphenoxy)-N-hydroxy-1,3-thiazole-5-carboximidoyl chloride The title compound was prepared as described in Example 1E, substituting Example 9E for Example 1D. $^1$H NMR (300 MHz, DMSO-d$_6$) δ ppm 0.98 (d, J=6.99 Hz, 6H) 1.93-2.11 (m, 1H) 3.81 (d, J=6.62 Hz, 2H) 7.03 (dd, J=9.19, 2.94 Hz, 1H) 7.24 (d, J=2.94 Hz, 1H) 7.51 (d, J=9.19 Hz, 1H) 7.66 (s, 1H) 12.47 (s, 1H). MS (ESI) m/z 341.7 (M−19)$^+$.

Example 9G 2-(1-{3-[2-(2-chloro-4-isobutoxyphenoxy)-1,3-thiazol-5-yl]isoxazol-5-yl}ethyl)-1H-isoindole-1,3(2H)-dione The title compound was prepared as described in Example 1F, substituting Example 9F for Example 1E. $^1$H NMR (300 MHz, CDCl$_3$) δ ppm 1.02 (d, J=6.62 Hz, 6H) 1.91 (d, J=7.35 Hz, 3H) 2.06-2.15 (m, 1H) 3.71 (d, J=6.62 Hz, 2H) 5.67 (q, J=7.11 Hz, 1H) 6.51 (s, 1H) 6.85 (dd, J=9.01, 2.76 Hz, 1H) 7.01 (d, J=2.94 Hz, 1H) 7.26 (d, J=9.01 Hz, 1H) 7.50 (s, 1H) 7.71-7.79 (m, 2H) 7.82-7.90 (m, 2H). MS (ESI) m/z 556.1 (M+33)$^+$.

Example 9H

N-(1-{3-[2-(2-chloro-4-isobutoxyphenoxy)-1,3-thiazol-5-yl]isoxazol-5-yl}ethyl)cyclopropanecarboxamide The title compound was prepared as described in Example 1G, substituting Example 9G for Example 1F and substituting cyclopropanecarbonyl chloride for acetic anhydride $^1$H NMR (300 MHz, DMSO-d$_6$) δ ppm 0.65-0.84 (m, 4H) 0.99 (d, J=6.62 Hz, 6H) 1.44 (d, J=7.35 Hz, 3H) 1.93-2.11 (m, 1H) 1.95-2.09 (m, 1H) 3.82 (d, J=6.62 Hz, 2H) 5.14 (t, J=7.54 Hz, 1H) 6.90 (s, 1H) 7.04 (dd, J=8.82, 2.94 Hz, 1H) 7.26 (d, J=2.94 Hz, 1H) 7.54 (d, J=9.19 Hz, 1H) 7.96 (s, 1H) 8.73 (d, J=8.09 Hz, 1H), MS (ESI) m/z 462.1 (M+H)$^+$.

Example 10

N-(1-{3-[2-(2-chloro-4-isobutoxyphenoxy)-1,3-thiazol-5-yl]isoxazol-5-yl}ethyl)-2-methylpropanamide The title compound was prepared as described for Example 1G, substituting Example 9G for Example 1F, and substituting isobutyryl chloride for acetic anhydride. $^1$H NMR (300 MHz, DMSO-d$_6$) δ ppm 0.99 (d, J=6.99 Hz, 6H) 1.02 (d, J=6.99 Hz, 6H) 1.42 (d, J=6.99 Hz, 3H) 1.95-2.09 (m, 1H) 2.33-2.46 (m, 1H) 3.81 (d, J=6.62 Hz, 2H) 5.10 (t, J=7.17 Hz, 1H) 6.85 (s, 1H) 7.04 (dd, J=9.01, 2.76 Hz, 1H) 7.26 (d, J=2.57 Hz, 1H) 7.54 (d, J=8.82 Hz, 1H) 7.95 (s, 1H) 8.38 (d, J=8.09 Hz, 1H). MS (ESI) m/z 464.1 (M+H)$^+$.

Example 11

N-(1-{3-[2-(2-chloro-4-isobutoxyphenoxy)-1,3-thiazol-5-yl]isoxazol-5-yl}ethyl)acetamide The title compound was prepared as described for Example 1G, substituting Example 9G for Example 1F. $^1$H NMR (300 MHz, DMSO-d$_6$) δ ppm 0.99 (d, J=6.62 Hz, 6H) 1.42 (d, J=7.35 Hz, 3H) 1.87 (s, 3H) 1.95-2.10 (m, 1H) 3.82 (d, J=6.62

Hz, 2H) 5.10 (t, J=7.17 Hz, 1H) 6.90 (s, 1H) 7.04 (dd, J=9.01, 3.13 Hz, 1H) 7.25 (d, J=2.94 Hz, 1H) 7.54 (d, J=8.82 Hz, 1H) 7.94 (s, 1H) 8.51 (d, J=8.09 Hz, 1H). MS (ESI) m/z 436.1 (M+H)+.

Example 12

N-(1-{3-[2-(2-chloro-4-isobutoxyphenoxy)-1,3-thiazol-5-yl]isoxazol-5-yl}ethyl)propanamide The title compound was prepared as described in Example 1G, substituting Example 9G for Example 1F, and substituting propionyl chloride for acetic anhydride. $^1$H NMR (300 MHz, DMSO-$d_6$) δ ppm 0.95-1.02 (m, 9H) 1.42 (d, J=6.99 Hz, 3H) 1.95-2.08 (m, 1H) 2.14 (q, J=7.35 Hz, 1H) 3.82 (d, J=6.25 Hz, 2H) 5.02-5.18 (m, 1H) 6.88 (s, 1H) 7.04 (dd, J=8.82, 2.94 Hz, 1H) 7.25 (d, J=2.94 Hz, 1H) 7.54 (d, J=9.19 Hz, 1H) 7.94 (s, 1H) 8.42 (d, J=8.09 Hz, 1H). MS (ESI) m/z 450.1 (M+H)+.

Example 13 methyl 1-{3-[2-(2-chloro-4-isobutoxyphenoxy)-1,3-thiazol-5-yl]isoxazol-5-yl}ethylcarbamate The title compound was prepared as described in Example 1G, substituting Example 9G for Example 1F, and substituting methyl chloroformate for acetic anhydride. $^1$H NMR (300 MHz, DMSO-$d_6$) δ ppm 0.99 (d, J=6.62 Hz, 6H) 1.44 (d, J=6.99 Hz, 3H) 1.96-2.11 (m, 1H) 3.56 (s, 3H) 3.82 (d, J=6.62 Hz, 2H) 4.79-4.95 (m, 1H) 6.90 (s, 1H) 7.04 (dd, J=9.19, 2.94 Hz, 1H) 7.25 (d, J=2.94 Hz, 1H) 7.53 (d, J=9.19 Hz, 1H) 7.90 (d, J=8.46 Hz, 1H) 7.96 (s, 1H). MS (ESI) m/z 452.2 (M+H)+.

Example 14

N-(1-{3-[2-(2-chloro-4-isobutoxyphenoxy-1,3-thiazol-5-yl]isoxazol-5-yl}ethyl-N'-methylurea The title compound was prepared as described in Example 1G, substituting Example 9G for Example 1F and substituting methyl isocyanate for acetic anhydride. $^1$H NMR (300 MHz, DMSO-$d_6$) δ ppm 0.99 (d, J=6.99 Hz, 6H) 1.40 (d, J=6.99 Hz, 3H) 1.94-2.11 (m, 1 H) 2.56 (d, J=4.41 Hz, 3H) 3.81 (d, J=6.62 Hz, 2H) 4.88-5.02 (m, 1H) 5.79 (d, J=4.78 Hz, 1H) 6.57 (d, J=8.09 Hz, 1H) 6.82 (s, 1H) 7.04 (dd, J=8.82, 2.94 Hz, 1H) 7.25 (d, J=2.94 Hz, 1H) 7.53 (d, J=9.19 Hz, 1H) 7.94 (s, 1H). MS (ESI) m/z 451.1 (M+H)+.

Example 15

N-((1R)-1-{3-[2-(4-isopropoxyphenoxy)-1,3-thiazol-5-yl]isoxazol-5-yl}ethyl)acetamide Example 15A 2-[(1R)-1-methylprop-2-ynyl]-1H-isoindole-1,3(2H)-dione To a solution of S-(−)-propargyl-2-ol (2.5 g, 0.035 mol), phthalimide (5.4 g, 0.037 mol) and triphenylphosphine (14.1 g, 0.055 mol) in tetrahydrofuran was added a solution of diethyl azodicarboxylate (24.9 mL, 0.055 mol) in toluene at 0° C. drop wise. Then the reaction mixture was stirred at room temperature for 3 hours. The solvent was removed and the residue was dissolved in ether and stored in freezer overnight. The solution was filtered and the filtrate was concentrated and purified on silica gel (5~30% ethyl acetate in hexane) to give 4.15 g of the title compound (60% yield). $^1$H NMR (500 MHz, CDCl$_3$) δ ppm 1.72 (d, J=7.32 Hz, 6H) 2.35 (d, J=2.44 Hz, 1H) 5.18-5.25 (m, 1H) 7.70-7.75 (m, 2H) 7.83-7.89 (m, 2H). MS (ESI) m/z 232.0 (M+33)+.

Example 15B 2-((1R)-1-{3-[2-(4-isopropoxyphenoxy)-1,3-thiazol-5-yl]isoxazol-5-yl}ethyl)-1H-isoindole-1,3(2H)-dione The title compound was prepared using procedure as described in Example 1F, substituting Example 15A for Example 1F-1. 1H NMR (300 MHz, CHLOROFORM-D) δ ppm 1.35 (d, J=5.88 Hz, 6H) 1.91 (d, J=6.99 Hz, 3H) 4.42-4.61 (m, 1H) 5.59-5.75 (m, 1H) 6.50 (s, 1H) 6.86-6.96 (m, 2H) 7.13-7.24 (m, 2H) 7.53 (s, 1H) 7.69-7.79 (m, 2H) 7.81-7.90 (m, 2H). MS (ESI), m/z 476.2 (M+H)+. [α]: +76.0 (c=1, CHCl$_3$).

Example 15C

N-((1R)-1-{3-[2-(4-isopropoxyphenoxy)-1,3-thiazol-5-yl]isoxazol-5-yl}ethyl)acetamide The title compound was prepared using the procedure described in Example 1G, substituting Example 155B for 1F, $^1$H NMR (300 MHz, DMSO-$d_6$) δ ppm 1.29 (d, J=5.88 Hz, 6H) 1.42 (d, J=6.99 Hz, 3H) 1.87 (s, 3H) 4.55-4.72 (m, 1H) 5.10 (t, J=7.35 Hz, 1H) 6.89 (s, 1H) 6.97-7.07 (m, 2H) 7.29-7.39 (m, 2H) 7.95 (s, 1H) 8.51 (d, J=8.09 Hz, 1H). MS (ESI) m/z 388.1 (M+H)+. [α]: +91.6 (c=1, CHCl$_3$). The ee was determined by chiral HPLC (Chiralcel OD-H; Mobile Phase: Hexanes (0.2% diethylamine)/isopropyl alcohol=98/2; Flow rate: 0.8 mL/min) to be 100%

Example 16

N-((1S)-1-{3-[2-(4-isopropoxyphenoxy)-1,3-thiazol-5-yl]isoxazol-5-yl}ethyl)acetamide Example 16A 2-[(1S)-1-methylprop-2-ynyl]-1H-isoindole-1,3(2H)-dione To a solution of R-(+)-propargyl-2-ol (2.46 g, 20.8 mmol), phthalimide (3.065 g, 20.5 mmol) and triphenylphosphine (8.2 g, 31.3 mmol) in tetrahydrofuran (30 mL) at 0° C., was slowly added a solution of 40% diethyl azodicarboxylate in toluene (14 mL, 31.3 mmol). The reaction mixture was stirred at room temperature for 4 hours and the solvent was removed under vacuum. The residue was dissolved in a mixture of 5:1 ether:hexane and stirred at room temperature overnight. The resulting solid triphenylphosphine oxide was filtered off, washed with ether, and the filtrate was concentrated and purified using silica gel column chromatography using a gradient of 5 to 25% ethyl acetate in hexane to provide the title compound (2.56 gm). $^1$H NMR (300 MHz, DMSO-$d_6$) δ ppm 7.82-7.94 (m, 4H) 5.00-5.20 (m, 1H) 3.34 (d, J=2.57 Hz, 1H) 1.62 (d, J=7.35 Hz, 3H). MS (DCI): m/z 200 (M+H)+. The enantiomeric excess was determined by chiral HPLC (Chiralcel OD-H; Mobile Phase: Hex (0.2% diethylamine)/isopropyl alcohol=98/2; Flow rate: 0.8 mL/min) to be >96%,

Example 16B 2-((1S-1-{3-[2-(4-isopropoxyphenoxy)-1,3-thiazol-5-yl]isoxazol-5-yl}ethyl)-1H-isoindole-1,3(2H)-dione The title compound was prepared using procedure as described in Example 1F, substituting Example 16A for Example 1F-1. $^1$H NMR (300 MHz, CHLOROFORM-D) δ ppm 1.35 (d, J=5.88 Hz, 6H) 1.91 (d, J=6.99 Hz, 3H) 4.42-4.61 (m, 1H) 5.59-5.75 (m, 1H) 6.50 (s, 1H) 6.86-6.96 (m, 2H) 7.13-7.24 (m, 2H) 7.53 (s, 1H) 7.69-7.79 (m, 2H) 7.81-7.90 (m, 2H). MS (ESI), m/z 476.2 (M+H)$^+$. [α]: −74.7 (c=1, CHCl$_3$).

Example 16C

N-((1S)-1-{3-[2-(4-isopropoxyphenoxy)-1,3-thiazol-5-yl]isoxazol-5-yl}ethyl)acetamide The title compound was prepared according the procedure described in Example 1G, substituting Example 16B for Example 1F. $^1$H NMR (300 MHz, CDCl$_3$) δ ppm 7.52 (s, 1H) 7.15-7.24 (m, 2H) 6.86-6.98 (m, 2H) 6.36 (s, 1H) 5.79 (d, J=8.09 Hz, 1 H) 5.26-5.47 (m, 1H) 4.53 (quintet, J=6.25 Hz, 1H) 2.03 (s, 3H) 1.57 (d, J=6.99 Hz, 3H) 1.35 (d, J=6.25 Hz, 6H). MS (DCI): m/z 388 (M+H)$^+$. [α]: −86.8 (c=1, CHCl$_3$). The enantiomeric excess was determined by chiral HPLC (Chiralcel OD-H; Mobile Phase: Hex (0.2% diethylamine)/isopropyl alcohol=98/2; Flow rate: 0.8 mL/min) to be 99%.

Example 17

N-(1-{3-[4-(4-isopropoxyphenoxy)phenyl]isoxazol-5-yl}ethyl)acetamide

Example 17A 4-isopropoxyphenol

To a mixture of hydroquinone (20.0 g, 0.182 mmol) and 2-iodopropane (30.9 g, 0.182 mmol) in ethanol (25 mL) at refluxing was added KOH (88%, 12.2 mg, 0.191 mmol) in water (30 mL) over a period of 60 minutes. The resulting mixture was refluxed for 3 hours. The mixture was poured into 1N NaOH and extracted with ether (1×). The aqueous layer was acidified with 10% HCl to pH ~5 and extracted with ether (2×). The combined extracts were washed with brine, dried over MgSO$_4$ and concentrated. The residue was purified on silica gel eluting with ethyl acetate:hexane (1:8) to provide the title compound (13.01 g, 47.0%).

Example 17B 4-(4-isopropoxyphenoxy)benzaldehyde

To a mixture of Example 17A (1.50 g, 9.86 mmol), 4-bromobenzaldehyde (2.20 g, 11.9 mmol.), (K$_2$CO$_3$ (2.85 g, 20.6 mmol) and pyridine (50 mL) at 80° C. was added Cu(II) oxide (1.95 g, 24.5 mmol). After the addition, the mixture was refluxed vigorously for 20 hours. After cooling, dichloromethane was added and the mixture was filtered through Celite. The filtrate was concentrated to dryness. The residue was dissolved in ether, which was washed with 10% HCl (2×), 1N NaOH (2×), brine (1×), dried over MgSO$_4$, and concentrated to dryness. The residue was purified on silica gel eluting with a hexane and ethyl acetate gradient to give the desired product as a white solid (1.42 g, 56%).

Example 17C 4-(4-isopropoxyphenoxy)benzaldehyde oxime

To a solution of Example 17B (1.42 g, 5.56 mmol) in pyridine (10 mL) was added hydroxylamine hydrochloride (3.30 g, 47.5 mmol). The mixture was heated to reflux with a heat gun. After cooling, the mixture was poured into 10% HCl. The precipitates were collected and washed with 10% HCl followed by water, and then dried under vacuum at 50° C. overnight to give the desired product as a white solid (1.48 g, 98%).

Example 17D

N-hydroxy-4-(4-isopropoxyphenoxy)benzenecarboximidoyl chloride

To a solution of Example 17C (1.48 g, 5.56 mmol) in N,N-dimethyl formamide (15 mL) was added N-chlorosuccinimide (0.70 g, 5.24 mmol) at room temperature. The mixture was stirred at room temperature overnight. The mixture was poured into water. The aqueous layer was extracted with ether washed with water, then brine, and dried over MgSO$_4$ and concentrated to give the title compound as an oil (1.67 g, 100%),

Example 17E 2-(1-{3-[4-(4-isopropoxyphenoxy)phenyl]isoxazol-5-yl}ethyl)-1H-isoindole-1,3(2H)-dione To a solution of Example 17D (1.67 g, 5.46 mmol) in toluene (50 mL) was added K$_2$CO$_3$ (2.25 g, 16.3 mmol) and Example 1F-1 (1.10 g, 5.52 mmol). The mixture was heated to reflux for 3 hours. The reaction was diluted with dichloromethane and the solid was filtered off. The filtrate was concentrated. The residue was purified on silica gel eluting with ethyl acetate:hexane gradient to give the desired product as a white solid (1.68 g, 66%).

Example 17F

1-{3-[4-(4-isopropoxyphenoxy)phenyl]isoxazol-5-yl}ethanamine

To a solution of Example 17E (168 g, 3.59 mmol) in dichloromethane (25 ml) and ethanol (2.5 mL) was added hydrazine monohydrate (100 mL, 20.6 mmol). The mixture was stirred at room temperature overnight. The reaction was filtered and the filtrate concentrated. The residue was dissolved in dichloromethane again and filtered. The filtrate was concentrated to give the amine as a colorless oil (1.20 g, theory: 100%).

Example 17G

N-(1-{3-[4-(4-isopropoxyphenoxy)phenyl]isoxazol-5-yl}ethyl)acetamide

A solution of Example 17F (600 mg, 1.79 mmol) in tetrahydrofuran (5 mL) and triethyl amine (1.0 mL) was cooled to 0° C. To this was added acetyl chloride (300 μL, 4.22 mmol) at 0° C. The mixture was stirred at room temperature for 30 minutes. The reaction was diluted with dichloroethane, which was washed with water and concentrated. The residue was purified on silica gel eluting with hexane and ethyl acetate gradient to give the desired product as a white solid (500 mg, 77%). MS (DCI): m/z 381 (M+H); $^1$H NMR (300 MHz, CDCl$_3$) δ ppm 7.66-7.76 (m, 2H), 6.95-7.04 (m, 4H), 6.86-6.93 (m, 2H), 6.40 (s, 1H), 5.82 (d, J=8.46 Hz, 1H), 5.32-5.47 (m, 1H), 4.43-4.59 (m, 1H), 2.04 (s, 3H), 1.58 (d, J=6.99 Hz, 3H), 1.35 (d, J=6.25 Hz, 6H).

Example 18

N-(1-{3-[2-(2-chloro-4-methoxyphenoxy)-1,3-thiazol-5-yl]isoxazol-5-yl}ethyl)acetamide Example 18A 2-(2-chloro-4-methoxyphenoxy)-1,3-thiazole-5-carbaldehyde This reaction was carried out by using the same procedure as described in Example 1C, substituting Example 9A for Example 1B. $^1$H NMR (500 MHz, CDCl$_3$) δ ppm 3.83 (s, 3H) 6.88 (dd, J=9.00, 2.90 Hz, 1H) 7.04 (d, J=3.05 Hz, 1H) 7.22-7.31 (m, 1H) 7.89 (s, 1H), 9.84 (s, 1H). MS (ESI) m/z 305.0 (M+37)$^+$.

Example 18B 2-(2-chloro-4-methoxyphenoxy)-1,3-thiazole-5-carbaldehyde oxime

The title compound was prepared using the method described for Example 1D, substituting Example 18S for Example 1C. $^1$H NMR (300 MHz, DMSO-d$_6$) δ ppm 3.82 (s, 3H) 7.03 (dd, J=9.19, 2.94 Hz, 1H) 7.25 (d, J=2.94 Hz, 1H) 7.52 (d, J=8.82 Hz, 1 H) 7.68 (s, 1H) 7.81 (s, 1H) 12.02 (s, 1H). MS (ESI) m/z 285.0 (M+H)$^+$.

Example 18C 2-(2-chloro-4-methoxyphenoxy)-N-hydroxy-1,3-thiazole-5-carboximidoyl chloride The title compound was prepared using the method described for Example 1E, substituting Example 18B for Example 1D $^1$H NMR (300 MHz, DMSO-d$_6$) δ ppm 3.82 (s, 3 H) 7.04 (dd, J=9.19, 2.94 Hz, 1H) 7.26 (d, J=2.94 Hz, 1H) 7.54 (d, J=8.82 Hz, 1 H) 7.66 (s, 1H) 12.48 (s, 1H). MS (ESI) m/z 300.0 (M−18)$^+$.

Example 18D 2-(1-{3-[2-(2-chloro-4-methoxyphenoxy)-1,3-thiazol-5-yl]isoxazol-5-yl}ethyl)-1H-isoindole-1,3(2H)-dione The title compound was prepared using the method described for Example 1F, substituting Example 18C for Example 1E $^1$H NMR (300 MHz, CDCl$_3$) δ ppm 1.91 (d, J=7.35 Hz, 3H) 3.82 (s, 3H) 5.68 (q, J=7.35 Hz, 1H) 6.51 (s, 1H) 6.87 (dd, J=9.19 Hz, 1H) 7.02 (d, J=2.94 Hz, 1H) 7.28 (none, 1H) 7.30 (s, 1H) 7.50 (s, 1H) 7.70-7.80 (m, 2H) 7.82-7.91 (m, 2H). MS (ESI) m/z 482.1 (M+H)$^+$.

Example 18E

N-(1-{3-[2-(2-chloro-4-methoxyphenoxy)-1,3-thiazol-5-yl]isoxazol-5-yl}ethyl)acetamide The title compound was prepared using the method described for Example 1G, substituting Example 18D for Example 1F. $^1$H NMR (300 MHz, DMSO-d$_6$) δ ppm 1.42 (d, J=6.99 Hz, 3H) 1.87 (s, 3H) 3.83 (s, 3H) 5.10 (t, J=7.17 Hz, 1H) 6.89 (s, 1H) 7.05 (dd, J=9.01, 3.13 Hz, 1H) 7.27 (d, J=2.94 Hz, 1H) 7.56 (d, J=9.19 Hz, 1H) 7.94 (s, 1H) 8.51 (d, J=8.09 Hz, 1H). MS (ESI) m/z 394.0 (M+H)$^+$.

Example 19 methyl 1-{3-[2-(2-chloro-4-methoxyphenoxy)-1,3-thiazol-5-yl]isoxazol-5-yl}ethylcarbamate The title compound was synthesized by using the procedure as described for Example 1G, substituting Example 18D for Example 1F, and substituting methyl chloroformate for acetic anhydride. $^1$H NMR (300 MHz, DMSO-d$_6$) δ ppm 1.44 (d, J=6.99 Hz, 3H) 3.57 (s, 3H) 3.83 (s, 3H) 4.78-4.95 (m, 1H) 6.90 (s, 1H) 7.05 (dd, J=9.19, 2.94 Hz, 1H) 7.27 (d, J=3.31 Hz, 1H) 7.56 (d, J=9.19 Hz, 1H) 7.91 (d, J=8.09 Hz, 1H) 7.96 (s, 1H). MS (ESI) m/z 410.0 (M+H)$^+$.

Example 20

N-(1-{3-[2-(2-chloro-4-methoxyphenoxy)-1,3-thiazol-5-yl]isoxazol-5-yl}ethyl)-2-methylpropanamide The title compound was synthesized using the procedure as described for Example 1G, substituting Example 18D for Example 1F, and substituting isobutyryl chloride for acetic anhydride. $^1$H NMR (300 MHz, DMSO-d$_6$) δ ppm 1.02 (d, J=6.62 Hz, 6H) 1.43 (d, J=6.99 Hz, 3H) 2.31-2.47 (m, 1H) 3.83 (s, 3H) 5.11 (t, J=7.35 Hz, 1H) 6.86 (s, 1 H) 7.05 (dd, J=9.19, 2.94 Hz, 1H) 7.27 (d, J=2.94 Hz, 1H) 7.56 (d, J=8.82 Hz, 1H) 7.95 (s, 1H) 8.39 (d, J=8.09 Hz, 1H). MS (ESI) m/z 422.1 (M+H)$^+$.

Example 21

N-(1-{3-[2-(2-chloro-4-methoxyphenoxy)-1,3-thiazol-5-yl]isoxazol-5-yl}ethyl)cyclopropanecarboxamide The title compound was synthesized using the procedure as described for Example 1G, substituting Example 18D for Example 1F, and substituting cyclopropanecarbonyl chloride for acetic anhydride. $^1$H NMR (300 MHz, DMSO-d$_6$) δ ppm 0.62-0.77 (m, 4H) 1.44 (d, J=6.99 Hz, 3H) 1.51-1.65 (m, 1H) 3.83 (s, 3H) 5.14 (t, J=7.35 Hz, 1H) 6.90 (s, 1H) 7.05 (dd, J=9.19, 2.94 Hz, 1H) 7.27 (d, J=2.94 Hz, 1H) 7.56 (d, J=8.82 Hz, 1 H) 7.96 (s, 1H) 8.73 (d, J=7.72 Hz, 1H), MS (ESI) m/z 420.1 (M+H)$^+$.

Example 22 methyl 1-{3-[4-(4-isopropoxyphenoxy)phenyl]isoxazol-5-yl}ethylcarbamate

A solution of Example 17F (340 mg, 1.00 mmol) in tetrahydrofuran (5 mL) and triethyl amine (1.0 mL) was cooled to 0° C. To this was added methyl chloroformate (200 µL, 2.59 mmol) at 0° C. The mixture was stirred at room temperature for 30 minutes. The reaction was diluted with dichloromethane, which was washed with water (1×) and concentrated. The residue was purified on silica gel eluting with hexane and ethyl acetate gradient to give the desired product as a white solid (234 mg, 59%). MS (DCI): m/z 397 (M+H); $^1$H NMR (300 MHz, CDCl$_3$) δ ppm 7.65-7.77 (m, 2H), 6.94-7.07 (m, 4H), 6.85-6.93 (m, 2H), 6.40 (s, 1H), 5.01-5.16 (m, 1H), 4.44-4.58 (m, 1H), 3.71 (s, 3H), 1.58 (d, J=6.99 Hz, 3H), 1.35 (d, J=6.25 Hz, 6H).

Example 23

N-(1-{3-[4-(4-isopropoxyphenoxy)phenyl]isoxazol-5-yl}ethyl)urea

To a solution of Example 17F (377 mg, 1.12 mmol) in dichloromethane (10 mL) at 0° C. was added trichloroacetyl isocyanate (145 µL, 1.22 mmol). The mixture was stirred at 0° C. for 10 minutes. The reaction was concentrated and the residue was dissolved in methanol (~60 mL) and a small amount of Na$_2$CO$_3$ was added. The mixture was stirred at room temperature for 3 hours before being concentrated. The residue was dissolved in dichloromethane, which was washed with water (1×) and concentrated. The residue was purified on silica gel eluting with hexane and ethyl acetate gradient to give the desired product as a white solid (286 mg, 67%), MS (DCI): m/z 382 (M+H); $^1$H NMR (300 MHz, DMSO-d$_6$) δ ppm 7.78-7.86 (m, 2H), 6.99-7.08 (m, 4H), 6.94-6.99 (m, 2H), 6.75 (s, 1H), 6.61 (d, J=8.46 Hz, 1H), 5.59 (br s, 2H), 4.90-5.02 (m, 1H), 4.53-4.63 (m, 1H), 1.41 (d, J=6.99 Hz, 3H), 1.27 (d, J=5.88 Hz, 6H).

Example 24

N-(1-{5-[5-(4-isopropoxyphenoxy)-1,3,4-thiadiazol-2-yl]thien-2-yl}ethyl)acetamide Example 24A 2-bromo-5-(4-methoxyphenoxy)-1,3,4-thiadiazole 2,5-dibromo-1,3,4-thiadiazole (2 g, 8.16 mmol), (prepared according to Example 1 as described in U.S. Pat. No. 5,847,149) was dissolved in N,N-dimethyl formamide (65 mL) and the resulting solution was treated with K$_2$CO$_3$ (1.69 g, 12.24 mmol) and 4-methoxyphenol (1.01 g, 8.16 mmol). The reaction mixture was heated at 90° C. for 1.5 hours, cooled to 25° C., poured into water (150 mL) and extracted with diethyl ether (2×150 mL) The combined organic layers were washed with 1N NaOH (1×100 mL), water (3×100 mL) and brine (1×100 mL), dried (Na$_2$SO$_4$), filtered and evaporated to provide 2.3 g of a light yellow oil. The residue was purified by flash chromatography on silica gel eluting with a solvent gradient from 1% to 14% ethyl acetate in hexanes to provide 1.86 g (79%) of the title compound, $^1$H NMR (300 MHz, DMSO-d$_6$) δ ppm 7.40 (d, J=9.19 Hz, 2H) 7.04 (d, J=9.19 Hz, 2H) 3.79 (s, 3H); MS (APCI) m/z 289 (M+H)$^+$.

Example 24B

4-[(5-bromo-1,3,4-thiadiazol-2-yl)oxy]phenol

A solution of Example 24A (1.63 g, 5.67 mmol) in CH$_2$Cl$_2$ (75 mL) was cooled to −78° C. and the resulting suspension was treated with BBr$_3$ (22.67 mmol, 2.14 mL) drop wise over 2 minutes. The reaction was stirred at 25° C. for 2 hours and was poured into a 200 mL ice/water mixture. The resulting bilayer was stirred vigorously for 0.5 hours and a white precipitate formed. The solids were filtered, washed with water (1×20 mL) and dried in a vacuum oven to provide 1.35 g (87%) of the title compound as a white solid. $^1$H NMR (300 MHz, DMSO-d$_6$) δ ppm 9.79 (br. s, 1H) 7.27 (d, J=9.19 Hz, 2H) 6.84 (d, J=9.19 Hz, 2H); MS (DCI) m/z 275 (M+H)$^+$.

Example 24C 2-bromo-5-(4-isopropoxyphenoxy)-1,3,4-thiadiazole

A solution of Example 24B (1.4 g, 5.11 mmol) in N,N-dimethyl formamide (20 mL) was treated with K$_2$CO$_3$ (1.06 g, 7.66 mmol) and 2-iodopropane (5.1 mL, 51.1 mmol) and the reaction mixture was sealed in a screw-top pressure vessel and heated at 85° C. for 2 hours. The reaction was cooled to 25° C., poured into water (200 mL), and extracted with diethyl ether (2×100 mL). The combined organic layers were washed with water (3×80 mL) and brine (80 mL), dried (Na$_2$SO$_4$), filtered and evaporated to provide 1.6 g of a light brown solid. The residue was purified by flash chromatography on silica gel eluting with a solvent gradient from 1% to 14% ethyl acetate in hexanes to provide 0.8 g (50%) of the title compound as a clear colorless oil. $^1$H NMR (300 MHz, DMSO-d$_6$) δ ppm 7.37 (d, J=9.19 Hz, 2H) 7.01 (d, J=9.19 Hz, 2H) 4.63 (heptet, J=5.88 Hz, 1H) 1.27 (d, J=5.88 Hz, 6H); MS (ESI) m/z 316.9 (M+H)$^+$.

Example 24D 2-(4-isopropoxyphenoxy)-5-thien-2-yl-1,3,4-thiadiazole

A solution of Example 24C (0.58 g, 1835 mmol) and 2-tributylstannylthiophene (0.816 ml, 2.57 mmol) in DME (15 mL) was degassed by bubbling nitrogen into the reaction mixture via a 20-gauge needle for 10 minutes. PdCl$_2$(PPh$_3$)$_2$ was added and the reaction was heated at reflux under a nitrogen atmosphere for 20 hours. The reaction was cooled to 25° C. and concentrated under reduced pressure on a rotary evaporator to provide 1.6 g of a golden oil. The concentrate was purified by flash chromatography on silica gel eluting with a solvent gradient from 1% to 15% ethyl acetate in hexanes to provide 0.51 g (88%) of the title compound as a pale purple oil which crystallized on standing, $^1$H NMR (300 MHz, DMSO-d$_6$) δ ppm 7.79 (d, J=5.15 Hz, 1H) 7.66 (d, J=3.68 Hz, 1H) 7.40 (d, J=9.19 Hz, 2H) 7.18 (dd, J=5.15, 3.68 Hz, 1H) 7.03 (d, J=9.19 Hz, 2H) 4.64 (heptet, J=5.88 Hz, 1H) 1.28 (d, J=5.88 Hz, 6H); MS (DCI) m/z 319 (M+H)$^+$.

Example 24E

1-{5-[5-(4-isopropoxyphenoxy)-1,3,4-thiadiazol-2-yl]thien-2-yl}ethanol

A solution of Example 24D (0.35 g, 1.1 mmol) in tetrahydrofuran (14 mL) was cooled to −78° C. under a nitrogen atmosphere and was treated with n-butyllithium (2.5M in hexanes, 0.925 mL, 2.31 mmol) drop wise over 5 minutes. After stirring at −78° C. for 10 min, acetaldehyde (0.309 mL, 5.5 mmol) was added and the reaction was allowed to warm to −30° C. The reaction was stirred for 10 min at −30° C. and 1N HCl (20 mL) was added. The resulting bilayer was stirred at 25° C. for 5 min and was extracted with ethyl ether (80 mL). The organic phase was washed with brine (20 mL), dried (Na$_2$SO$_4$), filtered, and evaporated to provide 0.74 g of a light brown oil. The residue was purified by flash chromatography on silica gel eluting with a solvent gradient from 10% to 35% ethyl acetate in hexanes to provide 0.34 g (86%) of the title compound as a pale green oil. $^1$H NMR (300 MHz, DMSO-d$_6$) δ ppm 7.48 (d, J=3.68 Hz, 1H) 7.39 (d, J=9.19 Hz, 2H) 7.02 (d, J=9.19 Hz, 2H) 6.96 (dd, J=3.68, 0.74 Hz, 1H) 5.78 (d, J=5.15 Hz, 1H) 4.88-5.06 (m, 1H) 4.63 (heptet, J=5.88 Hz, 1H) 1.43 (d, J=6.25 Hz, 3H) 1.28 (d, J=5.88 Hz, 6H); MS (ESI) m/z 363 (M+H)$^+$.

Example 24F 2-(1-{5-[5-(4-isopropoxyphenoxy)-1,3,4-thiadiazol-2-yl]thien-2-yl}ethyl)-1H-isoindole-1,3(2H)-dione A solution of Example 24E (0.37 g, 1.025 mmol), phthalimide (0.151 g, 1.025 mmol), and triphenyl phosphine (0.537 g, 2.05 mmol) in tetrahydrofuran (5 mL) was treated with diisopropyl azodicarboxylate (0.385 mL, 1.85 mmol) and the resulting solution was stirred at 25° C. for 3 hours. The reaction was concentrated under reduced pressure on a rotary evaporator to provide 1.4 g of a yellow oil. The concentrate was purified by flash chromatography on silica gel eluting with a solvent gradient from 1% to 20% ethyl acetate in hexanes to provide 0.49 g (98%) of the title compound as a white solid. $^1$H NMR (300 MHz, DMSO-d$_6$) δ ppm 7.76-7.98 (m, 4H) 7.51 (d, J=3.68 Hz, 1H) 7.38 (d, J=9.19 Hz, 2H) 7.14 (dd, J=3.68, 0.92 Hz, 1H) 7.01 (d, J=9.19 Hz, 2H) 5.60-5.77 (m, 1H) 4.55-4.70 (m, 1H) 1.88 (d, J=7.35 Hz, 3H) 1.27 (d, J=5.88 Hz, 6H); MS (ESI) m/z 492 (M+H)$^+$.

Example 24G

1-{5-[5-(4-isopropoxyphenoxy)-1,3,4-thiadiazol-2-yl]thien-2-yl}ethanamine

A solution of Example 24F (0.48 g, 0.98 mmol) in CH$_2$Cl$_2$/ethanol (1:1, v/v, 12 mL) was treated with hydrazine hydrate (0.476 mL, 9.79 mmol). The reaction was stirred at 25° C. for 5 hours and was concentrated under reduced pressure on a rotary evaporator to provide a residual oil. The concentrate was treated with CH$_2$Cl$_2$ (15 mL) and a white suspension formed. The suspension was filtered and the filtrate was concentrated on a rotary evaporator to provide 0.32 g of a pale yellow oil. The concentrate was purified by flash chromatography on silica gel eluting with a solvent gradient from 98:1:1 to 97:2:1 CH$_2$Cl$_2$/CH$_3$OH/NH$_4$OH to provide 0.09 g (25%) of the title compound as a colorless oil. $^1$H NMR (300 MHz, DMSO-d$_6$) δ ppm 7.46 (d, J=3.68 Hz, 1H) 7.38 (d, J=9.19 Hz, 2H) 7.02 (d, J=9.19 Hz, 2H) 6.96 (dd, J=3.68, 0.74 Hz, 1H) 4.63 (heptet, J=5.88 Hz, 1H) 4.17-4.29 (m, 1H) 1.35 (d, J=6.62 Hz, 3H) 1.28 (d, J=5.88 Hz, 6H); MS (APCI) m/z 362 (M+H)$^+$.

Example 24H

N-(1-{5-[5-(4-isopropoxyphenoxy)-1,3,4-thiadiazol-2-yl]thien-2-yl}ethyl)acetamide A solution of Example 24G (0.044 g, 0.122 mmol) in CH$_2$Cl$_2$ (2 mL) was treated with triethyl amine (0.051 mL, 0.366 mmol) followed by acetyl chloride (0.0173 mL, 0.244 mmol). The reaction was stirred at 25° C. for 1 hour and was concentrated under reduced pressure on a rotary evaporator. The residual white solids (0.075 g) were purified by flash chromatography on silica gel eluting with a solvent gradient of 30% to 50% ethyl acetate in hexanes to provide 0.035 g (71%) of the title compound as a white solid. $^1$H NMR (300 MHz, DMSO-d$_6$) δ ppm 8.49 (d, J=8.09 Hz, 1H) 7.49 (d, J=3.68 Hz, 1H) 7.39 (d, J=9.19 Hz, 2H) 7.02 (d, J=9.19 Hz, 2H) 6.99 (dd, J=3.68, 0.74 Hz, 1H) 5.09-5.20 (m, 1 H) 4.63 (heptet, J=5.88 Hz, 1H) 1.85 (s, 3H) 1.45 (d, J=6.99 Hz, 3H) 1.28 (d, J=5.88 Hz, 6H); MS (ESI) m/z 404 (M+H)$^+$.

Example 25

N-(1-{3-[2-(2-chloro-4-isopropoxyphenoxy)-1,3-thiazol-5-yl]isoxazol-5-yl}ethyl)acetamide Example 25A 2-(2-chloro-4-isopropoxyphenoxy)-1,3-thiazole To a mixture of Example 9B (2.3 g, 0.01 mol), isopropanol (1.2 mL, 0.015 mol) and triphenylphosphine (3.93 g, 0.015 mol) in dry tetrahydrofuran was added diethyl azodicarboxylate (2.61 g, 0.015 mol) drop wise and the reaction was stirred at room temperature overnight. The solvent was removed and the residue was purified on silica gel (ethyl acetate/hexane, 5~35%) to give 2.4 g of product as a light yellow oil (89% yield), $^1$H NMR (300 MHz, CDCl$_3$) δ ppm 1.35 (d, J=5.88 Hz, 6H) 4.42-4.57 (m, 1H) 6.76-6.86 (m, 2H) 6.99 (d, J=2.94 Hz, 1H) 7.19 (d, J=3.68 Hz, 1H) 7.23 (s, 1H), MS (ESI) m/z 269.9 (M+H)$^+$.

Example 25B 2-(2-chloro-4-isopropoxyphenoxy)-1,3-thiazole-5-carbaldehyde

The title compound was prepared as described in Example 1C, substituting Example 25A for Example 1B. $^1$H NMR (300 MHz, CDCl$_3$) δ ppm 1.36 (d, J=5.88 Hz, 6H) 4.41-4.62 (m, 1H) 6.85 (dd, J=9.01, 2.76 Hz, 1H) 7.01 (d, J=2.57 Hz, 1H) 7.23 (d, J=8.82 Hz, 1H) 7.90 (s, 1H) 9.84 (s, 1H). M/Z: 297.9 (M+H)$^+$.

Example 25C 2-(2-chloro-4-isopropoxyphenoxy)-1,3-thiazole-5-carbaldehyde oxime

The title compound was prepared as described in Example 1D, substituting Example 25B for Example 1C, $^1$H NMR (300 MHz, DMSO-d$_6$) δ ppm 1.28 (d, J=5.88 Hz, 6H) 4.56-4.78 (m, 1H) 7.00 (dd, J=8.82, 2.94 Hz, 1H) 7.21 (d, J=2.94 Hz, 1H) 7.48 (d, J=9.19 Hz, 1H) 7.68 (s, 1H) 7.81 (s, 1H) 12.02 (s, 1H). MS (ESI) m/z 313.0 (M+H)$^+$.

Example 25D 2-(2-chloro-4-isopropoxyphenoxy)-N-hydroxy-1,3-thiazole-5-carboximidoyl chloride The title compound was prepared as described in Example 1E, substituting Example 25C for Example 1D, $^1$H NMR (300 MHz, DMSO-d$_6$) δ ppm 1.28 (d, J=6.25 Hz, 6H) 4.58-

4.77 (m, 1H) 7.01 (dd, J=9.19, 2.94 Hz, 1H) 7.22 (d, J=2.94 Hz, 1H) 7.50 (d, J=9.19 Hz, 1H) 7.66 (s, 1H) 12.47 (s, 1H) MS (ESI) m/z 328.0 (M−18)+.

Example 25E 2-(1-{3-[2-(2-chloro-4-isopropoxyphenoxy)-1,3-thiazol-5-yl]isoxazol-5-yl}ethyl)-1H-isoindole-1,3(2H)-dione The title compound was prepared as described in Example 1F, substituting Example 25D for Example 1E. $^1$H NMR (300 MHz, CDCl$_3$) δ ppm 1.91 (d, J=7.35 Hz, 3H) 3.82 (s, 3H) 5.68 (q, J=7.35 Hz, 1H) 6.51 (s, 1H) 6.87 (dd, J=9.19, 2.94 Hz, 1H) 7.02 (d, J=2.94 Hz, 1H) 7.28 (none, 1H) 7.30 (s, 1H) 7.50 (s, 1H) 7.70-7.80 (m, 2H) 7.82-7.91 (m, 2H). MS (ESI) m/z 542.2 (M+33)+.

Example 25F

N-(1-{3-[2-(2-chloro-4-isopropoxyphenoxy)-1,3-thiazol-5-yl]isoxazol-5-yl}ethyl)acetamide This reaction was carried out by using the same procedure as described for Example 1G, substituting Example 25E for Example 1F. $^1$H NMR (300 MHz, DMSO-d$_6$) δ ppm 1.29 (d, J=6.25 Hz, 6H) 1.42 (d, J=6.99 Hz, 3H) 1.87 (s, 3H) 4.61-4.77 (m, 1H) 5.10 (t, J=7.35 Hz, 1H) 6.90 (s, 1H) 7.02 (dd, J=9.19, 2.94 Hz, 1H) 7.23 (d, J=2.94 Hz, 1H) 7.53 (d, J=8.82 Hz, 1H) 7.94 (s, 1H) 8.52 (d, J=8.09 Hz, 1H). MS (ESI) m/z 422.1 (M+H)+.

Example 26 methyl 1-{3-[2-(2-chloro-4-isopropoxyphenoxy)-1,3-thiazol-5-yl]isoxazol-5-yl}ethylcarbamate The title compound was synthesized by using the procedure as described for Example 1G, substituting Example 25E for Example 1F, and substituting methyl chloroformate for acetic anhydride. $^1$H NMR (300 MHz, DMSO-d$_6$) δ ppm 1.29 (d, J=5.88 Hz, 6H) 1.44 (d, J=6.99 Hz, 3H) 3.56 (s, 3H) 4.63-4.76 (m, 1H) 4.79-4.95 (m, 1H) 6.90 (s, 1H) 7.02 (dd, J=9.19, 2.94 Hz, 1H) 7.23 (d, J=2.94 Hz, 1H) 7.52 (d, J=9.19 Hz, 1H) 7.86-7.93 (m, 1H) 7.96 (s, 1H). MS (ESI) m/z 438.1 (M+H)+.

Example 27

N-(1-{3-[2-(2-chloro-4-isopropoxyphenoxy)-1,3-thiazol-5-yl]isoxazol-5-yl}ethyl)-2-methylpropanamide The title compound was synthesized by using the procedure as described for Example 1G, substituting Example 25E for Example 1F, and substituting isobutyryl chloride for acetic anhydride. $^1$H NMR (300 MHz, DMSO-d$_6$) δ ppm 1.02 (d, J=6.99 Hz, 6H) 1.29 (d, J=5.88 Hz, 6H) 2.32-2.47 (m, 1H) 4.62-4.77 (m, 1H) 5.03-5.18 (m, 1H) 6.86 (s, 1H) 7.02 (dd, J=9.19, 2.94 Hz, 1H) 7.23 (d, J=2.94 Hz, 1H) 7.52 (d, J=8.82 Hz, 1H) 7.95 (s, 1H) 8.38 (d, J=8.09 Hz, 1H). MS (ESI) m/z 450.1 (M+H)+.

Example 28

N-1-{3-[2-(2-chloro-4-isopropoxyphenoxy)-1,3-thiazol-5-yl]isoxazol-5-yl}ethyl)cyclopropanecarboxamide The title compound was synthesized by using the procedure as described for Example 1G, substituting Example 25E for Example 1F, and substituting cyclopropanecarbonyl chloride for acetic anhydride. $^1$H NMR (300 MHz, DMSO-d$_6$) δ ppm 0.63-0.75 (m, 4H) 1.29 (d, J=5.88 Hz, 6H) 1.44 (d, J=6.99 Hz, 3H) 1.52-1.65 (m, 1H) 4.59-4.77 (m, 1H) 5.14 (t, J=7.35 Hz, 1H) 6.90 (s, 1H) 7.02 (dd, J=8.82, 2.94 Hz, 1H) 7.23 (d, J=2.57 Hz, 1H) 7.52 (d, J=9.19 Hz, 1H) 7.96 (s, 1H) 8.73 (d, J=7.72 Hz, 1H). MS (ESI) m/z 448.0 (M+H)+.

Example 29

N-[1-(3-{2-[4-(isopropylamino)phenoxy]-1,3-thiazol-5-yl}isoxazol-5-yl)ethyl]acetamide Example 29A tert-butyl 4-(1,3-thiazol-2-yloxy)phenylcarbamate N-Boc-4-hydroxy-aniline (3.9 g, 0.019 mol) was combined with 2-bromothiazole (2.4 mL, 0.027 mol) in DMSO (20 mL) at room temperature. K$_2$CO$_3$ (3.9 g, 0.028 mol) was added and with rapid stirring, the reaction mixture was heated at about 140° C. for 5 hours. After cooling to room temperature, the reaction mixture was poured into water (300 mL), extracted with ethyl acetate (2×) and the combined organics were dried over MgSO$_4$. Decolorizing charcoal was added, stirred for 30 minutes and filtered through a plug of celite and silica (1:1) to obtain an amber filtrate. The solvent was removed by rotary evaporation and the residue was purified by flash column chromatography (ethyl acetate:hexanes; 5%-50% ethyl acetate gradient) to give the title compound (1.4 g, 4.8 mmol, 25%) MS (ESI APCI) m/z 293.0 (M+H+); $^1$H NMR (300 MHz, DMSO-d$_6$) δ 9.49 (s, 1H) 7.53 (d, J=9.0 Hz, 2H) 7.21-7.28 (m, 2H) 7.16-7.19 (m, 2H) 1.48 (s, 9H).

Example 29B tert-butyl 4-[(5-formyl-1,3-thiazol-2-yl)oxy]phenylcarbamate

Example 29A (2.5 g, 8.6 mmol) was dissolved in anhydrous tetrahydrofuran (8.6 ml) and added drop wise to a −78° C. solution of n-butyl lithium (2.5 M hexanes, 7.4 mL) under nitrogen. The reaction mixture was stirred at −78° C. for 20 minutes upon which time a tetrahydrofuran (8.6 mL) solution of formylmorpholine (3.0 mL, 30.1 mmol) was added drop wise. The reaction was stirred at −78° C. for 15 minutes and then slowly warmed to room temperature. The reaction mixture was poured into saturated aqueous NH$_4$Cl and extracted with ethyl acetate (2×). The combined organics were dried over Na$_2$SO$_4$, filtered and concentrated by rotary evaporation. The residue was purified by flash column chromatography (ethyl acetate:hexanes; 5%-50% ethyl acetate gradient) to give the title compound as an oil (1.37 g, 4.3 mmol). $^1$H NMR (300 MHz, DMSO-d$_6$) δ 9.86 (s, 1H) 9.52 (s, 1H) 8.30 (s, 1H) 7.57 (d, J=9.0 Hz, 2H) 7.34 (d, J=9.0 Hz, 2H) 1.40 (s, 9H).

Example 29C tert-butyl 4-({5-[(E)-(hydroxyimino)methyl]-1,3-thiazol-2-yl}oxy)phenylcarbamate Example 29B (1.0 g, 3.1 mmol) was combined with hydroxyamine hydrochloride (2.15 g, 31 mmol) in pyridine (3.75 mL, 46.5 mmol) and the reaction solution was stirred for 1.5 h at room temperature. The reaction was poured into saturated aqueous $NH_4Cl$ and was extracted with ethyl acetate (3×). The combined organics were washed with 5% aqueous citric acid (3×), dried ($Na_2SO_4$), filtered and concentrated by rotary evaporation. The residue was placed on high vacuum overnight to give the title compound (1.03 g, 3.07 mmol, 99%) as a white solid that was used in the next step without further purification. MS (ESI APCI) m/z 336.0 $(M+H^+)$.

Example 29D tert-butyl 4-({5-[(Z)-chloro(hydroxyimino)methyl]-1,3-thiazol-2-yl}oxy)phenylcarbamate Example 29C (1.03 g, 3.1 mmol) was dissolved in N,N-dimethyl formamide (10 mL) and N-chlorosuccinimide (435 mg, 3.2 mmol) was added in portions over 1 hour. The reaction was stirred overnight. Water was added and a fine white solid precipitated which was collected by filtration to give the title compound as a white solid, which was used in the next step without further purification.

Example 29E tert-butyl 4-[(5-{5-[1-(acetylamino)ethyl]isoxazol-3-yl}-1,3-thiazol-2-yl)oxy]phenylcarbamate Example 29D (541 mg, 1.5 mmol), N-(1-methyl-prop-2-ynyl)-acetamide (406 mg, 3.75 mmol; prepared as described in Gardner, J. N. et al Can. J. Chem. 51, 1973) and $K_2CO_3$ (1.0 g, 7.2 mmol) were combined in toluene (4 mL) and heated to reflux for 3.2 hours. The reaction was diluted with $CH_2Cl_2$ and filtered. The filtrate was concentrated by rotary evaporation and the residue was purified by flash column chromatography (eluting with ethyl acetate:hexanes; 5%-100% ethyl acetate gradient) to give the title compound as a solid (525 mg, 1.18 mmol, 79%). MS (ESI APCI) m/z 445.0 $(M+H^+)$; $^1H$ NMR (300 MHz, DMSO-$d_6$) δ 9.55 (s, 1H) 8.50 (d, J=6.0 Hz, 1H) 7.96 (s, 1H) 7.56 (d, J=9.00 Hz, 2H) 7.33 (d, J=9.0 Hz, 2H) 6.89 (s, 1H) 5.02-5.16 (m, 1H) 1.87 (s, 3H) 1.49 (s, 9H) 1.42 (D, J=6.0 Hz, 3H).

Example 29F

N-(1-{3-[2-(4-aminophenoxy)-1,3-thiazol-5-yl]isoxazol-5-yl}ethyl)acetamide

Example 29E (525 mg, 1.2 mmol) was dissolved in $CH_2Cl_2$ (6 mL). To this solution, trifluoroacetic acid (2.1 mL, 35% v/v) was added and the resulting solution was stirred for 3 hours. The reaction was concentrated by rotary evaporation and the residue was placed on high vacuum overnight to give the title compound (154 mg) as an amber oil, which was used in the next step without further purification. MS (ESI APCI) m/z 345.2 $(M+H^+)$.

Example 29G

N-[1-(3-{2-[4-(isopropylamino)phenoxy]-1,3-thiazol-5-yl}isoxazol-5-yl)ethyl]acetamide Example 29F (48.3 mg, 0.12 mmol) was dissolved in a 1 mL buffer solution (prepared by mixing 6 mL, acetic acid and 8.5 g sodium acetate in 250 mL methanol). To this was added acetone, (26 µL, 0.36 mmol) and $NaCNBH_3$ (23 mg, 0.36 mmol). The reaction solution was stirred at 60° C. for 3 hours, filtered through a syringe filter and purified by HPLC (water: acetonitrile; gradient of 5% to 90% acetonitrile) to provide the title compound (28.7 mg, 0.07 mmol, 62%) as a solid. MS (ESI APCI) m/z 387.1 $(M+H^+)$; $^1H$ NMR (300 MHz, DMSO-$d_6$) δ 8.48 (d, J=6.00 Hz, 1H) 7.93 (s, 1H) 7.11 (d, J=9.00 Hz, 2H) 6.87 (s, 1H) 6.61 (d, J=9.00 Hz, 2H) 5.67 (d, J=9.00 Hz, 1H) 5.03-5.17 (m, 1H) 3.44-3.61 (m, 1H) 1.86 (s, 3H) 1.41 (d, J=6.00 Hz, 3H) 1.14 (d, J=6.00 Hz, 6H).

Example 30

N-[1-(3-{2-[2-chloro-4-(cyclopropylmethoxy)phenoxy]-1,3-thiazol-5-yl}isoxazol-5-yl)ethyl]acetamide

Example 30A 2-(2-chloro-4-methoxyphenoxy-1,3-thiazole

To a suspension of 2-chloro-4-methoxyphenol (10 g, 63 mmol) and $K_2CO_3$ (9.7 g, 69.4 mmol) in N,N-dimethyl formamide (120 mL) was added 2-bromothiazole (11.4 g, 69.4 mmol). The suspension was heated at 150° C. for 4 hours, cooled to ambient temperature, and poured into water (1000 mL). The mixture was extracted with ether (2×300 mL) and the combined ether layers were dried ($MgSO_4$), filtered and concentrated. The resulting black oil was purified by flash chromatography on silica gel eluting with a solvent gradient from 10% to 25% ethyl acetate in hexanes to provide 12.3 g of the title compound (81%) as a light yellow liquid. $^1H$ NMR (300 MHz, DMSO-$d_6$) δ ppm 3.81 (s, 3H) 7.01 (dd, J=9.01, 3.13 Hz, 1H) 7.18-7.21 (m, 1H) 7.23 (t, J=3.13 Hz, 2H) 7.47 (d, J=9.19 Hz, 1H); MS (ESI) m/z 241.9 $(M+H)^+$.

Example 30B 2-(2-chloro-4-methoxyphenoxy)-1,3-thiazole-5-carbaldehyde

To a solution of Example 30A (12 g, 49.9 mmol) in tetrahydrofuran (100 mL) was added butyllithium (2.5 M in hexanes, 21 mL, 52.5 mmol) drop wise over 10 minutes at −78° C. under nitrogen. The mixture was stirred at −78° C. for 1 hour, and was treated with 4-formylmorpholine (5.3 mL, 52.4 mmol) drop wise over 5 minutes. The reaction was allowed to warm to 25° C. and was stirred for 2 hours. The reaction was cooled to 0° C. and quenched with saturated $NH_4Cl$ (600 mL). The resulting mixture was extracted with ethyl acetate (2×200 mL) and the combined organic layers were washed with brine, dried ($MgSO_4$), filtered, and concentrated to provide 13.2 g of the title compound (98%) as a light yellow liquid. $^1H$ NMR (300 MHz, DMSO-$d_6$) δ ppm 3.83 (s, 3H) 7.06 (dd, J=9.19, 2.94 Hz, 1H) 7.28 (d, J=2.94 Hz, 1H) 7.57 (d, J=9.19 Hz, 1H) 8.28 (s, 1H) 9.88 (s, 1H); MS (ESI) m/z 269.9 $(M+H)^+$.

Example 30C 2-(2-chloro-4-methoxyphenoxy-1,3-thiazole-5-carbaldehyde oxime

To a solution of Example 30B (13.05 g, 48.4 mmol) in pyridine (38.8 g, 484 mmol) was added hydroxylamine hydrochloride (33.7 g, 484 mmol). The mixture was heated at 80° C. for 0.5 hours, cooled to ambient temperature, treated with water (1000 mL) and filtered. The collected solids were dried in a vacuum oven to provide 13.2 g of the title compound (96%) as an off-white solid. $^1$H NMR (300 MHz, DMSO-$d_6$) δ ppm 3.82 (s, 3H) 7.03 (dd, J=9.01, 3.13 Hz, 1H) 7.25 (d, J=2.94 Hz, 1H) 7.52 (d, J=8.82 Hz, 1H) 7.68 (s, 1H) 7.81 (s, 1H) 12.02 (s, 1H); MS (ESI) m/z 284.9 (M+H)$^+$.

Example 30D 2-(2-chloro-4-methoxyphenoxy-N-hydroxy-1,3-thiazole-5-carboximidoyl chloride To a solution of Example 30C (12 g, 42 mmol) in N,N-dimethyl formamide (80 mL) was added N-chlorosuccinimide (5.6 g, 42 mmol). The mixture was stirred at ambient temperature for 16 hours, water (1000 mL) was added and the resulting suspension was filtered. The solids were dried in a vacuum oven to provide 12.8 g of the title compound (95%) as an off-white solid. $^1$H NMR (300 MHz, DMSO-$d_6$) δ ppm 3.82 (s, 3H) 7.04 (dd, J=8.82, 2.94 Hz, 1H) 7.26 (d, J=2.94 Hz, 1H) 7.54 (d, J=9.19 Hz, 1H) 7.66 (s, 1H) 12.48 (s, 1H); MS (ESI) m/z 319.9 (M+H)$^+$.

Example 30E 2-(1-{3-[2-(2-chloro-4-methoxyphenoxy)-1,3-thiazol-5-yl]isoxazol-5-yl}ethyl)-1H-isoindole-1,3(2H)-dione To a solution of Example 30D (8.13 g, 25.5 mmol) in toluene (200 mL) was added potassium carbonate (10.7 g, 76.5 mmol), followed by Example 1F-1 (5.07 g, 25.5 mmol). The mixture was refluxed for 4 hours, cooled to 25° C., diluted with dichloromethane (400 mL), and filtered. The filtrate was concentrated and purified by flash chromatography on silica gel eluting with a solvent gradient from 10% to 40% ethyl acetate in hexanes to give 7.1 g of the title compound (58%) as a light brown solid, $^1$H NMR (300 MHz, DMSO-$d_6$) δ ppm 1.81 (d, J=6.99 Hz, 3H) 3.82 (s, 3H) 5.57-5.69 (m, 1H) 7.04 (dd, J=8.82, 2.94 Hz, 1H) 7.18 (s, 1H) 7.26 (d, J=2.94 Hz, 1H) 7.56 (d, J=8.82 Hz, 1H) 7.86-7.96 (m, 5H); MS (ESI) m/z 481.8 (M+H)$^+$, 514.1 (M+Na)$^+$.

Example 30F 2-(1-{3-[2-(2-chloro-4-hydroxyphenoxy)-1,3-thiazol-5-yl]isoxazol-5-yl}ethyl)-1H-isoindole-1,3(2H)-dione To a solution of Example 30E (1.2 g, 2.5 mmol) in dichloromethane (20 mL) was added boron tribromide (0.95 mL, 10 mmol) at −78° C. Upon addition, the mixture was allowed to stir at 25° C. for 16 hours. The reaction was then cooled to 0° C., treated with methanol (5 mL) and diluted with dichloromethane (80 mL). The resulting mixture was washed with water (120 mL) and brine (150 mL). The organic layer was dried (MgSO$_4$), filtered and concentrated. The concentrate was purified by flash chromatography on silica gel eluting with a solvent gradient from 20% to 60% ethyl acetate in hexanes to yield 900 mg of the title compound (77%) as a off-white solid. $^1$H NMR (300 MHz, DMSO-$d_6$) δ ppm 1.81 (d, J=6.99 Hz, 3H) 5.55-5.70 (m, 1H) 6.84 (dd, J=8.82, 2.94 Hz, 1H) 6.99 (d, J=2.57 Hz, 1H) 7.17 (s, 1H) 7.42 (d, J=8.82 Hz, 1H) 7.80-7.98 (m, 5H); MS (ESI) m/z 468.0 (M+H)$^+$, 500.0 (M+Na)$^+$.

Example 30G

2-[1-(3-{2-[2-chloro-4-(cyclopropylmethoxy)phenoxy]-1,3-thiazol-5-yl}isoxazol-5-yl)ethyl]-1H-isoindole-1,3(2H)-dione To a solution of Example 30F (550 mg, 1.18 mmol), cyclopropylmethanol (0.14 mL, 1.76 mmol) and triphenylphosphine (462 mg, 1.76 mmol) in tetrahydrofuran (10 mL) was added diethyl azodicarboxylate (0.28 mL, 1.76 mmol) at ambient temperature. The reaction was stirred for 16 hours, concentrated and purified by flash chromatography on silica gel eluting with a solvent gradient from 10% to 30% ethyl acetate in hexanes to provide 480 mg of the title compound as a white solid (78%). $^1$H NMR (300 MHz, DMSO-$d_6$) δ ppm 0.28-0.39 (m, 2H) 0.53-0.65 (m, 2H) 1.12-1.30 (m, 1H) 1.82 (d, J=7.35 Hz, 3H) 3.88 (d, J=6.99 Hz, 2H) 5.56-5.69 (m, J=7.11, 7.11, 7.11 Hz, 1H) 7.03 (dd, J=8.82, 2.94 Hz, 1H) 7.17 (s, 1H) 7.23 (d, J=2.94 Hz, 1H) 7.53 (d, J=8.82 Hz, 1H) 7.83-7.97 (m, 5H); MS (ESI) m/z 522.1 (M+H)$^+$

Example 30H 1-(3-{2-[2-chloro-4-(cyclopropylmethoxy)phenoxy]-1,3-thiazol-5-yl}isoxazol-5-yl)ethanamine To a solution of Example 30G (276 mg, 0.53 mmol) in ethanol (6 mL) was added hydrazine monohydrate (0.16 mL, 3.2 mmol). The reaction was heated at 60° C. for 45 minutes and filtered. The filtrate was concentrated and purified on silica gel eluting with 90:8:2 dichloromethane/methanol/concentrated ammonium hydroxide to provide 201 mg of the title compound (97%) as an amber liquid. $^1$H NMR (300 MHz, DMSO-$d_6$) δ ppm 0.29-0.38 (m, 2H) 0.53-0.65 (m, 2H) 1.12-1.23 (m, 1H) 1.34 (d, J=7.35 Hz, 3 H) 3.88 (d, J=7.35 Hz, 2H) 3.97-4.15 (m, 1H) 6.84 (s, 1H) 7.03 (dd, J=9.19, 2.94 Hz, 1H) 7.24 (d, J=2.94 Hz, 1H) 7.53 (d, J=9.19 Hz, 1H) 7.91 (s, 1H); MS (ESI) m/z 392.0 (M+H)$^+$.

Example 30I

N-[1-(3-{2-[2-chloro-4-(cyclopropylmethoxy)phenoxy]-1,3-thiazol-5-yl}isoxazol-5-yl)ethyl]acetamide To a solution of Example 30H (50 mg, 0.13 mmol) and triethylamine (54 uL, 0.39 mmol) in dichloromethane (1 mL) was added acetic anhydride (15 uL, 0.16 mmol) at ambient temperature. The reaction was stirred for, 10 minutes and was concentrated on a rotary evaporator. The concentrate was purified by reverse-phase HPLC on an Atlantis C18 column (1.9×10 cm, 5 μm particle size) using a gradient of 5% to 95% acetonitrile:0.1% aqueous trifluoroacetic acid to provide 36 mg (64%) of the title compound as a white solid. $^1$H NMR (300 MHz, DMSO-$d_6$) δ ppm 0.28-0.39 (m, 2H) 0.53-0.65 (m, 2H) 1.15-1.29 (m, 1H) 1.42 (d, J=6.99 Hz, 3H) 1.87 (s, 3H) 3.88 (d, J=6.9 Hz, 2H) 5.03-5.17 (m, 1H) 6.89 (s, 1H)

7.03 (dd, J=9.19, 2.94 Hz, 1H) 7.24 (d, J=2.57 Hz, 1H) 7.54 (d, J=8.82 Hz, 1 H) 7.94 (s, 1H) 8.51 (d, J=8.09 Hz, 1H); MS (ESI) m/z 434.1 (M−H)+.

Example 31 methyl 1-(3-{2-[2-chloro-4-(cyclopropylmethoxy) phenoxy]-1,3-thiazol-5-yl}isoxazol-5-yl)ethylcarbamate To a solution of Example 30H (50 mg, 0.13 mmol) and diisopropylethylamine (68 uL, 0.39 mmol) in dichloromethane (1 mL) was added methyl chloroformate (12 uL, 0.16 mmol) at ambient temperature. The reaction was stirred for 10 minutes and was concentrated on a rotary evaporator. The concentrate was purified by reverse-phase HPLC on an Atlantis C18 column (1.9×10 cm, 5 μm particle size) using a gradient of 5% to 95% acetonitrile: 0.1% aqueous trifluoroacetic acid to provide 42 mg (71%) of the title compound as a white solid. 1H NMR (300 MHz, DMSO-D6) δ ppm 0.29-0.38 (m, 2H) 0.55-0.64 (m, 2H) 1.13-1.29 (m, 1H) 1.43 (d, J=6.99 Hz, 3H) 3.56 (s, 3H) 3.88 (d, J=6.99 Hz, 2H) 4.80-4.93 (m, J=7.35, 7.35 Hz, 1H) 6.90 (s, 1H) 7.03 (dd, J=9.19, 2.94 Hz, 1H) 7.24 (d, J=2.94 Hz, 1H) 7.53 (d, J=9.19 Hz, 1H) 7.90 (d, J=8.46 Hz, 1H) 7.96 (s, 1H); MS (ESI) m/z 450.2 (M+H)+.

Example 32

N-[1-(3-{2-[2-chloro-4-(cyclopropylmethoxy)phenoxy]-1,3-thiazol-5-yl}isoxazol-5-yl)ethyl]-N'-methylurea To a solution of Example 30H (50 mg, 0.13 mmol) in dichloromethane (1 mL) was added methyl isocyanate (50 uL, 2.6 mmol) at ambient temperature. The reaction was stirred for 4 hours and was concentrated on a rotary evaporator. The concentrate was purified by reverse-phase HPLC on an Atlantis C18 column (1.9×10 cm, 5 μm particle size) using a gradient of 5% to 95% acetonitrile:0.1% aqueous trifluoroacetic acid to provide 45 mg (77%) of the title compound as a white solid. 1H NMR (300 MHz, DMSO-$d_6$) δ ppm 0.29-0.38 (m, 2H) 0.53-0.64 (m, 2H) 1.17-1.30 (m, 1H) 1.40 (d, J=7.35 Hz, 3H) 2.56 (d, J=4.78 Hz, 3H) 3.88 (d, J=6.99 Hz, 2H) 4.87-5.04 (m, 1H) 5.80 (q, J=4.78 Hz, 1H) 6.57 (d, J=8.09 Hz, 1H) 6.82 (s, 1H) 7.03 (dd, J=9.19, 2.94 Hz, 1H) 7.24 (d, J=2.94 Hz, 1H) 7.53 (d, J=9.19 Hz, 1H) 7.94 (s, 1H); MS (ESI) m/z 449.1 (M+H)+.

Example 33

N-(1-{5-[5-(4-isopropoxyphenoxy)-1,3,4-thiadiazol-2-yl]thien-2-yl}ethyl)-N'-methylurea A solution of Example 24G (0.044 g, 0.122 mmol) in CH$_2$Cl$_2$ (2 mL) was treated with methyl isocyanate (0.035 g, 0.61 mmol). The reaction was stirred at 25° C. for 1 hour and was concentrated under reduced pressure on a rotary evaporator. The residual white solids (0.046 g) were purified by flash chromatography on silica gel eluting with a solvent gradient from 50% to 70% ethyl acetate in hexanes to provide 0.025 g (49%) of the title compound as a white solid, 1H NMR (300 MHz, DMSO-$d_6$) δ ppm 7.48 (d, J=3.68 Hz, 1H) 7.39 (d, J=9.19 Hz, 2H) 7.02 (d, J=9.19 Hz, 2H) 6.96 (dd, J=3.86, 0.92 Hz, 1H) 6.53 (d, J=8.09 Hz, 1H) 5.75 (q, J=4.78 Hz, 1H) 4.94-5.05 (m, 1H) 4.63 (heptet, J=5.88 Hz, 1H) 2.56 (d, J=4.78 Hz, 3H) 1.42 (d, J=6.99 Hz, 3H) 1.28 (d, J=5.88 Hz, 6H); MS (ESI) m/z 419 (M+H+.

Example 34

N-{1-[3-(2-{4-[(cyclopropylmethyl)amino]phenoxy}-1,3-thiazol-5-yl)isoxazol-5-yl] ethyl}acetamide Example 29F (154 mg, 0.45 mmol) was dissolved in a 3 mL buffer solution (prepared by mixing 6 mL acetic acid and 8.5 g sodium acetate in 250 mL methanol). To this was added cyclopropanecarboxaldehyde (34 μL, 0.45 mmol) and NaCNBH$_3$ (28 mg, 0.45 mmol). The reaction solution was stirred at 70° C. for 1 hour, and then poured into saturated aqueous Na$_2$CO$_3$ and extracted (2×) with ethyl acetate. The combined organics were dried (Na$_2$SO$_4$), filtered and concentrated by rotary evaporation. The residue was purified by flash column chromatography (ethyl acetate:hexanes: 5%-100% gradient) to give the title compound (57 mg, 0.14 mmol, 32%). MS (ESI APCI) m/z 399.1 (M+H+); 1H NMR (300 MHz, DMSO-$d_6$) δ 8.49 (d, J=6.00 Hz, 1H) 7.93 (s, 1H) 7.12 (d, J=9.00 Hz, 2H) 6.87 (s, 1H) 6.65 (d, J=9.00 Hz, 2H) 5.87-6.04 (m, 1H) 4.94-5.16 (m, 1H) 2.84-2.98 (m, 2H) 1.86 (s, 3H) 1.39 (d, J=6.00 Hz, 3H) 0.97-1.12 (m, 1H) 0.41-0.57 (m, 2H) 0.15-0.31 (m, 2H).

Example 3S

N-(1-{3-[2-(2-chloro-4-isopropoxyphenoxy)-1,3-thiazol-5-yl]isoxazol-5-yl}ethyl)urea

Example 35A

1-{3-[2-(2-chloro-4-isopropoxyphenoxy)-1,3-thiazol-5-yl]isoxazol-5-yl}ethanamine The title compound was prepared using the procedure as described in step 1 of Example 1G, substituting Example 25E for Example 1F.

Example 35B

N-(1-{3-[2-(2-chloro-4-isopropoxyphenoxy)-1,3-thiazol-5-yl]isoxazol-5-yl}ethyl)urea The title compound was synthesized by using the procedure as described for Example 2F, substituting Example 35A for Example 2E. 1H NMR (300 MHz, DMSO-$d_6$) δ ppm 1.29 (d, J=6.25 Hz, 6H) 1.40 (d, J=6.99 Hz, 3H) 4.59-4.78 (m, 1H) 4.83-5.02 (m, 1H) 5.61 (s, 2H) 6.63 (d, J=8.09 Hz, 1H) 6.84 (s, 1H) 7.02 (dd, J=8.82, 2.94 Hz, 1H) 7.23 (d, J=2.94 Hz, 1H) 7.53 (d, J=8.82 Hz, 1H) 7.95 (s, 1H). MS (ESI) m/z 423.0 (M+H)+.

Example 36

N-(1-{3-[2-(2-chloro-4-isopropoxyphenoxy)-1,3-thiazol-5-yl]isoxazol-5-yl}ethyl)-N'-methylurea The title compound was prepared as described for Example 1G, substituting Example 25E for Example 1F, and substituting methyl isocyanate for acetic anhydride. 1H NMR (300 MHz, DMSO-$d_6$) δ ppm 1.29 (d, J=5.88 Hz, 6H) 1.40 (d, J=6.99 Hz, 3H) 2.56 (d, J=4.78 Hz, 3H) 4.62-4.76 (m, 1H) 4.88-5.04 (m, 1H) 5.80 (q, J=4.41 Hz, 1H) 6.58 (d, J=8.09 Hz, 1H) 6.83 (s, 1H) 7.02 (dd, J=9.19, 2.94 Hz, 1H) 7.23 (d, J=2.94 Hz, 1H) 7.52 (d, J=9.19 Hz, 1H) 7.94 (s, 1H). MS (ESI) m/z 437.1 (M+H)$^+$.

Example 37

N-[1-(3-{2-[2-chloro-4-(tetrahydrofuran-3-yl-methoxy)phenoxy]-1,3-thiazol-5-yl}isoxazol-5-yl) ethyl]acetamide

Example 37A

1-{3-[2-(2-chloro-4-methoxyphenoxy)-1,3-thiazol-5-yl]isoxazol-5-yl}ethanamine

To a solution of Example 30E (510 mg, 1.06 mmol) in ethanol (6 mL) was added hydrazine monohydrate (0.31 mL, 6.3 mol). The reaction was heated at 60° C. for 45 minutes and filtered. The filtrate was concentrated and purified by flash chromatography on silica gel eluting with 90:8:2 dichloromethane/methanol/concentrated ammonium hydroxide to provide 358 mg of the title compound,

Example 37B

N-(1-{3-[2-(2-chloro-4-methoxyphenoxy)-1,3-thiazol-5-yl]isoxazol-5-yl}ethyl)acetamide To a solution of Example 37A (358 mg, 1.02 mmol) and triethylamine (426 µL, 3.06 mmol) in dichloromethane (5 mL) was added acetic anhydride (116 µl, 1.22 mmol) at ambient temperature. The reaction was stirred for 10 minutes and was then concentrated on a rotary evaporator. The concentrate was purified by flash chromatography on silica gel eluting with a solvent gradient from 30% to 80% ethyl acetate in hexanes to give 338 mg (94%) of the title compound as a white solid. $^1$H NMR (300 MHz, DMSO-d$_6$) δ ppm 1.42 (d, J=7.35 Hz, 3H) 1.87 (s, 3H) 3.82 (s, 3H) 4.98-5.18 (m, 1H) 6.89 (s, 1H) 7.05 (dd, J=9.19, 2.94 Hz, 1H) 7.27 (d, J=2.94 Hz, 1H) 7.56 (d, J=9.19 Hz, 1H) 7.94 (s, 1H) 8.51 (d, J=7.72 Hz, 1H); MS (ESI) m/z 394.0 (M+H)$^+$.

Example 37C

N-(1-{3-[2-(2-chloro-4-hydroxyphenoxy)-1,3-thiazol-5-yl]isoxazol-5-yl}ethyl)acetamide To a solution of Example 37B (370 mg, 0.94 mmol) in dichloromethane (10 mL) was added boron tribromide (0.36 mL, 3.76 mmol) at −78° C. Upon addition, the mixture was allowed to stir at 25° C. for 16 hours. The reaction was then cooled to 0° C., treated with methanol (5 mL) and diluted with dichloromethane (80 mL). The resulting mixture was washed with water (120 mL) and brine (150 mL). The organic layer was dried (MgSO$_4$), filtered and concentrated. The concentrate was purified by flash chromatography on silica gel eluting with a solvent gradient from 20% to 90% ethyl acetate in hexanes to provide 179 mg of the title compound (51%) as a off-white solid. $^1$H NMR (300 MHz, DMSO-d$_6$) δ ppm 1.42 (d, J=6.99 Hz, 3H) 1.87 (s, 3H) 5.02-5.16 (m, 1H) 6.85 (dd, J=9.01, 2.76 Hz, 1H) 6.89 (s, 1H) 7.00 (d, J=2.57 Hz, 1H) 7.43 (d, J=8.82 Hz, 1H) 7.94 (s, 1H) 8.51 (d, J=8.09 Hz, 1H) 10.19 (s, 1H); MS (ESI) m/z 394.0 (M+H)$^+$.

Example 37D

N-[1-(3-{2-[2-chloro-4-(tetrahydrofuran-3-yl-methoxy)phenoxy]-1,3-thiazol-5-yl}isoxazol-5-yl-ethyl]acetamide To a solution of Example 37C (32 mg, 0.084 mmol), (tetrahydro-furan-3-yl)-methanol (13 µL, 0.13 mmol) and triphenylphosphine (33 mg, 0.13 mmol) in tetrahydrofuran (1 mL) was added diethyl azodicarboxylate (22 µL, 0.13 mmol) at ambient temperature. The reaction was stirred for 16 hours, concentrated on a rotary evaporator, and purified by reverse-phase HPLC on an Atlantis C18 column (1.9×10 cm, 5 µm particle size) using a gradient of 5% to 95% acetonitrile:0.1% aqueous trifluoroacetic acid to provide 16 mg (41%) of the title compound as a off-white solid. $^1$H NMR (300 MHz, DMSO-d$_6$) δ ppm 1.42 (d, J=7.35 Hz, 3H) 1.55-1.77 (m, 1H) 1.87 (s, 3H) 1.94-2.12 (m, 1H) 2.65 (d, J=7.72 Hz, 1 H) 3.54 (dd, J=8.46, 5.52 Hz, 1H) 3.60-3.71 (m, 1H) 3.72-3.84 (m, 2H) 3.91-4.06 (m, 2H) 5.03-5.17 (m, J=7.17, 7.17 Hz, 1H) 6.90 (s, 1H) 7.06 (dd, J=8.82, 2.94 Hz, 1H) 7.29 (d, J=2.94 Hz, 1H) 7.55 (d, J=8.82 Hz, 1H) 7.94 (s, 1H) 8.51 (d, J=8.09 Hz, 1H); MS (ESI) m/z 464.1 (M+H)$^+$.

Example 38

N-[1-(3-{2-[2-chloro-4-(tetrahydrofuran-3-yloxy) phenoxy]-1,3-thiazol-5-yl}isoxazol-5-yl)ethyl]acetamide The title compound was prepared according to the procedure described in Example 37D substituting tetrahydro-furan-3-ol for (tetrahydro-furan-3-yl)-methanol. The crude product was purified by reverse-phase HPLC on an Atlantis C18 column (1.9×10 cm, 5 µm particle size) using a gradient of 5% to 100% acetonitrile:0.1% aqueous trifluoroacetic acid to provide the title compound. $^1$H NMR (300 MHz, DMSO-d$_6$) δ ppm 1.42 (d, J=6.99 Hz, 3H) 1.87 (s, 3H) 1.91-2.04 (m, 1H) 2.16-2.34 (m, 1H) 3.68-3.95 (m, 4H) 5.00-5.18 (m, 2H) 6.90 (s, 1H) 7.04 (dd, J=9.01, 3.13 Hz, 1H) 7.26 (d, J=2.94 Hz, 1H) 7.56 (d, J=9.19 Hz, 1H) 7.94 (s, 1H) 8.51 (d, J=7.72 Hz, 1H); MS (EST) m/z 450.1 (M+H)$^+$.

Example 39

N-(1-{3-[2-(2-chloro-4-ethoxyphenoxy)-1,3-thiazol-5-yl]isoxazol-5-yl}ethyl)acetamide The title compound was prepared according to the procedure described in Example 37D substituting ethanol for (tetrahydro-furan-3-yl)-methanol. The crude product was purified by reverse-phase HPLC on an Atlantis C18 column (1.9× 10 cm, 5 µm particle size) using a gradient of 5% to 100% acetonitrile:0.1% aqueous trifluoroacetic acid to provide the title compound. $^1$H NMR (300 MHz, DMSO-d$_6$) δ ppm 1.34 (t, J=6.99 Hz, 3H) 1.42 (d, J=6.99 Hz, 3H) 1.87 (s, 3H) 4.09 (q, J=6.99 Hz, 2H) 5.02-5.17 (m, J=7.35, 7.35 Hz, 1H) 6.89 (s, 1H) 7.03 (dd, J=8.82, 2.94 Hz, 1H) 7.25 (d, J=2.94 Hz, 1H) 7.54 (d, J=9.19 Hz, 1H) 7.94 (s, 1H) 8.51 (d, J=7.72 Hz, 1H); MS m/z 408.0 (M+H)$^+$.

Example 40

N-(1-{3-[2-(4-isopropoxyphenoxy)-1,3-thiazol-5-yl]-1,2,4-oxadiazol-5-yl}ethyl)acetamide

Example 40A 2-(4-isopropoxyphenoxy)-1,3-thiazole-5-carbonitrile

To a solution of Example 1A (1.18 g, 7.75 mmol) in N,N-dimethylformamide (50 mL) was added potassium carbonate (1.1 g, 7.96 mmol), 2-chlorothiazole-5-carbonitrile (CAS 51640-36-9, 1.12 g, 7.75 mmol) and then the reaction was stirred at room temperature overnight. The reaction mixture was diluted with ethyl acetate (100 mL) and washed with water (3×50 mL) and brine (50 mL). The organics were dried over magnesium sulfate, filtered, and evaporated. The product was purified via silica-gel column chromatography using dichloromethane as the eluent. The title compound was obtained as white solid (2.0 g), $^1$H NMR (300 MHz, CDCl$_3$) δ ppm 7.76 (s, 1H) 7.12-7.23 (m, 2H) 6.87-7.00 (m, 2H) 4.44-4.65 (heptet, J=6.25 Hz, 1H) 1.36 (d, J=6.25 Hz, 6H), MS (DCI): m/z 261 (M+H)$^+$.

Example 40B

N'-hydroxy-2-(4-isopropoxyphenoxy)-1,3-thiazole-5-carboximidamide

To a solution of Example 40A (1 g, 3.84 mmol) in a mixture of 20:1 ethanol:water (35 mL) was added hydroxyamine hydrochloride (667 mg, 9.6 mmol) followed by triethylamine (3 mL, 21.5 mmol). The reaction mixture was refluxed for an hour. After evaporation of the solvent, water was added and the solution was stirred for several hours. The product was isolated by filtration, after washing with water, and then was dried under vacuum to provide the title compound (911 mg). $^1$H NMR (300 MHz, DMSO-d$_6$) δ ppm 9.66 (s, 1H) 7.61 (s, 1H) 7.19-7.33 (m, 2H) 6.92-7.06 (m, 2H) 6.00 (s, 2H) 4.52-4.71 (m, 1H) 1.27 (d, J=5.88 Hz, 6H). MS (DCI): m/z 294 (M+H).

Example 40C 2-(1-{3-[2-(4-isopropoxyphenoxy)-1,3-thiazol-5-yl]-1,2,4-oxadiazol-5-yl}ethyl)-1H-isoindole-1,3(2H)-dione To a solution of Example 40B (616 mg, 2.1 mmol) in pyridine (15 mL) was added 2-(1,3-dioxoisoindolin-2-yl)propanoyl chloride (CAS#5364-22-7) (598 mg, 2.52 mmol) and the solution was stirred for an hour at room temperature and then at reflux for an additional hour. The reaction mixture was cooled down, methanol was added, and after stirring for 15 minutes the solvent was removed under vacuum. The title compound was purified via silica-gel column chromatography using a gradient of 25 to 50% ethyl acetate in hexane to provide 855 mg, $^1$H NMR (300 MHz, CDCl$_3$) δ ppm 7.84-7.96 (m, 3H) 7.73-7.83 (m, 2H) 7.15-7.24 (m, 2H) 6.86-6.99 (m, 2H) 5.68 (q, J=7.35 Hz, 1H) 4.43-4.63 (m, 1H) 1.98 (d, J=7.35 Hz, 3H) 1.35 (d, J=5.88 Hz, 6H). MS (DCI): m/z 477 (M+H)$^+$.

Example 40D

1-{3-[2-(4-isopropoxyphenoxy)-1,3-thiazol-5-yl]-1,2,4-oxadiazol-5-yl}ethanamine

A solution of Example 40C (372 mg, 0.78 mmol) in 9:1 dichloromethane:ethanol (25 mL) was charged with hydrazine hydrate (379 uL, 7.8 mmol) and refluxed for 4 hours. The solvent was removed under vacuum and the reaction mixture was stirred in dichloromethane for 3 hours. The solid was removed by filtration and the residue was concentrated under vacuum to yield 265 mg of the title compound. $^1$H NMR (300 MHz, CDCl$_3$) δ ppm 7.91 (s, 1H) 7.15-7.25 (m, 2H) 6.88-7.00 (m, 2H) 4.46-4.61 (m, 1H) 4.28-4.41 (m, J=6.86 Hz, 1H) 1.58 (d, J=6.99 Hz, 3H) 1.36 (d, J=5.88 Hz, 6H). MS (DCI): m/z 347 (M+H)$^+$.

Example 40E

N-(1-{3-[2-(4-isopropoxyphenoxy)-1,3-thiazol-5-yl]-1,2,4-oxadiazol-5-yl}ethyl)acetamide To a solution of Example 40D (265 mg, 0.76 mmol) in tetrahydrofuran (5 mL) at room temperature, was added diisopropylethyl amine (400 uL) followed by acetic anhydride (150 μL, 1.59 mmol). After an hour the reaction was quenched with methanol and stirred for additional hour. The solvent was removed under vacuum and the product was purified via silica-gel column chromatography using a gradient of 25 to 75% ethyl acetate in hexane to provide the title compound (152 mg). $^1$H NMR (300 MHz, CDCl$_3$) δ ppm 7.90 (s, 1H) 7.17-7.25 (m, 2H) 6.89-6.99 (m, 2H) 6.09 (d, J=7.72 Hz, 1H) 5.33-5.53 (m, 1H) 4.54 (heptet, J=6.0 Hz, 1H) 2.08 (s, 3H) 1.62 (d, J=7.0 Hz, 3H) 1.36 (d, J=6.0 Hz, 6.0H).). MS (DCI): m/z 389 (M+H).

Example 41

N-[1-(3-{2-[4-(isobutylamino)phenoxy]-1,3-thiazol-5-yl}isoxazol-5-yl)ethyl]acetamide The title compound was prepared as in Example 34, substituting isobutyraldehyde for cyclopropanecarboxaldehyde. MS (ESI APCI) m/z 401.2 (M+H$^+$); $^1$H NMR (300 MHz, DMSO-d$_6$) δ 8.50 (d, J=8.09 Hz, 1H) 7.93 (s, 1H) 7.11 (d, J=8.82 Hz, 2H) 6.87 (s, 1H) 6.63 (d, J=8.82 Hz, 2H) 5.92 (t, J=5.52 Hz, 1H) 4.99-5.18 (m, 1H) 2.83 (t, J=6.25 Hz, 2H) 1.76-1.94 (m, 4H) 1.41 (d, J=7.35 Hz, 3H) 0.93 (d, J=6.60 Hz, 6H).

Example 42

N-(1-{3-[5-(4-isopropoxyphenoxy)thien-2-yl]isoxazol-5-yl}ethyl)acetamide

Example 42A 5-(4-isopropoxyphenoxy)thiophene-2-carbaldehyde

NaH (60%, 480 mg, 12.0 mmol) was added in several portions to a stirred solution of Example 17A (1.52 g, 10.0 mmol) in DMSO (15 mL) at room temperature. After 20 min, 4-nitrothiophene-2-carbaldehyde (1.57 g, 10.0 mmol) was added in one portion. The mixture was stirred at room temperature for 30 minutes. The reaction mixture was poured into water, extracted with ether (2×). The ether layer was washed with 10% NaOH (1×), brine (1×), dried over MgSO$_4$ and concentrated. The residue was purified on silica gel eluting with ethyl acetate: hexane gradient to give the desired product as a brown oil (206 mg, 7.8%).

Example 42B

N-1-{3-[5-(4-isopropoxyphenoxy)thien-2-yl]isoxazol-5-yl}ethyl)acetamide

The title compound was prepared using the procedure as described in Example 17C by substituting Example 42A for Example 17B and following subsequent reaction conditions in Examples 21D-G. MS (DCI): m/z 387 (M+H); $^1$H NMR (300 MHz, CDCl$_3$) δ ppm 7.02-7.14 (m, 3H), 6.82-6.92 (m, 2H), 6.40 (d, J=3.68 Hz, 1H), 6.31 (s, 1H), 5.81 (d, J=8.46 Hz, 1H), 5.27-5.43 (m, 1H), 4.37-4.58 (m, 1H), 2.03 (s, 3H), 1.58 (d, J=6.99 Hz, 3H), 1.56 (d, J=6.99 Hz, 3H); 1.34 (d, J=6.25 Hz, 6H).

Example 43

N-(1-{3-[5-(4-isopropoxyphenoxy)-2-furyl]isoxazol-5-yl}ethyl)acetamide

Example 43A 5-(4-isopropoxyphenoxy)-2-furaldehyde

The title compound (22% yield) was prepared as described in Examples 46A, substituting 5-nitro-furan-2-carbaldehyde for 5-nitro-thiophene-2-carbaldehyde.

Example 43B

1-{3-[5-(4-isopropoxyphenoxy)-2-furyl]isoxazol-5-yl}ethanamine

The desired product was prepared by substituting Example 43A for Example 17B and following subsequent reaction conditions in Examples 21C-F.

Example 43C

N-(1-{3-[5-(4-isopropoxyphenoxy)-2-furyl]isoxazol-5-yl}ethyl)acetamide

The title compound (37% yield) was prepared by substituting Example 43B for Example 17F and following reaction conditions in Example 17G. MS (DCI): m/z 371 (M+H); $^1$H NMR (300 MHz, CDCl$_3$) δ ppm 6.99-7.12 (m, 2H), 6.83-6.93 (m, 3H), 6.81 (d, J=3.31 Hz, 1H), 6.33 (s, 1H), 5.50 (d, J=3.31 Hz, 1H), 5.30-5.42 (m, 1H), 4.38-4.56 (m, 1H), 2.03 (s, 3H), 1.55 (d, J=6.98 Hz, 3H); 1.33 (d, J=6.25 Hz, 6H).

Example 44

N-(1-{3-[5-(4-isopropoxyphenoxy)-2-furyl]isoxazol-5-yl}ethyl)-N'-methylurea

To a solution of Example 431B (38 mg, 0.116 mmol) in dichloromethane (2 mL) was added methyl isocyanate (35 μL, 061 mmol) at room temperature. The mixture was stirred at room temperature overnight. The reaction mixture was purified directly on silica gel eluting with ethyl acetate:hexane gradient to give the desired product as a white solid (22 mg, 51%). MS (DCI): m/z 386 (M+H); $^1$H NMR (300 MHz, CDCl$_3$) δ ppm 6.99-7.10 (m, 2H), 6.82-6.92 (m, 3H), 6.80 (d, J=3.68 Hz, 1H), 6.33 (s, 1H), 5.50 (d, J=3.68 Hz, 1H), 5.09-5.26 (m, J=6.62 Hz, 1H), 4.65 (br, S, 1H), 4.40-4.55 (m, 1H), 2.79 (s, 3H), 1.55 (d, J=6.98 Hz, 3H), 1.33 (d, J=6.25 Hz, 6H).

Example 45

N-[1-(3-{2-[2-chloro-4-(cyclohexyloxy)phenoxy]-1,3-thiazol-5-yl}isoxazol-5-yl)ethyl]acetamide The title compound was prepared according to the procedure described in Example 37D, substituting cyclohexanol for (tetrahydro-furan-3-yl)-methanol. The crude product was purified by reverse-phase HPLC on an Atlantis C18 column (1.9×10 cm, 5 μm particle size) using a gradient of 5% to 100% acetonitrile:0.1% aqueous trifluoroacetic acid to provide the title compound, $^1$H NMR (300 MHz, DMSO-d$_6$) δ ppm 1.42 (d, J=7.35 Hz, 3H) 1.44-1.61 (m, 3H) 1.63-1.78 (m, J=4.78 Hz, 4H) 1.87 (s, 3H) 1.89-2.02 (m, J=5.15 Hz, 3H) 4.92-5.03 (m, 1H) 5.04-5.17 (m, J=7.35, 7.35 Hz, 1H) 6.90 (s, 1H) 7.04 (dd, J=9.19, 2.94 Hz, 1H) 7.26 (d, J=2.94 Hz, 1H) 7.52 (d, J=8.82 Hz, 1H) 7.94 (s, 1H) 8.51 (d, J=7.72 Hz, 1H); MS (ESI) m/z 462.1 (M+H)$^+$.

Example 46

N-[1-{2-[2-chloro-4-(cyclopentyloxy)phenoxy]-1,3-thiazol-5-yl}isoxazol-5-yl)ethyl]acetamide The title compound was prepared according to the procedure described in Example 37D, substituting cyclopentanol for (tetrahydro-furan-3-yl)-methanol. The crude product was purified by reverse-phase HPLC on an Atlantis C18 column (1.9×10 cm, 5 μm particle size) using a gradient of 5% to 100% acetonitrile:0.1% aqueous trifluoroacetic acid to provide the title compound. $^1$H NMR (300 MHz, DMSO-d$_6$) δ ppm 1.13-1.26 (m, 2H) 1.42 (d, J=6.99 Hz, 3H) 1.65-1.79 (m, 4H) 1.87 (s, 3H) 1.89-1.98 (m, 2H) 4.85-4.94 (m, J=5.70, 5.70 Hz, 1H) 5.02-5.19 (m, J=7.35, 7.35 Hz, 1H) 6.90 (s, 1H) 7.00 (dd, J=9.01, 2.76 Hz, 1H) 7.20 (d, J=2.94 Hz, 1H) 7.53 (d, J=8.82 Hz, 1H) 7.94 (s, 1H) 8.51 (d, J=7.72 Hz, 1H); MS (ESI) m/z 448.1 (M+H)$^+$.

Example 47

N-[1-(3-{2-[2-chloro-4-(tetrahydro-2H-pyran-4-yloxy)phenoxy]-1,3-thiazol-5-yl}isoxazol-5-yl)ethyl]acetamide The title compound was prepared according to the procedure described in Example 37D, substituting tetrahydro-pyran-4-ol for (tetrahydro-furan-3-yl)-methanol. The crude product was purified by reverse-phase HPLC on an Atlantis C18 column (1.9×10 cm, 5 μm particle size) using a gradient of 5% to 100% acetonitrile:0.1% aqueous trifluoroacetic acid to provide the title compound. $^1$H NMR (300 MHz, DMSO-d$_6$) δ ppm 1.18 (d, J=6.25 Hz, 1H) 1.42 (d, J=7.35 Hz, 3H) 1.50-1.68 (m, 2H) 1.87 (s, 3H) 1.91-2.05 (m, J=13.05, 3.86 Hz, 1H) 3.75-3.95 (m, 4H) 4.58-4.73 (m, 1H) 5.03-5.18 (m, J=7.17, 7.17 Hz, 1 H) 6.90 (s, 1H) 7.09 (dd, J=9.19, 2.94 Hz, 1H) 7.33 (d, J=2.94 Hz, 1H) 7.54 (d, J=8.82 Hz, 1 H) 7.94 (s, 1H) 8.51 (d, J=7.72 Hz, 1H); MS (ESI) m/z 464.1 (M–H)$^+$.

Example 48

N-[1-(3-{2-[4-(cyclopropylmethoxy)phenoxy]-1,3-thiazol-5-yl}isoxazol-5-yl)ethyl]acetamide

Example 48A 2-(4-methoxyphenoxy)-1,3-thiazole

The title compound was prepared according to the procedure described in Example 30A, substituting 4-methoxyphenol for 2-chloro-4-methoxyphenol. The crude product was purified by flash chromatography on silica gel eluting with a solvent gradient from 10% to 20% ethyl acetate in hexanes to provide the title compound as a light yellow liquid. $^1$H NMR (300 MHz, DMSO-d$_6$) δ ppm 3.78 (s, 3H) 6.96-7.06 (m, 2H) 7.17 (d, J=3.68 Hz, 1H) 7.24-7.32 (m, 3H); MS (ESI) m/z 208.0 (M+H)$^+$.

Example 48B 2-(4-methoxyphenoxy)-1,3-thiazole-5-carbaldehyde

The title compound was prepared according to the procedure described in Example 30B, substituting Example 48A for Example 30A. The crude product was purified by flash chromatography on silica gel eluting with a solvent gradient from 5% to 25% ethyl acetate in hexanes to provide the title compound as a light yellow liquid. $^1$H NMR (300 MHz, DMSO-d$_6$) δ ppm 3.80 (s, 3H) 7.06 (m, 2H) 7.30-7.51 (m, 2H) 8.29 (s, 1H) 9.86 (s, 1H); MS (ESI) m/z 236.0 (M+H)$^+$.

Example 48C 2-(4-methoxyphenoxy)-1,3-thiazole-5-carbaldehyde oxime

The title compound was prepared according to the procedure described in Example 30C, substituting Example 48B for Example 30B. The crude product was purified by flash chromatography on silica gel eluting with a solvent gradient from 10% to 30% ethyl acetate in hexanes to provide the title compound as a off-white solid, $^1$H NMR (300 MHz, DMSO-d$_6$) δ ppm 3.79 (s, 3H) 6.91-7.15 (m, 2H) 7.22-7.41 (m, 2H) 7.69 (s, 1H) 7.79 (s, 1H) 11.93 (s, 1H); MS (ESI) m/z 251.0 (M+H)$^+$.

Example 48D

N-hydroxy-2-(4-methoxyphenoxy)-1,3-thiazole-5-carboximidoyl chloride

The title compound was prepared according to the procedure described in Example 30D, substituting Example 48C for Example 30C. $^1$H NMR (300 MHz, DMSO-d$_6$) δ ppm 3.79 (s, 3H) 7.04 (d, J=8.82 Hz, 2H) 7.36 (d, J=8.82 Hz, 2H) 7.67 (s, 1H) 12.41 (s, 1H); MS (ESI) m/z 284.8 (M−H)$^+$.

Example 48E 2-(1-{3-[2-(4-methoxyphenoxy)-1,3-thiazol-5-yl]isoxazol-5-yl}ethyl)-1H-isoindole-1,3(2H)-dione The title compound was prepared according to the procedure described in Example 30E, substituting Example 48D for Example 30D. The crude product was purified by flash chromatography on silica gel eluting with a solvent gradient from 10% to 60% ethyl acetate in hexanes to provide the title compound. $^1$H NMR (300 MHz, DMSO-d$_6$) δ ppm 1.82 (d, J=6.99 Hz, 3H) 3.79 (s, 3H) 5.57-5.69 (m, 1H) 6.99-7.09 (m, 2H) 7.17 (s, 1H) 7.33-7.41 (m, 2H) 7.85-7.93 (m, 4H) 7.94 (s, 1H); MS (ESI) m/z 448.1 (M+H)$^+$.

Example 48F 2-(1-{3-[2-(4-hydroxyphenoxy)-1,3-thiazol-5-yl]isoxazol-5-yl}ethyl)-1H-isoindole-1,3(2H)-dione The title compound was prepared according to the procedure described in Example 30F, substituting Example 48E for Example 30E. The crude product was purified by flash chromatography on silica gel eluting with a solvent gradient from 30% to 90% ethyl acetate in hexanes to provide the title compound.

Example 48G

2-[1-(3-{2-[4-(cyclopropylmethoxy)phenoxy]-1,3-thiazol-5-yl}isoxazol-5-yl)ethyl]-1H-isoindole-1,3(2H)-dione The title compound was prepared according to the procedure described in Example 30O, substituting Example 48F for Example 30F. The crude product was purified by flash chromatography on silica gel eluting with a solvent gradient from 5% to 20% ethyl acetate in hexanes to provide the title compound. $^1$H NMR (300 MHz, DMSO-d$_6$) δ ppm 0.28-0.37 (m, 2H) 0.51-0.63 (m, 2H) 1.09-1.28 (m, 1H) 1.81 (d, J=6.99 Hz, 3H) 3.84 (d, J=6.99 Hz, 2H) 4.65-4.87 (m, 1H) 6.96-7.07 (m, 2H) 7.16 (s, 1H) 7.29-7.39 (m, 2H) 7.86-7.93 (m, 4H) 7.93 (s, 1H); MS (ESI) m/z 488.1 (M+H)$^+$.

Example 48H 1-(3-{2-[4-(cyclopropylmethoxy)phenoxy]-1,3-thiazol-5-yl}isoxazol-5-yl)ethanamine The title compound was prepared according to the procedure described in Example 30H, substituting Example 48G for Example 30G. The crude product was taken to the next step without further purification.

Example 48I

N-[1-(3-{2-[4-(cyclopropylmethoxy)phenoxy]-1,3-thiazol-5-yl}isoxazol-5-yl)ethyl]acetamide The title compound was prepared according to the procedure described in Example 30I, substituting Example 48H for Example 30H. The crude product was purified by reverse-phase HPLC on an Atlantis C18 column (1.9×10 cm, 5 μm particle size) using a gradient of 5% to 100% acetonitrile:0.1% aqueous trifluoroacetic acid to provide the title compound. $^1$H NMR (300 MHz, DMSO-d$_6$) δ ppm 0.27-0.41 (m, 2H) 0.53-0.66 (m, 2H) 1.18-1.31 (m, 1H) 1.42 (d, J=6.99 Hz, 3H) 1.87 (s, 3H) 3.85 (d, J=6.99 Hz, 2H) 5.08 (q J=7.35 Hz, 1H) 6.88 (s, 1H) 6.97-7.10 (m, 2H) 7.22-7.45 (m, 2H) 7.95 (s, 1H) 8.50 (d, J=7.72 Hz, 1H); MS (ESI) m/z 400 (M+H)$^+$.

Example 49 methyl 1-(3-{2-[4-(cyclopropylmethoxy)phenoxy]-1,3-thiazol-5-yl}isoxazol-5-yl)ethylcarbamate The title compound was prepared according to the procedure described in Example 31, substituting Example 48H for Example 30H. The crude product was purified by reverse-phase HPLC on an Atlantis C18 column (1.9×10 cm, 5 μm particle size) using a gradient of 5% to 100% acetonitrile:0.1% aqueous trifluoroacetic acid to provide the title compound. $^1$H NMR (300 MHz, DMSO-d$_6$) δ ppm 0.28-0.38 (m, 2H) 0.53-0.64 (m, 2H) 1.16-1.30 (m, 1H) 1.43 (d, J=6.99 Hz, 3H) 3.56 (s, 3H) 3.85 (d, J=6.99 Hz, 2H) 4.79-4.93 (m, 1H) 6.89 (s, 1H) 6.99-7.07 (m, 2H) 7.30-7.39 (m, 2H) 7.89 (d, J=8.46 Hz, 1H) 7.97 (s, 1H); MS (ESI) m/z 416.1 (M+H)$^+$.

Example 50

N-[1-(3-{2-[4-(cyclopropylmethoxy)phenoxy]-1,3-thiazol-5-yl}isoxazol-5-yl)ethyl]urea To a solution of Example 48H (50 mg, 0.14 mmol) in dichloromethane (1 mL) was added trichloroacetyl isocyanate (24 µL, 0.196 mmol) at 0° C. The reaction was stirred for 15 minutes and concentrated. The resulting oil was dissolved in methanol (2 mL) and heated to reflux for 4 hours. The crude product was purified by reverse-phase HPLC on an Atlantis C18 column (1.9×10 cm, 5 µm particle size) using a gradient of 5% to 100% acetonitrile:0.1% aqueous trifluoroacetic acid to provide 36 mg of the title compound (64%) as a white solid. $^1$H NMR (300 MHz, DMSO-$d_6$) δ ppm 0.28-0.39 (m, 2H) 0.53-0.66 (m, 2H) 1.15-1.31 (m, 1H) 1.39 (d, J=7.35 Hz, 3H) 3.85 (d, J=6.99 Hz, 2H) 4.81-5.01 (m, J=7.35, 7.35 Hz, 1H) 5.59 (s, 2H) 6.61 (d, J=8.09 Hz, 1H) 6.82 (s, 1H) 6.97-7.11 (m, 2H) 7.27-7.43 (m, 2H) 7.96 (s, 1H); MS (ESI) m/z 401.0 (M+H)$^+$.

Example 51

N-[1-(3-{2-[4-(cyclopropylmethoxy)phenoxy]-1,3-thiazol-5-yl}isoxazol-5-yl)ethyl]-N'-methylurea The title compound was prepared according to the procedure described in Example 32, substituting Example 48H for Example 30H. The crude product was purified by reverse-phase HPLC on an Atlantis C18 column (1.9×10 cm, 5 µm particle size) using a gradient of 5% to 100% acetonitrile:0.1% aqueous trifluoroacetic acid to provide the title compound as a white solid. $^1$H NMR (300 MHz, DMSO-$d_6$) δ ppm 0.29-0.38 (m, 2H) 0.53-0.64 (m, 2H) 1.13-1.32 (m, 1H) 1.39 (d, J=6.99 Hz, 3H) 2.56 (s, 3H) 3.85 (d, J=6.99 Hz, 2H) 4.83-5.03 (m, 1H) 5.79 (s, 1H) 6.57 (d, J=8.46 Hz, 1H) 6.82 (s, 1H) 6.94-7.11 (m, 2H) 7.26-7.42 (m, 2H) 7.95 (s, 1H); MS (ESI) m/z 415.1 (M+H)$^+$.

Example 52

N-{1-[3-(2-{3-chloro-4-[(cyclopropylmethyl)amino]phenoxy}-1,3-thiazol-5-yl)isoxazol-5-yl]ethyl}acetamide Example 52A tert-butyl 2-chloro-4-hydroxyphenylcarbamate 4-Amino-3-chloro-phenol hydrochloride (20 g, 0.11 mol) was dissolved in tetrahydrofuran (92 mL) and triethylamine (15.5 mL, 0.11 mol) at room temperature. To this solution was added di-tert-butyl dicarbonate (24 g, 0.12 mol) as a solid portion-wise over 15 minutes. The resulting reaction solution was heated to reflux for 1.5 hours, cooled to room temperature and poured into saturated aqueous NH$_4$Cl. It was then extracted with ethyl acetate (2×) and the combined organics were dried (Na$_2$SO$_4$), filtered and concentrated by rotary evaporation. The resulting solid was triturated with hexanes to give the title compound (23.5 g, 0,096 mmol 80%) as a light brown solid. MS (ESI APCI) m/z 241.9 (M−H$^+$); $^1$H NMR (300 MHz, DMSO-$d_6$) δ 9.75 (s, 1H) 8.40 (s, 1H) 7.18 (d, J=8.46 Hz, 1H) 6.82 (d, J=2.57 Hz, 1H) 6.68 (dd, J=8.64, 2.76 Hz, 1H) 1.46 (s, 9H).

Example 52B 2-chloro-4-(1,3-thiazol-2-yloxy)aniline

Example 52A (10.0 g, 41.0 mmol) was dissolved in DMSO (20 mL). To this solution was added K$_2$CO$_3$ (7.9 g, 57.2 mmol) and 2-bromothiazole (5.1 mL, 57.4 mmol) and the mixture was heated at 140° C. for 5 hours. The reaction mixture was cooled to room temperature, diluted with ethyl acetate and poured into a large excess of water. The aqueous layer was extracted with ethyl acetate (2×) and the combined organics were dried (Na$_2$SO$_4$), filtered and concentrated by rotary evaporation. The residue was purified by flash column chromatography (ethyl acetate:hexanes; 5%-75% ethyl acetate gradient) to give the title compound (7.95 g, 35.0 mmol, 85%). MS (ESI APCI) m/z 227.0 (M+H$^+$); $^1$H NMR (300 MHz, DMSO-$d_6$) δ 7.29 (d, J=2.57 Hz, 1H) 7.25 (d, J=3.68 Hz, 1H) 7.14 (d, J=3.68 Hz, 1H) 7.06 (dd, J=8.82, 2.57 Hz, 1H) 6.84 (d, J=8.82 Hz, 1H) 5.47 (s, 2H).

Example 52C tert-butyl 2-chloro-4-(1,3-thiazol-2-yloxy)phenylcarbamate

Example 52B (7.95 g, 35 mmol) was dissolved in tetrahydrofuran (50 mL) and to this solution was added di-tert-butyl dicarbonate (8.24 g, 37.8 mmol) in portions over 15 minutes. The resulting solution was heated to reflux for 5 hours. The reaction was then cooled to room temperature, poured into water and extracted twice with ethyl acetate. The combined organics were dried (Na$_2$SO$_4$), filtered and concentrated by rotary evaporation. The residue was purified by flash column chromatography to provide the title compound (5.38 g, 16.5 mmol, 47%). MS (ESI APCI) m/z 327.0 (M+H$^+$). $^1$H NMR (300 MHz, DMSO-$d_6$) δ 8.78 (s, 1H) 7.60 (d, J=8.82 Hz, 1H) 7.56 (d, J=2.57 Hz, 1H) 7.31 (dd, J=6.25, 2.57 Hz, 1H) 7.25-7.29 (m, 2H) 1.46 (s, 9H), Example 52D tert-butyl 2-chloro-4-[(5-formyl-1,3-thiazol-2-yl)oxy]phenylcarbamate Example 52C (217 mg, 0.66 mmol) was dissolved in anhydrous tetrahydrofuran (2.2 ml) and added drop wise to a −78° C. solution of n-butyl lithium (2.5 M hexanes, 0.58 mL) under nitrogen. The reaction mixture was stirred at −78° C. for 30 min and then a tetrahydrofuran (2.2 mL) solution of formylmorpholine was added drop wise. The reaction was stirred at −78° C. for 15 minutes and then slowly warned to room temperature. The reaction mixture was poured into saturated aqueous NH$_4$Cl and extracted with ethyl acetate (2×). The combined organics were dried (Na$_2$SO$_4$), filtered and concentrated by rotary evaporation. The residue was purified by flash column chromatography (ethyl acetate:hexanes: 5%-50% ethyl acetate gradient) to give the title compound as an oil (164 mg, 0.46 mmol, 77%). MS (ESI APCI) m/z 355.0 (M+H$^+$); $^1$H NMR (300 MHz, DMSO-$d_6$) δ 9.90 (s, 1H) 8.85 (s, 1H) 8.29 (s, 1H) 7.71 (d, J=2.57 Hz, 1H) 7.67 (d, J=9.19 Hz, 1H) 7.41 (dd, J=9.01, 2.76 Hz, 1H) 1.47 (s, 9H).

Example 52E tert-butyl 2-chloro-4-({15-[(E)-(hydroxyimino)methyl]-1,3-thiazol-2-yl}oxy)phenylcarbamate Example 52D (164 mg, 0.46 mmol) was combined with hydroxyamine hydrochloride (480 mg, 6.9 mmol) in pyridine (0.93 mL, 11.5 mmol) and the reaction solution was stirred for 1.5 hours at room temperature. The reaction was poured into saturated aqueous NH$_4$Cl and was extracted with ethyl acetate (3×) The combined organics were washed with 5% aqueous citric acid (3×), dried (Na$_2$SO$_4$), filtered and concentrated by rotary evaporation. The residue was placed on high vacuum overnight to give the title compound (160 mg, 0.43 mmol, 93%) as a white solid that was used in the next step without further purifications MS (ESI APCI) m/z 370.0 (M+H$^+$).

Example 52F tert-butyl 2-chloro-4-({5-[(Z)-chloro(hydroxyimino) methyl]-1,3-thiazol-2-yl}oxy)phenylcarbamate Example 52E (160 mg, 0.59 mmol) was dissolved in N,N-dimethyl formamide (1.5 mL) and N-chlorosuccinimide (79.0 mg, 0.59 mmol) was added in portions over 30 minutes. The reaction was stirred overnight. Water was added and a fine white solid precipitated which was collected by filtration to give the title compound (131 mg) as a white solid that was used in the next step without further purification.

Example 52G tert-butyl 4-[(5-{5-[1-(acetylamino)ethyl]isoxazol-3-yl}-1,3-thiazol-2-yl)oxy]-2-chlorophenylcarbamate Example 52F (131 mg, 0.34 mmol), N-(1-Methyl-prop-2-ynyl)-acetamide (406 mg, 3.75 mmol; prepared as described in Gardner, J. N. et al Can. J. Chem. 51, 1973) and K$_2$CO$_3$ (141 mg, 1.0 mmol) were combined in ethyl acetate (1 mL) and stirred at room temperature overnight. The reaction was diluted with ethyl acetate and filtered. The filtrate was concentrated by rotary evaporator to give the title compound that was used in the next step without further purification. LC/MS (ESI APCI) m/z 478.7 (M+H$^+$).

Example 52H

N-{1-[3-(2-{3-chloro-4-[(cyclopropylmethyl)amino] phenoxy}-1,3-thiazol-5-yl)isoxazol-5-yl] ethyl}acetamide Example 52G (33.7 mg, 0.070 mmol) was dissolved in CH$_2$Cl$_2$ (1 mL). Trifluoroacetic acid (0.4 ml, 40% v/v) was added drop wise and the reaction solution was stirred for 1.5 hours. At that time, the reaction was concentrated and placed on high vacuum for 30 minutes. To the remaining residue was added a buffer solution (1 mL of a solution prepared from 6 ml, acetic acid and 8.5 g sodium acetate in 250 mL methanol). To this was added cyclopropanecarboxaldehyde (5 μL, 0.07 mmol) and NaCNBH$_3$ (4.3 mg, 0.07 mmol). The reaction solution was stirred at 70° C. for 1 hour, cooled to room temperature and filtered. The filtrate was purified by reverse phase-HPLC (water:acetonitrile; gradient of 5% to 90% acetonitrile) to give the title compound (20.0 mg, 0.046 mmol, 66%). MS (ESI APCI) m/z 433.1 (M+H$^+$); $^1$H NMR (300 MHz, DMSO-d$_6$) δ 8.50 (d, J=8.09 Hz, 1H) 7.94 (s, 1H) 7.47 (d, J=2.94 Hz, 1H) 7.24 (dd, J=9.01, 2.76 Hz, 1H) 6.88 (s, 1H) 6.82 (d, J=8.82 Hz, 1H) 5.45 (t, J=5.70 Hz, 1H) 5.09 (t, J=7.35 Hz, 1H) 3.05 (t, J=6.25 Hz, 2H) 1.87 (s, 3H) 1.42 (d, J=7.35 Hz, 3H) 1.03-1.20 (m, 1H) 0.40-0.52 (m, 2H) 0.20-0.31 (m, 2H).

Example 53

N-[1-(3-{2-[4-(tetrahydro-2H-pyran-4-yloxy)phenoxy]-1,3-thiazol-5-yl}isoxazol-5-yl)ethyl]acetamide

Example 53A

1-{3-[2-(4-methoxyphenoxy)-1,3-thiazol-5-yl]isoxazol-5-yl}ethanamine

To a solution of Example 48E (1.06 g, 2.4 mmol) in ethanol (15 mL) was added hydrazine monohydrate (0.698 mL, 144 mmol). The reaction was heated at 60° C. for 45 minutes and then filtered. The filtrate was concentrated and purified by flash chromatography on silica gel eluting with 90:8:2 dichloromethane/methanol/concentrated ammonium hydroxide to provide 746 mg of title compound (98%). $^1$H NMR (300 MHz, DMSO-d$_6$) δ ppm 1.34 (d, J=6.62 Hz, 3H) 3.80 (s, 3H) 3.99-4.16 (m, 1H) 6.66-6.74 (m, 2H) 6.81-6.85 (m, 1H) 6.99-7.11 (m, 2H) 7.33-7.41 (m, 2H) 7.92 (s, 1H); MS (ESI) m/z 318.0 (M+H)$^+$.

Example 53B

N-(1-{3-[2-(4-methoxyphenoxy)-1,3-thiazol-5-yl] isoxazol-5-yl}ethyl)acetamide

To a solution of Example 53A (740 mg, 2.33 mmol) and triethylamine (975 μL, 7 mmol) in dichloromethane (15 mL) was added acetic anhydride (282 μL, 2.8 mmol) at ambient temperature. The reaction was stirred for 20 minutes, concentrated, and purified by flash chromatography on silica gel eluting with a solvent gradient from 30% to 80% ethyl acetate in hexanes to provide 796 mg (95%) of the title compound as a white solid. $^1$H NMR (300 MHz, DMSO-d$_6$) δ ppm 1.42 (d, J=6.99 Hz, 3H) 1.87 (s, 3H) 3.80 (s, 3H) 5.09 (m, 1H) 6.89 (s, 1H) 6.99-7.12 (m, 2H) 7.27-7.46 (m, 2H) 7.95 (s, 1H) 8.51 (d, J=8.09 Hz, 1H); MS (ESI) m/z 360.0 (M+H)$^+$.

Example 53C

N-(1-{3-[2-(4-hydroxyphenoxy)-1,3-thiazol-5-yl] isoxazol-5-yl}ethyl)acetamide

To a solution of Example 53B (726 mg, 2.02 mmol) in dichloromethane (20 mL) was added boron tribromide (763 μL, 8.08 mmol) at −78° C. Upon addition, the mixture was allowed to stir at 25° C. for 16 hours. The reaction was then cooled to 0° C., treated with methanol (10 mL) and diluted with dichloromethane (80 mL). The resulting mixture was washed with water (120 mL) and brine (150 mL). The organic layer was dried (MgSO$_4$), filtered and concentrated. The concentrate was purified by flash chromatography on silica gel eluting with a solvent gradient from 40% to 90% ethyl acetate in hexanes to provide 384 mg of the title compound (55%) as a white solid. $^1$H NMR (300 MHz, DMSO-d$_6$) δ ppm 1.41 (d, J=6.99 Hz, 3H) 1.87 (s, 3H) 4.93-5.24 (m, 1H) 6.55 (s, 1H) 6.82-6.95 (m, 2H) 7.16-7.34 (m, 2H) 7.95 (s, 1H) 8.53 (d, J=8.09 Hz, 1H) 11.78 (s, 1H); MS (ESI) m/z 346.0 (M+H)$^+$.

Example 53D

N-[1-(3-{2-[4-(tetrahydro-2H-pyran-4-yloxy)phenoxy]-1,3-thiazol-5-yl}isoxazol-5-yl)ethyl]acetamide To a solution of Example 53C (50 mg, 0.14 mmol), tetrahydro-pyran-4-ol (21 μL, 0.22 mmol) and triphenylphosphine (57 mg, 0.22 mmol) in tetrahydrofuran (1 mL) was added diethyl azodicarboxylate (38 μL, 0.22 mmol) at ambient temperature. The reaction was stirred for 16 hours, concentrated and purified by reverse-phase HPLC on an Atlantis C18 column (1.9×10 cm, 5 μm particle size) using a gradient of 5% to 95% acetonitrile:0.1% aqueous trifluoroacetic acid to provide 28 mg (47%) of the title compound, $^1$H NMR (300 MHz, DMSO-d$_6$) δ ppm 1.42 (d, J=7.35 Hz, 3H) 1.52-1.68 (m, 2H) 1.89 (s, 3H) 1.91-2.05 (m, 2H) 3.43-3.58 (m, 2H) 3.77-3.96 (m, 2H) 4.51-4.68 (m, 1H) 5.01-5.18 (m, 1H) 6.89 (s, 1H)

7.05-7.19 (m, 2H) 7.29-7.45 (m, 2H) 7.95 (s, 1H) 8.51 (d, J=7.72 Hz, 1H); MS (ESI) m/z 430.1 (M+H)+.

Example 54

N-[1-(3-{2-[4-(tetrahydrofuran-3-yloxy)phenoxy]-1,3-thiazol-5-yl}isoxazol-5-yl)ethyl]acetamide The title compound was prepared according to the procedure described in Example 53D, substituting tetrahydro-furan-3-ol for tetrahydro-pyran-4-ol. The crude product was purified by reverse-phase HPLC on an Atlantis C18 column (1.9×10 cm, 5 μm particle size) using a gradient of 5% to 95% acetonitrile:0.1% aqueous trifluoroacetic acid to provide the title compound. $^1$H NMR (300 MHz, DMSO-$d_6$) δ ppm 1.42 (d, J=6.99 Hz, 3H) 1.87 (s, 3H) 1.92-2.06 (m, 1H) 2.13-2.33 (m, 1H) 3.65-3.98 (m, 4H) 4.98-5.18 (m, 2 H) 6.89 (s, 1H) 7.00-7.11 (m, 2H) 7.32-7.43 (m, 2H) 7.95 (s, 1H) 8.51 (d, J=8.09 Hz, 1H); MS (ESI) m/z 416.0 (M+H)+.

Example 55

N-[1-(3-{2-[4-(cyclohexyloxy)phenoxy]-1,3-thiazol-5-yl}isoxazol-5-ylethyl]acetamide The title compound was prepared according to the procedure described in Example 53D, substituting cyclohexanol for tetrahydro-pyran-4-ol. The crude product was purified by reverse-phase HPLC on an Atlantis C18 column (1.9×10 cm, 5 μm particle size) using a gradient of 5% to 95% acetonitrile:0.1% aqueous trifluoroacetic acid to provide the title compound. $^1$H NMR (500 MHz, DMSO-$d_6$) δ ppm 1.11-1.32 (m, 2H) 1.42 (d, J=7.32 Hz, 3 H) 1.49-1.60 (m, 2H) 1.66-1.77 (m, 4H) 1.87 (s, 3H) 1.90-1.99 (m, 2H) 4.28-4.41 (m, 1H) 5.02-5.17 (m, 1H) 6.87 (s, 1H) 6.97-7.11 (m, 2H) 7.29-7.37 (m, 2 H) 7.93 (s, 1H) 8.48 (d, J=7.93 Hz, 1H); MS (ESI) m/z 428.1 (M+H)+.

Example 56

N-[1-(3-{2-[4-(cyclopentyloxy)phenoxy]-1,3-thiazol-5-yl}isoxazol-5-yl)ethyl]acetamide The title compound was prepared according to the procedure described in Example 53D, substituting cyclopentanol for tetrahydro-pyran-4-ol. The crude product was purified by reverse-phase HPLC on an Atlantis C18 column (1.9×10 cm, 5 μm particle size) using a gradient of 5% to 95% acetonitrile:0.1% aqueous trifluoroacetic acid to provide the title compound. $^1$H NMR (300 MHz, DMSO-$d_6$) δ ppm 1.15-1.27 (m, 2H) 1.42 (d, J=7.35 Hz, 3H) 1.53-1.64 (m, 1H) 1.65-1.79 (m, 4H) 1.87 (s, 3H) 1.88-2.01 (m, 1H) 4.76-4.90 (m, 1H) 5.02-5.16 (m, 1H) 6.88 (s, 1H) 6.94-7.03 (m, 2H) 7.27-7.42 (m, 2 H) 7.95 (s, 1H) 8.50 (d, J=8.09 Hz, 1H); MS (ESI) m/z 414.1 (M+H)+.

Example 57

N-(1-{3-[4-chloro-2-(4-isopropoxyphenoxy)-1,3-thiazol-5-yl]isoxazol-5-yl}ethyl)acetamide Example 57A 2,4-dichloro-1,3-thiazole-5-carbaldehyde oxime Hydroxylamine hydrochloride (385 mg, 5.54 mmol) was added to a solution of sodium bicarbonate (465 mg, 5.54 mmol) in water (17 mL) at room temperature. Then a solution of 2,4-dichloro-5-thiazolecarboxaldehyde (100 g, 5.49 mmol) in ethanol (17 mL) was added The mixture was clear yellow and the precipitates started to appear in ~20 minutes More water (~40 mL) was added. After stirring for 1 hour, the reaction was filtered. The solid was washed with water and dried under vacuum overnight to give the title compound as a white sold (883 mg, 82%).

Example 57B 2,4-dichloro-N-hydroxy-1,3-thiazole-5-carboximidoyl chloride

The title compound was prepared using the procedure as described in Example 17D, substituting Example 57A for Example 17C.

Example 57C

2-{1-[3-(2,4-dichloro-1,3-thiazol-5-yl)isoxazol-5-yl]ethyl}-1H-isoindole-1,3(2H)-dione The title compound was prepared using the procedure as described in Example 17E, substituting Example 57B for Example 17D.

Example 57D 2-(1-{3-[4-chloro-2-(4-isopropoxyphenoxy)-1,3-thiazol-5-yl]isoxazol-5-yl}ethyl)-1H-isoindole-1,3(2H)-dione To a solution of Example 17A (150 mg, 0.99 mmol) and Example 57C (348 mg, 0.88 mmol) in DMSO (5 mL) was added $K_2CO_3$ (146 mg, 1.06 mmol) at room temperature. The mixture was stirred at 80° C. overnight. The mixture was poured into water. The aqueous layer was extracted with ether (3×). The combined extracts were washed with waster (1×), brine (1×), dried over MgSO4 and concentrated. The residue was purified on silica gel eluting with ethyl acetate: hexane gradient to give the desired product as a white solid (188 mg, 37%).

Example 57B

1-{3-[4-chloro-2-(4-isopropoxyphenoxy)-1,3-thiazol-5-yl]isoxazol-5-yl}ethanamine The title compound (100% yield) was prepared using the procedure as described in Example 17F, substituting Example 57D for Example 17E.

Example 57F

N-(1-{3-[4-chloro-2-(4-isopropoxyphenoxy)-1,3-thiazol-5-yl]isoxazol-5-yl}ethyl)acetamide The title compound (59% yield) was prepared using the procedure as described in Example 17G, substituting Example 57E for Example 17F. MS (DCI): m/z 422, 424 (M+H); $^1$H NMR (300 MHz, CDCl$_3$) δ ppm 7.15-7.23 (m, 2H), 6.86-6.99 (m, 2H), 6.78 (s, 1H), 5.76 (br, s, 1H), 5.32-5.48 (m, 1H), 4.44-4.61 (m, 1H), 2.03 (s, 3H), 1.58 (d, J=6.99 Hz, 3H), 1.36 (d, J=5.89 Hz, 6H).

Example 58

N-(1-{3-[4-chloro-2-(4-isopropoxyphenoxy)-1,3-thiazol-5-yl]isoxazol-5-yl}ethyl)-N'-methylurea The title compound (56% yield) was prepared using the procedure as described in Example 17G, substituting Example 57D for Example 17F, MS (DCI): m/z 437, 439 (M+H), 454, 456 (M+NH4); $^1$H NMR (300 MHz, CDCl$_3$) δ ppm 7.14-7.23 (m, 2H), 6.84-6.97 (m, 2H), 6.77 (s, 1H), 5.16-5.30 (m, 1H), 4.47-4.62 (m, 1H), 4.28 (br, s, 1H), 2.80 (d, J=4.78 Hz, 3H), 1.58 (d, J=6.99 Hz, 3H), 1.35 (d, J=6.25 Hz, 6H).

Example 59 methyl 1-{3-[4-chloro-2-(4-isopropoxyphenoxy)-1,3-thiazol-5-yl]isoxazol-5-yl}ethylcarbamate The title compound (64% yield) was prepared using the procedure as described in Example 22, substituting Example 57E for Example 17F. MS (DCI): m/z 438, 440 (M+H); $^1$H NMR (300 MHz, CDCl$_3$) δ ppm 7.15-7.23 (m, 2H), 6.88-6.96 (m, 2H), 6.78 (s, 1 H), 4.95-5.12 (m, 1H), 4.46-4.63 (m, 1H), 3.71 (s, 3H), 1.58 (d, J=6.99 Hz, 3H), 1.35 (d, J=5.88 Hz, 6H).

Example 60

N-(1-{3-[4-chloro-2-(4-isopropoxyphenoxy)-1,3-thiazol-5-yl]isoxazol-5-yl}ethyl)urea The title compound (45% yield) was prepared using the procedure as described in Example 23, substituting Example 57E for Example 17F. MS (DCI): m/z 423, 425 (M+H); $^1$H NMR (300 MHz, CDCl$_3$) δ ppm 7.15-7.22 (m, 2H), 6.87-6.99 (m, 2H), 6.79 (s, 1H), 5.12-5.30 (m, J=7.35 Hz, 1H), 4.73-4.82 (m, 1H), 4.45-4.63 (m, 1H), 4.37 (br, s, 2H), 1.57 (d, J=6.99 Hz, 3H), 1.35 (d, J=5.88 Hz, 6H).

Example 61

N-[1-(3-{2-[3-(isobutylamino)phenoxy]-1,3-thiazol-5-yl}isoxazol-5-yl)ethyl]acetamide

Example 61A 3-(Thiazol-2-yloxy)-phenylamine

The title compound was using the procedure as described in Example 29A, substituting 3-amino phenol for N-Boc-4-hydroxy-aniline. This material was used in the next step without rigorous purification.

Example 61B

[3-(Thiazol-2-yloxy)-phenyl]-carbamic acid tert-butyl ester

Example 61A (8.6 g, 0.045 mol) was dissolved in tetrahydrofuran (80 mL) and to this solution was added di-tert-butyl dicarbonate (10.3 g, 0.047 mol) portion wise over 15 min. The resulting reaction solution was heated to reflux for 5 h. The reaction was then cooled to room temperature, poured into water and extracted (2×) with ethyl acetate. The combined organics were dried over Na$_2$SO$_4$, filtered and concentrated by rotary evaporation. The residue was passed through a plug of silica gel using hexanes and ethyl acetate to elute, the solvents were removed by rotary evaporation and the residue was used without further purification.

Example 61C

N-(1-{3-[2-(3-Amino-phenoxy)-thiazol-5-yl]-isoxazol-5-yl}-ethyl)-acetamide

The title compound was prepared by substituting Example 61B for Example 29A in the preparation of Example 29B and then following the procedures for Examples 33B-33F.

Example 61D

N-[1-(3-{2-[3-(isobutylamino)phenoxy]-1,3-thiazol-5-yl}isoxazol-5-yl)ethyl]acetamide Example 61C (55 mg, 0.16 mmol) was dissolved in a buffer solution (1.5 mL of a solution prepared from 6 mL acetic acid and 8.5 g sodium acetate in 250 mL methanol). To this was added isobutyraldehyde (15 μL, 0.16 mmol) and NaCNBH$_3$ (10 mg, 0.16 mmol). The reaction solution was stirred at 70° C. for 1 hour, cooled, filtered and purified by reverse phase-HPLC (water:acetonitrile; gradient of 5% to 90% acetonitrile) to give the title compound (19 mg, 0.047 mmol, 29%). MS (ESI APCI) M/z 401.2 (M+H$^+$); $^1$H NMR (300 MHz, DMSO-d$_6$) δ 8.51 (d, J=8.09 Hz, 1H) 7.96 (s, 1H) 7.16 (t, J=7.91 Hz, 2 H) 6.89 (s, 1H) 6.41-6.61 (m, 2H) 6.06 (t, J=5.70 Hz, 1H) 5.02-5.15 (m, 1H) 2.82 (appt, J=6.25 Hz, 2H) 1.87 (s, 3H) 1.75-1.92 (m, 1H) 1.42 (d, J=6.99 Hz, 3H) 0.92 (d, J=6.62 Hz, 6H).

Example 62 methyl 1-{3-[2-(4-isopropoxyphenoxy)-1,3-thiazol-5-yl]-1,2,4-oxadiazol-5-yl}ethylcarbamate The title compound was prepared using the procedure as described in Example 40E, substituting methylchloroformate for acetic anhydride. $^1$H NMR (300 MHz, CDCl$_3$) δ ppm 7.90 (s, 1H) 7.17-7.25 (m, 2H) 6.88-6.98 (m, 2H) 5.06-5.39 (m, 1H) 4.53 (heptet, J=6.25 Hz, 1H) 3.72 (s, 3H) 1.63 (d, J=6.62 Hz, 3H) 1.36 (d, J=6.25 Hz, 6 H).). MS (DCI): m/z 405 (M+H).

Example 63

N-(1-{3-[2-(4-isopropoxyphenoxy)-1,3-thiazol-5-yl]-1,2,4-oxadiazol-5-yl}ethyl)-N'-ethylurea The title compound was prepared using the procedure as described in Example 40E, substituting methylisocyanate for acetic anhydride. In addition, the reaction was performed in the absence of diisopropylethyl amine. $^1$H NMR (300 MHz, CDCl$_3$) δ ppm 7.90 (s, 1H) 7.16-7.25 (m, 2H) 6.87-6.98 (m, 2H) 5.23-5.43 (m, 1H) 4.94 (d, J=8.09 Hz, 1H) 4.48-4.62 (m, 1H) 4.37-4.49 (m, 1H) 2.81 (d, J=4.78 Hz, 3H) 1.60 (d, J=7.35 Hz, 3H) 1.36 (d, J=6.25 Hz, 6H).). MS (DCI): m/z 404 (M+H).

Example 64

N-(1-{3-[2-(4-isopropoxyphenoxy)-1,3-thiazol-5-yl]-1,2,4-oxadiazol-5-yl}ethyl)urea To a solution Example 40D (140 mg) in dichloromethane (5 mL) was added trichloroacetyl isocyanate (100 uL) and the reaction was stirred at room temperature overnight. The solvent was removed under vacuum, and then the mixture was dissolved in methanol (5 mL), potassium carbonate (100 mg) was added and the mixture was stirred at room temperature for 2 hours. To the reaction mixture was added dichloromethane and the dichloromethane layer was washed with water and brine. The organics were dried over magnesium sulfate, filtered, and evaporated. The crude product was purified via silica-gel chromatography using a gradient (13 to 100% ethyl acetate in hexane), and yielded 45 mg of the title compound as white solid. $^1$H NMR (300 MHz, CDCl$_3$) δ ppm 7.92 (s, 1H) 7.16-7.25 (m, 2H) 6.88-6.98 (m, 2H) 5.50 (d, J=8.46 Hz, 1H) 5.21-5.37 (m, 1H) 4.63 (s, 2H) 4.46-4.59 (m, 1H) 1.56-1.60 (d, J=6.99 Hz, 3H) 1.36 (d, J=6.25 Hz, 6H).). MS (DCI): m/z 390 (M+H).

Example 65

N-{1-[3-(2-{3-[(cyclopropylmethyl)amino]phenoxy}-1,3-thiazol-5-yl)isoxazol-5-yl]ethyl}acetamide The title compound was prepared using the procedure as described in Example 61D, substituting cyclopropanecarboxaldehyde for isobutyraldehyde. MS (ESI APCI) m/z 399.2 (M+H$^+$); $^1$H NMR (300 MHz, DMSO-d$_6$) δ 8.51 (d, J=8.09 Hz, 1H) 7.96 (s, 1H) 7.18 (t, J=8.09 Hz, 2H) 6.89 (s, 1H) 6.45-6.65 (m, 2H) 5.76 (s, 1H) 5.01-5.16 (m, 1H) 2.90 (d, J=6.62 Hz, 2H) 1.87 (s, 3H) 1.42 (d, J=6.99 Hz, 3H) 0.94-1.09 (m, 1H) 0.39-0.53 (m, 2H) 0.16-0.27 (m, 2H).

Example 66

N-[1-(3-{2-[3-(isopropylamino)phenoxy]-1,3-thiazol-5-yl}isoxazol-5-yl)ethyl]acetamide The title compound was prepared using the procedure as described in Example 61D, substituting acetone for isobutyraldehyde. MS (ESI APCI) m/z 387.2 (M+H$^+$); $^1$H NMR (300 MHz, DMSO-d$_6$) δ 8.51 (d, J=8.09 Hz, 1H) 7.96 (s, 1H) 7.16 (t, J=8.09 Hz, 2H) 6.89 (s, 1H) 6.37-6.60 (m, 2H) 5.84 (d, J=8.09 Hz, 1H) 4.96-5.19 (m, 1H) 3.45-3.62 (m, J=14.16, 6.43 Hz, 1H) 1.87 (s, 3H) 1.42 (d, J=7.35 Hz, 3H) 1.12 (d, J=625 Hz, 6H).

Example 67 tert-butyl 4-[(5-{5-[1-(acetylamino)ethyl]-1,2,4-oxadiazol-3-yl}-1,3-thiazol-2-yl)oxy]phenylcarbamate

Example 67A tert-butyl 4-[(5-cyano-1,3-thiazol-2-yl)oxy]phenylcarbamate 2-chloro-thiazole-5-carbonitrile (900 mg 6.2 mmol; prepared according to procedure described in WO 01/17995, p. 103) and N-Boc-4-hydroxy-aniline (1.3 g, 6.2 mmol) were combined in N,N-dimethyl formamide (5 mL). To this solution, K$_2$CO$_3$ (2.6 g, 18.8 mmol) was added and the resulting reaction mixture was stirred at room temperature overnight. The reaction mixture was then poured into water and extracted with ethyl acetate (2×). The combined organics were dried (Na$_2$SO$_4$), filtered and concentrated by rotary evaporation. The residue was purified by flash column chromatography (ethyl acetate:hexanes: 5%-50% ethyl acetate gradient) to give the title compound (2.0 g, 6.2 mmol, 100%) as a white solid. MS (ESI APCI) m/z 316.0 (M−H$^+$); $^1$H NMR (300 MHz, DMSO-d$_6$) δ 9.59 (s, 1H) 8.24 (s, 1H) 7.58 (d, J=9.0 Hz, 2H) 7.36 (d, J=9.0 Hz, 2H) 1.48 (s, 9H).

Example 67B tert-butyl 4-({5-[(Z)-amino(hydroxyimino)methyl]-1,3-thiazol-2-yl}oxy)phenylcarbamate Example 67A (2.0 g, 6.2 mmol) was dissolved in ethanol: H$_2$O (10.5 mL, 95:5) and triethylamine (9.0 mL, 63.0 mmol) was added. To this solution was added hydroxylamine hydrochloride (122 g, 18.9 mmol) and the reaction was stirred for 2 hours. The reaction solution was then concentrated by rotary evaporation and water was added. A small amount of methanol was added and the mixture was sonicated for 1 hour to give a free-flowing solid which was collected by filtration and dried under high vacuum to give the title compound (2.0 g, 5.7 mmol, 92%) as a white solid, MS (ESI APCI) m/z 351.1 (M+H$^+$); $^1$H NMR (300 MHz, DMSO-d$_6$) δ 9.67 (s, 2H) 9.50 (s, 1H) 7.62 (s, 1H) 7.53 (d, J=9.0 Hz, 2H) 7.25 (d, J=9.0 Hz, 2H) 6.00 (s, 1H) 1.48 (s, 9H).

Example 67C tert-butyl 4-({5-[(Z)-({[2-(acetylamino)propanoyl]oxy}imino)(amino)methyl]-1,3-thiazol-2-yl}oxy)phenylcarbamate Example 67B (1.73 g, 5.0 mmol) was dissolved in CH$_2$Cl$_2$:N,N-dimethyl formamide (17 mL, 3:1). To this solution was added N-acetyl-DL-alanine (0.72 g, 5.5 mmol), 1-ethyl-3-[3-(dimethylamino)propyl]-carbodiimide (1.25 g, 6.5 mmol), 1 hydroxybenzotriazole hydrate (67.0 mg, 0.5 mmol) and then diisopropylethylamine (1.31 mL, 7.5 mmol). The reaction solution was stirred overnight at room temperature, poured into saturated NaHCO$_3$, and extracted with ethyl acetate (2×). The combined organics were washed with water, dried (Na$_2$SO$_4$), filtered and concentrated by rotary evaporation. The residue was purified by flash column chromatography (ethyl acetate:hexanes; 5%-75% ethyl acetate gradient) to give the title compound (2.12 g, 4.6 mmol, 92%). MS (ESI APCI) m/z 464.2 (M+H$^+$); $^1$H NMR (300 MHz, DMSO-d$_6$) δ 9.53 (s, 2H) 8.34 (d, J=7.35 Hz, 1H) 7.87 (s, 1H) 7.55 (d, J=8.82 Hz, 2H) 7.29 (d, J=9.19 Hz, 2H) 7.03 (s, 1H) 4.36-4.49 (m, 1H) 1.85 (s, 3H) 1.48 (s, 9H) 1.31 (d, J=7.35 Hz, 3H).

Example 67D tert-butyl 4-[(5-{5-[1-(acetylamino)ethyl]-1,2,4-oxadiazol-3-yl}-1,3-thiazol-2-yl)oxy]phenylcarbamate Example 67C (200 mg, 0.43 mmol) was dissolved in pyridine (15 mL) and the resulting solution was heated at 115° C. for 5 hours. The reaction solution was cooled to room temperature, diluted with ethyl acetate, poured into 5% aqueous citric acid and separated. The aqueous layer was extracted with ethyl acetate (2×) and the combined organics were washed with 5% aqueous citric acid (4×), dried (Na$_2$SO$_4$), filtered and concentrated by rotary evaporation. The residue was purified by flash column chromatography (ethyl acetate:hexanes; 5%-100% ethyl acetate gradient) to give the title compound. MS (ESI APCI) m/z 446.2 (M+H$^+$); $^1$H NMR (500 MHz, DMSO-d$_6$) δ 9.53 (s, 1H) 8.69 (d, J=6.71 Hz, 1H) 7.98 (s, 1H) 7.58 (d, J=9.16 Hz, 2H) 7.35 (d, J=9.16 Hz, 2H) 508-5.20 (m, 1H) 1.88 (s, 3H) 1.45-1.52 (m, 12H).

Example 68

N-[1-(3-{2-[(6-isopropoxypyridin-3-yl)oxy]-1,3-thiazol-5-yl}isoxazol-5-yl)ethyl]acetamide

Example 68A 5-bromo-2-isopropoxypyridine

To isopropanol (11 mL, 143 mmol) under nitrogen at 25° C. was added sodium hydride (95%, 1.94 g, 76.7 mmol) portion wise over 5 minutes. The reaction was stirred for 16 hours and a solution of 2-fluoro-5-bromopyridine (9 g, 51 mmol) in N,N-dimethyl formamide (250 mL) was added over 10 minutes. The resulting mixture was heated at 130° C. for 4 hours and cooled to 25° C. The mixture was diluted with ether (500 mL) and washed with water (600 mL) and brine (300 mL). The organic layer was dried (MgSO$_4$), filtered, and concentrated to provide 10.1 g of the title compound (92%) as light yellow liquid. $^1$H NMR (300 MHz, DMSO-d$_6$) δ ppm 1.28 (d, J=6.25 Hz, 6H) 5.08-5.28 (m, 1H) 6.75 (d, J=8.82 Hz, 1H) 7.86 (dd, J=8.82, 2.57 Hz, 1H) 8.26 (d, J=2.57 Hz, 1H); MS (ESI) m/z 217.9 (M+H)$^+$.

Example 68B 6-isopropoxypyridin-3-ol

To a solution of Example 68A (7.9 g, 36.6 mmol) in tetrahydrofuran (100 mL) cooled to −78° C. under nitrogen was added butyllithium (1.6M in hexanes, 37 ml, 59.2 mmol) drop wise over 10 minutes. The reaction was stirred for 20 minutes and trimethyl borate (6.7 mL, 59.2 mmol) was added drop wise over 5 minutes. The resulting mixture was stirred for 2 hours at −78+ C. and peracetic acid (32% in acetic acid, 13 mL, 59.2 mmol) was added. After 10 minutes at −78° C. the reaction was warmed to 0° C. and stirred for 1 hour. The reaction was cooled to −10° C. and treated with 10% aqueous sodium bisulfite (30 mL). The mixture was concentrated to ⅓ volume and extracted with ether (300 mL). The organic phase was washed with water (300 mL) and brine (200 mL), dried (MgSO$_4$), filtered, and concentrated to provide 5.2 g of the title compound (92%) as a light yellow liquid. $^1$H NMR (300 MHz, DMSO-d$_6$) δ ppm 1.23 (d, J=6.25 Hz, 6H) 4.95-5.17 (m, 1H) 6.57 (d, J=8.82 Hz, 1H) 7.14 (dd, J=8.82, 2.94 Hz, 1H) 7.65 (d, J=2.94 Hz, 1H) 9.21 (s, 1H); MS (DCI) m/z 154.0 (M+H)$^+$.

Example 68C 2-isopropoxy-5-(1,3-thiazol-2-yloxy)pyridine

The title compound was prepared according to the procedure described in Example 30A, substituting Example 68B for 2-chloro-4-methoxyphenol. The crude product was purified by flash chromatography on silica gel eluting with a solvent gradient from 5% to 20% ethyl acetate in hexanes to provide the title compound as a light yellow liquid. $^1$H NMR (300 MHz, DMSO-d$_6$) δ ppm 1.30 (d, J=5.88 Hz, 6H) 5.13-5.30 (m, 1H) 6.84 (d, J=8.82 Hz, 1H) 7.18-7.30 (m, 2H) 7.78 (dd, J=8.82, 2.94 Hz, 1H) 8.22 (d, J=2.94 Hz, 1H); MS (ESI) m/z 236.9 (M+H)$^+$.

Example 68D

2-[(6-isopropoxypyridin-3-yl)oxy]-1,3-thiazole-5-carbaldehyde

The title compound was prepared according to the procedure described in Example 30B, substituting Example 68C for Example 30A. The crude product was purified by flash chromatography on silica gel eluting with a solvent gradient from 10% to 25% ethyl acetate in hexanes to provide Example 68D as a light yellow liquid. $^1$H NMR (300 MHz, DMSO-d$_6$) δ ppm 1.31 (d, J=6.25 Hz, 6H) 5.14-5.31 (m, 1H) 6.88 (d, J=9.56 Hz, 1H) 7.87 (dd, J=19.19, 2.94 Hz, 1H) 8.28 (s, 1H) 8.29 (d, J=2.57 Hz, 1H) 9.89 (s, 1H); MS (ESI) m/z 264.7 (M+H)$^+$.

Example 68E

2-[(6-isopropoxypyridin-3-yl)oxy]-1,3-thiazole-5-carbaldehyde oxime

The title compound was prepared according to the procedure described in Example 30C, substituting Example 68D for Example 30B. The crude product was purified by flash chromatography on silica gel eluting with a solvent gradient from 5% to 25% ethyl acetate in hexanes to provide the title compound as an off-white solid. $^1$H NMR (300 MHz, DMSO-d$_6$) δ ppm 1.31 (d, J=6.25 Hz, 6H) 5.08-5.30 (m, 1H) 6.85 (d, J=9.56 Hz, 1H) 7.69 (s, 1H) 7.77-7.87 (m, 2H) 8.25 (d, J=2.57 Hz, 1H) 12.03 (s, 1H); MS (ESI) m/z 280.0 (M+H)$^+$.

Example 68F

N-hydroxy-2-[(6-isopropoxypyridin-3-yl)oxy]-1,3-thiazole-5-carboximidoyl chloride The title compound was prepared according to the procedure described in Example 30D, substituting Example 68E for Example 30C. $^1$H NMR (300 MHz, DMSO-d$_6$) δ ppm 1.30 (d, J=6.25 Hz, 6H) 5.15-5.30 (m, 1H) 6.86 (d, J=9.56 Hz, 1H) 7.67 (s, 1H) 7.83 (dd, J=9.01, 3.13 Hz, 1H) 8.27 (d, J=2.57 Hz, 1H) 12.48 (s, 1H).

Example 68G

2-[1-(3-{2-[(6-isopropoxypyridin-3-yl)oxy]-1,3-thiazol-5-yl}isoxazol-5-yl)ethyl]-1H-isoindole-1,3(2H)-dione The title compound was prepared according to the procedure described in Example 30E, substituting Example 68F for Example 30D. The crude product was purified by flash chromatography on silica gel eluting with a solvent gradient from 10% to 60% ethyl acetate in hexanes to provide Example 68G as a white solid. $^1$H NMR (300 MHz, DMSO-d$_6$) δ ppm 1.31 (d, J=6.25 Hz, 6H) 1.82 (d, J=7.35 Hz, 3H) 5.11-5.31 (m, 1H) 5.55-5.71 (m, 1H) 5.76 (s, 1H) 6.87 (d, J=8.82 Hz, 1H) 7.18 (s, 1H) 7.74-8.02 (m, 5H) 8.28 (d, J=2.57 Hz, 1H); MS (ESI) m/z 477.1 (M+H)$^+$.

Example 68H 1-(3-{2-[6-isopropoxypyridin-3-yl)oxy]-1,3-thiazol-5-yl}isoxazol-5-yl)ethanamine The title compound was prepared according to the procedure described in Example 30H, substituting Example 68G for Example 30G. The crude product was purified by flash chromatography on silica gel eluting with 90:8:2 dichloromethane/methanol/concentrated ammonium hydroxide to provide the title compound. $^1$H NMR (300 MHz, DMSO-d$_6$) δ ppm 1.31 (d, J=6.25 Hz, 6H) 1.82 (d, J=7.35 Hz, 3H) 4.02-5.14 (m, 1H) 5.18-5.28 (m, 1H) 6.86 (s, 1H) 6.87 (d, J=8.82 Hz, 1H) 7.18 (s, 1H) 7.82 (dd, J=9.19, 2.94 Hz, 1H) 8.28 (d, J=2.57 Hz, 1H); MS (ESI) m/z 347.1 (M+H)+.

Example 68I

N-[1-(3-{2-[(6-isopropoxypyridin-3-yl)oxy]-1,3-thiazol-5-yl}isoxazol-5-yl)ethyl]acetamide The title compound was prepared according to the procedure described in Example 30I, substituting Example 68H for Example 30H. The crude product was purified by reverse-phase HPLC on an Atlantis C18 column (1.9×10 cm, 5 μm particle size) using a gradient of 5% to 100% acetonitrile: 0.1% aqueous trifluoroacetic acid to provide the title compound as a white solid. $^1$H NMR (300 MHz, DMSO-$d_6$) δ ppm 1.31 (d, J=6.25 Hz, 6H) 1.42 (d, J=6.99 Hz, 3H) 1.87 (s, 3H) 5.03-5.16 (m, 1H) 5.18-5.30 (m, 1H) 6.87 (d, J=9.56 Hz, 1H) 6.90 (s, 1H) 7.86 (dd, J=9.19, 2.94 Hz, 1H) 7.95 (s, 1H) 8.29 (d, J=2.57 Hz, 1H) 8.52 (d, J=8.09 Hz, 1H); MS (ESI) m/z 389.1 (M−H)+.

Example 69

N-[1-(3-{4-[(5-isopropoxypyridin-2-yl)oxy]phenyl}isoxazol-5-yl)ethyl]acetamide

Example 69A 2-fluoro-5-isopropoxypyridine

To a solution of 2-fluoro-5-hydroxypyridine (6.000 g, 53.05 mmol) in N,N-dimethyl formamide (50 mL) cooled with an ice bath was added NaH (2.80 g, 60%, 70.0 mml) in several potions. After the addition, the mixture was stirred at 0° C. for 10 minutes. 2-iodopropane (6.5 mL, 65.00 mmol) was added. The mixture was stirred at room temperature for 2 hours. The mixture was poured into water, extracted with ether (2×), the combined extracts were washed with 1N NaOH (1×), water (1×), brine (1×), dried over MgSO$_4$ and concentrated to give the product that was used directly without further purification.

Example 69B 2-(4-bromophenoxy)-5-isopropoxypyridine

To a mixture of Example 69A (~53.05 mmol) and 4-bromophenol (13.80 g, 79.76 mmol) in DMSO (50 mL) cooled with an ice-bath was added NaH (60%, 3.20 g, 80.0 mmol) in several portions. After the addition, the mixture was stirred at room temperature for 10 minutes. To this was added 18-crown-6 (16.0 mL, 80.6 mmol). The reaction mixture was heated to 160° C. for 60 hours. The mixture was poured into 1N NaOH, extracted with ethyl acetate (2×). The combined extracts were washed with water (1×), brine (1×), dried over MgSO$_4$ and concentrated. The residue was purified on silica gel eluting with ethyl acetate and hexane to give the desired product as yellow oil (11.1 g).

Example 69C

4-[(5-isopropoxypyridin-2-yl)oxy]benzaldehyde

To a solution of Example 69B (1.00 g, 3.25 mmol) in tetrahydrofuran (10 mL) was added n-butyl lithium (2.5 M in hexanes, 1.35 mL, 3.38 mmol) at −78° C. The mixture was stirred for 30 minutes, and then 4-formylmorpholine (380 μL, 3.80 mmol) was added. The mixture was stirred for 30 minutes and warmed to room temperature before quenching with water. The aqueous layer was extracted with ether (1×). The ether layer was washed with brine (1×), dried over MgSO$_4$ and concentrated to give the title compound as colorless viscous oil.

Example 69D 1-(3-{4-[(5-isopropoxypyridin-2-yl)oxy]phenyl}isoxazol-5-yl)ethanamine The title compound was prepared by substituting Example 69C for Example 17B and following subsequent reaction conditions in Examples 21C-F.

Example 69E

N-[1-(3-{4-[(5-isopropoxypyridin-2-yl)oxy]phenyl}isoxazol-5-yl)ethyl]acetamide

The title compound was prepared in 68% yield by substituting Example 69D for Example 17F, following the procedure described in Example 17G. MS (DCI): m/z 382 (M+H); $^1$H NMR (300 MHz, CDCl$_3$) δ ppm 7.88 (d, J=2.94 Hz, 1H), 7.72-7.83 (m, 2 H), 7.27-7.38 (m, 1H), 7.09-7.21 (m, 2H), 6.91 (d, J=8.82 Hz, 1H), 6.42 (s, 1 H), 5.82 (m, 1H), 5.30-5.50 (m, 1H), 4.35-4.61 (m, 1H), 2.04 (s, 3H), 1.59 (d, J=6.99 Hz, 3H), 1.35 (d, J=5.88 Hz, 6H).

Example 70

N-(1-{3-[6-(4-isopropoxyphenoxy)pyridin-3-yl]isoxazol-5-yl}ethyl)acetamide

The title compound was prepared by substituting 5-bromo-2-fluoropyridine for 2-bromothiazole in Example 1B and following the reaction conditions in Examples 1B-G. MS (DCI): m/z 382 (M+H); $^1$H NMR (300 MHz, CDCl$_3$) δ ppm 8.53 (s, 1H), 8.11 (dd, J=8.46, 2.57 Hz, 1H), 7.03-7.13 (m, 2H), 6.87-7.02 (m, 3H), 6.38-6.41 (s, 1H), 5.83 (d, J=8.09 Hz, 1H), 5.32-5.48 (m, 1H), 4.41-4.60 (m, 1H), 2.04 (s, 3H), 1.59 (d, J=7.35 Hz, 3H), 1.35 (d, J=5.88 Hz, 6H).

Example 71

N-[1-(3-{2-[4-(isobutylamino)phenoxy]-1,3-thiazol-5-yl}-1,2,4-oxadiazol-5-yl)ethyl]acetamide Example 67D (222 mg, 0.50 mmol) was dissolved in CH$_2$Cl$_2$ (3 mL) and to this solution was added trifluoroacetic acid (0.9 mL, 30% v/v). The reaction was stirred for 1.5 hours upon which time the volatiles were removed by evaporation and the residue was placed on high vacuum. The crude material (83.2 mg) was then dissolved in a buffer solution (1.2 mL of a solution consisting of 6 mL, acetic acid and 8.5 g sodium acetate in 250 mL methanol). To this was added isobutyraldehyde (24 μL, 0.26 mmol) and NaCNBH$_3$ (16.5 mg, 0.26 mmol). The reaction solution was stirred at 70° C. for 1 hour, cooled, filtered and purified by reverse phase HPLC (water: acetonitrile; gradient of 5% to 90% acetonitrile) to give the title compound. MS (ESI APCI) m/z 402.2 (M+H+); $^1$H NMR (300 MHz, DMSO-$d_6$) δ 8.71 (d, J=6.99 Hz, 1H) 7.97 (s, 1H) 7.15 (d, J=9.19 Hz, 2H) 6.66 (d, J=8.82 Hz, 2H) 5.76 (s, 1H) 5.07-5.20 (m, 1H) 2.85 (d, J=6.62 Hz, 2H) 1.89-1.80 (m, 4H) 1.49 (d, J=6.99 Hz, 3H) 0.95 (d, J=6.62 Hz, 6H).

Example 72 tert-butyl 4-[(5-{5-[1-(acetylamino)ethyl]-1,2,4-oxadiazol-3-yl}-1,3-thiazol-2-yl)oxy]-2-chlorophenylcarbamate

Example 72A tert-butyl 4-({5-[(Z)-({[2-(acetylamino)propanoyl]oxy}imino)(amino)methyl]-1,3-thiazol-2-yl}oxy)-2-chlorophenylcarbamate The title compound was prepared in the same manner as 74C by substituting Example 52A for N-Boc-4-hydroxyaniline in the preparation of Example 67A and then following the reaction conditions for Examples 74A-74C. MS (ESI APCI) m/z 498.1 (M+H$^+$); $^1$H NMR (300 MHz, DMSO-d$_6$) δ 8.81 (s, 1H) 8.35 (d, J=6.99 Hz, 1H) 7.89 (s, 1H) 7.58-7.67 (m, 2H) 7.36 (dd, J=9.01, 2.76 Hz, 1H) 7.07 (bs, 2H) 4.34-4.51 (m, 1H) 1.86 (s, 3H) 1.47 (s, 9H) 1.32 (d, J=7.35 Hz, 3H).

Example 72B tert-butyl 4-[(5-{5-[1-(acetylamino)ethyl]-1,2,4-oxadiazol-3-yl}-1,3-thiazol-2-yl)oxy]-2-chlorophenylcarbamate Example 72A (1.64 g, 3.3 mmol) was dissolved in pyridine (25 mL) and the solution was heated to reflux for 3 hours. The reaction was concentrated by rotary evaporation and diluted with ethyl acetate. The organics were washed with 5% aqueous citric acid twice and the combined organics were dried (Na$_2$SO$_4$), filtered and concentrated by rotary evaporation. The residue was purified by flash column chromatography (ethyl acetate:hexanes; 5%-100% ethyl acetate gradient) to provide the title compound (710 mg, 1.5 mmol, 45%): MS (ESI APCI) m/z 480.1 (M+H$^+$); $^1$H NMR (300 MHz, DMSO-d$_6$) δ 8.84 (s, 1H) 8.73 (d, J=6.99 Hz, 1H) 7.99 (s, 1H) 7.71 (d, J=2.57 Hz, 1H) 7.66 (d, J=8.82 Hz, 1H) 7.42 (dd, J=8.82, 2.57 Hz, 1H) 5.09-5.23 (m, 1H) 1.88 (s, 3H) 1.50 (d, J=7.35 Hz, 3H) 1.47 (s, 9H).

Example 73

1-{3-[2-(4-isopropoxyphenoxy)-1,3-thiazol-5-yl]-1,2,4-oxadiazol-5-yl}ethanamine

A solution of Example 40C (372 mg) in 9:1 dichloromethane:ethanol (25 mL) was charged with hydrazine hydrate (379 uL) and refluxed for 4 hours. The solvent was dried in vacuum and the reaction mixture was stirred in dichloromethane for 3 hours. The solid was removed by filtration and the residue was concentrated under vacuum to yield 265 mg of the title product. $^1$H NMR (300 MHz, CDCl$_3$) δ ppm 7.91 (s, 1H) 7.15-7.25 (m, 2H) 6.88-7.00 (m, 2H) 4.46-4.61 (m, 1H) 4.28-4.41 (m, J=6.86 Hz, 1H) 1.58 (d, J=6.99 Hz, 3H) 1.36 (d, J=5.88 Hz, 6H) MS (DCI): m/z 347 (M+H).

Example 74

N-{1-[3-(2-{3-chloro-4-[(cyclopropylmethyl)amino]phenoxy}-1,3-thiazol-5-yl)-1,2,4-oxadiazol-5-yl]ethyl}acetamide Example 111 (34.0 mg, 0.090 mmol) was dissolved in a buffer solution (1.0 mL of a solution consisting of 6 mL acetic acid and 8.5 g sodium acetate in 250 mL methanol). To this was added cyclopropanecarboxaldehyde (6.7 μL, 0.09 mmol) and NaCNBH$_3$ (17.1 mg, 0.27 mmol). The reaction solution was stirred at 70° C. for 1 hour, cooled, filtered and purified by reverse phase-HPLC (water:acetonitrile; gradient of 5% to 90% acetonitrile) to give the title compound (14.0 mg, 0.032 mmol, 36%). MS (ESI APCI) m/z 434.0 (M+H$^+$); $^1$H NMR (300 MHz, DMSO-d$_6$) δ 8.71 (d, J=6.99 Hz, 1H) 7.98 (s, 1H) 7.51 (d, J=2.94 Hz, 1H) 7.26 (dd, J=8.82, 2.94 Hz, 1H) 6.84 (d, J=9.19 Hz, 1H) 5.06-5.22 (m, 1H) 3.05 (d, J=6.62 Hz, 2H) 1.87 (s, 3H) 1.49 (d, J=6.99 Hz, 3H) 1.03-1.19 (m, 1H) 0.41-0.53 (m, 2H) 0.26 (q, J=4.66 Hz, 2H).

Example 75

N-[1-(3-{2-[3-chloro-4-(isobutylamino)phenoxy]-1,3-thiazol-5-yl}-1,2,4-oxadiazol-5-yl)ethyl]acetamide The title compound was prepared using the procedure as described in Example 74, substituting isobutyraldehyde for cyclopropanecarboxaldehyde. MS (ESI APCI) m/z 436.1 (M+H$^+$); $^1$H NMR (300 MHz, DMSO-d$_6$) δ 8.71 (d, J=6.99 Hz, 1H) 7.97 (s, 1H) 7.49 (d, J=2.94 Hz, 1H) 7.25 (dd, J=9.01, 2.76 Hz, 1H) 6.78 (d, J=9.19 Hz, 2H) 5.05-5.23 (m, 1H) 2.99 (d, J=699 Hz, 2H) 1.81-1.98 (m, 4H) 1.49 (d, J=6.99 Hz, 3H) 0.92 (d, J=6.62 Hz, 6H).

Example 76

N-[1-(3-{2-[3-chloro-4-(isopropylamino)phenoxy]-1,3-thiazol-5-yl}-1,2,4-oxadiazol-5-yl)ethyl]acetamide The title compound was prepared using the procedure as described in Example 74, substituting acetone for cyclopropanecarboxaldehyde. MS (ESI APCI) m/z 422.1 (M+H$^+$); $^1$H NMR (300 MHz, DMSO-d$_6$) δ 8.71 (d, J=6.99 Hz, 1H) 7.98 (s, 1H) 7.50 (d, J=2.57 Hz, 1H) 7.27 (dd, J=9.01, 2.76 Hz, 1H) 6.83 (d, J=9.19 Hz, 2H) 5.08-5.22 (m, 1H) 3.60-3.78 (m, 1H) 1.87 (s, 3H) 1.49 (d, J=735 Hz, 3H) 1.21 (d, J=6.25 Hz, 6H).

Example 77

N-[1-(3-{2-[4-(isopropylamino)phenoxy]-1,3-thiazol-5-yl}-1,2,4-oxadiazol-5-yl)ethyl]acetamide The title compound was prepared using the procedure as described in Example 71, substituting acetone for isobutyraldehyde, MS (ESI APCI) m/z 388.3 (M+H$^+$); $^1$H NMR (300 MHz, DMSO-d$_6$) δ 8.71 (d, J=6.99 Hz, 1H) 7.98 (s, 1H) 7.17-7.28 (m, 1 H) 6.79 (s, 1H) 5.06-5.22 (m, 1H) 3.51-3.64 (m, 1H) 1.87 (s, 3H) 1.49 (d, J=6.99 Hz, 3 H) 1.16 (d, J=6.25 Hz, 6H).

Example 78

N-(1-{3-[2-(4-isopropoxyphenoxy)-1,3-thiazol-5-yl]-1,2,4-oxadiazol-5-yl}ethyl)cyclopropanecarboxamide The title compound was prepared using the procedure as described in Example 40E, substituting cyclopropanecarbonyl chloride for acetic anhydride. $^1$H NMR (300 MHz, CDCl$_3$) δ ppm 7.91 (s, 1H) 7.16-7.25 (m, 2H) 6.88-6.99 (m, 2H) 6.22 (d, J=8.09 Hz, 1H) 5.36-5.56 (m, 1H) 4.44-4.63 (m, 1H) 1.63 (d, J=6.99 Hz, 3H) 1.39-1.51 (m, 1H) 1.36 (d, J=5.88 Hz, 6H) 0.94-1.07 (m, 2H) 0.73-0.88 (m, 2H). MS (DCI): m/z 387 (M+H)$^+$.

Example 79

N-(1-{3-[2-(4-isopropoxyphenoxy)-1,3-thiazol-5-yl]-1,2,4-oxadiazol-5-yl}ethyl)methanesulfonamide The title compound was prepared using the procedure as described in Example 40E, substituting methanesulfonyl chloride for acetic anhydride. $^1$H NMR (300 MHz, CDCl$_3$) δ ppm 7.91 (s, 1H) 7.16-7.25 (m, 2H) 6.88-6.99 (m, 2H) 4.92-5.08 (m, 2H) 4.46-4.62 (m, 1H) 3.03 (s, 3H) 1.65-1.77 (m, 3H) 1.36 (d, J=6.25 Hz, 6 H). MS (DCI): m/z 425 (M+H).

Example 80

N-(1-{3-[2-(4-isopropoxyphenoxy)-1,3-thiazol-5-yl]-1,2,4-oxadiazol-5-yl}ethyl)-2-methylpropanamide The title compound was prepared using the procedure as described in Example 40E, substituting isobutyryl chloride for acetic anhydride $^1$H NMR (300 MHz, CDCl$_3$) δ ppm 7.89 (s, 1H) 7.15-7.25 (m, 2H) 6.86-6.99 (m, 2H) 6.03 (d, J=7.72 Hz, 1 H) 5.33-5.51 (m, 1H) 4.45-4.63 (m, 1H) 2.34-2.55 (m, 1H) 1.61 (d, J=7.35 Hz, 3H) 1.36 (d, J=6.25 Hz, 6H) 1.20 (d, J=6.99 Hz, 3H) 1.20 (d, J=6.62 Hz, 3H). MS (DCI): m/z 416 (M+H)$^+$.

Example 81

N-[1-(3-{2-[(6-isopropoxypyridin-3-yl)oxy]-1,3-thiazol-5-yl}-1,2,4-oxadiazol-5-yl)ethyl]acetamide Example 81A 2-[(6-isopropoxypyridin-3-yl)oxy]-1,3-thiazole-5-carbonitrile To a 0° C. solution of Example 68E (464 mg, 1.66 mmol) in pyridine (10 mL) was added methanesulfonyl chloride (0.53 mL, 6.64 mmol). The reaction was warmed to 25° C., stirred for 4 hours and diluted with dichloromethane (50 mL). The mixture was washed with 10% HCl (2×50 mL) and brine (50 mL), dried (MgSO$_4$), filtered, and concentrated. The concentrate was purified by flash chromatography on silica gel eluting with a solvent gradient from 10% to 20% ethyl acetate in hexanes to provide 363 mg of the title compound (84%) as a off-white solid, $^1$H NMR (300 MHz, DMSO-d$_6$) δ ppm 1.31 (d, J=6.25 Hz, 6H) 5.14-5.30 (m, 1H) 6.89 (d, J=9.19 Hz, 1H) 7.87 (dd, J=9.01, 3.13 Hz, 1H) 8.23 (s, 1 H) 8.31 (d, J=2.57 Hz, 1H); MS (ESI) m/z 262.0 (M+H)$^+$.

Example 81B

N'-hydroxy-2-[(6-isopropoxypyridin-3-yl)oxy]-1,3-thiazole-5-carboximidamide

To a solution of Example 81A (343 mg, 1.3 mmol) and triethylamine (0.9 ml, 6.5 mmol) in ethanol/water (95:5, v/v, 10 mL) was added hydroxylamine hydrochloride (228 mg, 3.25 mmol). The reaction was heated at reflux for 15 minutes and concentrated on a rotary evaporator. The residual solids were dissolved in dichloromethane (50 mL), and washed with water (50 mL) and brine (50 mL), dried (MgSO$_4$), filtered, and concentrated. The concentrate was purified by flash chromatography on silica gel eluting with a solvent gradient from 10% to 30% ethyl acetate in hexanes to provide 372 mg of the title compound (96%) as a off-white solid. $^1$H NMR (300 MHz, DMSO-d$_6$) δ ppm 1.30 (d, J=6.25 Hz, 6H) 5.11-5.33 (m, 1H) 6.03 (s, 2H) 6.84 (d, J=9.19 Hz, 1H) 7.61 (s, 1H) 7.78 (dd, J=9.01, 3.13 Hz, 1H) 8.22 (d, J=2.94 Hz, 1H) 9.71 (s, 1H); MS (ESI) m/z 295.0 (M+H)$^+$.

Example 81C tert-butyl 2-{[((1Z)-amino {2-[(6-isopropoxypyridin-3-yl)oxy]-1,3-thiazol-5-yl}methylene)amino]oxy}-1-methyl-2-oxoethylcarbamate A solution of Example 81B (370 mg, 1.25 mmol) and N-Boc-alanine (286 mg, 1.51 mmol) in dichloromethane (10 mL) was treated with 1-ethyl-3-[3-(dimethylamino)propyl]-carbodiimide (361 mg, 1.88 mmol). The reaction was stirred for 15 minutes at 25° C. Dichloromethane (50 mL) was added and the resulting mixture was washed with saturated sodium carbonate (50 mL) and brine (50 mL). The organic layers were dried (MgSO$_4$), filtered, and concentrated. The concentrate was purified by flash chromatography on silica gel eluting with a solvent gradient from 10% to 30% ethyl acetate in hexanes to provide 482 ng of the title compound (83%) as white solid. $^1$H NMR (300 MHz, DMSO-d$_6$) δ ppm 1.26-1.35 (m, J=5.70, 5.70 Hz, 9H) 1.39 (s, 9H) 4.12-426 (m, 1H) 5.14-5.31 (m, 1 H) 6.86 (d, J=8.82 Hz, 1H) 7.05 (s, 2H) 7.37 (d, J=7.72 Hz, 1H) 7.83 (dd, J=9.19, 2.94 Hz, 1H) 7.87 (s, 1H) 8.26 (d, J=2.94 Hz, 1H); MS (ESI) m/z 466.0 (M+H)$^+$.

Example 81D tert-butyl 1-(3-{2-[(6-isopropoxypyridin-3-yl)oxy]-1,3-thiazol-5-yl}-1,2,4-oxadiazol-5-yl)ethylcarbamate Example 81C (480 mg, 1.03 mmol) was dissolved in pyridine (10 mL) and heated to reflux for 4 hours. The mixture was concentrated under reduced pressure on a rotary evaporator. The concentrate was diluted with ethyl acetate (50 mL), washed with 0.5 M HCl (2×50 mL) and brine (50 mL), dried (MgSO$_4$), filtered, and concentrated to provide 452 mg of the title compound (98%) as a white solid. $^1$H NMR (300 MHz, DMSO-d$_6$) δ ppm 1.31 (d, J=6.25 Hz, 6H) 1.39 (s, 9H) 1.48 (d, J=6.99 Hz, 3H) 4.87-5.01 (m, 1H) 5.15-5.30 (m, 1H) 6.88 (d, J=9.19 Hz, 1H) 7.78 (d, J=7.72 Hz, 1H) 7.88 (dd, J=9.01, 3.13 Hz, 1 H) 7.98 (s, 1H) 8.31 (d, J=2.94 Hz, 1H); MS (ESI) m/z 448.1 (M+H)$^+$.

Example 81E 1-(3-{2-[(6-isopropoxypyridin-3-yl)oxy]-1,3-thiazol-5-yl}-1,2,4-oxadiazol-5-yl)ethanamine Example 81D (450 mg, 110 mmol) was treated with 4 M HCl in dioxane (10 mL). The mixture was stirred 30 minutes and concentrated to provide 460 mg of the title compound as a brown solid, which was used directly in the next step without further purification, Example 81F N-[1-(3-{2-[(6-isopropoxypyridin-3-yl)oxy]-1,3-thiazol-5-yl}-1,2,4-oxadiazol-5-yl)ethyl]acetamide The title compound was prepared according to the procedure described in Example 30I, substituting Example 81E for Example 30H. The crude product was purified by reverse-phase HPLC on an Atlantis C18 column (1.9×10 cm, 5 μm particle size) using a gradient of 5% to 100% acetonitrile: 0.1% aqueous trifluoroacetic acid to provide the title compound as an off-white solid. $^1$H NMR (300 MHz, DMSO-d$_6$) δ ppm 1.31 (d, J=6.25 Hz, 6H) 1.50 (d, J=7.35 Hz, 3H) 1.88 (s, 3H) 5.04-5.33 (m, 2H) 6.88 (d, J=9.19 Hz, 1 H) 7.88 (dd, J=9.01, 3.13 Hz, 1H) 7.98 (s, 1H) 8.31 (d, J=2.94 Hz, 1H) 8.73 (d, J=6.99 Hz, 1H); MS (ESI) m/z 390.1 (M+H)$^+$.

Example 82

N-[1-(3-{6-[(6-isopropoxypyridin-3-yl)oxy]pyridin-3-yl}isoxazol-5-yl)ethyl]acetamide Example 82A 3-Bromo-6-[(6-isopropoxypyridin-3-yl)oxy]-pyridine The mixture of Example 68B (1.0821 g, 7.064 mmol), 5-bromo-2-fluoropyridine (1.245 g, 7.074 mmol, 1.0 eq.), and K$_2$CO$_3$ (1.17 g, 8.47 mmol, 1.2 eq.) in dimethylsulfoxide (8 mL) was heated to 160° C. under microwave for 30 min. The reaction mixture was poured into water. The aqueous layer was extracted with ether (1×). The ether layer was washed with 10% NaOH (1×), brine (1×), dried over MgSO$_4$, filtered and concentrated. The product was purified on silica gel eluting with ethyl acetate: hexane gradient to give the desired product as a solid (0.845 mg, 39%).

Example 82B 1-(3-{6-[(6-isopropoxypyridin-3-yl)oxy]pyridin-3-yl}isoxazol-5-yl)ethanamine The title compound was prepared by substituting Example 82A for Example 68C in Example 68D and follow the procedures in Examples 75D-H.

Example 82C

N-[1-(3-{6-[(6-isopropoxypyridin-3-yl)oxy]pyridin-3-yl}isoxazol-5-yl)ethyl]acetamide The title compound was prepared using the procedure described in Example 17G, substituting Example 82B for Example 17F, MS (DCI): m/z 340 (M+H); $^1$H NMR (300 MHz, CDCl$_3$) δ ppm 8.19 (d, J=1.84 Hz, 1H), 7.99 (d, J=2.57 Hz, 1H), 7.69 (dd, J=8.46, 2.21 Hz, 1H), 7.38 (dd, J=8.82, 2.94 Hz, 1H), 6.87 (d, J=8.46 Hz, 1H), 6.72 (d, J=8.82 Hz, 1H), 5.65-5.76 (m, 1H), 5.17-5.34 (m, 1H), 4.95-5.12 (m, 1H), 2.01 (s, 3H), 1.49 (d, J=6.62 Hz, 3H), 1.36 (d, J=6.25 Hz, 6H).

Example 83

N-[1-(3-{6-[(6-isopropoxypyridin-3-yl)oxy]pyridin-3-yl}isoxazol-5-yl)ethyl]urea

The title compound was prepared using the procedure described in Example 23, substituting Example 82B for Example 17F. MS (DCI): m/z 341 (M+H); $^1$H NMR (300 MHz, DMSO-d$_6$) δ ppm 8.16 (d, J=1.47 Hz, 1H), 8.02 (d, J=2.57 Hz, 1H), 7.56 (dd, J=8.82, 2.94 Hz, 1H), 7.08 (d, J=9.19 Hz, 1H), 6.80 (d, J=8.46 Hz, 1H), 6.46 (d, J=8.46 Hz, 1H), 5.53 (s, 2H), 5.13-5.28 (m, 1H), 4.57-4.75 (m, 1H), 1.34 (d, J=6.99 Hz, 3 H), 1.30 (d, J=5.88 Hz, 6H).

Example 84

N-[1-(3-{6-[(6-isopropoxypyridin-3-yl)oxy]pyridin-3-yl}isoxazol-5-yl)ethyl]-N'-methylurea The title compound was prepared in 87% yield using the procedure described in Example 44, substituting Example 82B for Example 43B. MS (DCI): m/z 355 (M+H); $^1$H NMR (300 MHz, DMSO-d$_6$) δ ppm 8.16 (d, J=1.84 Hz, 1H), 8.02 (d, J=2.94 Hz, 1H), 7.86 (dd, J=8.64, 2.39 Hz, 1H), 7.56 (dd, J=8.82, 2.94 Hz, 1H), 7.07 (d, J=8.46 Hz, 1H), 6.80 (d, J=8.46 Hz, 1H), 6.41 (d, J=8.46 Hz, 1H), 5.62-5.81 (m, 1H), 5.04-5.30 (m, 1H), 4.58-4.79 (m, 1H), 2.55 (d, J=4.41 Hz, 3H), 1.35 (d, J=6.99 Hz, 3H), 1.30 (d, J=5.88 Hz, 6H).

Example 85 methyl 1-(3-{6-[(6-isopropoxypyridin-3-yl)oxy]pyridin-3-yl}isoxazol-5-yl)ethylcarbamate The title compound was prepared using the procedure described in Example 22, substituting Example 82B for Example 17F. MS (DCI): m/z 356 (M+H); $^1$H NMR (300 MHz, CDCl$_3$) δ ppm 8.18 (d, J=2.21 Hz, 1H), 7.99 (d, J=2.94 Hz, 1H), 7.69 (dd, J=8.46, 2.57 Hz, 1H), 7.38 (dd, J=8.82, 2.94 Hz, 1H), 6.87 (d, J=8.82 Hz, 1H), 6.71 (d, J=8.82 Hz, 1H), 5.16-5.38 (m, 1H), 4.90 (m, 1H), 4.77 (m, 1H), 3.71 (s, 3H), 1.50 (d, J=6.99 Hz, 3H), 1.35 (d J=6.25 Hz, 6H).

Example 86

N-[1-(3-{2-[3-(cyclopropylmethoxy)phenoxy]-1,3-thiazol-5-yl}isoxazol-5-yl)ethyl]acetamide Example 86A 2-(3-methoxyphenoxy)-1,3-thiazole The title compound was prepared according to the procedure described in Example 30A, substituting 3-methoxyphenol for 2-chloro-4-methoxyphenol. The crude product was purified by flash chromatography on silica gel eluting with a solvent gradient from 5% to 20% ethyl acetate in hexanes to provide the title compound as a light yellow liquid. $^1$H NMR (300 MHz, DMSO-d$_6$) δ ppm 3.77 (s, 3H) 6.86-6.98 (m, 3H) 7.21-7.26 (d, J=3.68 Hz, 1H) 7.30 (d, J=3.68 Hz, 1H) 7.38 (t, J=8.09 Hz, 1H); MS (DCI) m/z 207.9 (M+H)$^+$.

Example 86B 2-(3-methoxyphenoxy)-1,3-thiazole-5-carbaldehyde

The title compound was prepared according to the procedure described in Example 30B, substituting Example 86A for Example 30A. The crude product was purified by flash chromatography on silica gel eluting with a solvent gradient from 10% to 25% ethyl acetate in hexanes to provide the title compound as a light yellow liquid. $^1$H NMR (500 MHz, DMSO-d$_6$) δ ppm 3.79 (s, 3H) 6.94-7.03 (m, 2H) 7.06 (t, J=2.44 Hz, 1H) 7.44 (t, J=8.30 Hz, 1H) 8.29 (s, 1H) 9.88 (s, 1H); MS (DCI) m/z 235.9 (M+H)+.

Example 86C 2-(3-methoxyphenoxy)-1,3-thiazole-5-carbaldehyde oxime

The title compound was prepared according to the procedure described in Example 30C, substituting Example 86B for Example 30B. The crude product was purified by flash chromatography on silica gel eluting with a solvent gradient from 10% to 30% ethyl acetate in hexanes to provide the title compound as a off-white solid. $^1$H NMR (300 MHz, methanol-$d_4$) δ ppm 3.82 (s, 3H) 6.77-6.99 (m, 2H) 7.27-7.46 (m, 1H) 7.63 (d, J=14.34 Hz, 1H) 8.15 (s, 1H); MS (DCI) m/z 250.9 (M+H)+.

Example 86D

N-hydroxy-2-(3-methoxyphenoxy)-1,3-thiazole-5-carboximidoyl chloride

The title compound was prepared according to the procedure described in Example 30D, substituting Example 86C for Example 30C. The crude product was used directly for the next step without further purification. $^1$H NMR (500 MHz, DMSO-$d_6$) δ ppm 3.78 (s, 3H) 6.90-6.99 (m, 2H) 6.99-7.07 (m, 1H) 7.41 (t, J=8.40 Hz, 1H) 7.69 (s, 1 H) 12.43 (s, 1H); MS (DCI) m/z 284.9 (M+H)+.

Example 86E 2-(1-{3-[2-(3-methoxyphenoxy)-1,3-thiazol-5-yl]isoxazol-5-yl}ethyl)-1H-isoindole-1,3(2H)-dione The title compound was prepared according to the procedure described in Example 30E, substituting Example 86D for Example 30D. The crude product was purified by flash chromatography on silica gel eluting with a solvent gradient from 10% to 60% ethyl acetate in hexanes to provide the title compound as a light brown solid. $^1$H NMR (300 MHz, DMSO-$d_6$) δ ppm 1.82 (d, J=6.99 Hz, 3H) 3.78 (s, 3H) 5.56-5.71 (m, 1H) 6.89-7.08 (m, 3H) 7.18 (s, 1H) 7.42 (t, J=8.09 Hz, 1H) 7.83-8.05 (m, 5H); MS (ESI) m/z 448.1 (M+H)+.

Example 86F 2-(1-{3-[2-(3-hydroxyphenoxy)-1,3-thiazol-5-yl]isoxazol-5-yl}ethyl)-1H-isoindole-1,3(2H)-dione The title compound was prepared according to the procedure described in Example 30F, substituting Example 86E for Example 30E. The crude product was used directly in the next step without purification.

Example 86G

2-[1-(3-{2-[3-(cyclopropylmethoxy)phenoxy]-1,3-thiazol-5-yl}isoxazol-5-yl)ethyl]-1H-isoindole-1,3(2H)-dione The title compound was prepared according to the procedure described in Example 30G, substituting Example 86F for Example 30F. The crude product was purified by flash chromatography on silica gel eluting with a solvent gradient from 10% to 25% ethyl acetate in hexanes to provide the title compound as a off-white solid. $^1$H NMR (300 MHz, DMSO-$d_6$) δ ppm 0.29-0.36 (m, 2H) 0.50-0.64 (m, 2H) 1.12-1.26 (m, 1H) 1.82 (d, J=7.35 Hz, 3H) 3.84 (d, J=6.99 Hz, 2H) 5.64 (q, J=7.11 Hz, 1H) 6.86-7.05 (m, 3H) 7.18 (s, 1H) 7.39 (t, J=8.09 Hz, 1H) 7.83-7.94 (m, 4H) 7.95 (s, 1H); MS (ESI) m/z 488.1 (M+H)+.

Example 86H 1-(3-{2-[3-(cyclopropylmethoxy)phenoxy]-1,3-thiazol-5-yl}isoxazol-5-yl)ethanamine The title compound was prepared according to the procedure described in Example 30H, substituting Example 86G for Example 30G. It was used directly for the next step without further purification.

Example 86I

N-[1-(3-{2-[3-(cyclopropylmethoxy)phenoxy]-1,3-thiazol-5-yl}isoxazol-5-yl)ethyl]acetamide The title compound was prepared according to the procedure described in Example 30I, substituting Example 86H for Example 30H. The crude product was purified by reverse-phase HPLC on an Atlantis C18 column (1.9×10 cm, 5 μm particle size) using a gradient of 5% to 100% acetonitrile:0.1% aqueous trifluoroacetic acid to provide the title compound as a off-white solid. $^1$H NMR (300 MHz, DMSO-$d_6$) δ ppm 0.27-0.38 (m, 2H) 0.50-0.64 (m, 2 H) 1.12-1.28 (m, 1H) 1.42 (d, J=6.99 Hz, 3H) 1.87 (s, 3H) 3.84 (d, J×6.99 Hz, 2H) 5.01-5.18 (m, 1H) 6.90 (s, 1H) 6.91-7.06 (m, 3H) 7.40 (t, J=8.27 Hz, 1H) 7.97 (s, 1H) 8.51 (d, J=8.09 Hz, 1H); MS (ESI) m/z 400.1 (M+H)+.

Example 87 methyl 1-(3-{2-[3-(cyclopropylmethoxy)phenoxy]-1,3-thiazol-5-yl}isoxazol-5-yl)ethylcarbamate The title compound was prepared according to the procedure described in Example 31 substituting Example 86H for Example 30H. The crude product was purified by reverse-phase HPLC on an Atlantis C18 column (1.9×10 cm, 5 μm particle size) using a gradient of 5% to 100% acetonitrile:0.1% aqueous trifluoroacetic acid to provide the title compound. $^1$H NMR (300 MHz, DMSO-$d_6$) δ ppm 0.26-0.38 (m, 2H) 0.48-0.65 (m, 2H) 1.16-1.29 (m, 1H) 1.44 (d, J=6.99 Hz, 3H) 3.57 (s, 3H) 3.84 (d, J=6.99 Hz, 2H) 4.76-4.98 (m, 1H) 6.90 (s, 1H) 6.91-7.02 (m, 3H) 7.40 (t, J=8.09 Hz, 1H) 7.90 (d, J=8.09 Hz, 1H) 7.99 (s, 1H); MS (ESI) m/z 416.1 (M+H)+.

Example 88

N-[1-(3-{2-[3-(cyclopropylmethoxy)phenoxy]-1,3-thiazol-5-yl}isoxazol-5-yl)ethyl]-N'-methylurea The title compound was prepared according to the procedure described in Example 32, substituting Example 86H for Example 30H. The crude product was purified by reverse-phase HPLC on an Atlantis C18 column (1.9×10 cm, 5 μm particle size) using a gradient of 5% to 100% acetonitrile:0.1% aqueous trifluoroacetic acid to provide the title compound. $^1$H NMR (300 MHz, DMSO-$d_6$) δ ppm 0.25-0.36 (m, 2H) 0.48-0.58 (m, 2H) 1.09-1.25 (m, 1H) 1.40 (d, J=6.99 Hz, 3H) 2.56 (d, J=4.78 Hz, 3H) 3.72 (d, J=6.99 Hz, 2 H) 4.87-5.03 (m, 1H) 5.82 (q, J=4.78 Hz, 1H) 6.57 (d, J=8.09 Hz, 1H)

6.83 (s, 1H) 6.88-7.08 (m, 3H) 7.39 (t, J=8.09 Hz, 1H) 8.01 (s, 1H); MS (ESI) m/z 415.0 (M+H)+.

Example 89

N-[1-(3-{2-[3-(cyclopropylmethoxy)phenoxy]-1,3-thiazol-5-yl}isoxazol-5-yl)ethyl]urea The title compound was prepared according to the procedure described in Example 50, substituting Example 86H for Example 48H. The crude product was purified by reverse-phase HPLC on an Atlantis C18 column (1.9×10 cm, 5 μm particle size) using a gradient of 5% to 100% acetonitrile: 0.1% aqueous trifluoroacetic acid to provide the title compound, $^1$H NMR (300 MHz, DMSO-$d_6$) δ ppm 0.28-0.39 (m, 2H) 0.53-0.64 (m, 2H) 1.13-1.29 (m, 1H) 1.39 (d, J=7.35 Hz, 3H) 3.85 (d, J=6.99 Hz, 2H) 4.81-5.01 (m, 1H) 5.59 (s, 2H) 6.61 (d, J=8.09 Hz, 1H) 6.90 (s, 1H) 6.91-7.06 (m, 3H) 7.40 (t, J=8.27 Hz, 1H) 7.97 (s, 1H); MS (ESI) m/z 401.1 (M+H)+.

Example 90

N-(1-{3-[2-(3-isopropoxyphenoxy)-1,3-thiazol-5-yl]isoxazol-5-yl}ethyl)acetamide

Example 90A 2-(1-{3-[2-(3-isopropoxyphenoxy)-1,3-thiazol-5-yl]isoxazol-5-yl}ethyl)-1H-isoindole-1,3(2H)-dione To a solution of Example 86F (250 mg, 0.68 mmol), isopropanol (78 μL, 1.02 mmol) and triphenylphosphine (267 mg, 1.02 mmol) in tetrahydrofuran (5 mL) was added diethyl azodicarboxylate (175 μL, 1.02 mmol) at 25° C. The reaction was stirred for 16 hours and concentrated. The concentrate was purified by flash chromatography on silica gel eluting with a solvent gradient from 10% to 30% ethyl acetate in hexanes to provide 272 mg of the title compound (84%) as a off-white solid. $^1$H NMR (300 MHz, DMSO-$d_6$) δ ppm 1.26 (d, J=5.88 Hz, 6H) 1.82 (d, J=6.99 Hz, 3H) 4.55-4.74 (m, 1H) 5.64 (q, J=6.99 Hz, 1H) 6.83-7.05 (m, 3H) 7.18 (s, 1H) 7.38 (t, J=8.27 Hz, 1H) 7.83-7.95 (m, 4H) 7.96 (s, 1H); MS (ESI) m/z 476.1 (M+H)+.

Example 90B

1-{3-[2-(3-isopropoxyphenoxy)-1,3-thiazol-5-yl]isoxazol-5-yl}ethanamine

The title compound was prepared according to the procedure described in Example 30H, substituting Example 90A for Example 30G. It was used directly for the next step without further purification.

Example 90C

N-(1-{3-[2-(3-isopropoxyphenoxy)-1,3-thiazol-5-yl]isoxazol-5-yl}ethyl)acetamide

The title compound was prepared according to the procedure described in Example 30I, substituting Example 90B for Example 30H. The crude product was purified by reverse-phase HPLC on an Atlantis C18 column (1.9×10 cm, 5 μm particle size) using a gradient of 5% to 100% acetonitrile: 0.1% aqueous trifluoroacetic acid to provide the title compound as an off-white solid. $^1$H NMR (300 MHz, DMSO-$d_6$) δ ppm 1.27 (d, J=5.88 Hz, 6H) 1.42 (d, J=6.99 Hz, 3H) 1.87 (s, 3H) 4.58-4.74 (m, 1H) 5.02-5.17 (m, 1H) 6.90 (s, 1H) 6.92-7.05 (m, 3H) 7.39 (t, J=8.27 Hz, 1H) 7.97 (s, 1H) 8.51 (d, J=8.09 Hz, 1H); MS (ESI) m/z 388.1 (M−H)+.

Example 91 methyl 1-{3-[2-(3-isopropoxyphenoxy)-1,3-thiazol-5-yl]isoxazol-5-yl}ethylcarbamate The title compound was prepared according to the procedure described in Example 31, substituting Example 90B for Example 30H. The crude product was purified by reverse-phase HPLC on an Atlantis C18 column (1.9×10 cm, 5 μm particle size) using a gradient of 5% to 100% acetonitrile: 0.1% aqueous trifluoroacetic acid to provide the title compound as an off-white solid. $^1$H NMR (300 MHz, DMSO-$d_6$) δ ppm 1.27 (d, J=5.88 Hz, 6H) 1.44 (d, J=6.99 Hz, 3H) 3.57 (s, 3H) 4.60-4.72 (m, 1H) 4.81-4.93 (m, 1H) 6.90 (s, 1H) 6.92-7.04 (m, 3H) 7.39 (t, J=8.27 Hz, 1H) 7.90 (d, J=8.46 Hz, 1H) 7.99 (s, 1H); MS (ESI) m/z 404.0 (M+H)+.

Example 92

N-(1-{3-[2-(3-isopropoxyphenoxy)-1,3-thiazol-5-yl]isoxazol-5-yl}ethyl)-N'-methylurea The title compound was prepared according to the procedure described in Example 32, substituting Example 90B for Example 30H. The crude product was purified by reverse-phase HPLC on an Atlantis C18 column (1.9×10 cm, 5 μm particle size) using a gradient of 5% to 100% acetonitrile: 0.1% aqueous trifluoroacetic acid to provide the title compound as an off-white solid. $^1$H NMR (300 MHz, CDCl$_3$) δ ppm 1.35 (d, J=6.25 Hz, 6H) 1.56 (d, J=7.22 Hz, 3H) 2.80 (d, J=4.78 Hz, 3H) 4.46-4.57 (m, 1H) 5.14-5.27 (m, 1H) 6.37 (s, 1H) 6.77-6.90 (m, 3H) 7.28-7.36 (m, 1H) 7.53 (s, 1H); MS (ESI) m/z 403.1 (M+H)+.

Example 93

N-(1-{3-[2-(3-isopropoxyphenoxy)-1,3-thiazol-5-yl]isoxazol-5-yl}ethyl)urea

The title compound was prepared according to the procedure described in Example 50, substituting Example 90B for Example 48H. The crude product was purified by reverse-phase HPLC on an Atlantis C18 column (1.9×10 cm, 5 μm particle size) using a gradient of 5% to 100% acetonitrile: 0.1% aqueous trifluoroacetic acid to provide Example 93 as an off-white solid. $^1$H NMR (300 MHz, CDCl$_3$) δ ppm 1.35 (d, J=5.88 Hz, 6H) 1.57 (d, J=7.18 Hz, 3H) 4.41 (s, 2H) 4.46-4.64 (m, 1H) 4.86 (d, J=8.09 Hz, 1H) 5.09-5.25 (m, 1H) 6.38 (s, 1H) 6.73-6.94 (m, 3H) 7.27-7.36 (m, 1H) 7.53 (s, 1H); MS (ESI) m/z 389.1 (M+H)+.

Example 94

N-[1-(3-{2-[3-(isopropylamino)phenoxy]-1,3-thiazol-5-yl}-1,2,4-oxadiazol-5-yl)ethyl]acetamide Example 94A 2-(3-aminophenoxy)-1,3-thiazole-5-carbonitrile 2-chloro-thiazole-5-carbonitrile (1.09 g, 7.5 mmol; prepared as described in WO 01/17995, p. 103) and 3-amino phenol (820 mg, 7.5 mmol) were combined in N,N-dimethyl formamide (5 mL). To this solution, K₂CO₃ (3.1 g, 22.5 mmol) was added and the resulting reaction mixture was stirred at room temperature overnight. The reaction mixture was then poured into water and extracted with ethyl acetate (2×). The combined organics were dried (Na₂SO₄), filtered and concentrated by rotary evaporation. The residue was purified by flash column chromatography (ethyl acetate:hexanes; 5%-75% ethyl acetate gradient) to give the title compound (1.63 g, 7.5 mmol, 100%) as a white solid. MS (ESI APCI) m/z 217.9 (M+H⁺), ¹H NMR (300 MHz, DMSO-d₆) δ 8.24 (s, 1H) 7.14 (t, J=7.91 Hz, 2H) 6.40-6.64 (m, 2H) 5.54 (s, 2H).

Example 94B tert-butyl 3-[(5-cyano-1,3-thiazol-2-yl)oxy]phenylcarbamate

The title compound was prepared using the procedure as described in Example 52C, substituting Example 94A for Example 52B. MS (ESI APCI) m/z 316.8 (M−H⁺). ¹H NMR (300 MHz, DMSO-d₆) δ 9.69 (s, 1H) 8.25 (s, 1H) 7.58 (s, 1H) 7.34-7.45 (m, 2H) 6.98-7.09 (m, 1H) 1.47 (s, 9H).

Example 94C tert-butyl 3-[(5-{5-[1-(acetylamino)ethyl]-1,2,4-oxadiazol-3-yl}-1,3-thiazol-2-yl)oxy]phenylcarbamate The title compound was prepared by substituting Example 94B for Example 67A in the preparation of Example 67B and then following the procedures in examples 74B-74D). MS (ESI APCI) m/z 446.1 (M+H⁺); ¹H NMR (300 MHz, DMSO-d₆) δ 9.66 (s, 1H) 8.72 (d, J=6.99 Hz, 1H) 8.00 (s, 1H) 7.58 (s, 1H) 7.29-7.42 (m, 2H) 7.04 (dd, J=5.88, 3.31 Hz, 1H) 5.09-5.23 (m, 1H) 1.88 (s, 3H) 1.43-1.54 (m, 12H).

Example 94D

N-[1-(3-{2-[3-(isopropylamino)phenoxy]-1,3-thiazol-5-yl}-1,2,4-oxadiazol-5-yl)ethyl]acetamide The title compound was prepared using the procedure as described in Example 71, substituting Example 94C for Example 67D, and substituting acetone for isobutyraldehyde. MS (ESI APCI) m/z 388.2 (M+H⁺); ¹H NMR (300 MHz, DMSO-d₆) δ 8.72 (d, J=6.99 Hz, 1H) 7.99 (s, 1H) 7.20 (t, J=8.09 Hz, 1H) 6.48-6.65 (m, 3H) 5.05-5.22 (m, 1H) 3.45-3.62 (m, 1H) 1.87 (s, 3H) 1.49 (d, J=6.99 Hz, 3H) 1.13 (d, J=6.25 Hz, 6H).

Example 95

N-{1-[3-(2-{3-[(cyclopropylmethyl)amino]phenoxy}-1,3-thiazol-5-yl)-1,2,4-oxadiazol-5-yl]ethyl}acetamide The title compound was prepared using the procedure as described in Example 71, substituting cyclopropanecarboxaldehyde for isobutyraldehyde, and substituting Example 94C for Example 67D. MS (ESI APCI) m/z 400.6 (M+H⁺); ¹H NMR (300 MHz, DMSO-d₆) δ 8.72 (d, J=6.99 Hz, 1H) 7.99 (s, 1H) 7.19 (t, J=8.09 Hz, 1H) 6.49-6.67 (m, 3H) 5.76 (s, 1H) 5.06-5.23 (m, 1H) 2.90 (d, J=6.62 Hz, 2H) 1.87 (s, 3H) 1.49 (d, J=6.99 Hz, 3H) 0.93-1.10 (m, 1H) 0.39-0.56 (m, 2H) 0.13-0.28 (m, 2H).

Example 96

N-[1-(3-{2-[3-(isobutylamino)phenoxy]-1,3-thiazol-5-yl}-1,2,4-oxadiazol-5-yl)ethyl]acetamide The title compound was prepared using the procedure as described in Example 71, substituting Example 94C for Example 67D. MS (ESI APCI) m/z 402.2 (M+H⁺); ¹H NMR (300 MHz, DMSO-d₆) δ 8.72 (d, J=6.99 Hz, 1H) 7.99 (s, 1H) 7.17 (t, J=8.09 Hz, 1H) 6.43-6.63 (m, 3H) 5.07-5.21 (m, 1H) 2.78-2.87 (m, 2H) 1.74-1.91 (m, 4H) 1.49 (d, J=6.99 Hz, 3H) 0.92 (d, J=6.62 Hz, 6H).

Example 97 methyl 1-(3-{2-[(6-isopropoxypyridin-3-yl)oxy]-1,3-thiazol-5-yl}-1,2,4-oxadiazol-5-yl)ethylcarbamate The title compound was prepared according to the procedure as described in Example 31, substituting Example 81E for Example 30H. The crude product was purified by reverse-phase HPLC on an Atlantis C18 column (1.9×10 cm, 5 μm particle size) using a gradient of 5% to 100% acetonitrile: 0.1% aqueous trifluoroacetic acid to provide the title compound as a white solid. ¹H NMR (300 MHz, DMSO-d₆) δ ppm 1.31 (d, J=6.25 Hz, 6H) 1.51 (d, J=7.35 Hz, 3H) 3.57 (s, 3H) 4.94-5.08 (m, 1H) 5.14-5.32 (m, 1H) 6.88 (d, J=9.19 Hz, 1H) 7.88 (dd, J=8.82, 2.94 Hz, 1H) 7.99 (s, 1H) 8.10 (d, J=7.35 Hz, 1H) 8.31 (d, J=2.94 Hz, 1H); MS (ESI) m/z 406.0 (M+H)⁺.

Example 98

N-[1-(3-{2-[(6-isopropoxypyridin-3-yl)oxy]-1,3-thiazol-5-yl}-1,2,4-oxadiazol-5-yl)ethyl]urea The title compound was prepared according to the procedure as described in Example 50, substituting Example 81E for Example 48H. The crude product was purified by reverse-phase HPLC on an Atlantis C18 column (1.9×10 cm, 5 μm particle size) using a gradient of 5% to 100% acetonitrile: 0.1% aqueous trifluoroacetic acid to provide the title compound as a white solid ¹H NMR (300 MHz, DMSO-d₆) δ ppm 1.31 (d, J=6.25 Hz, 6H) 1.46 (d, J=7.72 Hz, 3H) 4.92-5.09 (m, 1H) 5.16-5.32 (m, 1H) 5.72 (s, 2H) 6.82 (d, J=7.35 Hz, 1H) 6.88 (d, J=9.56 Hz, 1H) 7.88 (dd, J=9.01, 3.13 Hz, 1H) 7.97 (s, 1H) 8.31 (d, J=2.57 Hz, 1H); MS m/z 391.0 (M+H)⁺.

Example 99

N-[1-(3-{2-[(6-isopropoxypyridin-3-yl)oxy]-1,3-thiazol-5-yl}-1,2,4-oxadiazol-5-yl)ethyl]-N'-ethylurea The title compound was prepared according to the procedure as described in Example 32, substituting Example 81E for Example 30H. The crude product was purified by reverse-phase HPLC on an Atlantis C18 column (1.9×10 cm, 5 μm particle size) using a gradient of 5% to 100% acetonitrile: 0.1% aqueous trifluoroacetic acid to provide the title compound as a white solid. ¹H NMR (300 MHz, CDCl₃) δ ppm 1.36 (d, J=6.25 Hz, 6H) 1.60 (d, J=7.35 Hz, 3H) 2.81 (d, J=4.78 Hz, 3H) 4.50-4.60 (m, 1H) 5.02 (d, J=7.72 Hz, 1H) 5.22-5.41 (m, 2H) 6.75 (d, J=9.19 Hz, 1H) 7.56 (dd, J=9.01, 3.13 Hz, 1H) 7.86 (s, 1H) 8.16 (d, J=2.94 Hz, 1H); MS m/z 405.1 (M+H)⁺.

Example 100

1-{3-[2-(4-isopropoxyphenoxy)-1,3-thiazol-5-yl]-1,2,4-thiadiazol-5-yl}ethyl methanesulfonate

Example 100A 2-(4-isopropoxyphenoxy)-1,3-thiazole-5-carboxamide

A mixture of Example 40A (1.0 g, 0.0038 mol) in 10 mL of concentrated hydrochloric acid was stirred at room temperature for 16 hours. The suspension gradually dissolved into a yellow solution. Water was added and the solution stirred for 2 hours. The precipitate was then filtered off and dried in vacuum oven for 2 hours at 50° C. to give 1.02 g of product as a white solid (96% yield). $^1$H NMR (300 MHz, DMSO-$d_6$) δ ppm 1.28 (d, J=5.88 Hz, 6H) 4.54-4.70 (m, 1H) 6.96-7.05 (m, 2H) 7.24-7.35 (m, 2H) 7.49 (s, 1H) 7.88 (s, 1H) 7.99 (s, 1H). MS (ESI), M/Z: 279.0 (M+H)$^+$.

Example 100B

5-[2-(4-isopropoxyphenoxy)-1,3-thiazol-5-yl]-1,3,4-oxathiazol-2-one

A mixture of Example 100A (1.89 g, 0.0066 mol) and chlorocarbonylsulfenyl chloride (0.64 g, 0.01 mol) in toluene was heated at reflux for 6 hours. The solvent was removed and the residue was purified on silica gel (5~30% ethyl acetate in hexane) to give 2.05 g of product as an off-white solid (92% yield). $^1$H NMR (300 MHz, CDCl$_3$) δ ppm 1.36 (d, J=6.25 Hz, 6H) 4.46-4.63 (m, 1H) 6.89-6.98 (m, 2H) 7.14-7.24 (m, 2H) 7.80 (s, 1H). MS (ESI), M/Z: 369.0 (M+32)$^+$.

Example 100C

1-{3-[2-(4-isopropoxyphenoxy)-1,3-thiazol-5-yl]-1,2,4-thiadiazol-5-yl}ethanone

A mixture of Example 100B (2.0 g, 0.0057 mol) and excess pyruvonitrile (2 mL) in xylene was heated at reflux in a pressure tube overnight. The solvent was removed and the residue was purified on silica gel (5~30% ethyl acetate in hexane) to give 1.74 g of product as a light yellow solid (84% yield). $^1$H NMR (300 MHz, CDCl$_3$) δ ppm 1.36 (d, J=6.25 Hz, 6H) 2.77 (s, 3H) 4.46-4.61 (m, 1H) 6.89-6.99 (m, 2H) 7.18-7.25 (m, 2H) 8.03 (s, 1H). MS (ESI), M/Z: 394.0 (M+33)$^+$.

Example 100D

1-{3-[2-(4-isopropoxyphenoxy)-1,3-thiazol-5-yl]-1,2,4-thiadiazol-5-yl}ethanol

To a solution of Example 100C (1.7 g, 0.0047 mol) in a mixture of methanol and tetrahydrofuran (1:1) was added sodium borohydride (0.36 g, 0.0094 mol) and the reaction mixture was stirred at room temperature overnight. The solvent was removed and the residue was partitioned between ethyl acetate and water. The organic layer was washed with brine, dried over magnesium sulfate and filtered. The filtrate was concentrated and purified on silica gel (ethyl acetate/hexane, 10~50%) to give 1.43 g of product as a white solid (84% yield). $^1$H NMR (300 MHz, CDCl$_3$) δ ppm 1.35 (d, J=5.88 Hz, 6H) 1.70 (d, J=6.62 Hz, 3H) 2.87 (s, 1H) 4.45-4.61 (m, 1H) 5.27 (q, J=6.62 Hz, 1H) 6.87-6.98 (m, 2 H) 7.16-7.25 (m, 2H) 7.94 (s, 1H). MS (ESI), M/Z: 364.0 (M+H)$^+$.

Example 100E

1-{3-[2-(4-isopropoxyphenoxy)-1,3-thiazol-5-yl]-1,2,4-thiadiazol-5-yl}ethyl methanesulfonate To a solution of Example 100D (136 g, 0.0037 mol), triethylamine (0.95 g, 0.0094 mol) and 4-(dimethylamino)pyridine in dichloromethane at 0° C. was added methanesulfonyl chloride (0.52 g, 0.0045 mol) drop wise and the mixture was stirred for 2 hours at room temperature. More dichloromethane was added and the organic layer was washed with water, then brine and dried over magnesium sulfate and filtered. The filtrate was concentrated to give 1.5 g of product as a clear oil. $^1$H NMR (300 MHz, CDCl$_3$) δ ppm 1.36 (d, J=6.25 Hz, 6H) 1.90 (d, J=6.62 Hz, 3H) 3.15 (s, 3H) 4.45-4.61 (m, 1H) 6.10 (q, J=6.86 Hz, 1H) 6.87-6.99 (m, 2H) 7.17-7.25 (m, 2H) 7.96 (s, 1H). MS (ESI) m/z 442.0 (M+H)$^+$.

Example 101

N-(1-{3-[2-(4-isopropoxyphenoxy)-1,3-thiazol-5-yl]-1,2,4-thiadiazol-5-yl}ethyl)acetamide

Example 101A 2-(1-{3-[2-(4-isopropoxyphenoxy)-1,3-thiazol-5-yl]-1,2,4-thiadiazol-5-yl}ethyl)-1H-isoindole-1,3(2H)-dione The title compound was prepared as described in Example 2D, substituting Example 100D for Example 2C. $^1$H NMR (300 MHz, CDCl$_3$) δ ppm 1.35 (d, J=5.88 Hz, 6H) 2.01 (d, J=7.35 Hz, 3H) 4.44-4.61 (m, 1H) 5.91 (q, J=7.35 Hz, 1H) 6.85-6.97 (m, 2H) 7.15-7.24 (m, 2H) 7.72-7.82 (m, 2H) 7.83-7.95 (m, 3H), MS (ESI), M/Z: 525.1 (M+33)$^+$.

Example 101B

N-(1-{3-[2-(4-isopropoxyphenoxy)-1,3-thiazol-5-yl]-1,2,4-thiadiazol-5-yl}ethyl)acetamide The title compound was prepared as described in Example 1G, substituting Example 101A for Example 1F, $^1$H NMR (300 MHz, CDCl$_3$) δ ppm 1.36 (d, J=5.88 Hz, 6H) 1.67 (d, J=6.99 Hz, 3H) 2.43 (s, 3H) 4.46-4.60 (m, 1H) 5.44-5.56 (m, 1H) 6.03 (s, 1H) 6.87-6.99 (m, 2H) 7.18-7.25 (m, 2H) 7.95 (s, 1H) MS (ESI), M/Z: 405.0 (M+H)$^+$.

Example 102 methyl 1-{3-[2-(4-isopropoxyphenoxy)-1,3-thiazol-5-yl]-1,2,4-thiadiazol-5-yl}ethylcarbamate The title compound was prepared as described in Example 1G, substituting Example 101A for Example 1F, and substituting methyl chloroformate for acetic anhydride. $^1$H NMR (300 MHz, CDCl$_3$) δ ppm 1.36 (d, J=6.25 Hz, 6H) 1.62-1.71 (d, J=6.99 Hz, 3H) 3.73 (s, 3H) 4.45-4.62 (m, 1H) 5.18-5.32

(m, 1H) 6.88-6.97 (m, 2H) 7.17-7.25 (m, 3 H) 7.95 (s, 1H). MS (ESI), m/z: 421.0 (M+H)+.

Example 103 tert-butyl 4-[(5-{5-[1-(acetylamino)ethyl]-1,2,4-oxadiazol-3-yl}-1,3-thiazol-2-yl)oxy]-3-chlorophenylcarbamate

Example 103A (3-Chloro-4-hydroxy-phenyl)-carbamic acid tert-butyl ester

The title compound was prepared (88%) by substituting 4-Amino-2-chloro-phenol hydrochloride for 4-Amino-3-chloro-phenol hydrochloride in the preparation of Example 52A. $^1$H NMR (300 MHz, DMSO-$d_6$) δ 9.72 (s, 1H) 9.19 (s, 1H) 7.47 (s, 1H) 7.15 (dd, J=8.82, 2.57 Hz, 1H) 6.84 (d, J=8.82 Hz, 1H) 1.45 (s, 9H).

Example 103B tert-butyl 4-[(5-{5-[1-(acetylamino)ethyl]-1,2,4-oxadiazol-3-yl}-1,3-thiazol-2-yl)oxy]-3-chlorophenylcarbamate The title compound was prepared by substituting Example 103A for N-Boc-4-hydroxy-aniline in Example 67A and following the experimental procedures for Examples 74A-74D, MS (ESI APCI) m/z 480.1 (M+H+); $^1$H NMR (300 MHz, DMSO-$d_6$) δ 9.76 (s, 1H) 8.72 (d, J=6.99 Hz, 1H) 7.97 (s, 1H) 7.73-7.88 (m, 1H) 7.32-7.59 (m, 2H) 5.06-5.23 (m, 1H) 1.88 (s, 3H) 1.41-1.56 (m, 12H).

Example 104

N-[1-(3-{2-[2-chloro-4-(isopropylamino)phenoxy]-1,3-thiazol-5-yl}-1,2,4-oxadiazol-5-yl)ethyl]acetamide

Example 104A

N-(1-{3-[2-(4-amino-2-chlorophenoxy)-1,3-thiazol-5-yl]-1,2,4-oxadiazol-5-yl}ethyl)acetamide The title compound was prepared using the procedure as described in Example 29F, substituting Example 103B for Example 29E. MS (ESI APCI) m/z 380.4 (M+H+); $^1$H NMR (300 MHz, DMSO-$d_6$) δ 8.71 (d, J=6.99 Hz, 1H) 7.97 (s, 1H) 7.25 (d, J=8.82 Hz, 1H) 6.75 (d, J=2.57 Hz, 1H) 6.59 (dd, J=8.82, 2.57 Hz, 1H) 5.09-5.21 (m, 1H) 1.87 (s, 3H) 1.49 (d, J=6.99 Hz, 3H).

Example 1044B

N-[1-(3-{2-[2-chloro-4-(isopropylamino)phenoxy]-1,3-thiazol-5-yl}-1,2,4-oxadiazol-5-yl)ethyl]acetamide Example 104A (50 mg, 0.13 mmol) was dissolved in a buffer solution (1.5 mL of a solution prepared by mixing 6 mL, acetic acid and 8.5 g sodium acetate in 250 mL methanol). To this was added acetone (10 μL, 0.13 mmol) and NaCNBH$_3$ (16.3 mg, 0.26 mmol). The reaction solution was stirred at 70° C. for 1 hour, cooled, filtered and purified by reverse phase-HPLC (water:acetonitrile; gradient of 5% to 90% acetonitrile) to give the title compound (43.0 mg, 0.10 mmol, 77%), MS (ESI APCI) m/z 422.1 (M+H+). $^1$H NMR (300 MHz, DMSO-$d_6$) δ 8.71 (d, J=6.99 Hz, 1H) 7.97 (s, 1H) 7.31 (d, J=8.82 Hz, 1 H) 6.73 (d, J=2.94 Hz, 1H) 6.60 (dd, J=9.01, 2.76 Hz, 1H) 5.07-5.21 (m, 1H) 3.48-3.63 (m, 1H) 1.87 (s, 3H) 1.49 (d, J=6.99 Hz, 3H) 1.14 (d, J=6.25 Hz, 6H).

Example 105

N-{1-[3-(2-{2-chloro-4-[(cyclopropylmethyl)amino]phenoxy}-1,3-thiazol-5-yl)-1,2,4-oxadiazol-5-yl]ethyl}acetamide The title compound was prepared using the procedure as described in Example 104B, substituting cyclopropanecarboxaldehyde for acetone. MS (ESI APCI) m/z 434.2 (M+H+); $^1$H NMR (300 MHz, DMSO-$d_6$) δ 8.71 (d, J=6.99 Hz, 1H) 7.97 (s, 1H) 7.31 (d, J=19.19 Hz, 1H) 6.75 (d, J=2.57 Hz, 1H) 6.64 (dd, J=9.01, 2.76 Hz, 1H) 5.76 (s, 1H) 5.04-5.22 (m, 1H) 2.91 (d, J=6.62 Hz, 2H) 1.87 (s, 3H) 1.49 (d, J=7.35 Hz, 3H) 0.92-1.13 (m, 1H) 0.42-0.55 (m, 2H) 0.23 (q, J=4.66 Hz, 2H).

Example 106

N-[1-(3-{2-[2-chloro-4-(isobutylamino)phenoxy]-1,3-thiazol-5-yl}-1,2,4-oxadiazol-5-yl)ethyl]acetamide The title compound was prepared using the same procedure as described in Example 104B, substituting isobutyraldehyde for acetone. MS (ESI APCI) m/z 436.1 (M+H+); $^1$H NMR (300 MHz, DMSO-$d_6$) δ 8.71 (d, J=6.99 Hz, 1H) 7.97 (s, 1H) 7.30 (d, J=9.19 Hz, 1H) 6.74 (d, J=2.57 Hz, 1H) 6.62 (dd, J=8.82, 2.57 Hz, 1H) 5.76 (s, 1H) 4.97-5.29 (m, 1H) 2.85 (d, J=6.99 Hz, 2H) 1.74-1.93 (m, 4H) 1.49 (d, J=6.99 Hz, 3H) 0.94 (d, J=6.62 Hz, 6H).

Example 107

N-[1-(3-{2-[4-(benzylamino)-2-chlorophenoxy]-1,3-thiazol-5-yl}-1,2,4-oxadiazol-5-yl)ethyl]acetamide The title compound was prepared using the procedure as described in Example 104B, substituting benzaldehyde for acetone. MS (ESI APCI) m/z 470.3 (M+H+); $^1$H NMR (300 MHz, DMSO-$d_6$) δ 8.71 (d, J=6.99 Hz, 1H) 7.95 (s, 1H) 7.20-7.44 (m, 6H) 6.76 (d, J=2.57 Hz, 1H) 6.63 (dd, J=9.01, 2.76 Hz, 1H) 5.06-5.22 (m, 1H) 4.31 (s, 2H) 1.87 (s, 3H) 1.49 (d, J=6.99 Hz, 3H).

Example 108 methyl [(1-{3-[2-(4-isopropoxyphenoxy)-1,3-thiazol-5-yl]-1,2,4-oxadiazol-5-yl}ethyl)amino]acetate To a solution of Example 40D (100 mg, 0.22 mmol) in CH$_3$CN (1.0 mL) was added K$_2$CO$_3$ (150 mg, 1.1 mmol) and bromomethyl acetate (20 μL, 0.22 mmol). The reaction solution was heated to reflux with stirring for 2 hours, cooled, diluted with ethyl acetate and poured into water. The organics were separated, dried (Na$_2$SO$_4$), filtered and concentrated by rotary evaporation. The residue was purified by reverse phase HPLC (water:acetonitrile; gradient of 5% to 90% acetonitrile) to provide the title compound (23 mg, 0.054 mmol, 24%). MS (ESI APCI) m/z 419.19 (M+H+); $^1$H NMR (300 MHz, DMSO-$d_6$) δ 8.01 (s, 1H) 7.37 (d, J=8.82 Hz, 2H) 7.04

(d, J=9.19 Hz, 2H) 4.57-4.72 (m, 2H) 3.83 (bs, 2H) 3.66 (s, 3H) 1.57 (d, J=6.99 Hz, 3H) 1.29 (d, J=6.25 Hz, 6H).

Example 109

N-(1-{3-[2-(4-isopropoxyphenoxy)-1,3-thiazol-5-yl]-4-methylisoxazol-5-yl}ethyl)acetamide

Example 109A

2-(1-methylbut-2-ynyl)-1H-isoindole-1,3(2H)-dione

The title compound was prepared as described in Example 15A, substituting pent-3-yn-2-ol for S-(−) propargyl-2-ol. $^1$H NMR (300 MHz, CDCl$_3$) δ ppm 1.67 (d, J=6.99 Hz, 3H) 1.82 (d, J=2.21 Hz, 3H) 5.08-5.27 (m, 1H) 7.65-7.77 (m, 2H) 7.79-7.93 (m, 2H). MS (ESI), M/Z: 246.1 (M+33)$^+$.

Example 109B

2-(1-{3-[2-(4-isopropoxyphenoxy)-1,3-thiazol-5-yl]-4-methylisoxazol-5-yl}ethyl)-1H-isoindole-1,3(2H)-dione The title compound was prepared using the procedure as described in Example 1F, substituting Example 109A for Example 1F-1. $^1$H NMR (300 MHz, CDCl$_3$) δ ppm 1.35 (d, J=5.88 Hz, 6H) 1.95 (d, J=7.35 Hz, 3H) 2.14 (s, 3H) 4.43-4.60 (m, 1H) 5.70 (q, J=7.35 Hz, 1H) 6.86-6.96 (m, 2H) 7.14-7.23 (m, 2H) 7.50 (s, 1H) 7.68-7.78 (m, 2H) 7.81-7.90 (m, 2H). MS (ESI), M/Z: 490.0 (M+H)$^+$.

Example 109C

N-(1-{3-[2-(4-isopropoxyphenoxy)-1,3-thiazol-5-yl]-4-methylisoxazol-5-yl}ethyl)acetamide The title compound was prepared as described in Example 1G, substituting Example 109B for Example 1F. $^1$H NMR (300 MHz, CDCl$_3$) δ ppm 1.35 (d, J=5.88 Hz, 6H) 1.53 (d, J=699 Hz, 3H) 1.99 (s, 3H) 2.20 (s, 3H) 4.46-4.59 (m, 1H) 5.31-5.43 (m, 1H) 5.88 (d, J=8.46 Hz, 1H) 6.86-6.98 (m, 2H) 7.17-7.25 (m, 2H) 7.55 (s, 1H). MS (ESI), M/Z: 402.1 (M+H)$^+$.

Example 110

N-(1-{4-ethyl-3-[2-(4-isopropoxyphenoxy)-1,3-thiazol-5-yl]isoxazol-5-yl}ethyl)acetamide

Example 110A

2-(1-Methyl-pent-2-ynyl)-isoindole-1,3-dione

The title compound was prepared as described in Example 15A, substituting hex-3-yn-2-ol for S-(−)propargyl-2-ol. $^1$H NMR (300 MHz, CHLOROFORM-D) δ ppm 1.11 (t, J=7.54 Hz, 3H) 1.67 (d, J=6.99 Hz, 3H) 2.10-2.28 (m, 2H) 5.11-5.28 (m, 1H) 7.65-7.76 (m, 2H) 7.80-7.90 (m, 2H). MS (ESI), m/z: 260.0 (M+33)$^+$.

Example 110B

2-(1-{4-Ethyl-3-[2-(4-isopropoxy-phenoxy)-thiazol-5-yl]-isoxazol-5-yl}-ethyl)-isoindole-1,3-dione and 2-(1-{5-Ethyl-3-[2-(4-isopropoxy-phenoxy)-thiazol-5-yl]-isoxazol-4-yl}-ethyl)-isoindole-1,3-dione To a solution of Example 1E (1.6 g, 0.005 mol) and Example 110A (1.3 g, 0.0055 mol) in toluene was added potassium carbonate (1.95 g, 0.015 mol) and the reaction was heated at reflux for 6 h. The dark suspension was cooled and diluted with methylenechloride and filtered through Celite. The filtrate was then concentrated and the crude was purified on silica gel (ethyl acetate/hexane, 10~50%) to give 0.5 g of a mixture of two regioisomers as a light brown solid, MS (ESI), m/z: 504.2 (M+1)$^+$.

Example 110C

N-(1-{4-Ethyl-3-[2-(4-isopropoxy-phenoxy)-thiazol-5-yl]-isoxazol-5-yl}-ethyl)-acetamide The title compound was prepared using the procedure described in Example 1G, substituting Example 110B for Example 1F. $^1$H NMR (300 MHz, CDCl$_3$) δ ppm 1.17 (t, J=7.54 Hz, 3H) 1.35 (d, J=5.88 Hz, 6H) 1.53 (d, J=6.99 Hz, 3H) 1.99 (s, 3H) 2.51-2.75 (m, 2H) 4.45-4.60 (m, 1H) 5.31-5.46 (m, 1H) 5.94 (d, J=8.46 Hz, 1 H) 6.88-6.97 (m, 2H) 7.16-7.25 (m, 2H) 7.55 (s, 1H). MS (ESI), m/z: 416.1 (M+H)$^+$.

Example 111

N-(1-{3-[2-(4-Amino-3-chloro-phenoxy)-thiazol-5-yl]-[1,2,4]oxadiazol-5-yl}-ethyl)-acetamide Example 72A (1.64 g, 3.3 mmol) was dissolved in pyridine (25 mL) and the solution was heated to reflux for 3 hours. The reaction was concentrated by rotary evaporation and diluted with ethyl acetate. The organics were washed with 5% aqueous citric acid twice and the combined organics were dried (Na$_2$SO$_4$), filtered and concentrated by rotary evaporation. The residue was purified by flash column chromatography (ethyl acetate:hexanes; 5%-100% ethyl acetate gradient) to provide the title compound (1.34 mg, 0.35 mmol, 11%): MS (ESI APCI) m/z 380.1 (M+H$^+$); $^1$H NMR (300 MHz, DMSO-d$_6$) δ 8.71 (d, J=6.99 Hz, 1H) 7.97 (s, 1H) 7.43 (d, J=2.94 Hz, 1H) 7.15 (dd, J=8.82, 2.94 Hz, 1H) 6.87 (d, J=8.82 Hz, 1H) 5.58 (s, 2H) 5.09-5.21 (m, 1H) 1.87 (s, 3H) 1.49 (d, J=6.99 Hz, 3H).

It is understood that the foregoing detailed description and accompanying examples are merely illustrative and are not to be taken as limitations upon the scope of the invention, which is defined solely by the appended claims and their equivalents. Various changes and modifications including, but not limited to, those relating to the chemical structures, substituents, derivatives, intermediates, syntheses, formulations and/or methods of use of the invention, can be made without departing from the spirit and scope thereof

We claim:
1. A compound of formula (I)

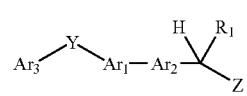

or a pharmaceutically acceptable salt thereof, wherein
R$_1$ is selected from the group consisting of hydrogen, cycloalkyl, alkyl and haloalkyl;
Y is selected from the group consisting of —(CR$_{4a}$R$_{4b}$)$_m$—, —O—, and —S—; wherein
m is 1, 2 or 3;

each of $R_{4a}$, $R_{4b}$, at each occurrence, is independently selected from the group consisting of hydrogen, alkyl, hydroxyalkyl, and haloalkyl when m is 1, 2 or 3; alternatively, $R_{4a}$ and $R_{4b}$ together with the carbon to which they are attached form a monocyclic cycloalkyl or heterocycle ring when m is 1;

$Ar_3$ is selected from the group consisting of

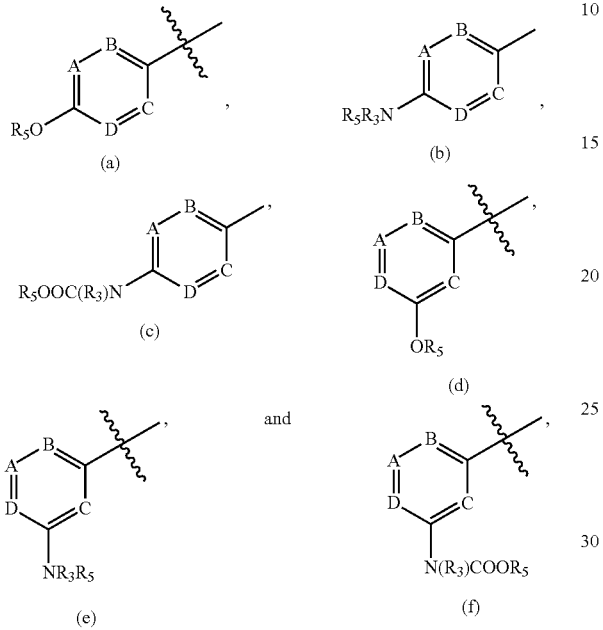

A, B, C and D are —C(R)—; or one of A, B, C and D is N and the others are —C(R)—; wherein R is selected from the group consisting of hydrogen, alkyl, alkenyl, —CN, —$NO_2$, halogen, hydroxy, alkoxy, —$NH_2$, —N(H)(alkyl), —N(alkyl)$_2$, —S(alkyl), —S(O)$_2$alkyl, —S(O)$_2$OH, —S(O)$_2$Oalkyl, —C(O)OH, —C(O)Oalkyl, —C(O)H, haloalkyl, cyanoalkyl, nitroalkyl, hydroxyalkyl, alkoxyalkyl, and haloalkoxyalkyl;

$R_3$, at each occurrence, is independently selected from the group consisting of hydrogen, alkyl, arylalkyl, haloalkyl, and heteroarylalkyl;

$R_5$, at each occurrence, is independently selected from the group consisting of hydrogen, alkyl, alkenyl, haloalkyl, alkoxyalkyl, haloalkoxyalkyl, —$R_8$, and -alkylenyl-$R_8$;

$Ar_1$ is selected from the group consisting of phenyl, pyridinyl, thienyl, furanyl, thiazolyl, and 1,3,4-thiadiazolyl;

$Ar_2$ is selected from the group consisting of thienyl, thiazolyl, isoxazolyl, 1,2,4-thiadiazolyl, and 1,2,4-oxadiazolyl, wherein each $Ar_2$ is independently unsubstituted or substituted with 1 or 2 substituents selected from the group consisting of alkyl, alkenyl, halogen, —CN, —$NO_2$, hydroxy, alkoxy, —$NH_2$, —N(H)(alkyl), —N(alkyl)$_2$, —C(O)OH, —C(O)Oalkyl, —C(O)H, —C(O)alkyl, and haloalkyl;

Z is selected from the group consisting of —$OR_{9a}$, -alkylenyl-$OR_{9a}$, —$NR_6R_{9b}$ and -alkylenyl-$NR_6R_{9b}$;

$R_6$, at each occurrence, is independently selected from the group consisting of hydrogen, alkyl and haloalkyl;

$R_{9a}$ at each occurrence, is independently selected from the group consisting of hydrogen, alkyl, haloalkyl, $R_8$, —C(O)$OR_{10}$, —S(O)$_2R_{10}$, —C(O)$NR_7R_{11}$, —S(O)$_2NR_7R_{11}$, —C(O)$R_{10}$, alkylenyl-$OR_{10}$, -alkylenyl-$NR_7R_{11}$, -alkylenyl-N($R_7$)C(O)$OR_{10}$, -alkylenyl-N($R_7$)C(O)$R_{10}$, -alkylenyl-C(O)$OR_{10}$, -alkylenyl-S(O)$_2R_{10}$, -alkylenyl-S(O)$_2NR_7R_{11}$, -alkylenyl-C(O)$NR_7R_{11}$, -alkylenyl-C(O)$R_{10}$, and -alkylenyl-$R_8$, $R_{9b}$, at each occurrence, is independently selected from the group consisting of hydrogen, alkyl, hydroxy, alkoxy, $R_8$, —C(=NH)$NH_2$, —C(O)$OR_{10}$, —S(O)$_2 R_{10}$, —C(O)$NR_7R_{12}$, —C(O)$ONH_2$, —S(O)$_2 NR_7R_{12}$, —C(O)$R_{10}$, —C(O)$CH_2$C(O)$R_{10}$, haloalkyl, -alkylenyl-$OR_{10}$, -alkylenyl-$NR_7R_{12}$, -alkylenyl-N($R_7$)C(O)$OR_{10}$, -alkylenyl-N($R_7$)C(O)$R_{10}$, -alkylenyl-C(O)$OR_{10}$, -alkylenyl-S(O)$_2R_{10}$, -alkylenyl-S(O)$_2NR_7R_{12}$, -alkylenyl-C(O)$NR_7R_{12}$, -alkylenyl-C(O)$R_{10}$, and -alkylenyl-$R_8$, $R_7$, at each occurrence, are each independently selected from the group consisting of hydrogen, alkyl and haloalkyl;

$R_{10}$, at each occurrence, is independently selected from the group consisting of hydrogen, alkyl, alkoxyalkyl, cyanoalkyl, haloalkyl, —$R_8$, and -alkylenyl-$R_8$;

$R_{11}$, at each occurrence, is independently selected from the group consisting of hydrogen, alkyl, hydroxy, alkoxy, alkoxyalkyl, cyanoalkyl, haloalkyl, —$R_8$, and -alkylenyl-$R_8$;

$R_{12}$, at each occurrence, is independently selected from the group consisting of hydrogen, alkyl, hydroxy, alkoxy, —$R_8$, alkoxyalkyl, cyanoalkyl, haloalkyl, -alkylenyl-C(O)$NH_2$, -alkylenyl-C(O)N(H) (alkyl), -alkylenyl-C(O)N (alkyl)$_2$, -alkylenyl-N(H)C(O)Oalkyl, -alkylenyl-N(alkyl)C(O)Oalkyl, and -alkylenyl-$R_8$; and $R_8$, at each occurrence, is independently selected from the group consisting of aryl, heteroaryl, heterocycle, cycloalkyl and cycloalkenyl;

the aryl moiety of the arylalkyl, and the heteroaryl moiety of the heteroarylalkyl represented by $R_3$ and the aryl, heteroaryl, heterocycle, cycloalkyl and cycloalkenyl represented by $R_8$ are each independently unsubstituted or substituted with 1, 2, 3 or 4 substituents independently selected from the group consisting of alkyl, alkenyl, —CN, —$NO_2$, halogen, ethylenedioxy, methylenedioxy, oxo, —$OR_a$, —OC(O)$R_a$, —OC(O)$OR_a$, —OS(O)$_2R_a$, —S (alkyl), —S(O) alkyl, —S(O)$_2$alkyl, —S(O)$_2OR_a$, —S(O)$_2NR_aR_b$, —C(O)$R_a$, —C(O)$NR_aR_b$, —C(O)$OR_a$, —C(O)$NR_aR_b$, —$NR_aR_b$, —$NOR_a$, —N($R_b$)C(O)$R_a$, —N($R_b$)C(O)$OR_a$, —N($R_b$)S(O)$_2R_a$, —N($R_b$)C(O)$NR_aR_b$, —N($R_b$)S(O)$_2NR_aR_b$, haloalkyl, cyanoalkyl, nitroalkyl, hydroxyalkyl, alkoxyalkyl, haloalkoxyalkyl, -alkylenyl-OC(O)$R_a$, -alkylenyl-OC(O)$OR_a$, -alkylenyl-OS(O)$_2$alkyl, -alkylenyl-S(alkyl), -alkylenyl-S(O)alkyl, -alkylenyl-S(O)$_2$alkyl, -alkylenyl-S(O)$_2OR_a$, -alkylenyl-S(O)$_2NR_aR_b$, -alkylenyl-C(O)$R_a$, -alkylenyl-C(O)$NR_aR_b$, -alkylenyl-C(O)$OR_a$, -alkylenyl-C(O)$NR_aR_b$, -alkylenyl-$NR_aR_b$, -alkylenyl-N($R_b$)C(O)$R_a$, -alkylenyl-N($R_b$)C(O)$OR_a$, -alkylenyl-N($R_b$)S(O)$_2R_a$, -alkylenyl-N($R_b$)C(O)$NR_aR_b$, and -alkylenyl-N($R_b$)S(O)$_2NR_aR_b$;

the phenyl, pyridinyl, thienyl, furanyl, thiazolyl, and 1,3,4-thiadiazolyl represented by $Ar_1$ are each independently unsubstituted or substituted with 1, 2, 3 or 4 substituents independently selected from the group consisting of alkyl, alkenyl, —CN, —NO$_2$, halogen, ethylenedioxy, methylenedioxy, oxo, —OR$_a$, —OC(O)R$_a$, —OC(O)OR$_a$, —OS(O)$_2$R$_a$, —S (alkyl), —S(O)alkyl, —S(O)$_2$alkyl, —S(O)$_2$OR$_a$, —S(O)$_2$NR$_a$R$_b$, —C(O)R$_a$, —C(O)NR$_a$R$_b$, —C(O)OR$_a$, —C(O)NR$_a$R$_b$, —NR$_a$R$_b$, —NOR$_a$, —N(R$_b$)C(O)R$_a$, —N(R$_b$)C(O)OR$_a$, —N(R$_b$)S(O)$_2$R$_a$, —N(R$_b$)C(O)NR$_a$R$_b$, —N(R$_b$)S(O)$_2$NR$_a$R$_b$, haloalkyl, cyanoalkyl, nitroalkyl, hydroxyalkyl, alkoxyalkyl, haloalkoxyalkyl, -alkylenyl-OC(O)R$_a$, -alkylenyl-OC(O)OR$_a$, -alkylenyl-OS(O)$_2$alkyl, -alkylenyl-S(alkyl), -alkylenyl-S(O)alkyl, -alkylenyl-S(O)$_2$alkyl, -alkylenyl-S(O)$_2$OR$_a$, -alkylenyl-S(O)$_2$NR$_a$R$_b$, -alkylenyl-C(O)R$_a$, -alkylenyl-C(O)NR$_a$R$_b$, -alkylenyl-C(O)OR$_a$, -alkylenyl-C(O)NR$_a$R$_b$, -alkylenyl-NR$_a$R$_b$, -alkylenyl-N(R$_b$)C(O)R$_a$, -alkylenyl-N(R$_b$)C(O)OR$_a$, -alkylenyl-N(R$_b$)S(O)$_2$R$_a$, -alkylenyl-N(R$_b$)C(O)NR$_a$R$_b$, and -alkylenyl-N(R$_b$)S(O)$_2$NR$_a$R$_b$;

the phenyl represented by Ar$_1$ is independently unsubstituted or substituted with 1, 2, 3 or 4 substituents independently selected from the group consisting of alkyl, alkenyl, —CN, —NO$_2$, halogen, ethylenedioxy, methylenedioxy, —OR$_a$, —OC(O)R$_a$—OC(O)OR$_a$, —OS(O)$_2$R$_a$, —S(alkyl), —S(O)alkyl, —S(O)$_2$alkyl, —S(O)$_2$OR$_a$, —S(O)$_2$NR$_a$R$_b$, —NR$_a$R$_b$, —NOR$_a$, —N(R$_b$)C(O)R$_a$, —N(R$_b$)C(O)OR$_a$, —N(R$_b$)S(O)$_2$R$_a$, —N(R$_b$)C(O)NR$_a$R$_b$, —N(R$_b$)S(O)$_2$NR$_a$R$_b$, haloalkyl, cyanoalkyl, nitroalkyl, hydroxyalkyl, alkoxyalkyl, haloalkoxyalkyl, -alkylenyl-OC(O)R$_a$, -alkylenyl-OC(O)OR$_a$, -alkylenyl-OS(O)$_2$alkyl, -alkylenyl-S(alkyl), -alkylenyl-S(O)alkyl, -alkylenyl-S(O)$_2$alkyl, -alkylenyl-S(O)$_2$OR$_a$, -alkylenyl-S(O)$_2$NR$_a$R$_b$, -alkylenyl-C(O)R$_a$, -alkylenyl-C(O)NR$_a$R$_b$, -alkylenyl-C(O)OR$_a$, -alkylenyl-C(O)NR$_a$R$_b$, -alkylenyl-NR$_a$R$_b$, -alkylenyl-N(R$_b$)C(O)R$_a$, -alkylenyl-N(R$_b$)C(O)OR$_a$, -alkylenyl-N(R$_b$)S(O)$_2$R$_a$, -alkylenyl-N(R$_b$)C(O)NR$_a$R$_b$, and -alkylenyl-N(R$_b$) S(O)$_2$NR$_a$R$_b$;

wherein R$_a$ at each occurrence is independently selected from the group consisting of hydrogen, alkyl, alkenyl and haloalkyl, and R$_b$ at each occurrence is independently selected from the group consisting of hydrogen and alkyl.

2. The compound of claim 1 or a pharmaceutically acceptable salt thereof, wherein Ar$_3$ is selected from the group consisting of

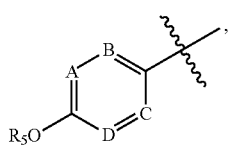
(a)

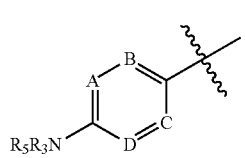
(b)

and

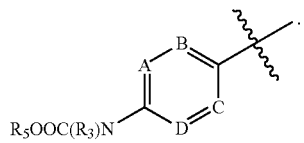
(c)

3. The compound of claim 2 or a pharmaceutically acceptable salt thereof, wherein R$_3$ is hydrogen and R$_5$ at each occurrence is independently selected from the group consisting of alkyl, —R$_8$ and -alkylenyl-R$_8$ wherein R$_8$ is selected from the group consisting of cycloalkyl, heterocycle and aryl.

4. The compound of claim 2 or a pharmaceutically acceptable salt thereof, wherein Ar$_3$ is

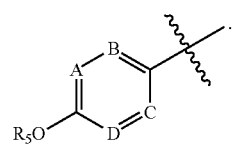
(a)

5. The compound of claim 2 or a pharmaceutically acceptable salt thereof, wherein Ar$_3$ is

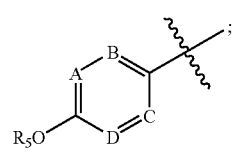
(a);

and

Ar$_1$ is unsubstituted or substituted thiazolyl.

6. The compound of claim 2 or a pharmaceutically acceptable salt thereof, wherein Ar$_3$ is

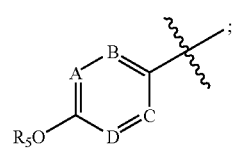
(a);

wherein R is selected from the group consisting of hydrogen, —I, —Br, —Cl, and —F;
Ar$_1$ is independently unsubstituted or substituted with one substituent selected from the group consisting of —I, —Br, —Cl, and —F;
Ar$_2$ is independently unsubstituted or substituted with one C$_1$-C$_6$ alkyl;
R$_1$ is selected from the group consisting of C$_1$-C$_6$ alkyl and haloalkyl;
Z is selected from the group consisting of —OR$_{9a}$ and —NR$_6$R$_{9b}$; wherein R$_{9a}$ is —S(O)$_2$(C$_1$-C$_6$ alkyl), R$_6$ is hydrogen, and R$_{9b}$ is selected from the group consisting of hydrogen, —C(O)NH$_2$, —C(O)N(H)(C$_1$-C$_6$ alkyl), —C(O)O(C$_1$-C$_6$ alkyl), —S(O)$_2$(C$_1$-C$_6$ alkyl), —CH$_2$—C(O)O(C$_1$-C$_6$ alkyl), and —C(O)R$_{10}$ wherein R$_{10}$ is C$_1$-C$_6$ alkyl or unsubstituted C$_3$-C$_6$ cycloalkyl;

and $R_5$ is selected from the group consisting of $C_1$-$C_6$ alkyl, —$R_8$, and —($C_1$-$C_6$ alkylenyl)-$R_3$; wherein $R_8$ at each occurrence is an unsubstituted ring selected from the group consisting of phenyl, cyclopropyl, cyclopentyl, cyclohexyl, tetrahydrofuranyl and tetrahydropyranyl.

7. The compound of claim 2 or a pharmaceutically acceptable salt thereof, wherein $Ar_3$ is

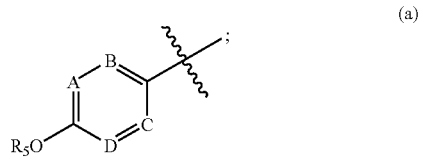

wherein R is selected from the group consisting of hydrogen, —I, —Br, —Cl, and —F;
$Ar_1$ is independently unsubstituted or substituted with one substituent selected from the group consisting of —I, —Br, —Cl, and —F;
$Ar_2$ is independently unsubstituted or substituted with one substituent selected from the group consisting of methyl and ethyl;
$R_1$ is selected from the group consisting of methyl and trifluoromethyl;
Z is selected from the group consisting of —$OR_{9a}$, and —$NR_6R_{9b}$; wherein $R_{9a}$ is —$S(O)_2$(methyl), $R_6$ is hydrogen, and $R_{9b}$ is selected from the group consisting of hydrogen, —$C(O)NH_2$, —$C(O)N(H)$(methyl), —$C(O)O$(methyl), —$S(O)_2$(methyl), —$CH_2$—$C(O)O$(methyl), and —$C(O)R_{10}$ wherein $R_{10}$ is methyl, ethyl, isopropyl or unsubstituted cyclopropyl; and
$R_5$ is selected from the group consisting of methyl, ethyl, isopropyl, 2-methylpropyl, —$R_8$, and —$CH_2$—$R_8$; wherein $R_8$ at each occurrence is an unsubstituted ring selected from the group consisting of phenyl, cyclopropyl, cyclopentyl, cyclohexyl, tetrahydrofuranyl and tetrahydropyranyl.

8. The compound of claim 4 selected from the group consisting of
N-(1-{3-[2-(4-isopropoxyphenoxy)-1,3-thiazol-5-yl]isoxazol-5-yl}ethyl)acetamide;
N-(1-{5-[2-(4-phenoxyphenoxy)-1,3-thiazol-5-yl]thien-2-yl}ethyl)urea;
N-(1-{5-[2-(4-isopropoxyphenoxy)-1,3-thiazol-5-yl]thien-2-yl}ethyl)acetamide;
N-{1-[2'-(4-isopropoxyphenoxy)-2,5'-bi-1,3-thiazol-5-yl]ethyl}acetamide;
N-(2,2,2-trifluoro-1-{5-[2-(4-isopropoxyphenoxy)-1,3-thiazol-5-yl]thien-2-yl}urea;
N-(1-{3-[2-(4-isopropoxyphenoxy)-1,3-thiazol-5-yl]isoxazol-5-yl}ethyl)propanamide;
N-(1-{3-[2-(4-isopropoxyphenoxy)-1,3-thiazol-5-yl]isoxazol-5-yl}ethyl)urea;
N-(1-{3-[2-(4-isopropoxyphenoxy)-1,3-thiazol-5-yl]isoxazol-5-yl}ethyl)-N'-methylurea;
N-(1-{3-[2-(2-chloro-4-isobutoxyphenoxy)-1,3-thiazol-5-yl]isoxazol-5-yl}ethyl)cyclopropanecarboxamide;
N-(1-{3-[2-(2-chloro-4-isobutoxyphenoxy)-1,3-thiazol-5-yl]isoxazol-5-yl}ethyl)-2-methylpropanamide;
N-(1-{3-[2-(2-chloro-4-isobutoxyphenoxy)-1,3-thiazol-5-yl]isoxazol-5-yl}ethyl)acetamide;
N-(1-{3-[2-(2-chloro-4-isobutoxyphenoxy)-1,3-thiazol-5-yl]isoxazol-5-yl}ethyl)propanamide;
methyl 1-{3-[2-(2-chloro-4-isobutoxyphenoxy)-1,3-thiazol-5-yl]isoxazol-5-yl}ethylcarbamate;
N-(1-{3-[2-(2-chloro-4-isobutoxyphenoxy)-1,3-thiazol-5-yl]isoxazol-5-yl}ethyl)-N'-methylurea;
N-((1R)-1-{3-[2-(4-isopropoxyphenoxy)-1,3-thiazol-5-yl]isoxazol-5-yl}ethyl)acetamide;
N-((1S)-1-{3-[2-(4-isopropoxyphenoxy)-1,3-thiazol-5-yl]isoxazol-5-yl}ethyl)acetamide;
N-(1-{3-[4-(4-isopropoxyphenoxy)phenyl]isoxazol-5-yl}ethyl)acetamide;
N-(1-{3-[2-(2-chloro-4-methoxyphenoxy)-1,3-thiazol-5-yl]isoxazol-5-yl}ethyl)acetamide;
methyl 1-{3-[2-(2-chloro-4-methoxyphenoxy)-1,3-thiazol-5-yl]isoxazol-5-yl}ethylcarbamate;
N-(1-{3-[2-(2-chloro-4-methoxyphenoxy)-1,3-thiazol-5-yl]isoxazol-5-yl}ethyl)-2-methylpropanamide;
N-(1-{3-[2-(2-chloro-4-methoxyphenoxy)-1,3-thiazol-5-yl]isoxazol-5-yl}ethyl)cyclopropanecarboxamide;
methyl 1-{3-[4-(4-isopropoxyphenoxy)phenyl]isoxazol-5-yl}ethylcarbamate;
N-(1-{3-[4-(4-isopropoxyphenoxy)phenyl]isoxazol-5-yl}ethyl)urea;
N-(1-{5-[5-(4-isopropoxyphenoxy)-1,3,4-thiadiazol-2-yl]thien-2-yl}ethyl)acetamide;
N-(1-{3-[2-(2-chloro-4-isopropoxyphenoxy)-1,3-thiazol-5-yl]isoxazol-5-yl}ethyl)acetamide;
methyl 1-{3-[2-(2-chloro-4-isopropoxyphenoxy)-1,3-thiazol-5-yl]isoxazol-5-yl}ethylcarbamate;
N-(1-{3-[2-(2-chloro-4-isopropoxyphenoxy)-1,3-thiazol-5-yl]isoxazol-5-yl}ethyl)-2-methylpropanamide;
N-(1-{3-[2-(2-chloro-4-isopropoxyphenoxy)-1,3-thiazol-5-yl]isoxazol-5-yl}ethyl)cyclopropanecarboxamide;
N-[1-(3-{2-[2-chloro-4-(cyclopropylmethoxy)phenoxy]-1,3-thiazol-5-yl}isoxazol-5-yl)ethyl]acetamide;
methyl 1-(3-{2-[2-chloro-4-(cyclopropylmethoxy)phenoxy]-1,3-thiazol-5-yl}isoxazol-5-yl)ethylcarbamate;
N-[1-(3-{2-[2-chloro-4-(cyclopropylmethoxy)phenoxy]-1,3-thiazol-5-yl}isoxazol-5-yl)ethyl]-N'-methylurea;
N-(1-{5-[5-(4-isopropoxyphenoxy)-1,3,4-thiadiazol-2-yl]thien-2-yl}ethyl)-N'-methylurea;
N-(1-{3-[2-(2-chloro-4-isopropoxyphenoxy)-1,3-thiazol-5-yl]isoxazol-5-yl}ethyl)urea;
N-(1-{3-[2-(2-chloro-4-isopropoxyphenoxy)-1,3-thiazol-5-yl]isoxazol-5-yl}ethyl)-N'-methylurea;
N-[1-(3-{2-[2-chloro-4-(tetrahydrofuran-3-ylmethoxy)phenoxy]-1,3-thiazol-5-yl}isoxazol-5-yl)ethyl]acetamide;
N-[1-(3-{2-[2-chloro-4-(tetrahydrofuran-3-yloxy)phenoxy]-1,3-thiazol-5-yl}isoxazol-5-yl)ethyl]acetamide;
N-(1-{3-[2-(2-chloro-4-ethoxyphenoxy)-1,3-thiazol-5-yl]isoxazol-5-yl}ethyl)acetamide;
N-(1-{3-[2-(4-isopropoxyphenoxy)-1,3-thiazol-5-yl]-1,2,4-oxadiazol-5-yl}ethyl)acetamide;
N-(1-{3-[5-(4-isopropoxyphenoxy)thien-2-yl]isoxazol-5-yl}ethyl)acetamide;
N-(1-{3-[5-(4-isopropoxyphenoxy)-2-furyl]isoxazol-5-yl}ethyl)acetamide;
N-(1-{3-[5-(4-isopropoxyphenoxy)-2-furyl]isoxazol-5-yl}ethyl)-N'-methylurea;
N-[1-(3-{2-[2-chloro-4-(cyclohexyloxy)phenoxy]-1,3-thiazol-5-yl}isoxazol-5-yl)ethyl]acetamide;
N-[1-(3-{2-[2-chloro-4-(cyclopentyloxy)phenoxy]-1,3-thiazol-5-yl}isoxazol-5-yl)ethyl]acetamide;

N-[1-(3-{2-[2-chloro-4-(tetrahydro-2H-pyran-4-yloxy)
phenoxy]-1,3-thiazol-5-yl}isoxazol-5-yl)ethyl]aceta-
mide;
N-[1-(3-{2-[4-(cyclopropylmethoxy)phenoxy]-1,3-thia-
zol-5-yl}isoxazol-5-yl)ethyl]acetamide;
methyl 1-(3-{2-[4-(cyclopropylmethoxy)phenoxy]-1,3-
thiazol-5-yl}isoxazol-5-yl)ethylcarbamate;
N-[1-(3-{2-[4-(cyclopropylmethoxy)phenoxy]-1,3-thia-
zol-5-yl}isoxazol-5-yl)ethyl]urea;
N-[1-(3-{2-[4-(cyclopropylmethoxy)phenoxy]-1,3-thia-
zol-5-yl}isoxazol-5-yl)ethyl]-N'-methylurea;
N-[1-(3-{2-[4-(tetrahydro-2H-pyran-4-yloxy)phenoxy]-
1,3-thiazol-5-yl}isoxazol-5-yl)ethyl]acetamide;
N-[1-(3-{2-[4-(tetrahydrofuran-3-yloxy)phenoxy]-1,3-
thiazol-5-yl}isoxazol-5-yl)ethyl]acetamide;
N-[1-(3-{2-[4-(cyclohexyloxy)phenoxy]-1,3-thiazol-5-
yl}isoxazol-5-yl)ethyl]acetamide;
N-[1-(3-{2-[4-(cyclopentyloxy)phenoxy]-1,3-thiazol-5-
yl}isoxazol-5-yl)ethyl]acetamide;
N-(1-{3-[4-chloro-2-(4-isopropoxyphenoxy)-1,3-thiazol-
5-yl]isoxazol-5-yl}ethyl)acetamide;
N-(1-{3-[4-chloro-2-(4-isopropoxyphenoxy)-1,3-thiazol-
5-yl]isoxazol-5-yl}ethyl)-N'-methylurea;
methyl 1-{3-[4-chloro-2-(4-isopropoxyphenoxy)-1,3-
thiazol-5-yl]isoxazol-5-yl}ethylcarbamate;
N-(1-{3-[4-chloro-2-(4-isopropoxyphenoxy)-1,3-thiazol-
5-yl]isoxazol-5-yl}ethyl)urea;
methyl 1-{3-[2-(4-isopropoxyphenoxy)-1,3-thiazol-5-yl]-
1,2,4-oxadiazol-5-yl}ethylcarbamate;
N-(1-{3-[2-(4-isopropoxyphenoxy)-1,3-thiazol-5-yl]-1,2,
4-oxadiazol-5-yl}ethyl)-N'-methylurea;
N-(1-{3-[2-(4-isopropoxyphenoxy)-1,3-thiazol-5-yl]-1,2,
4-oxadiazol-5-yl}ethyl)urea;
N-[1-(3-{2-[(6-isopropoxypyridin-3-yl)oxy]-1,3-thiazol-
5-yl}isoxazol-5-yl)ethyl]acetamide;
N-[1-(3-{4-[(5-isopropoxypyridin-2-yl)oxy]
phenyl}isoxazol-5-yl)ethyl]acetamide;
N-(1-{3-[6-(4-isopropoxyphenoxy)pyridin-3-yl]isoxazol-
5-yl}ethyl)acetamide;
1-{3-[2-(4-isopropoxyphenoxy)-1,3-thiazol-5-yl]-1,2,4-
oxadiazol-5-yl}ethanamine;
N-(1-{3-[2-(4-isopropoxyphenoxy)-1,3-thiazol-5-yl]-1,2,
4-oxadiazol-5-yl}ethyl)cyclopropanecarboxamide;
N-(1-{3-[2-(4-isopropoxyphenoxy)-1,3-thiazol-5-yl]-1,2,
4-oxadiazol-5-yl}ethyl)methanesulfonamide;
N-(1-{3-[2-(4-isopropoxyphenoxy)-1,3-thiazol-5-yl]-1,2,
4-oxadiazol-5-yl}ethyl)-2-methylpropanamide;
N-[1-(3-{2-[(6-isopropoxypyridin-3-yl)oxy]-1,3-thiazol-
5-yl}-1,2,4-oxadiazol-5-yl)ethyl]acetamide;
N-[1-(3-{6-[(6-isopropoxypyridin-3-yl)oxy]pyridin-3-
yl}isoxazol-5-yl)ethyl]acetamide;
N-[1-(3-{6-[(6-isopropoxypyridin-3-yl)oxy]pyridin-3-
yl}isoxazol-5-yl)ethyl]urea;
N-[1-(3-{6-[(6-isopropoxypyridin-3-yl)oxy]pyridin-3-
yl}isoxazol-5-yl)ethyl]-N'-methylurea;
methyl 1-(3-{6-[(6-isopropoxypyridin-3-yl)oxy]pyridin-
3-yl}isoxazol-5-yl)ethylcarbamate;
methyl 1-(3-{2-[(6-isopropoxypyridin-3-yl)oxy]-1,3-thia-
zol-5-yl}-1,2,4-oxadiazol-5-yl)ethylcarbamate;
N-[1-(3-{2-[(6-isopropoxypyridin-3-yl)oxy]-1,3-thiazol-
5-yl}-1,2,4-oxadiazol-5-yl)ethyl]urea;
N-[1-(3-{2-[(6-isopropoxypyridin-3-yl)oxy]-1,3-thiazol-
5-yl}-1,2,4-oxadiazol-5-yl)ethyl]-N'-methylurea;
1-{3-[2-(4-isopropoxyphenoxy)-1,3-thiazol-5-yl]-1,2,4-
thiadiazol-5-yl}ethyl methanesulfonate;
N-(1-{3-[2-(4-isopropoxyphenoxy)-1,3-thiazol-5-yl]-1,2,
4-thiadiazol-5-yl}ethyl)acetamide;
methyl 1-{3-[2-(4-isopropoxyphenoxy)-1,3-thiazol-5-yl]-
1,2,4-thiadiazol-5-yl}ethylcarbamate;
methyl [(1-{3-[2-(4-isopropoxyphenoxy)-1,3-thiazol-5-
yl]-1,2,4-oxadiazol-5-yl}ethyl)amino]acetate;
N-(1-{3-[2-(4-isopropoxyphenoxy)-1,3-thiazol-5-yl]-4-
methylisoxazol-5-yl}ethyl)acetamide; and
N-(1-{4-ethyl-3-[2-(4-isopropoxyphenoxy)-1,3-thiazol-
5-yl]isoxazol-5-yl}ethyl)acetamide;
or a pharmaceutically acceptable salt thereof.

9. The compound of claim 2 or a pharmaceutically acceptable salt thereof, wherein Ar$_3$ is selected from the group of formula consisting of

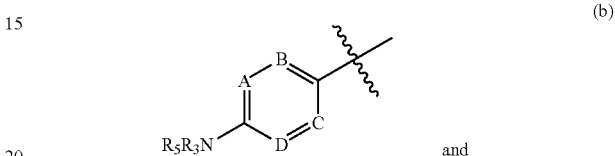

(b)

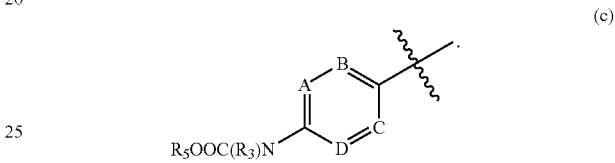

and (c)

10. The compound of claim 2 or a pharmaceutically acceptable salt thereof, wherein Ar$_3$ is selected from the group of formula consisting of

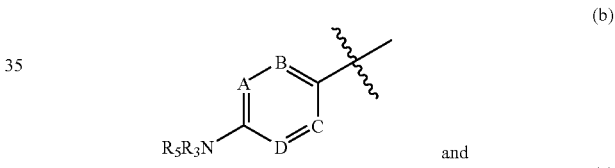

(b)

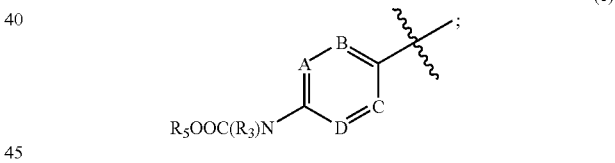

and (c)

;

and
Ar$_1$ is unsubstituted or substituted thiazolyl.

11. The compound of claim 2 or a pharmaceutically acceptable salt thereof, wherein Ar$_3$ is

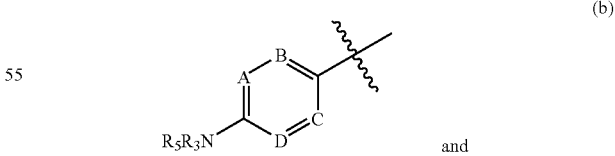

(b)

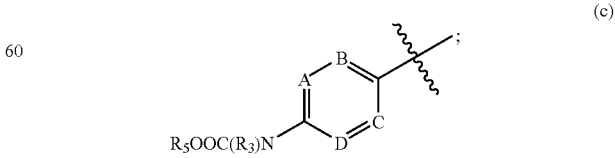

and (c)

;

wherein R is selected from the group consisting of hydrogen, —I, —Br, —Cl, and —F;

Ar$_1$ is independently unsubstituted or substituted with one substituent selected from the group consisting of —I, —Br, —Cl, and —F;

Ar$_2$ is independently unsubstituted or substituted with one C$_1$-C$_6$ alkyl;

R$_1$ is selected from the group consisting of C$_1$-C$_6$ alkyl and haloalkyl;

Z is selected from the group consisting of —OR$_{9a}$ and —NR$_6$R$_{9b}$; wherein R$_{9a}$ is —S(O)$_2$(C$_1$-C$_6$ alkyl), R$_6$ is hydrogen, and R$_{9b}$ is selected from the group consisting of hydrogen, —C(O)NH$_2$, —C(O)N(H)(C$_1$-C$_6$ alkyl), —C(O)O(C$_1$-C$_6$ alkyl), —S(O)$_2$(C$_1$-C$_6$ alkyl), —CH$_2$—C(O)O(C$_1$-C$_6$ alkyl), and —C(O)R$_{10}$ wherein R$_{10}$ is C$_1$-C$_6$ alkyl or unsubstituted C$_3$-C$_6$ cycloalkyl;

R$_3$ is hydrogen; and

R$_5$ at each occurrence is independently selected from the group consisting of C$_1$-C$_9$ alkyl, —R$_8$, and —(C$_1$-C$_6$ alkylenyl)-R$_8$; wherein R$_8$ at each occurrence is an unsubstituted ring selected from the group consisting of phenyl, cyclopropyl, cyclopentyl, cyclohexyl, tetrahydrofuranyl and tetrahydropyranyl.

12. The compound of claim 2 or a pharmaceutically acceptable salt thereof, wherein Ar$_3$ is selected from the group of formula consisting of

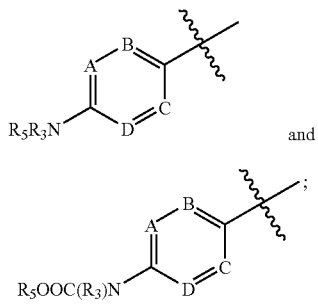

wherein R is selected from the group consisting of hydrogen, —I, —Br, —Cl, and —F;

Ar$_1$ is independently unsubstituted or substituted with one substituent selected from the group consisting of —I, —Br, —Cl, and —F;

Ar$_2$ is independently unsubstituted or substituted with one substituent selected from the group consisting of methyl and ethyl;

R$_1$ is selected from the group consisting of methyl and trifluoromethyl;

Z is selected from the group consisting of —OR$_{9a}$ and —NR$_6$R$_{9b}$; wherein R$_{9a}$ is —S(O)$_2$(methyl), R$_6$ is hydrogen, and R$_{9b}$ is selected from the group consisting of hydrogen, —C(O)NH$_2$, —C(O)N(H) (methyl), —C(O)O(methyl), —S(O)$_2$(methyl), —CH$_2$—C(O)O (methyl), and —C(O)R$_{10}$ wherein R$_{10}$ is methyl, ethyl, isopropyl or unsubstituted cyclopropyl;

R$_3$ is hydrogen; and

R$_5$ at each occurrence is independently selected from the group consisting of methyl, ethyl, isopropyl, 2-methylpropyl, tert-butyl, —R$_8$, and —CH$_2$—R$_8$; wherein R$_8$ at each occurrence is an unsubstituted ring selected from the group consisting of phenyl, cyclopropyl, cyclopentyl, cyclohexyl, tetrahydrofuranyl and tetrahydropyranyl.

13. The compound of claim 9 selected from the group consisting of

N-[1-(3-{2-[4-(isopropylamino)phenoxy]-1,3-thiazol-5-yl}isoxazol-5-yl)ethyl]acetamide;

N-{1-[3-(2-(4-[(cyclopropylmethyl)amino]phenoxy)-1,3-thiazol-5-yl]isoxazol-5-yl]ethyl}acetamide;

N-[1-(3-{(2-[4-(isobutylamino)phenoxy])-1,3-thiazol-5-yl}isoxazol-5-yl)ethyl]acetamide;

N-{1-[3-(2-{3-chloro-4-[(cyclopropylmethyl)amino]phenoxy}-1,3-thiazol-5-yl)isoxazol-5-yl]ethyl}acetamide;

tert-butyl 4-[(5-{5-[1-(acetylamino)ethyl]-1,2,4-oxadiazol-3-yl}-1,3-thiazol-2-yl)oxy]phenylcarbamate;

N-[1-(3-{2-[4-(isobutylamino)phenoxy]-1,3-thiazol-5-yl}-1,2,4-oxadiazol-5-yl)ethyl]acetamide;

tert-butyl 4-[(5-{5-[1-(acetylamino)ethyl]-1,2,4-oxadiazol-3-yl}-1,3-thiazol-2-yl)oxy]-2-chlorophenylcarbamate;

N-{1-[3-(2-{3-chloro-4-[(cyclopropylmethyl)amino]phenoxy}-1,3-thiazol-5-yl)-1,2,4-oxadiazol-5-yl]ethyl}acetamide;

N-[1-(3-{2-[3-chloro-4-(isobutylamino)phenoxy]-1,3-thiazol-5-yl}-1,2,4-oxadiazol-5-yl)ethyl]acetamide;

N-[1-(3-{2-[3-chloro-4-(isopropylamino)phenoxy]-1,3-thiazol-5-yl}-1,2,4-oxadiazol-5-yl)ethyl]acetamide;

N-[1-(3-{2-[4-(isopropylamino)phenoxy]-1,3-thiazol-5-yl}-1,2,4-oxadiazol-5-yl)ethyl]acetamide;

tert-butyl 4-[(5-{5-[1-(acetylamino)ethyl]-1,2,4-oxadiazol-3-yl}-1,3-thiazol-2-yl)oxy]-3-chlorophenylcarbamate;

N-[1-(3-{2-[2-chloro-4-(isopropylamino)phenoxy]-1,3-thiazol-5-yl}-1,2,4-oxadiazol-5-yl)ethyl]acetamide;

N-{1-[3-(2-{2-chloro-4-[(cyclopropylmethyl)amino]phenoxy}-1,3-thiazol-5-yl)-1,2,4-oxadiazol-5-yl]ethyl}acetamide;

N-[1-(3-{2-[2-chloro-4-(isobutylamino)phenoxy]-1,3-thiazol-5-yl}-1,2,4-oxadiazol-5-yl)ethyl]acetamide; and N-[1-(3-{2-[4-(benzylamino)-2-chlorophenoxy]-1,3-thiazol-5-yl}-1,2,4-oxadiazol-5-yl)ethyl]acetamide;

or a pharmaceutically acceptable salt thereof.

14. The compound of claim 1 or a pharmaceutically acceptable salt thereof, wherein Ar$_3$ is selected from the group consisting of

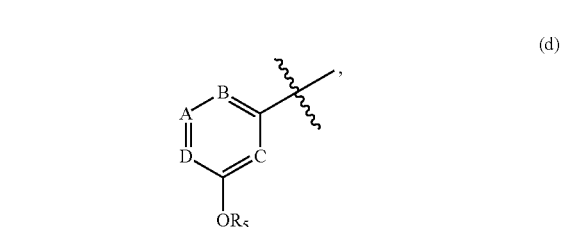

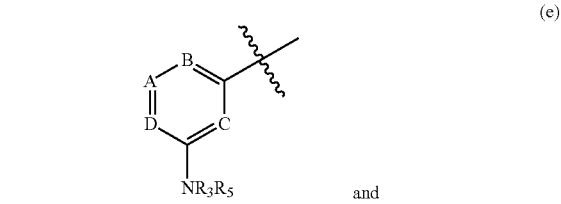

(f)

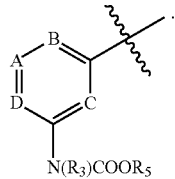

N(R₃)COOR₅

15. The compound of claim 14 or a pharmaceutically acceptable salt thereof, wherein Ar₃ is (d)

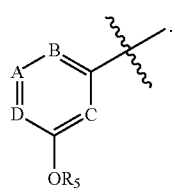

OR₅

16. The compound of claim 14 or a pharmaceutically acceptable salt thereof, wherein Ar₃ is (d)

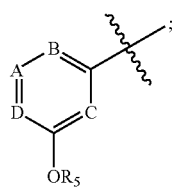

OR₅ wherein R is selected from the group consisting of —I, —Br, —Cl, and —F;

Ar₁ is independently unsubstituted or substituted with one substituent selected from the group consisting of hydrogen, —I, —Br, —Cl, and —F;

Ar₂ is independently unsubstituted or substituted with one $C_1$-$C_6$ alkyl;

R₁ is selected from the group consisting of $C_1$-$C_6$ alkyl and haloalkyl;

Z is selected from the group consisting of —OR$_{9a}$ and —NR₆R$_{9b}$; wherein R$_{9a}$ is —S(O)₂($C_1$-$C_6$ alkyl), R₆ is hydrogen, and R$_{9b}$ is selected from the group consisting of hydrogen, —C(O)NH₂, —C(O)N(H)($C_1$-$C_6$ alkyl), —C(O)O($C_1$-$C_6$ alkyl), —S(O)₂($C_1$-$C_6$ alkyl), —CH₂—C(O)O($C_1$-$C_6$ alkyl), and —C(O)R$_{10}$ wherein R$_{10}$ is $C_1$-$C_6$ alkyl or unsubstituted $C_3$-$C_6$ cycloalkyl; and R₅ is selected from the group consisting of $C_1$-$C_6$ alkyl, —R₈, and —($C_1$-$C_6$ alkylenyl)-R₈; wherein R₈ at each occurrence is an unsubstituted ring selected from the group consisting of phenyl, cyclopropyl, cyclopentyl, cyclohexyl, tetrahydrofuranyl and tetrahydropyranyl.

17. The compound of claim 14 or a pharmaceutically acceptable salt thereof, wherein Ar₃ is (d)

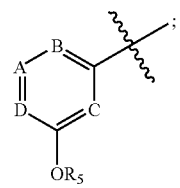

OR₅ wherein R is selected from the group consisting of hydrogen, —I, —Br, —Cl, and —F;

Ar₁ is independently unsubstituted or substituted with one substituent selected from the group consisting of —I, —Br, —Cl, and —F;

Ar₂ is independently unsubstituted or substituted with one substituent selected from the group consisting of methyl and ethyl;

R₁ is selected from the group consisting of methyl and trifluoromethyl;

Z is selected from the group consisting of —OR$_{9a}$ and —NR₆R$_{9b}$; wherein R$_{9a}$ is —S(O)₂(methyl), R₆ is hydrogen, and R$_{9b}$ is selected from the group consisting of hydrogen, —C(O)NH₂, —C(O)N(H)(methyl), —C(O)O(methyl), —S(O)₂(methyl), —CH₂—C(O)O(methyl), and —C(O)R$_{10}$ wherein R$_{10}$ is methyl, ethyl, isopropyl or unsubstituted cyclopropyl; and R₅ is selected from the group consisting of methyl, ethyl, isopropyl, 2-methylpropyl, —R₈, and —CH₂—R₈; wherein R₈ at each occurrence is an unsubstituted ring selected from the group consisting of phenyl, cyclopropyl, cyclopentyl, cyclohexyl, tetrahydrofuranyl and tetrahydropyranyl.

18. The compound of claim 15 selected from the group consisting of

N-[-(3-{2-[3-(cyclopropylmethoxy)phenoxy]-1,3-thiazol-5-yl}isoxazol-5-yl)ethyl]acetamide;

methyl 1-(3-{2-[3-(cyclopropylmethoxy)phenoxy]-1,3-thiazol-5-yl}isoxazol-5-yl)ethylcarbamate;

N-[1-(3-{2-[3-(cyclopropylmethoxy)phenoxy]-1,3-thiazol-5-yl}isoxazol-5-yl)ethyl]-N'-methylurea;

N-[1-(3-{2-[3-(cyclopropylmethoxy)phenoxy]-1,3-thiazol-5-yl}isoxazol-5-yl)ethyl]urea;

N-(1-{3-[2-(3-isopropoxyphenoxy)-1,3-thiazol-5-yl] isoxazol-5-yl}ethyl)acetamide;

methyl 1-{3-[2-(3-isopropoxyphenoxy)-1,3-thiazol-5-yl] isoxazol-5-yl}ethylcarbamate;

N-(1-{3-[2-(3-isopropoxyphenoxy)-1,3-thiazol-5-yl] isoxazol-5-yl}ethyl)-N'-methylurea; and N-(1-{3-[2-(3-isopropoxyphenoxy)-1,3-thiazol-5-yl] isoxazol-5-yl}ethyl)urea; or a pharmaceutically acceptable salt thereof.

19. The compound of claim 13 or a pharmaceutically acceptable salt thereof, wherein Ar₃ is selected from the group of formula consisting of (e)

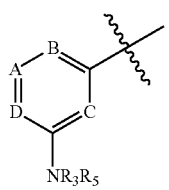

NR₃R₅    and

-continued

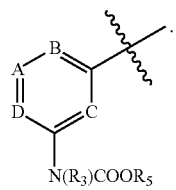
(f)

20. The compound of claim 14 or a pharmaceutically acceptable salt thereof, wherein $Ar_3$ is selected from the group of formula consisting of

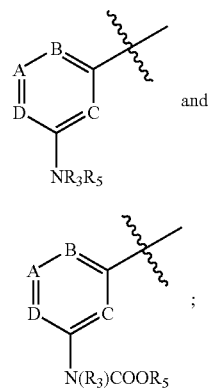

wherein R is selected from the group consisting of hydrogen, —I, —Br, —Cl, and —F;
$Ar_1$ is independently unsubstituted or substituted with one substituent selected from the group consisting of —I, —Br, —Cl, and —F;
$Ar_2$ is independently unsubstituted or substituted with one $C_1$-$C_6$ alkyl;
$R_1$ is selected from the group consisting of $C_1$-$C_6$ alkyl and haloalkyl;
Z is selected from the group consisting of $OR_{9a}$ and —$NR_6R_{9b}$; wherein $R_{9a}$ is —$S(O)_2(C_1$-$C_6$ alkyl), $R_6$ is hydrogen, and $R_{9b}$ is selected from the group consisting of hydrogen, —$C(O)NH_2$, —$C(O)N(H)(C_1$-$C_6$ alkyl), —$C(O)O(C_1$-$C_6$ alkyl), —$S(O)_2(C_1$-$C_6$ alkyl), —$CH_2$—$C(O)O(C_1$-$C_6$ alkyl), and —$C(O)R_{10}$ wherein $R_{10}$ is $C_1$-$C_6$ alkyl or unsubstituted $C_3$-$C_6$ cycloalkyl;
$R_3$ is hydrogen; and
$R_5$ at each occurrence is independently selected from the group consisting of $C_1$-$C_9$ alkyl, —$R_8$, and —$(C_1$-$C_6$ alkylenyl)-$R_8$; wherein $R_8$ at each occurrence is an unsubstituted ring selected from the group consisting of phenyl, cyclopropyl, cyclopentyl, cyclohexyl, tetrahydrofuranyl and tetrahydropyranyl.

21. The compound of claim 14 or a pharmaceutically acceptable salt thereof, wherein $Ar_3$ is selected from the group of formula consisting of

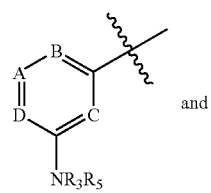

-continued

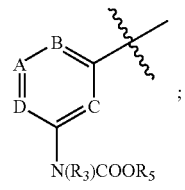
(f)

wherein R is selected from the group consisting of hydrogen, —I, —Br, —Cl, and —F;
$Ar_1$ is independently unsubstituted or substituted with one substituent selected from the group consisting of —I, —Br, —Cl, and —F;
$Ar_2$ is independently unsubstituted or substituted with one substituent selected from the group consisting of methyl and ethyl;
$R_1$ is selected from the group consisting of methyl and trifluoromethyl;
Z is selected from the group consisting of —$OR_{9a}$ and —$NR_6R_{9b}$; wherein $R_{9a}$ is —$S(O)_2$(methyl), $R_6$ is hydrogen, and $R_{9b}$ is selected from the group consisting of hydrogen, —$C(O)NH_2$, —$C(O)N(H)$(methyl), —$C(O)O$(methyl), —$S(O)_2$(methyl), —$CH_2$—$C(O)O$ (methyl), and —$C(O)R_{10}$ wherein $R_{10}$ is methyl, ethyl, isopropyl or unsubstituted cyclopropyl;
$R_3$ is hydrogen; and
$R_5$ is at each occurrence is independently selected from the group consisting of methyl, ethyl, isopropyl, 2-methylpropyl, tert-butyl, —$R_8$, and —$CH_2$—$R_8$; wherein $R_8$ at each occurrence is an unsubstituted ring selected from the group consisting of phenyl, cyclopropyl, cyclopentyl, cyclohexyl, tetrahydrofuranyl and tetrahydropyranyl.

22. The compound of claim 19 selected from the group consisting of

N-[1-(3-{2-[3-(isobutylamino)phenoxy]-1,3-thiazol-5-yl}isoxazol-5-yl)ethyl]acetamide;

N-{1-[3-(2-{3-[(cyclopropylmethyl)amino]phenoxy}-1,3-thiazol-5-yl)isoxazol-5-yl]ethyl}acetamide;

N-[1-(3-{2-[3-(isopropylamino)phenoxy]-1,3-thiazol-5-yl}isoxazol-5-yl)ethyl]acetamide;

N-[1-(3-{2-[3-(isopropylamino)phenoxy]-1,3-thiazol-5-yl}-1,2,4-oxadiazol-5-yl)ethyl]acetamide;

N-{1-[3-(2-(3-[(cyclopropylmethyl)amino]phenoxy)-1,3-thiazol-5-yl)-1,2,4-oxadiazol-5-yl]ethyl}acetamide; and N-[1-(3-{2-[3-(isobutylamino)phenoxy]-1,3-thiazol-5-yl}-1,2,4-oxadiazol-5-yl)ethyl]acetamide;

or a pharmaceutically acceptable salt thereof.

23. A method of inhibiting ACC comprising administering to a patient in need thereof a therapeutically effective amount of a compound of claim 1.

24. A method of inhibiting ACC-1 comprising administering to a patient in need thereof a therapeutically effective amount of a compound of claim 1.

25. A method of inhibiting ACC-2 comprising administering to a patient in need thereof a therapeutically effective amount of a compound of claim 1.

26. A method of treating metabolic syndrome comprising administering to a patient in need thereof a therapeutically effective amount of a compound of claim 1.

27. A method of treating type II diabetes comprising administering to a patient in need thereof a therapeutically effective amount of a compound of claim 1.

28. A method of treating obesity comprising administering to a patient in need thereof a therapeutically effective amount of a compound of claim 1.

29. A pharmaceutical composition comprising a therapeutically effective amount of a compound of claim 1 in combination with a pharmaceutically acceptable carrier.

* * * * *